US009951338B2

(12) United States Patent
Jimenez et al.

(10) Patent No.: US 9,951,338 B2
(45) Date of Patent: Apr. 24, 2018

(54) SIRNA AND THEIR USE IN METHODS AND COMPOSITIONS FOR INHIBITING THE EXPRESSION OF THE PDK1 GENE

(71) Applicant: SYLENTIS SAU, Madrid (ES)

(72) Inventors: Ana Isabel Jimenez, Madrid (ES);
Covadonga Pañeda, Madrid (ES);
Tamara Martinez, Madrid (ES)

(73) Assignee: SYLENTIS SAU, Madrid (ES)

( * ) Notice: Subject to any disclaimer, the term of this patent is extended or adjusted under 35 U.S.C. 154(b) by 0 days.

(21) Appl. No.: 15/030,188

(22) PCT Filed: Oct. 21, 2014

(86) PCT No.: PCT/EP2014/072516
§ 371 (c)(1),
(2) Date: Apr. 18, 2016

(87) PCT Pub. No.: WO2015/059124
PCT Pub. Date: Apr. 30, 2015

(65) Prior Publication Data
US 2016/0237440 A1 Aug. 18, 2016

(30) Foreign Application Priority Data

Oct. 22, 2013 (EP) ..................................... 13382414

(51) Int. Cl.
*C12N 15/113* (2010.01)
*A61K 31/7115* (2006.01)
*A61K 31/712* (2006.01)

(52) U.S. Cl.
CPC ...... *C12N 15/1137* (2013.01); *C12N 2310/14* (2013.01); *C12N 2310/321* (2013.01); *C12N 2310/50* (2013.01); *C12Y 207/11001* (2013.01)

(58) Field of Classification Search
None
See application file for complete search history.

(56) References Cited

U.S. PATENT DOCUMENTS

2005/0255487 A1* 11/2005 Khvorova ............ A61K 31/713
435/6.11
2007/0270365 A1* 11/2007 Jimenez .............. C12N 15/1137
514/44 A
2013/0123328 A1* 5/2013 Yu ........................ A61K 31/436
514/44 A

FOREIGN PATENT DOCUMENTS

WO   WO 2004/015107   2/2004
WO   WO 2008/104978   9/2008
WO   WO 2011/148193   12/2011

OTHER PUBLICATIONS

WO 2005116204-A/96132: Double Strand Polynucleotides Generating RNA Interference, retrieved from EBI Accession No. EM_PAT: FW689606, Database Accession No. FW689606, 2011, XP-002734078.
Sequence 364410 from Patent EP 2213738, retrieved from EBI Accession No. EM_PAT:HD487694, Database Accession No. HD487694, 2010, XP-002734079.
Pañeda et al., "Recent Advances in Ocular Nucleic Acid-Based Therapies: The Silent Era," InTech, pp. 157-186, Sep. 19, 2012.
Parrales et al., "Thrombin Activation of PI3K/PDK1/Akt Signaling Promotes Cyclin D1 Upregulation and RPE Cell Proliferation," Biochimica et Biophysica Acta, vol. 1813,, pp. 1758-1766, 2011.
Shumilina et al., "Phosphoinositide-dependent Kinase PDK1 in the Regulation of $Ca^{2+}$ Entry into Mast Cells," Cellular Physiology and Biochemistry, vol. 26, pp. 699-706, 2010.
Yu et al., "Silencing of PDK1 Gene Expression by RNA Interference Suppresses Growth of Esophageal Cancer," Asian Pacific Journal of Cancer Prevention, vol. 13, pp. 4147-4151, 2012.
Angaji et al., "Application of RNA interference in treating human diseases," J. of Genetics, 89(4), pp. 527-537, 2010.
Baba et al., "Essential function for the calcium sensor STIM1 in mast cell activation and anaphylactic responses," Nature Immunology, 9(1), pp. 81-88, 2008.
Bacsi et al., "Effect of pollen-mediated oxidative stress on immediate hypersensitivity reactions and late-phase inflammation in allergic conjunctivitis," J. Allergy Clin Immunol., 116(4), pp. 836-843, 2005.
Bramsen et al., "A large-scale chemical modification screen identifies design rules to generate siRNAs with high activity, high stability and low toxicity," Nucleic Acids Research, 37(9), pp. 2867-2881, 2009.
Cerutti et al., "Domains in gene silencing and cell differentiation proteins: the novel PAZ domain and redefinition of the Piwi domain," Protein Sequence Motifs, pp. 481-482, 2000.
Chang et al., "Structural Diversity Repertoire of Gene Silencing Small Interfering RNAs," Nucleic Acid Therapeutics, 21(3), pp. 125-131, 2011.
Collins et al., "Structural domains in RNAi," FEBS Lett., 579(26), pp. 5841-5849, 2005.
Deleavey et al., "Designing Chemically Modified Oligonucleotides for Targeted Gene Silencing," Chemistry & Biology, 19, pp. 937-954 , 2012.
Demo et al., "Quantitative Measurement of Mast Cell Degranulation Using a Novel Flow Cytometric Annexin-V Binding Assay," Cytometry, 36, pp. 340-348, 1999.
Doench et al., "Specificity of microRNA target selection in translational repression," Genes Dev., 18, pp. 504-511, 2004.
Elbashir et al., "RNA interference is mediated by 21-and 22-nucleotide RNAs," Genes & Development, 15, pp. 188-200, 2001.

(Continued)

*Primary Examiner* — Richard A Schnizer
(74) *Attorney, Agent, or Firm* — Margaret B. Brivanlou; King & Spalding LLP

(57) ABSTRACT

The invention relates to siRNA molecules and their use in methods and pharmaceutical compositions for inhibiting the expression of the PDK1 gene. The invention also relates to the use of said siRNAs molecules in the treatment and/or prevention of an eye condition characterized by increased expression and/or activity of PDK1 gene, preferably said eye condition is conjunctivitis and/or an ocular allergy such as seasonal allergic conjunctivitis, perennial allergic conjunctivitis, vernal keratoconjunctivitis, atopic keratoconjunctivitis, and giant papillary conjunctivitis.

15 Claims, 44 Drawing Sheets

(56) References Cited

OTHER PUBLICATIONS

Fire et al., "Potent and specific genetic interference by double-stranded RNA in Caenorhabditis elegans," Nature, 39, pp. 806-811, 1998.
Hutvagner et al., A microRNA in a Multiple-Turnover RNAi Enzyme Complex, Science, 297, pp. 2056-2060, 2002.
Kari et al., "Updates in the treatment of ocular allergies," J. of Asthma and Allergy, 3, pp. 149-158, 2010.
Kay, "Allergy and Allergic Diseases," N. Engl. J. Med., 344(1), pp. 30-37, 2001.
Kim et al., "Synthetic dsRNA Dicer substrates enhance RNAi potency and efficacy," Nature Biotechnology, 23(2), pp. 222-226, 2005.
Kornbrust et al., "Oligo Safety Working Group Exaggerated Pharmacology Subcommittee Consensus Document," Nucleic Acid Therapeutics, 23, pp. 21-28, 2013.
La Rosa et al., "Allergic conjunctivitis: a comprehensive review of the literature," Italian Journal of Pediatrics, 39, pp. 1-8, 2013.
Lewis et al., "Prediction of Mammalian MicroRNA Targets," Cell, 115, pp. 787-798, 2003.
Liu et al., "Argonaute2 is the Catalytic Engine of Mammalian RNAi," Science, 305, pp. 1437-1441, 2004.
Livak et al., "Analysis of Relative Gene Expression Data Using Real-Time Quantitative PCR and the $22^{-\Delta\Delta C}{}_T$ Method," Methods, 25, pp. 402-408, 2001.
Magone et al., "A Novel Murine Model of Allergic Conjunctivitis," Clinical Immunology and Immunopathology, 87(1), pp. 75-84, 1998.
Maniatis, "Separation of RNA According to Size: Electrophoresis of Glyoxylated RNA through Agarose Gels," Molecular Cloning, 5 pages, 1982.
Nykanen et al., "ATP Requirements and Small Interfering RNA Structure in the RNA Interference Pathway," Cell, 107, pp. 309-321, 2001.
Orban et al., "Decay of mRNAs targeted by RISC requires XRN1, the Ski complex, and the exosome," RNA, 11, pp. 459-469, 2005.
Ono et al., "Allergic conjunctivitis: Update on pathophysiology and prospects for future treatment," J. Allergy Clin. Immunol., pp. 118-122, 2005.
Parrish et al., "Functional Anatomy of a dsRNA Trigger: Differential Requirement for the Two Trigger Strands in RNA Interference," Molecular Cell, 6, pp. 1077-1087, 2000.
Popescu, "Antisense-and RNA Interference-Based Therapeutics Strategies in Allergy," J. Cell. Mol. Med., 19(4), pp. 840-853, 2005.
Rand et al., "Argonaute2 Cleaves the Anti-Guide Strand of siRNA during RISC Activation," Cell, 123, pp. 621-629, 2005.
Sanghvi, "A Status Update of Modified Oligonucleotides for Chemotherapeutics Applications," Curr. Protoc. Nucleic Acid Chem., 46, pp. 4.1.1-4.1.22, 2011.
Shumilina et al., "Phosphoinositide-dependent Kinase PDK1 in the Regulation of $Ca^{2+}$ Entry into Mast Cells," Cell Physiol Biochem, 26, pp. 699-706, 2010.
Song, et al., "Crystal Structure of Argonaute and Its Implications for RISC Slicer Activity," Science, 305, pp. 1434-1437, 2004.
Suzuki et al., "Inhibition of allergic responses by CD40 gene silencing," Allergy, 64, pp. 387-397, 2009.
Suzuki, et al., "A novel allergen-specific therapy for allergy using CD40-silenced dendritic cells," J. Allergy Clin. Immunol., pp. 737-743e6, 2010.
Walton et al., "Designing Highly Active siRNAs for Therapeutic Applications," FEBS J., 277(23), pp. 4806-4813, 2010.

\* cited by examiner

| PDK1 target sequences (cDNA) | | | |
|---|---|---|---|
| SEQ ID NO. 1 | CTATCACATGGTGTTTGAA | SEQ ID NO. 53 | TGTACTTGAAGTTATTAAA |
| SEQ ID NO. 2 | CAATACAAGTGGTTTATGT | SEQ ID NO. 54 | TACTTGAAGTTATTAAAGA |
| SEQ ID NO. 3 | TCTATCACATGGTGTTTGA | SEQ ID NO. 55 | TTAAAGATGGCTATGAAA |
| SEQ ID NO. 4 | GGCAAATATAATGAAAGAA | SEQ ID NO. 56 | TAAAGATGGCTATGAAAAT |
| SEQ ID NO. 5 | TGTTCAGTACTTTTTGGAT | SEQ ID NO. 57 | GTGTGATTTGTATTATATT |
| SEQ ID NO. 6 | ATTGGAAGCATAAATCCAA | SEQ ID NO. 58 | TGTGATTTGTATTATATTA |
| SEQ ID NO. 7 | CCATCCCATCTCTATCACA | SEQ ID NO. 59 | GTGATTTGTATTATATTAA |
| SEQ ID NO. 8 | CATCCCATCTCTATCACAT | SEQ ID NO. 60 | GGGTAATGAGGATTTGACT |
| SEQ ID NO. 9 | GGCAAATATAATGAAAGAA | SEQ ID NO. 61 | GATTTGACTGTGAAGATGA |
| SEQ ID NO. 10 | GCAAATATAATGAAAGAAA | SEQ ID NO. 62 | GTCAGACTGGCAAATATAA |
| SEQ ID NO. 11 | CAAATATAATGAAAGAAAT | SEQ ID NO. 63 | CGAACTAGAACTTGAAGAA |
| SEQ ID NO. 12 | CATTGGAAGCATAAATCCA | SEQ ID NO. 64 | ACTAGAACTTGAAGAACTA |
| SEQ ID NO. 13 | CAAGTGGTTTATGTACCAT | SEQ ID NO. 65 | CTAGAACTTGAAGAACTAA |
| SEQ ID NO. 14 | GGTTTATGTACCATCCCAT | SEQ ID NO. 66 | AGAACTTGAAGAACTAAAT |
| SEQ ID NO. 15 | TACCATCCCATCTCTATCA | SEQ ID NO. 67 | CTTGAAGAACTAAATGCAA |

FIG. 1

| SEQ ID NO. 16 | CCCATCTCTATCACATGGT | SEQ ID NO. 68 | TGAAGAACTAAATGCAAAA |
| --- | --- | --- | --- |
| SEQ ID NO. 17 | CATCTCTATCACATGGTGT | SEQ ID NO. 69 | GAAGAACTAAATGCAAAAT |
| SEQ ID NO. 18 | GCAAATATAATGAAAGAAA | SEQ ID NO. 70 | AGAACTAAATGCAAAATCA |
| SEQ ID NO. 19 | CAAATATAATGAAAGAAAT | SEQ ID NO. 71 | GCCAATACAAGTGGTTTAT |
| SEQ ID NO. 20 | TGGCAAATATAATGAAAGA | SEQ ID NO. 72 | GTGTTTGAACTTTTCAAGA |
| SEQ ID NO. 21 | GGGGTGGATCCTGTCACCA | SEQ ID NO. 73 | TGTTTGAACTTTTCAAGAA |
| SEQ ID NO. 22 | TTGGAAGCATAAATCCAAA | SEQ ID NO. 74 | GTGTTTACCCCCTATTCA |
| SEQ ID NO. 23 | AATACAAGTGGTTTATGTA | SEQ ID NO. 75 | TGTTTACCCCCTATTCAA |
| SEQ ID NO. 24 | GGTTTATGTACCATCCCAT | SEQ ID NO. 76 | GGGTAATGAGGATTTGACT |
| SEQ ID NO. 25 | AAATATAATGAAAGAAATA | SEQ ID NO. 77 | GATTTGACTGTGAAGATGA |
| SEQ ID NO. 26 | GGTACAAAGCTGGTATATC | SEQ ID NO. 78 | GTCAGACTGGCAAATATAA |
| SEQ ID NO. 27 | GCTAAAGCTATTTATGACT | SEQ ID NO. 79 | TCAGACTGGCAAATATAAT |
| SEQ ID NO. 28 | CTAAAGCTATTTATGACTT | SEQ ID NO. 80 | AGACTGGCAAATATAATGA |
| SEQ ID NO. 29 | TAAAGCTATTTATGACTTT | SEQ ID NO. 81 | GACTGGCAAATATAATGAA |
| SEQ ID NO. 30 | AAAGCTATTTATGACTTTA | SEQ ID NO. 82 | ACTGGCAAATATAATGAAA |
| SEQ ID NO. 31 | AGCTATTTATGACTTTACA | SEQ ID NO. 83 | TGGCAAATATAATGAAAGA |
| SEQ ID NO. 32 | CTATTTATGACTTTACAGA | SEQ ID NO. 84 | GGCAAATATAATGAAAGAA |

FIG.1 Cont'd

| SEQ ID NO. | Sequence | SEQ ID NO. | Sequence |
|---|---|---|---|
| SEQ ID NO. 33 | ATTTATGACTTTACAGATA | SEQ ID NO. 85 | GCAAATATAATGAAAGAAA |
| SEQ ID NO. 34 | TTATGACTTTACAGATACT | SEQ ID NO. 86 | CAAATATAATGAAAGAAAT |
| SEQ ID NO. 35 | CTGTGATACGGATCAGAAA | SEQ ID NO. 87 | AAATATAATGAAAGAAATA |
| SEQ ID NO. 36 | TCAGAAACCGACACAATGA | SEQ ID NO. 88 | GAAAGAAATAAGTCTCCTT |
| SEQ ID NO. 37 | CCAGAATGTTCAGTACTTT | SEQ ID NO. 89 | AGAAATAAGTCTCCTTCCA |
| SEQ ID NO. 38 | CAGAATGTTCAGTACTTTT | SEQ ID NO. 90 | AAATAAGTCTCCTTCCAGA |
| SEQ ID NO. 39 | AGAATGTTCAGTACTTTTT | SEQ ID NO. 91 | ATAAGTCTCCTTCCAGATA |
| SEQ ID NO. 40 | GCATTTCAATTAGAATGTT | SEQ ID NO. 92 | TAAGTCTCCTTCCAGATAA |
| SEQ ID NO. 41 | CATTTCAATTAGAATGTTA | SEQ ID NO. 93 | AAGTCTCCTTCCAGATAAT |
| SEQ ID NO. 42 | CAATTAGAATGTTACTCAA | SEQ ID NO. 94 | GTCTCCTTCCAGATAATCT |
| SEQ ID NO. 43 | TTAGAATGTTACTCAATCA | SEQ ID NO. 95 | CTTCCAGATAATCTTCTCA |
| SEQ ID NO. 44 | ACTCAATCAGCACTCTTTA | SEQ ID NO. 96 | AGATAATCTTCTCAGGACA |
| SEQ ID NO. 45 | TCAATCAGCACTCTTTATT | SEQ ID NO. 97 | TCAGGACACCATCCGTTCA |
| SEQ ID NO. 46 | CATCTCATCGAAAACACAT | SEQ ID NO. 98 | CAGGACACCATCCGTTCAA |
| SEQ ID NO. 47 | AAACACATTGGAAGCATAA | SEQ ID NO. 99 | AGGACACCATCCGTTCAAT |
| SEQ ID NO. 48 | AACACATTGGAAGCATAAA | SEQ ID NO. 100 | GGACACCATCCGTTCAATT |
| SEQ ID NO. 49 | ACACATTGGAAGCATAAAT | SEQ ID NO. 101 | CACCATCCGTTCAATTGGT |

FIG. 1 Cont'd

| SEQ ID NO. | | SEQ ID NO. | |
|---|---|---|---|
| 50 | GCAATGTACTTGAAGTTAT | 102 | ACCATCCGTTCAATTGGTA |
| 51 | CAATGTACTTGAAGTTATT | 103 | CATCCGTTCAATTGGTACA |
| 52 | ATGTACTTGAAGTTATTAA | 104 | TCCGTTCAATTGGTACAAA |
| 105 | GTTCAATTGGTACAAAGCT | 159 | CCCAGGGTGTGATTGAATA |
| 106 | TTGGTACAAAGCTGGTATA | 160 | CAGGGTGTGATTGAATACA |
| 107 | GGTACAAAGCTGGTATATC | 161 | AGGGTGTGATTGAATACAA |
| 108 | CAAAGCTGGTATATCCAGA | 162 | GTGTGATTGAATACAAGGA |
| 109 | GCTGGTATATCCAGAGTCT | 163 | GTGATTGAATACAAGGAGA |
| 110 | CTGGTATATCCAGAGTCTT | 164 | GGAGAGCTTTGGGGTGGAT |
| 111 | GGTATATCCAGAGTCTTCA | 165 | GCTTTGGGGTGGATCCTGT |
| 112 | CCAGAGTCTTCAGGAGCTT | 166 | GGGGTGGATCCTGTCACCA |
| 113 | GAGTCTTCAGGAGCTTCTT | 167 | CTGTCACCAGCCAGAATGT |
| 114 | GTCTTCAGGAGCTTCTTGA | 168 | TCACCAGCCAGAATGTTCA |
| 115 | CTTCAGGAGCTTCTTGATT | 169 | CCAGCCAGAATGTTCAGTA |
| 116 | TTCAGGAGCTTCTTGATTT | 170 | CAGCCAGAATGTTCAGTAC |
| 117 | TCAGGAGCTTCTTGATTTT | 171 | GCCAGAATGTTCAGTACTT |
| 118 | CAGGAGCTTCTTGATTTTA | 172 | CCAGAATGTTCAGTACTTT |

FIG. 1 Cont'd

| SEQ ID NO. 119 | AGGAGCTTCTTGATTTTAA | SEQ ID NO. 173 | CAGAATGTTCAGTACTTTT |
|---|---|---|---|
| SEQ ID NO. 120 | GGAGCTTCTTGATTTTAAG | SEQ ID NO. 174 | AGAATGTTCAGTACTTTTT |
| SEQ ID NO. 121 | CTTCTTGATTTTAAGGACA | SEQ ID NO. 175 | TCAGTACTTTTGGATCGA |
| SEQ ID NO. 122 | CTTGATTTTAAGGACAAAA | SEQ ID NO. 176 | CAGTACTTTTGGATCGAT |
| SEQ ID NO. 123 | GGACAAAAGTGCTGAGGAT | SEQ ID NO. 177 | TTGGATCGATTCTACATGA |
| SEQ ID NO. 124 | AAAGTGCTGAGGATGCTAA | SEQ ID NO. 178 | GGATCGATTCTACATGAGT |
| SEQ ID NO. 125 | AAGTGCTGAGGATGCTAAA | SEQ ID NO. 179 | CTACATGAGTCGCATTTCA |
| SEQ ID NO. 126 | GCTGAGGATGCTAAAGCTA | SEQ ID NO. 180 | TACATGAGTCGCATTTCAA |
| SEQ ID NO. 127 | CTGAGGATGCTAAAGCTAT | SEQ ID NO. 181 | ACATGAGTCGCATTTCAAT |
| SEQ ID NO. 128 | TGAGGATGCTAAAGCTATT | SEQ ID NO. 182 | CATGAGTCGCATTTCAATT |
| SEQ ID NO. 129 | GAGGATGCTAAAGCTATTT | SEQ ID NO. 183 | ATGAGTCGCATTTCAATTA |
| SEQ ID NO. 130 | AGGATGCTAAAGCTATTTA | SEQ ID NO. 184 | TGAGTCGCATTTCAATTAG |
| SEQ ID NO. 131 | GGATGCTAAAGCTATTTAT | SEQ ID NO. 185 | GAGTCGCATTTCAATTAGA |
| SEQ ID NO. 132 | GCTAAAGCTATTTATGACT | SEQ ID NO. 186 | AGTCGCATTTCAATTAGAA |
| SEQ ID NO. 133 | CTAAAGCTATTTATGACTT | SEQ ID NO. 187 | GTCGCATTTCAATTAGAAT |
| SEQ ID NO. 134 | TAAAGCTATTTATGACTTT | SEQ ID NO. 188 | CGCATTTCAATTAGAATGT |
| SEQ ID NO. 135 | TAAAGCTATTTATGACTTT | SEQ ID NO. 189 | GCATTTCAATTAGAATGTT |

FIG. 1 Cont'd

| SEQ ID NO. 136 | AGCTATTTATGACTTTACA | SEQ ID NO. 190 | CATTTCAATTAGAATGTTA |
| --- | --- | --- | --- |
| SEQ ID NO. 137 | CTATTTATGACTTTACAGA | SEQ ID NO. 191 | CAATTAGAATGTTACTCAA |
| SEQ ID NO. 138 | ATTTATGACTTTACAGATA | SEQ ID NO. 192 | TTAGAATGTTACTCAATCA |
| SEQ ID NO. 139 | TTATGACTTTACAGATACT | SEQ ID NO. 193 | GAATGTTACTCAATCAGCA |
| SEQ ID NO. 140 | GACTTTACAGATACTGTGA | SEQ ID NO. 194 | ACTCAATCAGCACTCTTTA |
| SEQ ID NO. 141 | CTTTACAGATACTGTGATA | SEQ ID NO. 195 | CTCAATCAGCACTCTTTAT |
| SEQ ID NO. 142 | CAGATACTGTGATACGGAT | SEQ ID NO. 196 | TCAATCAGCACTCTTTATT |
| SEQ ID NO. 143 | CTGTGATACGGATCAGAAA | SEQ ID NO. 197 | TCAGCACTCTTTATTGTTT |
| SEQ ID NO. 144 | GATACGGATCAGAAACCGA | SEQ ID NO. 198 | GCACTCTTTATTGTTTGGT |
| SEQ ID NO. 145 | CGGATCAGAAACCGACACA | SEQ ID NO. 199 | CTTTATTGTTTGGTGGAAA |
| SEQ ID NO. 146 | GGATCAGAAACCGACACAA | SEQ ID NO. 200 | TTTATTGTTTGGTGGAAAA |
| SEQ ID NO. 147 | GATCAGAAACCGACACAAT | SEQ ID NO. 201 | GTTTGGTGGAAAAGGCAAA |
| SEQ ID NO. 148 | TCAGAAACCGACACAATGA | SEQ ID NO. 202 | GGTGGAAAAGGCAAAGGAA |
| SEQ ID NO. 149 | CAGAAACCGACACAATGAT | SEQ ID NO. 203 | AGGCAAAGGAAGTCCATCT |
| SEQ ID NO. 150 | GAAACCGACACAATGATGT | SEQ ID NO. 204 | GGCAAAGGAAGTCCATCTC |
| SEQ ID NO. 151 | CCGACACAATGATGTCATT | SEQ ID NO. 205 | GCAAAGGAAGTCCATCTCA |
| SEQ ID NO. 152 | CACAATGATGTCATTCCCA | SEQ ID NO. 206 | CAAAGGAAGTCCATCTCAT |

FIG. 1 Cont'd

| SEQ ID NO. 153 | CAATGATGTCATTCCCACA | SEQ ID NO. 207 | GGAAGTCCATCTCATCGAA |
| --- | --- | --- | --- |
| SEQ ID NO. 154 | ATGATGTCATTCCCACAAT | SEQ ID NO. 208 | GAAGTCCATCTCATCGAAA |
| SEQ ID NO. 155 | CCACAATGGCCCAGGGTGT | SEQ ID NO. 209 | AAGTCCATCTCATCGAAAA |
| SEQ ID NO. 156 | CAATGGCCCAGGGTGTGAT | SEQ ID NO. 210 | GTCCATCTCATCGAAAACA |
| SEQ ID NO. 157 | GGCCCAGGGTGTGATTGAA | SEQ ID NO. 211 | CCATCTCATCGAAAACACA |
| SEQ ID NO. 158 | GCCCAGGGTGTGATTGAAT | SEQ ID NO. 212 | CATCTCATCGAAAACACAT |
| SEQ ID NO. 213 | ATCTCATCGAAAACACATT | SEQ ID NO. 267 | AGAACTAAATGCAAAATCA |
| SEQ ID NO. 214 | TCATCGAAAACACATTGGA | SEQ ID NO. 268 | CACCAGGACAGCCAATACA |
| SEQ ID NO. 215 | CATCGAAAACACATTGGAA | SEQ ID NO. 269 | ACCAGGACAGCCAATACAA |
| SEQ ID NO. 216 | CGAAAACACATTGGAAGCA | SEQ ID NO. 270 | CAGGACAGCCAATACAAGT |
| SEQ ID NO. 217 | GAAAACACATTGGAAGCAT | SEQ ID NO. 271 | GACAGCCAATACAAGTGGT |
| SEQ ID NO. 218 | AAAACACATTGGAAGCATA | SEQ ID NO. 272 | CAGCCAATACAAGTGGTTT |
| SEQ ID NO. 219 | AAACACATTGGAAGCATAA | SEQ ID NO. 273 | AGCCAATACAAGTGGTTTA |
| SEQ ID NO. 220 | AACACATTGGAAGCATAAA | SEQ ID NO. 274 | GCCAATACAAGTGGTTTAT |
| SEQ ID NO. 221 | ACACATTGGAAGCATAAAT | SEQ ID NO. 275 | CAATACAAGTGGTTTATGT |
| SEQ ID NO. 222 | CATTGGAAGCATAAATCCA | SEQ ID NO. 276 | ACAAGTGGTTTATGTACCA |
| SEQ ID NO. 223 | GGAAGCATAAATCCAAACT | SEQ ID NO. 277 | TCTATCACATGGTGTTTGA |

FIG. 1 Cont'd

| SEQ ID NO. 224 | GCATAAATCCAAACTGCAA | SEQ ID NO. 278 | CTATCACATGGTGTTTGAA |
|---|---|---|---|
| SEQ ID NO. 225 | CATAAATCCAAACTGCAAT | SEQ ID NO. 279 | TCACATGGTGTTTGAACTT |
| SEQ ID NO. 226 | AAATCCAAACTGCAATGTA | SEQ ID NO. 280 | CACATGGTGTTTGAACTTT |
| SEQ ID NO. 227 | CAAACTGCAATGTACTTGA | SEQ ID NO. 281 | ACATGGTGTTTGAACTTTT |
| SEQ ID NO. 228 | AAACTGCAATGTACTTGAA | SEQ ID NO. 282 | GTGTTTGAACTTTTCAAGA |
| SEQ ID NO. 229 | CTGCAATGTACTTGAAGTT | SEQ ID NO. 283 | TGTTTGAACTTTTCAAGAA |
| SEQ ID NO. 230 | GCAATGTACTTGAAGTTAT | SEQ ID NO. 284 | GTTTGAACTTTTCAAGAAT |
| SEQ ID NO. 231 | CAATGTACTTGAAGTTATT | SEQ ID NO. 285 | GAACTTTTCAAGAATGCAA |
| SEQ ID NO. 232 | ATGTACTTGAAGTTATTAA | SEQ ID NO. 286 | CTTTTCAAGAATGCAATGA |
| SEQ ID NO. 233 | TGTACTTGAAGTTATTAAA | SEQ ID NO. 287 | ATGCAATGAGAGCCACTAT |
| SEQ ID NO. 234 | TACTTGAAGTTATTAAAGA | SEQ ID NO. 288 | CAATGAGAGCCACTATGGA |
| SEQ ID NO. 235 | TATTAAAGATGGCTATGAA | SEQ ID NO. 289 | TGAGAGCCACTATGGAACA |
| SEQ ID NO. 236 | TTAAAGATGGCTATGAAAA | SEQ ID NO. 290 | GAGCCACTATGGAACACCA |
| SEQ ID NO. 237 | TAAAGATGGCTATGAAAAT | SEQ ID NO. 291 | CTATGGAACACCATGCCAA |
| SEQ ID NO. 238 | AGATGGCTATGAAAATGCT | SEQ ID NO. 292 | GGAACACCATGCCAACAGA |
| SEQ ID NO. 239 | GATGGCTATGAAAATGCTA | SEQ ID NO. 293 | CCATGCCAACAGAGGTGTT |
| SEQ ID NO. | GCTAGGCGTCTGTGTGATT | SEQ ID NO. | CATGCCAACAGAGGTGTTT |

FIG. 1 Cont'd

| SEQ ID NO. 240 | | SEQ ID NO. 294 | |
|---|---|---|---|
| SEQ ID NO. 241 | CTAGGCGTCTGTGTGATTT | SEQ ID NO. 295 | ATGCCAACAGAGGTGTTTA |
| SEQ ID NO. 242 | GGCGTCTGTGTGATTTGTA | SEQ ID NO. 296 | AGAGGTGTTTACCCCCCTA |
| SEQ ID NO. 243 | GCGTCTGTGTGATTTGTAT | SEQ ID NO. 297 | GAGGTGTTTACCCCCCTAT |
| SEQ ID NO. 244 | CGTCTGTGTGATTTGTATT | SEQ ID NO. 298 | AGGTGTTTACCCCCCTATT |
| SEQ ID NO. 245 | GTCTGTGTGATTTGTATTA | SEQ ID NO. 299 | GTGTTTACCCCCCTATTCA |
| SEQ ID NO. 246 | CTGTGTGATTTGTATTATA | SEQ ID NO. 300 | TGTTTACCCCCCTATTCAA |
| SEQ ID NO. 247 | TGTGTGATTTGTATTATAT | SEQ ID NO. 301 | TTACCCCCCTATTCAAGTT |
| SEQ ID NO. 248 | GTGTGATTTGTATTATATT | SEQ ID NO. 302 | ACCCCCCTATTCAAGTTCA |
| SEQ ID NO. 249 | TGTGATTTGTATTATATTA | SEQ ID NO. 303 | CCCCCCTATTCAAGTTCAT |
| SEQ ID NO. 250 | GTGATTTGTATTATATTAA | SEQ ID NO. 304 | CCCCTATTCAAGTTCATGT |
| SEQ ID NO. 251 | GATTTGTATTATATTAACT | SEQ ID NO. 305 | CCTATTCAAGTTCATGTCA |
| SEQ ID NO. 252 | TATTAACTCTCCCGAACTA | SEQ ID NO. 306 | ATGTCACGCTGGGTAATGA |
| SEQ ID NO. 253 | TTAACTCTCCCGAACTAGA | SEQ ID NO. 307 | CACGCTGGGTAATGAGGAT |
| SEQ ID NO. 254 | TAACTCTCCCGAACTAGA | SEQ ID NO. 308 | ACGCTGGGTAATGAGGATT |
| SEQ ID NO. 255 | CTCTCCCGAACTAGAACTT | SEQ ID NO. 309 | CGCTGGGTAATGAGGATTT |
| SEQ ID NO. 256 | CTCCCGAACTAGAACTTGA | SEQ ID NO. 310 | CTGGGTAATGAGGATTTGA |

FIG. 1 Cont'd

| SEQ ID NO. | Sequence | SEQ ID NO. | Sequence |
|---|---|---|---|
| 257 | TCCCGAACTAGAACTTGAA | 311 | GGGTAATGAGGATTTGACT |
| 258 | CCCGAACTAGAACTTGAAG | 312 | GTAATGAGGATTTGACTGT |
| 259 | CCGAACTAGAACTTGAAGA | 313 | AATGAGGATTTGACTGTGA |
| 260 | CGAACTAGAACTTGAAGAA | 314 | ATGAGGATTTGACTGTGAA |
| 261 | ACTAGAACTTGAAGAACTA | 315 | GAGGATTTGACTGTGAAGA |
| 262 | CTAGAACTTGAAGAACTAA | 316 | GATTTGACTGTGAAGATGA |
| 263 | AGAACTTGAAGAACTAAAT | 317 | TGACTGTGAAGATGAGTGA |
| 264 | CTTGAAGAACTAAATGCAA | 318 | GAAGATGAGTGACCGAGGA |
| 265 | TGAAGAACTAAATGCAAAA | 319 | GACCGAGGAGGTGGCGTTC |
| 266 | GAAGAACTAAATGCAAAAT | 320 | CCGAGGAGGTGGCGTTCCT |
| 321 | CGAGGAGGTGGCGTTCCTT | 375 | GGATGCTAAAGCTATTTAT |
| 322 | GAGGAGGTGGCGTTCCTTT | 376 | AAAGCTATTTATGACTTTA |
| 323 | GGAGGTGGCGTTCCTTTGA | 377 | ATTTATGACTTTACAGATA |
| 324 | GCAATGTACTTGAAGTTAT | 378 | CTTTACAGATACTGTGATA |
| 325 | GGAAGTCCATCTCATCGAA | 379 | CAGATACTGTGATACGGAT |
| 326 | GCTGAGGATGCTAAAGCTA | 380 | ACTGTGATACGGATCAGAA |

FIG. 1 Cont'd

| SEQ ID NO. 327 | CATTTCAATTAGAATGTTA | SEQ ID NO. 381 | CTGTGATACGGATCAGAAA |
| --- | --- | --- | --- |
| SEQ ID NO. 328 | CGAACTAGAACTTGAAGAA | SEQ ID NO. 382 | GGATCAGAAACCGACACAA |
| SEQ ID NO. 329 | GCATAAATCCAAACTGCAA | SEQ ID NO. 383 | GATCAGAAACCGACACAAT |
| SEQ ID NO. 330 | CAATGTACTTGAAGTTATT | SEQ ID NO. 384 | CAGAAACCGACACAATGAT |
| SEQ ID NO. 331 | CTGTGTGATTTGTATTATA | SEQ ID NO. 385 | ACCGACACAATGATGTCAT |
| SEQ ID NO. 332 | ACTAGAACTTGAAGAACTA | SEQ ID NO. 386 | CCGACACAATGATGTCATT |
| SEQ ID NO. 333 | GAATGTTACTCAATCAGCA | SEQ ID NO. 387 | GGCCCAGGGTGTGATTGAA |
| SEQ ID NO. 334 | GGATGCTAAAGCTATTTAT | SEQ ID NO. 388 | GCCCAGGGTGTGATTGAAT |
| SEQ ID NO. 335 | CTGTGATACGGATCAGAAA | SEQ ID NO. 389 | CCCAGGGTGTGATTGAATA |
| SEQ ID NO. 336 | AGGGTGTGATTGAATACAA | SEQ ID NO. 390 | AGGGTGTGATTGAATACAA |
| SEQ ID NO. 337 | CTTGAAGAACTAAATGCAA | SEQ ID NO. 391 | GGGTGTGATTGAATACAAG |
| SEQ ID NO. 338 | GTCTGTGTGATTTGTATTA | SEQ ID NO. 392 | GTGTGATTGAATACAAGGA |
| SEQ ID NO. 339 | GACTTACAGATACTGTGA | SEQ ID NO. 393 | GTGATTGAATACAAGGAGA |
| SEQ ID NO. 340 | GCGTCTGTGTGATTTGTAT | SEQ ID NO. 394 | TGAATACAAGGAGAGCTTT |
| SEQ ID NO. 341 | TGTGATTTGTATTATATTA | SEQ ID NO. 395 | GGAGAGCTTTGGGGTGGAT |
| SEQ ID NO. 342 | TGTACTTGAAGTTATTAAA | SEQ ID NO. 396 | CCAGCCAGAATGTTCAGTA |
| SEQ ID NO. 343 | CTTTACAGATACTGTGATA | SEQ ID NO. 397 | GCCAGAATGTTCAGTACTT |

FIG. 1 Cont'd

| SEQ ID NO. | | SEQ ID NO. | |
|---|---|---|---|
| 344 | GATTTGACTGTGAAGATGA | 398 | CCAGAATGTTCAGTACTTT |
| 345 | CCTATTCAAGTTCATGTCA | 399 | CAGAATGTTCAGTACTTTT |
| 346 | CAAATATAATGAAAGAAAT | 400 | AGAATGTTCAGTACTTTTT |
| 347 | CTGTCAGACTGGCAAATAT | 401 | AGTACTTTTGGATCGATT |
| 348 | TGTCAGACTGGCAAATATA | 402 | ACTTTTTGGATCGATTCTA |
| 349 | GTCAGACTGGCAAATATAA | 403 | GATTCTACATGAGTCGCAT |
| 350 | TCAGACTGGCAAATATAAT | 404 | ACATGAGTCGCATTTCAAT |
| 351 | GACTGGCAAATATAATGAA | 405 | CATGAGTCGCATTTCAATT |
| 352 | ACTGGCAAATATAATGAAA | 406 | AGTCGCATTTCAATTAGAA |
| 353 | GGCAAATATAATGAAAGAA | 407 | GTCGCATTTCAATTAGAAT |
| 354 | GCAAATATAATGAAAGAAA | 408 | GCATTTCAATTAGAATGTT |
| 355 | CAAATATAATGAAAGAAAT | 409 | CATTTCAATTAGAATGTTA |
| 356 | AAATATAATGAAAGAAATA | 410 | CAATTAGAATGTTACTCAA |
| 357 | AATATAATGAAAGAAATAA | 411 | GAATGTTACTCAATCAGCA |
| 358 | GAAAGAATAAGTCTCCTT | 412 | ACTCAATCAGCACTCTTTA |
| 359 | CAGATAATCTTCTCAGGAC | 413 | CTTTATTGTTTGGTGGAAA |
| SEQ ID NO. | GGACACCATCCGTTCAATT | SEQ ID NO. | GTTTGGTGGAAAAGGCAAA |

FIG. 1 Cont'd

| SEQ ID NO. 360 | | SEQ ID NO. 414 | |
|---|---|---|---|
| SEQ ID NO. 361 | ACCATCCGTTCAATTGGTA | SEQ ID NO. 415 | GGTGGAAAAGGCAAAGGAA |
| SEQ ID NO. 362 | TCCGTTCAATTGGTACAAA | SEQ ID NO. 416 | GTGGAAAAGGCAAAGGAAG |
| SEQ ID NO. 363 | CCAGAGTCTTCAGGAGCTT | SEQ ID NO. 417 | TGGAAAAGGCAAAGGAAGT |
| SEQ ID NO. 364 | TCAGGAGCTTCTTGATTTT | SEQ ID NO. 418 | CAAAGGAAGTCCATCTCAT |
| SEQ ID NO. 365 | CAGGAGCTTCTTGATTTTA | SEQ ID NO. 419 | GGAAGTCCATCTCATCGAA |
| SEQ ID NO. 366 | AGGAGCTTCTTGATTTTAA | SEQ ID NO. 420 | GAAGTCCATCTCATCGAAA |
| SEQ ID NO. 367 | GGAGCTTCTTGATTTTAAG | SEQ ID NO. 421 | CCATCTCATCGAAAACACA |
| SEQ ID NO. 368 | TCTTGATTTTAAGGACAAA | SEQ ID NO. 422 | CATCTCATCGAAAACACAT |
| SEQ ID NO. 369 | CTTGATTTTAAGGACAAAA | SEQ ID NO. 423 | CATCGAAAACACATTGGAA |
| SEQ ID NO. 370 | GGACAAAAGTGCTGAGGAT | SEQ ID NO. 424 | GAAAACACATTGGAAGCAT |
| SEQ ID NO. 371 | GCTGAGGATGCTAAAGCTA | SEQ ID NO. 425 | AAAACACATTGGAAGCATA |
| SEQ ID NO. 372 | CTGAGGATGCTAAAGCTAT | SEQ ID NO. 426 | AACACATTGGAAGCATAAA |
| SEQ ID NO. 373 | TGAGGATGCTAAAGCTATT | SEQ ID NO. 427 | ACACATTGGAAGCATAAAT |
| SEQ ID NO. 374 | AGGATGCTAAAGCTATTTA | SEQ ID NO. 428 | GCATAAATCCAAACTGCAA |
| SEQ ID NO. 429 | CATAAATCCAAACTGCAAT | SEQ ID NO. 483 | CGAGGAGGTGGCGTTCCTT |
| SEQ ID NO. 430 | AAATCCAAACTGCAATGTA | SEQ ID NO. 484 | TTTCTTTCATTATATTTGC |
| SEQ ID NO. | TCCAAACTGCAATGTACTT | SEQ ID NO. | TTCTTTCATTATATTTGCC |

FIG. 1 Cont'd

| | | | |
|---|---|---|---|
| 431 | | 485 | |
| SEQ ID NO. 432 | CTGCAATGTACTTGAAGTT | SEQ ID NO. 486 | ATAACTTCAAGTACATTGC |
| SEQ ID NO. 433 | TGCAATGTACTTGAAGTTA | SEQ ID NO. 487 | TTCTTCAAGTTCTAGTTCG |
| SEQ ID NO. 434 | GCAATGTACTTGAAGTTAT | SEQ ID NO. 488 | TTAATATAATACAAATCAC |
| SEQ ID NO. 435 | CAATGTACTTGAAGTTATT | SEQ ID NO. 489 | TCTTCACAGTCAAATCCTC |
| SEQ ID NO. 436 | ATGTACTTGAAGTTATTAA | SEQ ID NO. 490 | TCATCTTCACAGTCAAATC |
| SEQ ID NO. 437 | TGTACTTGAAGTTATTAAA | SEQ ID NO. 491 | TCTTCAAGTTCTAGTTCGG |
| SEQ ID NO. 438 | ACTTGAAGTTATTAAAGAT | SEQ ID NO. 492 | TAGTTCTTCAAGTTCTAGT |
| SEQ ID NO. 439 | AAGTTATTAAAGATGGCTA | SEQ ID NO. 493 | TTAGTTCTTCAAGTTCTAG |
| SEQ ID NO. 440 | AGTTATTAAAGATGGCTAT | SEQ ID NO. 494 | TATCACAGTATCTGTAAAG |
| SEQ ID NO. 441 | TATTAAAGATGGCTATGAA | SEQ ID NO. 495 | TTGCATTCTTGAAAAGTTC |
| SEQ ID NO. 442 | AAAGATGGCTATGAAAA | SEQ ID NO. 496 | TACAAATCACACAGACGCC |
| SEQ ID NO. 443 | TAAAGATGGCTATGAAAAT | SEQ ID NO. 497 | ATACAAATCACACAGACGC |
| SEQ ID NO. 444 | GGCGTCTGTGTGATTTGTA | SEQ ID NO. 498 | TAATACAAATCACACAGAC |
| SEQ ID NO. 445 | GCGTCTGTGTGATTTGTAT | SEQ ID NO. 499 | TTTAATAACTTCAAGTACA |
| SEQ ID NO. 446 | CGTCTGTGTGATTTGTATT | SEQ ID NO. 500 | TAACATTCTAATTGAAATG |
| SEQ ID NO. 447 | GTCTGTGTGATTTGTATTA | SEQ ID NO. 501 | ATAAATAGCTTTAGCATCC |
| SEQ ID NO. | CTGTGTGATTTGTATTATA | SEQ ID NO. | TTTCTGATCCGTATCACAG |

FIG. 1 Cont'd

| | | | |
|---|---|---|---|
| SEQ ID NO. 448 | | SEQ ID NO. 502 | |
| SEQ ID NO. 449 | GTGTGATTTGTATTATATT | SEQ ID NO. 503 | AAAGTACTGAACATTCTGG |
| SEQ ID NO. 450 | TGTGATTTGTATTATATTA | SEQ ID NO. 504 | TTATATTTGCCAGTCTGAC |
| SEQ ID NO. 451 | GTGATTTGTATTATATTAA | SEQ ID NO. 505 | TATAATACAAATCACACAG |
| SEQ ID NO. 452 | TCCCGAACTAGAACTTGAA | SEQ ID NO. 506 | TACTGAACATTCTGGCTGG |
| SEQ ID NO. 453 | CCGAACTAGAACTTGAAGA | SEQ ID NO. 507 | TTGTGTCGGTTTCTGATCC |
| SEQ ID NO. 454 | CGAACTAGAACTTGAAGAA | SEQ ID NO. 508 | TTTCCACCAAACAATAAAG |
| SEQ ID NO. 455 | ACTAGAACTTGAAGAACTA | SEQ ID NO. 509 | AAGTACTGAACATTCTGGC |
| SEQ ID NO. 456 | CTAGAACTTGAAGAACTAA | SEQ ID NO. 510 | AACATTCTAATTGAAATGC |
| SEQ ID NO. 457 | UAGAACUUGAAGAACUAAA | SEQ ID NO. 511 | TTCTGATCCGTATCACAGT |
| SEQ ID NO. 458 | AGAACTTGAAGAACTAAAT | SEQ ID NO. 512 | TTAAAATCAAGAAGCTCCT |
| SEQ ID NO. 459 | CTTGAAGAACTAAATGCAA | SEQ ID NO. 513 | TTAATAACTTCAAGTACAT |
| SEQ ID NO. 460 | GAAGAACTAAATGCAAA | SEQ ID NO. 514 | AATATAATACAAATCACAC |
| SEQ ID NO. 461 | TGAAGAACTAAATGCAAAA | SEQ ID NO. 515 | TTTTGTCCTTAAAATCAAG |
| SEQ ID NO. 462 | GAAGAACTAAATGCAAAAT | SEQ ID NO. 516 | TTTGTCCTTAAAATCAAGA |
| SEQ ID NO. 463 | AGAACTAAATGCAAAATCA | SEQ ID NO. 517 | TAGCATTTTCATAGCCATC |
| SEQ ID NO. 464 | ACCAGGACAGCCAATACAA | SEQ ID NO. 518 | TGAAGACTCTGGATATACC |
| SEQ ID NO. | CAGCCAATACAAGTGGTTT | SEQ ID NO. | TAGCTTTAGCATCCTCAGC |

FIG. 1 Cont'd

| | | | |
|---|---|---|---|
| 465 | | 519 | |
| SEQ ID NO. 466 | AGCCAATACAAGTGGTTTA | SEQ ID NO. 520 | TTCATTATATTTGCCAGTC |
| SEQ ID NO. 467 | GCCAATACAAGTGGTTTAT | SEQ ID NO. 521 | AATGACATCATTGTGTCGG |
| SEQ ID NO. 468 | TCACATGGTGTTTGAACTT | SEQ ID NO. 522 | TTGTATTCAATCACACCCT |
| SEQ ID NO. 469 | ACATGGTGTTTGAACTTTT | SEQ ID NO. 523 | TAACTTCAAGTACATTGCA |
| SEQ ID NO. 470 | TGGTGTTTGAACTTTTCAA | SEQ ID NO. 524 | TTCAAGTTCTAGTTCGGGA |
| SEQ ID NO. 471 | GGTGTTTGAACTTTTCAAG | SEQ ID NO. 525 | TTCAAACACCATGTGATAG |
| SEQ ID NO. 472 | TGTTTGAACTTTTCAAGAA | SEQ ID NO. 526 | ATCTTCACAGTCAAATCCT |
| SEQ ID NO. 473 | GTTTGAACTTTTCAAGAAT | SEQ ID NO. 527 | TAAAATCAAGAAGCTCCTG |
| SEQ ID NO. 474 | GAACTTTTCAAGAATGCAA | SEQ ID NO. 528 | TAATATAATACAAATCACA |
| SEQ ID NO. 475 | AGCCACTATGGAACACCAT | SEQ ID NO. 529 | TAGAATCGATCCAAAAAGT |
| SEQ ID NO. 476 | CTATGGAACACCATGCCAA | SEQ ID NO. 530 | ATCTTTAATAACTTCAAGT |
| SEQ ID NO. 477 | GGAACACCATGCCAACAGA | SEQ ID NO. 531 | TCCTTGTATTCAATCACAC |
| SEQ ID NO. 478 | CCATGCCAACAGAGGTGTT | SEQ ID NO. 532 | TTTCATTATATTTGCCAGT |
| SEQ ID NO. 479 | GTTCATGTCACGCTGGGTA | SEQ ID NO. 533 | TAAAGAGTGCTGATTGAGT |
| SEQ ID NO. 480 | CACGCTGGGTAATGAGGAT | SEQ ID NO. 534 | TATTCAATCACACCCTGGG |
| SEQ ID NO. 481 | GAGGATTTGACTGTGAAGA | SEQ ID NO. 535 | TGATCCGTATCACAGTATC |
| SEQ ID NO. | AGGATTTGACTGTGAAGAT | SEQ ID NO. | AATAACTTCAAGTACATTG |

FIG. 1 Cont'd

| | | | |
|---|---|---|---|
| 482 | | SEQ ID NO. 536 | |
| SEQ ID NO. 537 | ATAAACCACTTGTATTGGC | SEQ ID NO. 591 | TTCTAGTTCGGGAGAGTTA |
| SEQ ID NO. 538 | ATCACAGTATCTGTAAAGT | SEQ ID NO. 592 | AGACTCTGGATATACCAGC |
| SEQ ID NO. 539 | ATTCTTGAAAAGTTCAAAC | SEQ ID NO. 593 | ATAATACAAATCACACAGA |
| SEQ ID NO. 540 | TTGCATTTAGTTCTTCAAG | SEQ ID NO. 594 | TTGTATTGGCTGTCCTGGT |
| SEQ ID NO. 541 | TTCCACCAAACAATAAAGA | SEQ ID NO. 595 | AAAAGTTCAAACACCATGT |
| SEQ ID NO. 542 | ATCCTCAGCACTTTTGTCC | SEQ ID NO. 596 | AATCCTCATTACCCAGCGT |
| SEQ ID NO. 543 | TCAAATCCTCATTACCCAG | SEQ ID NO. 597 | ACAGTCAAATCCTCATTAC |
| SEQ ID NO. 544 | AACTTCAAGTACATTGCAG | SEQ ID NO. 598 | ATAGCTTTAGCATCCTCAG |
| SEQ ID NO. 545 | ATGCGACTCATGTAGAATC | SEQ ID NO. 599 | TTTGCCTTTTCCACCAAAC |
| SEQ ID NO. 546 | AAAAGTACTGAACATTCTG | SEQ ID NO. 600 | CTTAAAATCAAGAAGCTCC |
| SEQ ID NO. 547 | TCATTGCATTCTTGAAAAG | SEQ ID NO. 601 | ATCATTGTGTCGGTTTCTG |
| SEQ ID NO. 548 | TTCTTGAAAAGTTCAAACA | SEQ ID NO. 602 | ATAAAGAGTGCTGATTGAG |
| SEQ ID NO. 549 | ATTTCTTTCATTATATTTG | SEQ ID NO. 603 | CTTGAAAAGTTCAAACACC |
| SEQ ID NO. 550 | TTGAAAAGTTCAAACACCA | SEQ ID NO. 604 | ACCAAACAATAAAGAGTGC |
| SEQ ID NO. 551 | AGTCATAAATAGCTTTAGC | SEQ ID NO. 605 | TTCCTTTGCCTTTTCCACC |
| SEQ ID NO. 552 | TAAATAGCTTTAGCATCCT | SEQ ID NO. 606 | AATTGAAATGCGACTCATG |
| SEQ ID NO. | CTGTAAAGTCATAAATAGC | SEQ ID NO. | CAAATCCTCATTACCCAGC |

FIG. 1 Cont'd

| SEQ ID NO. 553 | | SEQ ID NO. 607 | |
|---|---|---|---|
| SEQ ID NO. 554 | TTCTAATTGAAATGCGACT | SEQ ID NO. 608 | TGAGAAGATTATCTGGAAG |
| SEQ ID NO. 555 | ATTTAGTTCTTCAAGTTCT | SEQ ID NO. 609 | ATGCTTCCAATGTGTTTTC |
| SEQ ID NO. 556 | TTTGTACCAATTGAACGGA | SEQ ID NO. 610 | TTGAAATGCGACTCATGTA |
| SEQ ID NO. 557 | TGTATTCAATCACACCCTG | SEQ ID NO. 611 | AAAGTTCAAACACCATGTG |
| SEQ ID NO. 558 | TTTCATAGCCATCTTTAAT | SEQ ID NO. 612 | AATTGAACGGATGGTGTCC |
| SEQ ID NO. 559 | AATACAAATCACACAGACG | SEQ ID NO. 613 | ATTTTGCATTTAGTTCTTC |
| SEQ ID NO. 560 | TTTAGTTCTTCAAGTTCTA | SEQ ID NO. 614 | ATCCAAAAAGTACTGAACA |
| SEQ ID NO. 561 | AAAAAGTACTGAACATTCT | SEQ ID NO. 615 | ACATGAACTTGAATAGGGG |
| SEQ ID NO. 562 | TATATTTGCCAGTCTGACA | SEQ ID NO. 616 | TTGGATTTATGCTTCCAAT |
| SEQ ID NO. 563 | ATAGCCATCTTTAATAACT | SEQ ID NO. 617 | ATTATATTTGCCAGTCTGA |
| SEQ ID NO. 564 | TCAAGAAGCTCCTGAAGAC | SEQ ID NO. 618 | AATCAAGAAGCTCCTGAAG |
| SEQ ID NO. 565 | ATGGGATGGTACATAAACC | SEQ ID NO. 619 | AAACACCTCTGTTGGCATG |
| SEQ ID NO. 566 | ATATTTGCCAGTCTGACAG | SEQ ID NO. 620 | AAATCACACAGACGCCTAG |
| SEQ ID NO. 567 | TCTAATTGAAATGCGACTC | SEQ ID NO. 621 | AAGTTCTAGTTCGGGAGAG |
| SEQ ID NO. 568 | ATGACATCATTGTGTCGGT | SEQ ID NO. 622 | AAACAATAAAGAGTGCTGA |
| SEQ ID NO. 569 | TAAACCACTTGTATTGGCT | SEQ ID NO. 623 | AAAATCAAGAAGCTCCTGA |

FIG. 1 Cont'd

| SEQ ID NO. 570 | ATTCTAATTGAAATGCGAC | SEQ ID NO. 624 | AAACCACTTGTATTGGCTG |
|---|---|---|---|
| SEQ ID NO. 571 | AATCGATCCAAAAAGTACT | SEQ ID NO. 625 | ATGAACTTGAATAGGGGGG |
| SEQ ID NO. 572 | AATCACACAGACGCCTAGC | SEQ ID NO. 626 | ATTACCCAGCGTGACATGA |
| SEQ ID NO. 573 | AGTCAAATCCTCATTACCC | SEQ ID NO. 627 | ACATCATTGTGTCGGTTTC |
| SEQ ID NO. 574 | ATCGATCCAAAAAGTACTG | SEQ ID NO. 628 | AAACACCATGTGATAGAGA |
| SEQ ID NO. 575 | ATTGTGTCGGTTTCTGATC | SEQ ID NO. 629 | CATAAATAGCTTTAGCATC |
| SEQ ID NO. 576 | TCAAGTACATTGCAGTTTG | SEQ ID NO. 630 | TGTTTTCGATGAGATGGAC |
| SEQ ID NO. 577 | AAATAGCTTTAGCATCCTC | SEQ ID NO. 631 | AGTTAATATAATACAAATC |
| SEQ ID NO. 578 | ATTCAATCACACCCTGGGC | SEQ ID NO. 632 | ATTGCAGTTTGGATTTATG |
| SEQ ID NO. 579 | AAGGAGACTTATTTCTTTC | SEQ ID NO. 633 | TGAACATTCTGGCTGGTGA |
| SEQ ID NO. 580 | TGCATTTAGTTCTTCAAGT | SEQ ID NO. 634 | ATCAAGAAGCTCCTGAAGA |
| SEQ ID NO. 581 | TTGTACCAATTGAACGGAT | SEQ ID NO. 635 | ACATTCTAATTGAAATGCG |
| SEQ ID NO. 582 | ATTGAAATGCGACTCATGT | SEQ ID NO. 636 | TGCTTCCAATGTGTTTTCG |
| SEQ ID NO. 583 | ATATAATACAAATCACACA | SEQ ID NO. 637 | AGCCATCTTTAATAACTTC |
| SEQ ID NO. 584 | ATTTATGCTTCCAATGTGT | SEQ ID NO. 638 | AAAGCTCTCCTTGTATTCA |
| SEQ ID NO. 585 | AAATCCTCATTACCCAGCG | SEQ ID NO. 639 | ATTGAACGGATGGTGTCCT |
| SEQ ID NO. | TTCCAATGTGTTTTCGATG | SEQ ID NO. | ATGTGTTTTCGATGAGATG |

FIG. 1 Cont'd

| | | | |
|---|---|---|---|
| SEQ ID NO. 586 | | SEQ ID NO. 640 | |
| SEQ ID NO. 587 | TTTTGCATTTAGTTCTTCA | SEQ ID NO. 641 | AACAATAAAGAGTGCTGAT |
| SEQ ID NO. 588 | TGTACCAATTGAACGGATG | SEQ ID NO. 642 | AAGTTCAAACACCATGTGA |
| SEQ ID NO. 589 | AAGAAGCTCCTGAAGACTC | SEQ ID NO. 643 | TGGTGATTTTGCATTTAGT |
| SEQ ID NO. 590 | ATCTGTAAAGTCATAAATA | SEQ ID NO. 644 | AGAGTGCTGATTGAGTAAC |
| SEQ ID NO. 645 | AATAGCTTTAGCATCCTCA | SEQ ID NO. 667 | ACCATGTGATAGAGATGGG |
| SEQ ID NO. 646 | AACCACTTGTATTGGCTGT | SEQ ID NO. 668 | ATAGAGATGGGATGGTACA |
| SEQ ID NO. 647 | TTGAATAGGGGGTAAACA | SEQ ID NO. 669 | AAGATTATCTGGAAGGAGA |
| SEQ ID NO. 648 | ATATACCAGCTTTGTACCA | SEQ ID NO. 670 | AGATTATCTGGAAGGAGAC |
| SEQ ID NO. 649 | ATGTGATAGAGATGGGATG | SEQ ID NO. 671 | CACTTTTGTCCTTAAAATC |
| SEQ ID NO. 650 | AAAGTCATAAATAGCTTTA | SEQ ID NO. 672 | GATATACCAGCTTTGTACC |
| SEQ ID NO. 651 | AATAAAGAGTGCTGATTGA | SEQ ID NO. 673 | AAGTACATTGCAGTTTGGA |
| SEQ ID NO. 652 | GACATGAACTTGAATAGGG | SEQ ID NO. 674 | AACATTCTGGCTGGTGACA |
| SEQ ID NO. 653 | ACATAAACCACTTGTATTG | SEQ ID NO. 675 | GTATTCAATCACACCCTGG |
| SEQ ID NO. 654 | CATAGCCATCTTTAATAAC | SEQ ID NO. 676 | ATCACACCCTGGGCCATTG |
| SEQ ID NO. 655 | AATGCGACTCATGTAGAAT | SEQ ID NO. 677 | AGCATCCTCAGCACTTTTG |
| SEQ ID NO. 656 | CAAGTACATTGCAGTTTGG | SEQ ID NO. 678 | ACTTGTATTGGCTGTCCTG |
| SEQ ID NO. | ATTTTCATAGCCATCTTTA | SEQ ID NO. | AATGTGTTTCGATGAGAT |

FIG. 1 Cont'd

| | | | |
|---|---|---|---|
| 657 | | 679 | |
| SEQ ID NO. 658 | AGTTTGGATTTATGCTTCC | SEQ ID NO. 680 | ACATTCTGGCTGGTGACAG |
| SEQ ID NO. 659 | CATAAACCACTTGTATTGG | SEQ ID NO. 681 | CAATTGAACGGATGGTGTC |
| SEQ ID NO. 660 | AACACCATGTGATAGAGAT | SEQ ID NO. 682 | ACCAATTGAACGGATGGTG |
| SEQ ID NO. 661 | ACACCATGTGATAGAGATG | SEQ ID NO. 683 | GAGAAGATTATCTGGAAGG |
| SEQ ID NO. 662 | ATGAGATGGACTTCCTTTG | SEQ ID NO. 684 | AGCTTTAGCATCCTCAGCA |
| SEQ ID NO. 663 | AGCTTTGTACCAATTGAAC | SEQ ID NO. 685 | AGAAGATTATCTGGAAGGA |
| SEQ ID NO. 664 | ACAGACGCCTAGCATTTTC | SEQ ID NO. 686 | CTTGAATAGGGGGTAAAC |
| SEQ ID NO. 665 | AGTTCTAGTTCGGGAGAGT | SEQ ID NO. 687 | GACTTCCTTTGCCTTTCC |
| SEQ ID NO. 666 | AAAGAGTGCTGATTGAGTA | | |

FIG.1 Cont'd

| PDK1 siRNAs | Sense strand 5'->3' | | Antisense strand 5'->3' |
|---|---|---|---|
| SEQ ID NO. 688 | CUAUCACAUGGUGUUUGAA | SEQ ID NO. 1375 | UUCAAACACCAUGUGAUAG |
| SEQ ID NO. 689 | CAAUACAAGUGGUUUAUGU | SEQ ID NO. 1376 | ACAUAAACCACUUGUAUUG |
| SEQ ID NO. 690 | UCUAUCACAUGGUGUUUGA | SEQ ID NO. 1377 | UCAAACACCAUGUGAUAGA |
| SEQ ID NO. 691 | GGCAAAUAUAAUGAAAGAA | SEQ ID NO. 1378 | UUCUUUCAUUAUAUUUGCC |
| SEQ ID NO. 692 | UGUUCAGUACUUUUUGGAU | SEQ ID NO. 1379 | AUCCAAAAAGUACUGAACA |
| SEQ ID NO. 693 | AUUGGAAGCAUAAAUCCAA | SEQ ID NO. 1380 | UUGGAUUUAUGCUUCCAAU |
| SEQ ID NO. 694 | CCAUCCCAUCUCUAUCACA | SEQ ID NO. 1381 | UGUGAUAGAGAUGGGAUGG |
| SEQ ID NO. 695 | CAUCCCAUCUCUAUCACAU | SEQ ID NO. 1382 | AUGUGAUAGAGAUGGGAUG |
| SEQ ID NO. 696 | GGCAAAUAUAAUGAAAGAA | SEQ ID NO. 1383 | UUCUUUCAUUAUAUUUGCC |
| SEQ ID NO. 697 | GCAAAUAUAAUGAAAGAAA | SEQ ID NO. 1384 | UUUCUUUCAUUAUAUUUGC |
| SEQ ID NO. 698 | CAAAUAUAAUGAAAGAAAU | SEQ ID NO. 1385 | AUUUCUUUCAUUAUAUUUG |
| SEQ ID NO. 699 | CAUUGGAAGCAUAAAUCCA | SEQ ID NO. 1386 | UGGAUUUAUGCUUCCAAUG |
| SEQ ID NO. 700 | CAAGUGGUUUAUGUACCAU | SEQ ID NO. 1387 | AUGGUACAUAAACCACUUG |
| SEQ ID NO. 701 | GGUUUAUGUACCAUCCCAU | SEQ ID NO. 1388 | AUGGGAUGGUACAUAAACC |
| SEQ ID NO. 702 | UACCAUCCCAUCUCUAUCA | SEQ ID NO. 1389 | UGAUAGAGAUGGGAUGGUA |
| SEQ ID NO. 703 | CCCAUCUCUAUCACAUGGU | SEQ ID NO. 1390 | ACCAUGUGAUAGAGAUGGG |
| SEQ ID NO. 704 | CAUCUCUAUCACAUGGUGU | SEQ ID NO. 1391 | ACACCAUGUGAUAGAGAUG |
| SEQ ID NO. 705 | GCAAAUAUAAUGAAAGAAA | SEQ ID NO. 1392 | UUUCUUUCAUUAUAUUUGC |
| SEQ ID NO. 706 | CAAATATAATGAAAGAAAT | SEQ ID NO. 1393 | ATTTCTTTCATTATATTTG |
| SEQ ID NO. 707 | TGGCAAATATAATGAAAGA | SEQ ID NO. 1394 | TCTTTCATTATATTTGCCA |
| SEQ ID NO. 708 | GGGGTGGATCCTGTCACCA | SEQ ID NO. 1395 | TGGTGACAGGATCCACCCC |
| SEQ ID NO. 709 | TTGGAAGCATAAATCCAAA | SEQ ID NO. 1396 | TTTGGATTTATGCTTCCAA |
| SEQ ID NO. 710 | AATACAAGTGGTTTATGTA | SEQ ID NO. 1397 | TACATAAACCACTTGTATT |
| SEQ ID NO. 711 | GGTTTATGTACCATCCCAT | SEQ ID NO. 1398 | ATGGGATGGTACATAAACC |
| SEQ ID NO. 712 | AAAUAUAAUGAAAGAAAUA | SEQ ID NO. 1399 | UAUUUCUUUCAUUAUAUUU |
| SEQ ID NO. 713 | GGUACAAAGCUGGUAUAUC | SEQ ID NO. 1400 | GAUAUACCAGCUUUGUACC |
| SEQ ID NO. 714 | GCUAAAGCUAUUUAUGACU | SEQ ID NO. 1401 | AGUCAUAAAUAGCUUUAGC |
| SEQ ID NO. 715 | CUAAAGCUAUUUAUGACUU | SEQ ID NO. 1402 | AAGUCAUAAAUAGCUUUAG |
| SEQ ID NO. 716 | UAAAGCUAUUUAUGACUUU | SEQ ID NO. 1403 | AAAGUCAUAAAUAGCUUUA |
| SEQ ID NO. 717 | AAAGCUAUUUAUGACUUUA | SEQ ID NO. 1404 | UAAAGUCAUAAAUAGCUUU |
| SEQ ID NO. 718 | AGCUAUUUAUGACUUUACA | SEQ ID NO. 1405 | UGUAAAGUCAUAAAUAGCU |
| SEQ ID NO. 719 | CUAUUUAUGACUUUACAGA | SEQ ID NO. 1406 | UCUGUAAAGUCAUAAAUAG |
| SEQ ID NO. 720 | AUUUAUGACUUUACAGAUA | SEQ ID NO. 1407 | UAUCUGUAAAGUCAUAAAU |
| SEQ ID NO. 721 | UUAUGACUUUACAGAUACU | SEQ ID NO. 1408 | AGUAUCUGUAAAGUCAUAA |

FIG. 2

| | | | |
|---|---|---|---|
| SEQ ID NO. 722 | CUGUGAUACGGAUCAGAAA | SEQ ID NO. 1409 | UUUCUGAUCCGUAUCACAG |
| SEQ ID NO. 723 | UCAGAAACCGACACAAUGA | SEQ ID NO. 1410 | UCAUUGUGUCGGUUUCUGA |
| SEQ ID NO. 724 | CCAGAAUGUUCAGUACUUU | SEQ ID NO. 1411 | AAAGUACUGAACAUUCUGG |
| SEQ ID NO. 725 | CAGAAUGUUCAGUACUUUU | SEQ ID NO. 1412 | AAAAGUACUGAACAUUCUG |
| SEQ ID NO. 726 | AGAAUGUUCAGUACUUUUU | SEQ ID NO. 1413 | AAAAAGUACUGAACAUUCU |
| SEQ ID NO. 727 | GCAUUUCAAUUAGAAUGUU | SEQ ID NO. 1414 | AACAUUCUAAUUGAAAUGC |
| SEQ ID NO. 728 | CAUUUCAAUUAGAAUGUUA | SEQ ID NO. 1415 | UAACAUUCUAAUUGAAAUG |
| SEQ ID NO. 729 | CAAUUAGAAUGUUACUCAA | SEQ ID NO. 1416 | UUGAGUAACAUUCUAAUUG |
| SEQ ID NO. 730 | UUAGAAUGUUACUCAAUCA | SEQ ID NO. 1417 | UGAUUGAGUAACAUUCUAA |
| SEQ ID NO. 731 | ACUCAAUCAGCACUCUUUA | SEQ ID NO. 1418 | UAAAGAGUGCUGAUUGAGU |
| SEQ ID NO. 732 | UCAAUCAGCACUCUUUAUU | SEQ ID NO. 1419 | AAUAAAGAGUGCUGAUUGA |
| SEQ ID NO. 733 | CAUCUCAUCGAAAACACAU | SEQ ID NO. 1420 | AUGUGUUUCGAUGAGAUG |
| SEQ ID NO. 734 | AAACACAUUGGAAGCAUAA | SEQ ID NO. 1421 | UUAUGCUUCCAAUGUGUUU |
| SEQ ID NO. 735 | AACACAUUGGAAGCAUAAA | SEQ ID NO. 1422 | UUUAUGCUUCCAAUGUGUU |
| SEQ ID NO. 736 | ACACAUUGGAAGCAUAAAU | SEQ ID NO. 1423 | AUUUAUGCUUCCAAUGUGU |
| SEQ ID NO. 737 | GCAAUGUACUUGAAGUUAU | SEQ ID NO. 1424 | AUAACUUCAAGUACAUUGC |
| SEQ ID NO. 738 | CAAUGUACUUGAAGUUAUU | SEQ ID NO. 1425 | AAUAACUUCAAGUACAUUG |
| SEQ ID NO. 739 | AUGUACUUGAAGUUAUUAA | SEQ ID NO. 1426 | UUAAUAACUUCAAGUACAU |
| SEQ ID NO. 740 | UGUACUUGAAGUUAUUAAA | SEQ ID NO. 1427 | UUUAAUAACUUCAAGUACA |
| SEQ ID NO. 741 | UACUUGAAGUUAUUAAAGA | SEQ ID NO. 1428 | UCUUUAAUAACUUCAAGUA |
| SEQ ID NO. 742 | UUAAAGAUGGCUAUGAAAA | SEQ ID NO. 1429 | UUUUCAUAGCCAUCUUUAA |
| SEQ ID NO. 743 | UAAAGAUGGCUAUGAAAAU | SEQ ID NO. 1430 | AUUUUCAUAGCCAUCUUUA |
| SEQ ID NO. 744 | GUGUGAUUUGUAUUAUAUU | SEQ ID NO. 1431 | AAUAUAAUACAAAUCACAC |
| SEQ ID NO. 745 | UGUGAUUUGUAUUAUAUUA | SEQ ID NO. 1432 | UAAUAUAAUACAAAUCACA |
| SEQ ID NO. 746 | GUGAUUUGUAUUAUAUUAA | SEQ ID NO. 1433 | UUAAUAUAAUACAAAUCAC |
| SEQ ID NO. 747 | GAUUUGUAUUAUAUUAACU | SEQ ID NO. 1434 | AGUUAAUAUAAUACAAAUC |
| SEQ ID NO. 748 | UUAACUCUCCCGAACUAGA | SEQ ID NO. 1435 | UCUAGUUCGGGAGAGUUAA |
| SEQ ID NO. 749 | CCGAACUAGAACUUGAAGA | SEQ ID NO. 1436 | UCUUCAAGUUCUAGUUCGG |
| SEQ ID NO. 750 | CGAACUAGAACUUGAAGAA | SEQ ID NO. 1437 | UUCUUCAAGUUCUAGUUCG |
| SEQ ID NO. 751 | ACUAGAACUUGAAGAACUA | SEQ ID NO. 1438 | UAGUUCUUCAAGUUCUAGU |
| SEQ ID NO. 752 | CUAGAACUUGAAGAACUAA | SEQ ID NO. 1439 | UUAGUUCUUCAAGUUCUAG |
| SEQ ID NO. 753 | AGAACUUGAAGAACUAAAU | SEQ ID NO. 1440 | AUUUAGUUCUUCAAGUUCU |
| SEQ ID NO. 754 | CUUGAAGAACUAAAUGCAA | SEQ ID NO. 1441 | UUGCAUUUAGUUCUUCAAG |
| SEQ ID NO. 755 | UGAAGAACUAAAUGCAAAA | SEQ ID NO. 1442 | UUUUGCAUUUAGUUCUUCA |
| SEQ ID NO. 756 | GAAGAACUAAAUGCAAAAU | SEQ ID NO. 1443 | AUUUUGCAUUUAGUUCUUC |
| SEQ ID NO. 757 | AGAACUAAAUGCAAAAUCA | SEQ ID NO. 1444 | UGAUUUUGCAUUUAGUUCU |
| SEQ ID NO. 758 | GCCAAUACAAGUGGUUUAU | SEQ ID NO. 1445 | AUAAACCACUUGUAUUGGC |
| SEQ ID NO. 759 | GUGUUUGAACUUUUCAAGA | SEQ ID NO. 1446 | UCUUGAAAAGUUCAAACAC |

FIG. 2 Cont'd

| | | | |
|---|---|---|---|
| SEQ ID NO. 760 | UGUUUGAACUUUUCAAGAA | SEQ ID NO. 1447 | UUCUUGAAAAGUUCAAACA |
| SEQ ID NO. 761 | GUGUUUACCCCCCUAUUCA | SEQ ID NO. 1448 | UGAAUAGGGGGGUAAACAC |
| SEQ ID NO. 762 | UGUUUACCCCCUAUUCAA | SEQ ID NO. 1449 | UUGAAUAGGGGGUAAACA |
| SEQ ID NO. 763 | GGGUAAUGAGGAUUUGACU | SEQ ID NO. 1450 | AGUCAAAUCCUCAUUACCC |
| SEQ ID NO. 764 | GAUUUGACUGUGAAGAUGA | SEQ ID NO. 1451 | UCAUCUUCACAGUCAAAUC |
| SEQ ID NO. 765 | GUCAGACUGGCAAAUAUAA | SEQ ID NO. 1452 | UUAUAUUUGCCAGUCUGAC |
| SEQ ID NO. 766 | UCAGACUGGCAAAUAUAAU | SEQ ID NO. 1453 | AUUAUAUUUGCCAGUCUGA |
| SEQ ID NO. 767 | AGACUGGCAAAUAUAAUGA | SEQ ID NO. 1454 | UCAUUAUAUUUGCCAGUCU |
| SEQ ID NO. 768 | GACUGGCAAAUAUAAUGAA | SEQ ID NO. 1455 | UUCAUUAUAUUUGCCAGUC |
| SEQ ID NO. 769 | ACUGGCAAAUAUAAUGAAA | SEQ ID NO. 1456 | UUUCAUUAUAUUUGCCAGU |
| SEQ ID NO. 770 | UGGCAAAUAUAAUGAAAGA | SEQ ID NO. 1457 | UCUUUCAUUAUAUUUGCCA |
| SEQ ID NO. 771 | GGCAAAUAUAAUGAAAGAA | SEQ ID NO. 1458 | UUCUUUCAUUAUAUUUGCC |
| SEQ ID NO. 772 | GCAAAUAUAAUGAAAGAAA | SEQ ID NO. 1459 | UUUCUUUCAUUAUAUUUGC |
| SEQ ID NO. 773 | CAAAUAUAAUGAAAGAAAU | SEQ ID NO. 1460 | AUUUCUUUCAUUAUAUUUG |
| SEQ ID NO. 774 | AAAUAUAAUGAAAGAAAUA | SEQ ID NO. 1461 | UAUUUCUUUCAUUAUAUUU |
| SEQ ID NO. 775 | GAAAGAAAUAAGUCUCCUU | SEQ ID NO. 1462 | AAGGAGACUUAUUUCUUUC |
| SEQ ID NO. 776 | AGAAAUAAGUCUCCUUCCA | SEQ ID NO. 1463 | UGGAAGGAGACUUAUUUCU |
| SEQ ID NO. 777 | AAAUAAGUCUCCUUCCAGA | SEQ ID NO. 1464 | UCUGGAAGGAGACUUAUUU |
| SEQ ID NO. 778 | AUAAGUCUCCUUCCAGAUA | SEQ ID NO. 1465 | UAUCUGGAAGGAGACUUAU |
| SEQ ID NO. 779 | UAAGUCUCCUUCCAGAUAA | SEQ ID NO. 1466 | UUAUCUGGAAGGAGACUUA |
| SEQ ID NO. 780 | AAGUCUCCUUCCAGAUAAU | SEQ ID NO. 1467 | AUUAUCUGGAAGGAGACUU |
| SEQ ID NO. 781 | GUCUCCUUCCAGAUAAUCU | SEQ ID NO. 1468 | AGAUUAUCUGGAAGGAGAC |
| SEQ ID NO. 782 | CUUCCAGAUAAUCUUCUCA | SEQ ID NO. 1469 | UGAGAAGAUUAUCUGGAAG |
| SEQ ID NO. 783 | AGAUAAUCUUCUCAGGACA | SEQ ID NO. 1470 | UGUCCUGAGAAGAUUAUCU |
| SEQ ID NO. 784 | UCAGGACACCAUCCGUUCA | SEQ ID NO. 1471 | UGAACGGAUGGUGUCCUGA |
| SEQ ID NO. 785 | CAGGACACCAUCCGUUCAA | SEQ ID NO. 1472 | UUGAACGGAUGGUGUCCUG |
| SEQ ID NO. 786 | AGGACACCAUCCGUUCAAU | SEQ ID NO. 1473 | AUUGAACGGAUGGUGUCCU |
| SEQ ID NO. 787 | GGACACCAUCCGUUCAAUU | SEQ ID NO. 1474 | AAUUGAACGGAUGGUGUCC |
| SEQ ID NO. 788 | CACCAUCCGUUCAAUUGGU | SEQ ID NO. 1475 | ACCAAUUGAACGGAUGGUG |
| SEQ ID NO. 789 | ACCAUCCGUUCAAUUGGUA | SEQ ID NO. 1476 | UACCAAUUGAACGGAUGGU |
| SEQ ID NO. 790 | CAUCCGUUCAAUUGGUACA | SEQ ID NO. 1477 | UGUACCAAUUGAACGGAUG |
| SEQ ID NO. 791 | UCCGUUCAAUUGGUACAAA | SEQ ID NO. 1478 | UUUGUACCAAUUGAACGGA |
| SEQ ID NO. 792 | GUUCAAUUGGUACAAAGCU | SEQ ID NO. 1479 | AGCUUUGUACCAAUUGAAC |
| SEQ ID NO. 793 | UUGGUACAAAGCUGGUAUA | SEQ ID NO. 1480 | UAUACCAGCUUUGUACCAA |
| SEQ ID NO. 794 | GGUACAAAGCUGGUAUAUC | SEQ ID NO. 1481 | GAUAUACCAGCUUUGUACC |
| SEQ ID NO. 795 | CAAAGCUGGUAUAUCCAGA | SEQ ID NO. 1482 | UCUGGAUAUACCAGCUUUG |
| SEQ ID NO. 796 | GCUGGUAUAUCCAGAGUCU | SEQ ID NO. 1483 | AGACUCUGGAUAUACCAGC |
| SEQ ID NO. 797 | CUGGUAUAUCCAGAGUCUU | SEQ ID NO. 1484 | AAGACUCUGGAUAUACCAG |

FIG. 2 Cont'd

| SEQ ID NO. 798 | GGUAUAUCCAGAGUCUUCA | SEQ ID NO. 1485 | UGAAGACUCUGGAUAUACC |
|---|---|---|---|
| SEQ ID NO. 799 | CCAGAGUCUUCAGGAGCUU | SEQ ID NO. 1486 | AAGCUCCUGAAGACUCUGG |
| SEQ ID NO. 800 | GAGUCUUCAGGAGCUUCUU | SEQ ID NO. 1487 | AAGAAGCUCCUGAAGACUC |
| SEQ ID NO. 801 | GUCUUCAGGAGCUUCUUGA | SEQ ID NO. 1488 | UCAAGAAGCUCCUGAAGAC |
| SEQ ID NO. 802 | CUUCAGGAGCUUCUUGAUU | SEQ ID NO. 1489 | AAUCAAGAAGCUCCUGAAG |
| SEQ ID NO. 803 | UUCAGGAGCUUCUUGAUUU | SEQ ID NO. 1490 | AAAUCAAGAAGCUCCUGAA |
| SEQ ID NO. 804 | UCAGGAGCUUCUUGAUUUU | SEQ ID NO. 1491 | AAAAUCAAGAAGCUCCUGA |
| SEQ ID NO. 805 | CAGGAGCUUCUUGAUUUUA | SEQ ID NO. 1492 | UAAAAUCAAGAAGCUCCUG |
| SEQ ID NO. 806 | AGGAGCUUCUUGAUUUUAA | SEQ ID NO. 1493 | UUAAAAUCAAGAAGCUCCU |
| SEQ ID NO. 807 | GGAGCUUCUUGAUUUUAAG | SEQ ID NO. 1494 | CUUAAAAUCAAGAAGCUCC |
| SEQ ID NO. 808 | CUUCUUGAUUUUAAGGACA | SEQ ID NO. 1495 | UGUCCUUAAAAUCAAGAAG |
| SEQ ID NO. 809 | CUUGAUUUUAAGGACAAAA | SEQ ID NO. 1496 | UUUUGUCCUUAAAAUCAAG |
| SEQ ID NO. 810 | GGACAAAAGUGCUGAGGAU | SEQ ID NO. 1497 | AUCCUCAGCACUUUUGUCC |
| SEQ ID NO. 811 | AAAGUGCUGAGGAUGCUAA | SEQ ID NO. 1498 | UUAGCAUCCUCAGCACUUU |
| SEQ ID NO. 812 | AAGUGCUGAGGAUGCUAAA | SEQ ID NO. 1499 | UUUAGCAUCCUCAGCACUU |
| SEQ ID NO. 813 | GCUGAGGAUGCUAAAGCUA | SEQ ID NO. 1500 | UAGCUUUAGCAUCCUCAGC |
| SEQ ID NO. 814 | CUGAGGAUGCUAAAGCUAU | SEQ ID NO. 1501 | AUAGCUUUAGCAUCCUCAG |
| SEQ ID NO. 815 | UGAGGAUGCUAAAGCUAUU | SEQ ID NO. 1502 | AAUAGCUUUAGCAUCCUCA |
| SEQ ID NO. 816 | GAGGAUGCUAAAGCUAUUU | SEQ ID NO. 1503 | AAAUAGCUUUAGCAUCCUC |
| SEQ ID NO. 817 | AGGAUGCUAAAGCUAUUUA | SEQ ID NO. 1504 | UAAAUAGCUUUAGCAUCCU |
| SEQ ID NO. 818 | GGAUGCUAAAGCUAUUUAU | SEQ ID NO. 1505 | AUAAAUAGCUUUAGCAUCC |
| SEQ ID NO. 819 | GCUAAAGCUAUUUAUGACU | SEQ ID NO. 1506 | AGUCAUAAAUAGCUUUAGC |
| SEQ ID NO. 820 | CUAAAGCUAUUUAUGACUU | SEQ ID NO. 1507 | AAGUCAUAAAUAGCUUUAG |
| SEQ ID NO. 821 | UAAAGCUAUUUAUGACUUU | SEQ ID NO. 1508 | AAAGUCAUAAAUAGCUUUA |
| SEQ ID NO. 822 | AAAGCUAUUUAUGACUUUA | SEQ ID NO. 1509 | UAAAGUCAUAAAUAGCUUU |
| SEQ ID NO. 823 | AGCUAUUUAUGACUUUACA | SEQ ID NO. 1510 | UGUAAAGUCAUAAAUAGCU |
| SEQ ID NO. 824 | CUAUUUAUGACUUUACAGA | SEQ ID NO. 1511 | UCUGUAAAGUCAUAAAUAG |
| SEQ ID NO. 825 | AUUUAUGACUUUACAGAUA | SEQ ID NO. 1512 | UAUCUGUAAAGUCAUAAAU |
| SEQ ID NO. 826 | UUAUGACUUUACAGAUACU | SEQ ID NO. 1513 | AGUAUCUGUAAAGUCAUAA |
| SEQ ID NO. 827 | GACUUUACAGAUACUGUGA | SEQ ID NO. 1514 | UCACAGUAUCUGUAAAGUC |
| SEQ ID NO. 828 | CUUUACAGAUACUGUGAUA | SEQ ID NO. 1515 | UAUCACAGUAUCUGUAAAG |
| SEQ ID NO. 829 | CAGAUACUGUGAUACGGAU | SEQ ID NO. 1516 | AUCCGUAUCACAGUAUCUG |
| SEQ ID NO. 830 | CUGUGAUACGGAUCAGAAA | SEQ ID NO. 1517 | UUUCUGAUCCGUAUCACAG |
| SEQ ID NO. 831 | GAUACGGAUCAGAAACCGA | SEQ ID NO. 1518 | UCGGUUUCUGAUCCGUAUC |
| SEQ ID NO. 832 | CGGAUCAGAAACCGACACA | SEQ ID NO. 1519 | UGUGUCGGUUUCUGAUCCG |
| SEQ ID NO. 833 | GGAUCAGAAACCGACACAA | SEQ ID NO. 1520 | UUGUGUCGGUUUCUGAUCC |
| SEQ ID NO. 834 | GAUCAGAAACCGACACAAU | SEQ ID NO. 1521 | AUUGUGUCGGUUUCUGAUC |
| SEQ ID NO. 835 | UCAGAAACCGACACAAUGA | SEQ ID NO. 1522 | UCAUUGUGUCGGUUUCUGA |

FIG. 2 Cont'd

| | | | |
|---|---|---|---|
| SEQ ID NO. 836 | CAGAAACCGACACAAUGAU | SEQ ID NO. 1523 | AUCAUUGUGUCGGUUUCUG |
| SEQ ID NO. 837 | GAAACCGACACAAUGAUGU | SEQ ID NO. 1524 | ACAUCAUUGUGUCGGUUUC |
| SEQ ID NO. 838 | CCGACACAAUGAUGUCAUU | SEQ ID NO. 1525 | AAUGACAUCAUUGUGUCGG |
| SEQ ID NO. 839 | CACAAUGAUGUCAUUCCCA | SEQ ID NO. 1526 | UGGGAAUGACAUCAUUGUG |
| SEQ ID NO. 840 | CAAUGAUGUCAUUCCCACA | SEQ ID NO. 1527 | UGUGGGAAUGACAUCAUUG |
| SEQ ID NO. 841 | AUGAUGUCAUUCCCACAAU | SEQ ID NO. 1528 | AUUGUGGGAAUGACAUCAU |
| SEQ ID NO. 842 | CCACAAUGGCCCAGGGUGU | SEQ ID NO. 1529 | ACACCCUGGGCCAUUGUGG |
| SEQ ID NO. 843 | CAAUGGCCCAGGGUGUGAU | SEQ ID NO. 1530 | AUCACACCCUGGGCCAUUG |
| SEQ ID NO. 844 | GGCCCAGGGUGUGAUUGAA | SEQ ID NO. 1531 | UUCAAUCACACCCUGGGCC |
| SEQ ID NO. 845 | GCCCAGGGUGUGAUUGAAU | SEQ ID NO. 1532 | AUUCAAUCACACCCUGGGC |
| SEQ ID NO. 846 | CCCAGGGUGUGAUUGAAUA | SEQ ID NO. 1533 | UAUUCAAUCACACCCUGGG |
| SEQ ID NO. 847 | CAGGGUGUGAUUGAAUACA | SEQ ID NO. 1534 | UGUAUUCAAUCACACCCUG |
| SEQ ID NO. 848 | AGGGUGUGAUUGAAUACAA | SEQ ID NO. 1535 | UUGUAUUCAAUCACACCCU |
| SEQ ID NO. 849 | GUGUGAUUGAAUACAAGGA | SEQ ID NO. 1536 | UCCUUGUAUUCAAUCACAC |
| SEQ ID NO. 850 | GUGAUUGAAUACAAGGAGA | SEQ ID NO. 1537 | UCUCCUUGUAUUCAAUCAC |
| SEQ ID NO. 851 | GGAGAGCUUUGGGGUGGAU | SEQ ID NO. 1538 | AUCCACCCCAAAGCUCUCC |
| SEQ ID NO. 852 | GCUUUGGGGUGGAUCCUGU | SEQ ID NO. 1539 | ACAGGAUCCACCCCAAAGC |
| SEQ ID NO. 853 | GGGGUGGAUCCUGUCACCA | SEQ ID NO. 1540 | UGGUGACAGGAUCCACCCC |
| SEQ ID NO. 854 | CUGUCACCAGCCAGAAUGU | SEQ ID NO. 1541 | ACAUUCUGGCUGGUGACAG |
| SEQ ID NO. 855 | UCACCAGCCAGAAUGUUCA | SEQ ID NO. 1542 | UGAACAUUCUGGCUGGUGA |
| SEQ ID NO. 856 | CCAGCCAGAAUGUUCAGUA | SEQ ID NO. 1543 | UACUGAACAUUCUGGCUGG |
| SEQ ID NO. 857 | CAGCCAGAAUGUUCAGUAC | SEQ ID NO. 1544 | GUACUGAACAUUCUGGCUG |
| SEQ ID NO. 858 | GCCAGAAUGUUCAGUACUU | SEQ ID NO. 1545 | AAGUACUGAACAUUCUGGC |
| SEQ ID NO. 859 | CCAGAAUGUUCAGUACUUU | SEQ ID NO. 1546 | AAAGUACUGAACAUUCUGG |
| SEQ ID NO. 860 | CAGAAUGUUCAGUACUUUU | SEQ ID NO. 1547 | AAAAGUACUGAACAUUCUG |
| SEQ ID NO. 861 | AGAAUGUUCAGUACUUUUU | SEQ ID NO. 1548 | AAAAAGUACUGAACAUUCU |
| SEQ ID NO. 862 | UCAGUACUUUUUGGAUCGA | SEQ ID NO. 1549 | UCGAUCCAAAAAGUACUGA |
| SEQ ID NO. 863 | CAGUACUUUUUGGAUCGAU | SEQ ID NO. 1550 | AUCGAUCCAAAAAGUACUG |
| SEQ ID NO. 864 | UUGGAUCGAUUCUACAUGA | SEQ ID NO. 1551 | UCAUGUAGAAUCGAUCCAA |
| SEQ ID NO. 865 | GGAUCGAUUCUACAUGAGU | SEQ ID NO. 1552 | ACUCAUGUAGAAUCGAUCC |
| SEQ ID NO. 866 | CUACAUGAGUCGCAUUUCA | SEQ ID NO. 1553 | UGAAAUGCGACUCAUGUAG |
| SEQ ID NO. 867 | UACAUGAGUCGCAUUUCAA | SEQ ID NO. 1554 | UUGAAAUGCGACUCAUGUA |
| SEQ ID NO. 868 | ACAUGAGUCGCAUUUCAAU | SEQ ID NO. 1555 | AUUGAAAUGCGACUCAUGU |
| SEQ ID NO. 869 | CAUGAGUCGCAUUUCAAUU | SEQ ID NO. 1556 | AAUUGAAAUGCGACUCAUG |
| SEQ ID NO. 870 | AUGAGUCGCAUUUCAAUUA | SEQ ID NO. 1557 | UAAUUGAAAUGCGACUCAU |
| SEQ ID NO. 871 | UGAGUCGCAUUUCAAUUAG | SEQ ID NO. 1558 | CUAAUUGAAAUGCGACUCA |
| SEQ ID NO. 872 | GAGUCGCAUUUCAAUUAGA | SEQ ID NO. 1559 | UCUAAUUGAAAUGCGACUC |
| SEQ ID NO. 873 | AGUCGCAUUUCAAUUAGAA | SEQ ID NO. 1560 | UUCUAAUUGAAAUGCGACU |

FIG. 2 Cont'd

| | | | |
|---|---|---|---|
| SEQ ID NO. 874 | GUCGCAUUUCAAUUAGAAU | SEQ ID NO. 1561 | AUUCUAAUUGAAAUGCGAC |
| SEQ ID NO. 875 | CGCAUUUCAAUUAGAAUGU | SEQ ID NO. 1562 | ACAUUCUAAUUGAAAUGCG |
| SEQ ID NO. 876 | GCAUUUCAAUUAGAAUGUU | SEQ ID NO. 1563 | AACAUUCUAAUUGAAAUGC |
| SEQ ID NO. 877 | CAUUUCAAUUAGAAUGUUA | SEQ ID NO. 1564 | UAACAUUCUAAUUGAAAUG |
| SEQ ID NO. 878 | CAAUUAGAAUGUUACUCAA | SEQ ID NO. 1565 | UUGAGUAACAUUCUAAUUG |
| SEQ ID NO. 879 | UUAGAAUGUUACUCAAUCA | SEQ ID NO. 1566 | UGAUUGAGUAACAUUCUAA |
| SEQ ID NO. 880 | GAAUGUUACUCAAUCAGCA | SEQ ID NO. 1567 | UGCUGAUUGAGUAACAUUC |
| SEQ ID NO. 881 | ACUCAAUCAGCACUCUUUA | SEQ ID NO. 1568 | UAAAGAGUGCUGAUUGAGU |
| SEQ ID NO. 882 | CUCAAUCAGCACUCUUUAU | SEQ ID NO. 1569 | AUAAAGAGUGCUGAUUGAG |
| SEQ ID NO. 883 | UCAAUCAGCACUCUUUAUU | SEQ ID NO. 1570 | AAUAAAGAGUGCUGAUUGA |
| SEQ ID NO. 884 | UCAGCACUCUUUAUUGUUU | SEQ ID NO. 1571 | AAACAAUAAAGAGUGCUGA |
| SEQ ID NO. 885 | GCACUCUUUAUUGUUUGGU | SEQ ID NO. 1572 | ACCAAACAAUAAAGAGUGC |
| SEQ ID NO. 886 | CUUUAUUGUUUGGUGGAAA | SEQ ID NO. 1573 | UUUCCACCAAACAAUAAAG |
| SEQ ID NO. 887 | UUUAUUGUUUGGUGGAAAA | SEQ ID NO. 1574 | UUUUCCACCAAACAAUAAA |
| SEQ ID NO. 888 | GUUUGGUGGAAAAGGCAAA | SEQ ID NO. 1575 | UUUGCCUUUUCCACCAAAC |
| SEQ ID NO. 889 | GGUGGAAAAGGCAAAGGAA | SEQ ID NO. 1576 | UUCCUUUGCCUUUUCCACC |
| SEQ ID NO. 890 | AGGCAAAGGAAGUCCAUCU | SEQ ID NO. 1577 | AGAUGGACUUCCUUUGCCU |
| SEQ ID NO. 891 | GGCAAAGGAAGUCCAUCUC | SEQ ID NO. 1578 | GAGAUGGACUUCCUUUGCC |
| SEQ ID NO. 892 | GCAAAGGAAGUCCAUCUCA | SEQ ID NO. 1579 | UGAGAUGGACUUCCUUUGC |
| SEQ ID NO. 893 | CAAAGGAAGUCCAUCUCAU | SEQ ID NO. 1580 | AUGAGAUGGACUUCCUUUG |
| SEQ ID NO. 894 | GGAAGUCCAUCUCAUCGAA | SEQ ID NO. 1581 | UUCGAUGAGAUGGACUUCC |
| SEQ ID NO. 895 | GAAGUCCAUCUCAUCGAAA | SEQ ID NO. 1582 | UUUCGAUGAGAUGGACUUC |
| SEQ ID NO. 896 | AAGUCCAUCUCAUCGAAAA | SEQ ID NO. 1583 | UUUUCGAUGAGAUGGACUU |
| SEQ ID NO. 897 | GUCCAUCUCAUCGAAAACA | SEQ ID NO. 1584 | UGUUUUCGAUGAGAUGGAC |
| SEQ ID NO. 898 | CCAUCUCAUCGAAAACACA | SEQ ID NO. 1585 | UGUGUUUUCGAUGAGAUGG |
| SEQ ID NO. 899 | CAUCUCAUCGAAAACACAU | SEQ ID NO. 1586 | AUGUGUUUUCGAUGAGAUG |
| SEQ ID NO. 900 | AUCUCAUCGAAAACACAUU | SEQ ID NO. 1587 | AAUGUGUUUUCGAUGAGAU |
| SEQ ID NO. 901 | UCAUCGAAAACACAUUGGA | SEQ ID NO. 1588 | UCCAAUGUGUUUUCGAUGA |
| SEQ ID NO. 902 | CAUCGAAAACACAUUGGAA | SEQ ID NO. 1589 | UUCCAAUGUGUUUUCGAUG |
| SEQ ID NO. 903 | CGAAAACACAUUGGAAGCA | SEQ ID NO. 1590 | UGCUUCCAAUGUGUUUUCG |
| SEQ ID NO. 904 | GAAAACACAUUGGAAGCAU | SEQ ID NO. 1591 | AUGCUUCCAAUGUGUUUUC |
| SEQ ID NO. 905 | AAAACACAUUGGAAGCAUA | SEQ ID NO. 1592 | UAUGCUUCCAAUGUGUUUU |
| SEQ ID NO. 906 | AAACACAUUGGAAGCAUAA | SEQ ID NO. 1593 | UUAUGCUUCCAAUGUGUUU |
| SEQ ID NO. 907 | AACACAUUGGAAGCAUAAA | SEQ ID NO. 1594 | UUUAUGCUUCCAAUGUGUU |
| SEQ ID NO. 908 | ACACAUUGGAAGCAUAAAU | SEQ ID NO. 1595 | AUUUAUGCUUCCAAUGUGU |
| SEQ ID NO. 909 | CAUUGGAAGCAUAAAUCCA | SEQ ID NO. 1596 | UGGAUUUAUGCUUCCAAUG |
| SEQ ID NO. 910 | GGAAGCAUAAAUCCAAACU | SEQ ID NO. 1597 | AGUUUGGAUUUAUGCUUCC |
| SEQ ID NO. 911 | GCAUAAAUCCAAACUGCAA | SEQ ID NO. 1598 | UUGCAGUUUGGAUUUAUGC |

FIG. 2 Cont'd

| SEQ ID NO. 912 | CAUAAAUCCAAACUGCAAU | SEQ ID NO. 1599 | AUUGCAGUUUGGAUUUAUG |
|---|---|---|---|
| SEQ ID NO. 913 | AAAUCCAAACUGCAAUGUA | SEQ ID NO. 1600 | UACAUUGCAGUUUGGAUUU |
| SEQ ID NO. 914 | CAAACUGCAAUGUACUUGA | SEQ ID NO. 1601 | UCAAGUACAUUGCAGUUUG |
| SEQ ID NO. 915 | AAACUGCAAUGUACUUGAA | SEQ ID NO. 1602 | UUCAAGUACAUUGCAGUUU |
| SEQ ID NO. 916 | CUGCAAUGUACUUGAAGUU | SEQ ID NO. 1603 | AACUUCAAGUACAUUGCAG |
| SEQ ID NO. 917 | GCAAUGUACUUGAAGUUAU | SEQ ID NO. 1604 | AUAACUUCAAGUACAUUGC |
| SEQ ID NO. 918 | CAAUGUACUUGAAGUUAUU | SEQ ID NO. 1605 | AAUAACUUCAAGUACAUUG |
| SEQ ID NO. 919 | AUGUACUUGAAGUUAUUAA | SEQ ID NO. 1606 | UUAAUAACUUCAAGUACAUU |
| SEQ ID NO. 920 | UGUACUUGAAGUUAUUAAA | SEQ ID NO. 1607 | UUUAAUAACUUCAAGUACA |
| SEQ ID NO. 921 | UACUUGAAGUUAUUAAAGA | SEQ ID NO. 1608 | UCUUUAAUAACUUCAAGUA |
| SEQ ID NO. 922 | UAUUAAAGAUGGCUAUGAA | SEQ ID NO. 1609 | UUCAUAGCCAUCUUUAAUA |
| SEQ ID NO. 923 | UUAAAGAUGGCUAUGAAAA | SEQ ID NO. 1610 | UUUUCAUAGCCAUCUUUAA |
| SEQ ID NO. 924 | UAAAGAUGGCUAUGAAAAU | SEQ ID NO. 1611 | AUUUCAUAGCCAUCUUUA |
| SEQ ID NO. 925 | AGAUGGCUAUGAAAAUGCU | SEQ ID NO. 1612 | AGCAUUUCAUAGCCAUCU |
| SEQ ID NO. 926 | GAUGGCUAUGAAAAUGCUA | SEQ ID NO. 1613 | UAGCAUUUCAUAGCCAUC |
| SEQ ID NO. 927 | GCUAGGCGUCUGUGUGAUU | SEQ ID NO. 1614 | AAUCACACGACGCCUAGC |
| SEQ ID NO. 928 | CUAGGCGUCUGUGUGAUUU | SEQ ID NO. 1615 | AAAUCACACAGACGCCUAG |
| SEQ ID NO. 929 | GGCGUCUGUGUGAUUUGUA | SEQ ID NO. 1616 | UACAAAUCACACAGACGCC |
| SEQ ID NO. 930 | GCGUCUGUGUGAUUUGUAU | SEQ ID NO. 1617 | AUACAAAUCACACAGACGC |
| SEQ ID NO. 931 | CGUCUGUGUGAUUUGUAUU | SEQ ID NO. 1618 | AAUACAAAUCACACAGACG |
| SEQ ID NO. 932 | GUCUGUGUGAUUUGUAUUA | SEQ ID NO. 1619 | UAAUACAAAUCACACAGAC |
| SEQ ID NO. 933 | CUGUGUGAUUUGUAUUAUA | SEQ ID NO. 1620 | UAUAAUACAAAUCACACAG |
| SEQ ID NO. 934 | UGUGUGAUUUGUAUUAUAU | SEQ ID NO. 1621 | AUAUAAUACAAAUCACACA |
| SEQ ID NO. 935 | GUGUGAUUUGUAUUAUAUU | SEQ ID NO. 1622 | AAUAUAAUACAAAUCACAC |
| SEQ ID NO. 936 | UGUGAUUUGUAUUAUAUUA | SEQ ID NO. 1623 | UAAUAUAAUACAAAUCACA |
| SEQ ID NO. 937 | GUGAUUUGUAUUAUAUUAA | SEQ ID NO. 1624 | UUAAUAUAAUACAAAUCAC |
| SEQ ID NO. 938 | GAUUUGUAUUAUAUUAACU | SEQ ID NO. 1625 | AGUUAAUAUAAUACAAAUC |
| SEQ ID NO. 939 | UAUUAACUCUCCCGAACUA | SEQ ID NO. 1626 | UAGUUCGGGAGAGUUAAUA |
| SEQ ID NO. 940 | UUAACUCUCCCGAACUAGA | SEQ ID NO. 1627 | UCUAGUUCGGGAGAGUUAA |
| SEQ ID NO. 941 | UAACUCUCCCGAACUAGAA | SEQ ID NO. 1628 | UUCUAGUUCGGGAGAGUUA |
| SEQ ID NO. 942 | CUCUCCCGAACUAGAACUU | SEQ ID NO. 1629 | AAGUUCUAGUUCGGGAGAG |
| SEQ ID NO. 943 | CUCCCGAACUAGAACUUGA | SEQ ID NO. 1630 | UCAAGUUCUAGUUCGGGAG |
| SEQ ID NO. 944 | UCCCGAACUAGAACUUGAA | SEQ ID NO. 1631 | UUCAAGUUCUAGUUCGGGA |
| SEQ ID NO. 945 | CCCGAACUAGAACUUGAAG | SEQ ID NO. 1632 | CUUCAAGUUCUAGUUCGGG |
| SEQ ID NO. 946 | CCGAACUAGAACUUGAAGA | SEQ ID NO. 1633 | UCUUCAAGUUCUAGUUCGG |
| SEQ ID NO. 947 | CGAACUAGAACUUGAAGAA | SEQ ID NO. 1634 | UUCUUCAAGUUCUAGUUCG |
| SEQ ID NO. 948 | ACUAGAACUUGAAGAACUA | SEQ ID NO. 1635 | UAGUUCUUCAAGUUCUAGU |
| SEQ ID NO. 949 | CUAGAACUUGAAGAACUAA | SEQ ID NO. 1636 | UUAGUUCUUCAAGUUCUAG |

FIG. 2 Cont'd

| | | | |
|---|---|---|---|
| SEQ ID NO. 950 | AGAACUUGAAGAACUAAAU | SEQ ID NO. 1637 | AUUUAGUUCUUCAAGUUCU |
| SEQ ID NO. 951 | CUUGAAGAACUAAAUGCAA | SEQ ID NO. 1638 | UUGCAUUUAGUUCUUCAAG |
| SEQ ID NO. 952 | UGAAGAACUAAAUGCAAAA | SEQ ID NO. 1639 | UUUUGCAUUUAGUUCUUCA |
| SEQ ID NO. 953 | GAAGAACUAAAUGCAAAAU | SEQ ID NO. 1640 | AUUUUGCAUUUAGUUCUUC |
| SEQ ID NO. 954 | AGAACUAAAUGCAAAAUCA | SEQ ID NO. 1641 | UGAUUUUGCAUUUAGUUCU |
| SEQ ID NO. 955 | CACCAGGACAGCCAAUACA | SEQ ID NO. 1642 | UGUAUUGGCUGUCCUGGUG |
| SEQ ID NO. 956 | ACCAGGACAGCCAAUACAA | SEQ ID NO. 1643 | UUGUAUUGGCUGUCCUGGU |
| SEQ ID NO. 957 | CAGGACAGCCAAUACAAGU | SEQ ID NO. 1644 | ACUUGUAUUGGCUGUCCUG |
| SEQ ID NO. 958 | GACAGCCAAUACAAGUGGU | SEQ ID NO. 1645 | ACCACUUGUAUUGGCUGUC |
| SEQ ID NO. 959 | CAGCCAAUACAAGUGGUUU | SEQ ID NO. 1646 | AAACCACUUGUAUUGGCUG |
| SEQ ID NO. 960 | AGCCAAUACAAGUGGUUUA | SEQ ID NO. 1647 | UAAACCACUUGUAUUGGCU |
| SEQ ID NO. 961 | GCCAAUACAAGUGGUUUAU | SEQ ID NO. 1648 | AUAAACCACUUGUAUUGGC |
| SEQ ID NO. 962 | CAAUACAAGUGGUUUAUGU | SEQ ID NO. 1649 | ACAUAAACCACUUGUAUUG |
| SEQ ID NO. 963 | ACAAGUGGUUUAUGUACCA | SEQ ID NO. 1650 | UGGUACAUAAACCACUUGU |
| SEQ ID NO. 964 | UCUAUCACAUGGUGUUUGA | SEQ ID NO. 1651 | UCAAACACCAUGUGAUAGA |
| SEQ ID NO. 965 | CUAUCACAUGGUGUUUGAA | SEQ ID NO. 1652 | UUCAAACACCAUGUGAUAG |
| SEQ ID NO. 966 | UCACAUGGUGUUUGAACUU | SEQ ID NO. 1653 | AAGUUCAAACACCAUGUGA |
| SEQ ID NO. 967 | CACAUGGUGUUUGAACUUU | SEQ ID NO. 1654 | AAAGUUCAAACACCAUGUG |
| SEQ ID NO. 968 | ACAUGGUGUUUGAACUUUU | SEQ ID NO. 1655 | AAAAGUUCAAACACCAUGU |
| SEQ ID NO. 969 | GUGUUUGAACUUUUCAAGA | SEQ ID NO. 1656 | UCUUGAAAAGUUCAAACAC |
| SEQ ID NO. 970 | UGUUUGAACUUUUCAAGAA | SEQ ID NO. 1657 | UUCUUGAAAAGUUCAAACA |
| SEQ ID NO. 971 | GUUUGAACUUUUCAAGAAU | SEQ ID NO. 1658 | AUUCUUGAAAAGUUCAAAC |
| SEQ ID NO. 972 | GAACUUUUCAAGAAUGCAA | SEQ ID NO. 1659 | UUGCAUUCUUGAAAAGUUC |
| SEQ ID NO. 973 | CUUUUCAAGAAUGCAAUGA | SEQ ID NO. 1660 | UCAUUGCAUUCUUGAAAAG |
| SEQ ID NO. 974 | AUGCAAUGAGAGCCACUAU | SEQ ID NO. 1661 | AUAGUGGCUCUCAUUGCAU |
| SEQ ID NO. 975 | CAAUGAGAGCCACUAUGGA | SEQ ID NO. 1662 | UCCAUAGUGGCUCUCAUUG |
| SEQ ID NO. 976 | UGAGAGCCACUAUGGAACA | SEQ ID NO. 1663 | UGUUCCAUAGUGGCUCUCA |
| SEQ ID NO. 977 | GAGCCACUAUGGAACACCA | SEQ ID NO. 1664 | UGGUGUUCCAUAGUGGCUC |
| SEQ ID NO. 978 | CUAUGGAACACCAUGCCAA | SEQ ID NO. 1665 | UUGGCAUGGUGUUCCAUAG |
| SEQ ID NO. 979 | GGAACACCAUGCCAACAGA | SEQ ID NO. 1666 | UCUGUUGGCAUGGUGUUCC |
| SEQ ID NO. 980 | CCAUGCCAACAGAGGUGUU | SEQ ID NO. 1667 | AACACCUCUGUUGGCAUGG |
| SEQ ID NO. 981 | CAUGCCAACAGAGGUGUUU | SEQ ID NO. 1668 | AAACACCUCUGUUGGCAUG |
| SEQ ID NO. 982 | AUGCCAACAGAGGUGUUUA | SEQ ID NO. 1669 | UAAACACCUCUGUUGGCAU |
| SEQ ID NO. 983 | AGAGGUGUUUACCCCCCUA | SEQ ID NO. 1670 | UAGGGGGGUAAACACCUCU |
| SEQ ID NO. 984 | GAGGUGUUUACCCCCCUAU | SEQ ID NO. 1671 | AUAGGGGGGUAAACACCUC |
| SEQ ID NO. 985 | AGGUGUUUACCCCCCUAUU | SEQ ID NO. 1672 | AAUAGGGGGGUAAACACCU |
| SEQ ID NO. 986 | GUGUUUACCCCCCUAUUCA | SEQ ID NO. 1673 | UGAAUAGGGGGGUAAACAC |
| SEQ ID NO. 987 | UGUUUACCCCCCUAUUCAA | SEQ ID NO. 1674 | UUGAAUAGGGGGGUAAACA |

FIG. 2 Cont'd

| | | | |
|---|---|---|---|
| SEQ ID NO. 988 | UUACCCCCCUAUUCAAGUU | SEQ ID NO. 1675 | AACUUGAAUAGGGGGGUAA |
| SEQ ID NO. 989 | ACCCCCCUAUUCAAGUUCA | SEQ ID NO. 1676 | UGAACUUGAAUAGGGGGGU |
| SEQ ID NO. 990 | CCCCCCUAUUCAAGUUCAU | SEQ ID NO. 1677 | AUGAACUUGAAUAGGGGGG |
| SEQ ID NO. 991 | CCCCUAUUCAAGUUCAUGU | SEQ ID NO. 1678 | ACAUGAACUUGAAUAGGGG |
| SEQ ID NO. 992 | CCUAUUCAAGUUCAUGUCA | SEQ ID NO. 1679 | UGACAUGAACUUGAAUAGG |
| SEQ ID NO. 993 | AUGUCACGCUGGGUAAUGA | SEQ ID NO. 1680 | UCAUUACCCAGCGUGACAU |
| SEQ ID NO. 994 | CACGCUGGGUAAUGAGGAU | SEQ ID NO. 1681 | AUCCUCAUUACCCAGCGUG |
| SEQ ID NO. 995 | ACGCUGGGUAAUGAGGAUU | SEQ ID NO. 1682 | AAUCCUCAUUACCCAGCGU |
| SEQ ID NO. 996 | CGCUGGGUAAUGAGGAUUU | SEQ ID NO. 1683 | AAAUCCUCAUUACCCAGCG |
| SEQ ID NO. 997 | CUGGGUAAUGAGGAUUUGA | SEQ ID NO. 1684 | UCAAAUCCUCAUUACCCAG |
| SEQ ID NO. 998 | GGGUAAUGAGGAUUUGACU | SEQ ID NO. 1685 | AGUCAAAUCCUCAUUACCC |
| SEQ ID NO. 999 | GUAAUGAGGAUUUGACUGU | SEQ ID NO. 1686 | ACAGUCAAAUCCUCAUUAC |
| SEQ ID NO. 1000 | AAUGAGGAUUUGACUGUGA | SEQ ID NO. 1687 | UCACAGUCAAAUCCUCAUU |
| SEQ ID NO. 1001 | AUGAGGAUUUGACUGUGAA | SEQ ID NO. 1688 | UUCACAGUCAAAUCCUCAU |
| SEQ ID NO. 1002 | GAGGAUUUGACUGUGAAGA | SEQ ID NO. 1689 | UCUUCACAGUCAAAUCCUC |
| SEQ ID NO. 1003 | GAUUUGACUGUGAAGAUGA | SEQ ID NO. 1690 | UCAUCUUCACAGUCAAAUC |
| SEQ ID NO. 1004 | UGACUGUGAAGAUGAGUGA | SEQ ID NO. 1691 | UCACUCAUCUUCACAGUCA |
| SEQ ID NO. 1005 | GAAGAUGAGUGACCGAGGA | SEQ ID NO. 1692 | UCCUCGGUCACUCAUCUUC |
| SEQ ID NO. 1006 | GACCGAGGAGGUGGCGUUC | SEQ ID NO. 1693 | GAACGCCACCUCCUCGGUC |
| SEQ ID NO. 1007 | CCGAGGAGGUGGCGUUCCU | SEQ ID NO. 1694 | AGGAACGCCACCUCCUCGG |
| SEQ ID NO. 1008 | CGAGGAGGUGGCGUUCCUU | SEQ ID NO. 1695 | AAGGAACGCCACCUCCUCG |
| SEQ ID NO. 1009 | GAGGAGGUGGCGUUCCUUU | SEQ ID NO. 1696 | AAAGGAACGCCACCUCCUC |
| SEQ ID NO. 1010 | GGAGGUGGCGUUCCUUUGA | SEQ ID NO. 1697 | UCAAAGGAACGCCACCUCC |
| SEQ ID NO. 1011 | GCAAUGUACUUGAAGUUAU | SEQ ID NO. 1698 | AUAACUUCAAGUACAUUGC |
| SEQ ID NO. 1012 | GGAAGUCCAUCUCAUCGAA | SEQ ID NO. 1699 | UUCGAUGAGAUGGACUUCC |
| SEQ ID NO. 1013 | GCUGAGGAUGCUAAAGCUA | SEQ ID NO. 1700 | UAGCUUUAGCAUCCUCAGC |
| SEQ ID NO. 1014 | CAUUUCAAUUAGAAUGUUA | SEQ ID NO. 1701 | UAACAUUCUAAUUGAAAUG |
| SEQ ID NO. 1015 | CGAACUAGAACUUGAAGAA | SEQ ID NO. 1702 | UUCUUCAAGUUCUAGUUCG |
| SEQ ID NO. 1016 | GCAUAAAUCCAAACUGCAA | SEQ ID NO. 1703 | UUGCAGUUUGGAUUUAUGC |
| SEQ ID NO. 1017 | CAAUGUACUUGAAGUUAUU | SEQ ID NO. 1704 | AAUAACUUCAAGUACAUUG |
| SEQ ID NO. 1018 | CUGUGUGAUUUGUAUUAUA | SEQ ID NO. 1705 | UAUAAUACAAAUCACACAG |
| SEQ ID NO. 1019 | ACUAGAACUUGAAGAACUA | SEQ ID NO. 1706 | UAGUUCUUCAAGUUCUAGU |
| SEQ ID NO. 1020 | GAAUGUUACUCAAUCAGCA | SEQ ID NO. 1707 | UGCUGAUUGAGUAACAUUC |
| SEQ ID NO. 1021 | GGAUGCUAAAGCUAUUUAU | SEQ ID NO. 1708 | AUAAAUAGCUUUAGCAUCC |
| SEQ ID NO. 1022 | CUGUGAUACGGAUCAGAAA | SEQ ID NO. 1709 | UUUCUGAUCCGUAUCACAG |
| SEQ ID NO. 1023 | AGGGUGUGAUUGAAUACAA | SEQ ID NO. 1710 | UUGUAUUCAAUCACACCCU |
| SEQ ID NO. 1024 | CUUGAAGAACUAAAUGCAA | SEQ ID NO. 1711 | UUGCAUUUAGUUCUUCAAG |
| SEQ ID NO. 1025 | GUCUGUGUGAUUUGUAUUA | SEQ ID NO. 1712 | UAAUACAAAUCACACAGAC |

FIG. 2 Cont'd

| | | | |
|---|---|---|---|
| SEQ ID NO. 1026 | GACUUUACAGAUACUGUGA | SEQ ID NO. 1713 | UCACAGUAUCUGUAAAGUC |
| SEQ ID NO. 1027 | GCGUCUGUGUGAUUUGUAU | SEQ ID NO. 1714 | AUACAAAUCACACAGACGC |
| SEQ ID NO. 1028 | UGUGAUUUGUAUUAUAUUA | SEQ ID NO. 1715 | UAAUAUAAUACAAAUCACA |
| SEQ ID NO. 1029 | UGUACUUGAAGUUAUUAAA | SEQ ID NO. 1716 | UUUAAUAACUUCAAGUACA |
| SEQ ID NO. 1030 | CUUUACAGAUACUGUGAUA | SEQ ID NO. 1717 | UAUCACAGUAUCUGUAAAG |
| SEQ ID NO. 1031 | GAUUUGACUGUGAAGAUGA | SEQ ID NO. 1718 | UCAUCUUCACAGUCAAAUC |
| SEQ ID NO. 1032 | CCUAUUCAAGUUCAUGUCA | SEQ ID NO. 1719 | UGACAUGAACUUGAAUAGG |
| SEQ ID NO. 1033 | CAAAUAUAAUGAAAGAAAU | SEQ ID NO. 1720 | AUUUCUUUCAUUAUAUUUG |
| SEQ ID NO. 1034 | CUGUCAGACUGGCAAAUAU | SEQ ID NO. 1721 | AUAUUUGCCAGUCUGACAG |
| SEQ ID NO. 1035 | UGUCAGACUGGCAAAUAUA | SEQ ID NO. 1722 | UAUAUUGCCAGUCUGACA |
| SEQ ID NO. 1036 | GUCAGACUGGCAAAUAUAA | SEQ ID NO. 1723 | UUAUAUUGCCAGUCUGAC |
| SEQ ID NO. 1037 | UCAGACUGGCAAAUAUAAU | SEQ ID NO. 1724 | AUUAUAUUGCCAGUCUGA |
| SEQ ID NO. 1038 | GACUGGCAAAUAUAAUGAA | SEQ ID NO. 1725 | UUCAUUAUAUUUGCCAGUC |
| SEQ ID NO. 1039 | ACUGGCAAAUAUAAUGAAA | SEQ ID NO. 1726 | UUUCAUUAUAUUUGCCAGU |
| SEQ ID NO. 1040 | GGCAAAUAUAAUGAAAGAA | SEQ ID NO. 1727 | UUCUUUCAUUAUAUUUGCC |
| SEQ ID NO. 1041 | GCAAAUAUAAUGAAAGAAA | SEQ ID NO. 1728 | UUUCUUUCAUUAUAUUUGC |
| SEQ ID NO. 1042 | CAAAUAUAAUGAAAGAAAU | SEQ ID NO. 1729 | AUUUCUUUCAUUAUAUUUG |
| SEQ ID NO. 1043 | AAAUAUAAUGAAAGAAAUA | SEQ ID NO. 1730 | UAUUUCUUUCAUUAUAUUU |
| SEQ ID NO. 1044 | AAUAUAAUGAAAGAAAUAA | SEQ ID NO. 1731 | UUAUUUCUUUCAUUAUAUU |
| SEQ ID NO. 1045 | GAAAGAAAUAAGUCUCCUU | SEQ ID NO. 1732 | AAGGAGACUUAUUUCUUUC |
| SEQ ID NO. 1046 | CAGAUAAUCUUCUCAGGAC | SEQ ID NO. 1733 | GUCCUGAGAAGAUUAUCUG |
| SEQ ID NO. 1047 | GGACACCAUCCGUUCAAUU | SEQ ID NO. 1734 | AAUUGAACGGAUGGUGUCC |
| SEQ ID NO. 1048 | ACCAUCCGUUCAAUUGGUA | SEQ ID NO. 1735 | UACCAAUUGAACGGAUGGU |
| SEQ ID NO. 1049 | UCCGUUCAAUUGGUACAAA | SEQ ID NO. 1736 | UUUGUACCAAUUGAACGGA |
| SEQ ID NO. 1050 | CCAGAGUCUUCAGGAGCUU | SEQ ID NO. 1737 | AAGCUCCUGAAGACUCUGG |
| SEQ ID NO. 1051 | UCAGGAGCUUCUUGAUUUU | SEQ ID NO. 1738 | AAAAUCAAGAAGCUCCUGA |
| SEQ ID NO. 1052 | CAGGAGCUUCUUGAUUUUA | SEQ ID NO. 1739 | UAAAAUCAAGAAGCUCCUG |
| SEQ ID NO. 1053 | AGGAGCUUCUUGAUUUUAA | SEQ ID NO. 1740 | UUAAAAUCAAGAAGCUCCU |
| SEQ ID NO. 1054 | GGAGCUUCUUGAUUUUAAG | SEQ ID NO. 1741 | CUUAAAAUCAAGAAGCUCC |
| SEQ ID NO. 1055 | UCUUGAUUUUAAGGACAAA | SEQ ID NO. 1742 | UUUGUCCUUAAAAUCAAGA |
| SEQ ID NO. 1056 | CUUGAUUUUAAGGACAAAA | SEQ ID NO. 1743 | UUUUGUCCUUAAAAUCAAG |
| SEQ ID NO. 1057 | GGACAAAAGUGCUGAGGAU | SEQ ID NO. 1744 | AUCCUCAGCACUUUUGUCC |
| SEQ ID NO. 1058 | GCUGAGGAUGCUAAAGCUA | SEQ ID NO. 1745 | UAGCUUUAGCAUCCUCAGC |
| SEQ ID NO. 1059 | CUGAGGAUGCUAAAGCUAU | SEQ ID NO. 1746 | AUAGCUUUAGCAUCCUCAG |
| SEQ ID NO. 1060 | UGAGGAUGCUAAAGCUAUU | SEQ ID NO. 1747 | AAUAGCUUUAGCAUCCUCA |
| SEQ ID NO. 1061 | AGGAUGCUAAAGCUAUUUA | SEQ ID NO. 1748 | UAAAUAGCUUUAGCAUCCU |
| SEQ ID NO. 1062 | GGAUGCUAAAGCUAUUUAU | SEQ ID NO. 1749 | AUAAAUAGCUUUAGCAUCC |
| SEQ ID NO. 1063 | AAAGCUAUUUAUGACUUUA | SEQ ID NO. 1750 | UAAAGUCAUAAAUAGCUUU |

FIG. 2 Cont'd

| | | | |
|---|---|---|---|
| SEQ ID NO. 1064 | AUUUAUGACUUUACAGAUA | SEQ ID NO. 1751 | UAUCUGUAAAGUCAUAAAU |
| SEQ ID NO. 1065 | CUUUACAGAUACUGUGAUA | SEQ ID NO. 1752 | UAUCACAGUAUCUGUAAAG |
| SEQ ID NO. 1066 | CAGAUACUGUGAUACGGAU | SEQ ID NO. 1753 | AUCCGUAUCACAGUAUCUG |
| SEQ ID NO. 1067 | ACUGUGAUACGGAUCAGAA | SEQ ID NO. 1754 | UUCUGAUCCGUAUCACAGU |
| SEQ ID NO. 1068 | CUGUGAUACGGAUCAGAAA | SEQ ID NO. 1755 | UUUCUGAUCCGUAUCACAG |
| SEQ ID NO. 1069 | GGAUCAGAAACCGACACAA | SEQ ID NO. 1756 | UUGUGUCGGUUUCUGAUCC |
| SEQ ID NO. 1070 | GAUCAGAAACCGACACAAU | SEQ ID NO. 1757 | AUUGUGUCGGUUUCUGAUC |
| SEQ ID NO. 1071 | CAGAAACCGACACAAUGAU | SEQ ID NO. 1758 | AUCAUUGUGUCGGUUUCUG |
| SEQ ID NO. 1072 | ACCGACACAAUGAUGUCAU | SEQ ID NO. 1759 | AUGACAUCAUUGUGUCGGU |
| SEQ ID NO. 1073 | CCGACACAAUGAUGUCAUU | SEQ ID NO. 1760 | AAUGACAUCAUUGUGUCGG |
| SEQ ID NO. 1074 | GGCCCAGGGUGUGAUUGAA | SEQ ID NO. 1761 | UUCAAUCACACCCUGGGCC |
| SEQ ID NO. 1075 | GCCCAGGGUGUGAUUGAAU | SEQ ID NO. 1762 | AUUCAAUCACACCCUGGGC |
| SEQ ID NO. 1076 | CCCAGGGUGUGAUUGAAUA | SEQ ID NO. 1763 | UAUUCAAUCACACCCUGGG |
| SEQ ID NO. 1077 | AGGGUGUGAUUGAAUACAA | SEQ ID NO. 1764 | UUGUAUUCAAUCACACCCU |
| SEQ ID NO. 1078 | GGGUGUGAUUGAAUACAAG | SEQ ID NO. 1765 | CUUGUAUUCAAUCACACCC |
| SEQ ID NO. 1079 | GUGUGAUUGAAUACAAGGA | SEQ ID NO. 1766 | UCCUUGUAUUCAAUCACAC |
| SEQ ID NO. 1080 | GUGAUUGAAUACAAGGAGA | SEQ ID NO. 1767 | UCUCCUUGUAUUCAAUCAC |
| SEQ ID NO. 1081 | UGAAUACAAGGAGAGCUUU | SEQ ID NO. 1768 | AAAGCUCUCCUUGUAUUCA |
| SEQ ID NO. 1082 | GGAGAGCUUUGGGGUGGAU | SEQ ID NO. 1769 | AUCCACCCCAAAGCUCUCC |
| SEQ ID NO. 1083 | CCAGCCAGAAUGUUCAGUA | SEQ ID NO. 1770 | UACUGAACAUUCUGGCUGG |
| SEQ ID NO. 1084 | GCCAGAAUGUUCAGUACUU | SEQ ID NO. 1771 | AAGUACUGAACAUUCUGGC |
| SEQ ID NO. 1085 | CCAGAAUGUUCAGUACUUU | SEQ ID NO. 1772 | AAAGUACUGAACAUUCUGG |
| SEQ ID NO. 1086 | CAGAAUGUUCAGUACUUUU | SEQ ID NO. 1773 | AAAAGUACUGAACAUUCUG |
| SEQ ID NO. 1087 | AGAAUGUUCAGUACUUUUU | SEQ ID NO. 1774 | AAAAAGUACUGAACAUUCU |
| SEQ ID NO. 1088 | AGUACUUUUUGGAUCGAUU | SEQ ID NO. 1775 | AAUCGAUCCAAAAAGUACU |
| SEQ ID NO. 1089 | ACUUUUUGGAUCGAUUCUA | SEQ ID NO. 1776 | UAGAAUCGAUCCAAAAAGU |
| SEQ ID NO. 1090 | GAUUCUACAUGAGUCGCAU | SEQ ID NO. 1777 | AUGCGACUCAUGUAGAAUC |
| SEQ ID NO. 1091 | ACAUGAGUCGCAUUUCAAU | SEQ ID NO. 1778 | AUUGAAAUGCGACUCAUGU |
| SEQ ID NO. 1092 | CAUGAGUCGCAUUUCAAUU | SEQ ID NO. 1779 | AAUUGAAAUGCGACUCAUG |
| SEQ ID NO. 1093 | AGUCGCAUUUCAAUUAGAA | SEQ ID NO. 1780 | UUCUAAUUGAAAUGCGACU |
| SEQ ID NO. 1094 | GUCGCAUUUCAAUUAGAAU | SEQ ID NO. 1781 | AUUCUAAUUGAAAUGCGAC |
| SEQ ID NO. 1095 | GCAUUUCAAUUAGAAUGUU | SEQ ID NO. 1782 | AACAUUCUAAUUGAAAUGC |
| SEQ ID NO. 1096 | CAUUUCAAUUAGAAUGUUA | SEQ ID NO. 1783 | UAACAUUCUAAUUGAAAUG |
| SEQ ID NO. 1097 | CAAUUAGAAUGUUACUCAA | SEQ ID NO. 1784 | UUGAGUAACAUUCUAAUUG |
| SEQ ID NO. 1098 | GAAUGUUACUCAAUCAGCA | SEQ ID NO. 1785 | UGCUGAUUGAGUAACAUUC |
| SEQ ID NO. 1099 | ACUCAAUCAGCACUCUUUA | SEQ ID NO. 1786 | UAAAGAGUGCUGAUUGAGU |
| SEQ ID NO. 1100 | CUUUAUUGUUUGGUGGAAA | SEQ ID NO. 1787 | UUUCCACCAAACAAUAAAG |
| SEQ ID NO. 1101 | GUUUGGUGGAAAAGGCAAA | SEQ ID NO. 1788 | UUUGCCUUUUCCACCAAAC |

FIG. 2 Cont'd

| SEQ ID NO. 1102 | GGUGGAAAAGGCAAAGGAA | SEQ ID NO. 1789 | UUCCUUUGCCUUUUCCACC |
|---|---|---|---|
| SEQ ID NO. 1103 | GUGGAAAAGGCAAAGGAAG | SEQ ID NO. 1790 | CUUCCUUUGCCUUUUCCAC |
| SEQ ID NO. 1104 | UGGAAAAGGCAAAGGAAGU | SEQ ID NO. 1791 | ACUUCCUUUGCCUUUUCCA |
| SEQ ID NO. 1105 | CAAAGGAAGUCCAUCUCAU | SEQ ID NO. 1792 | AUGAGAUGGACUUCCUUUG |
| SEQ ID NO. 1106 | GGAAGUCCAUCUCAUCGAA | SEQ ID NO. 1793 | UUCGAUGAGAUGGACUUCC |
| SEQ ID NO. 1107 | GAAGUCCAUCUCAUCGAAA | SEQ ID NO. 1794 | UUUCGAUGAGAUGGACUUC |
| SEQ ID NO. 1108 | CCAUCUCAUCGAAAACACA | SEQ ID NO. 1795 | UGUGUUUUCGAUGAGAUGG |
| SEQ ID NO. 1109 | CAUCUCAUCGAAAACACAU | SEQ ID NO. 1796 | AUGUGUUUUCGAUGAGAUG |
| SEQ ID NO. 1110 | CAUCGAAAACACAUUGGAA | SEQ ID NO. 1797 | UUCCAAUGUGUUUUCGAUG |
| SEQ ID NO. 1111 | GAAAACACAUUGGAAGCAU | SEQ ID NO. 1798 | AUGCUUCCAAUGUGUUUUC |
| SEQ ID NO. 1112 | AAAACACAUUGGAAGCAUA | SEQ ID NO. 1799 | UAUGCUUCCAAUGUGUUUU |
| SEQ ID NO. 1113 | AACACAUUGGAAGCAUAAA | SEQ ID NO. 1800 | UUUAUGCUUCCAAUGUGUU |
| SEQ ID NO. 1114 | ACACAUUGGAAGCAUAAAU | SEQ ID NO. 1801 | AUUUAUGCUUCCAAUGUGU |
| SEQ ID NO. 1115 | GCAUAAAUCCAAACUGCAA | SEQ ID NO. 1802 | UUGCAGUUUGGAUUUAUGC |
| SEQ ID NO. 1116 | CAUAAAUCCAAACUGCAAU | SEQ ID NO. 1803 | AUUGCAGUUUGGAUUUAUG |
| SEQ ID NO. 1117 | AAAUCCAAACUGCAAUGUA | SEQ ID NO. 1804 | UACAUUGCAGUUUGGAUUU |
| SEQ ID NO. 1118 | UCCAAACUGCAAUGUACUU | SEQ ID NO. 1805 | AAGUACAUUGCAGUUUGGA |
| SEQ ID NO. 1119 | CUGCAAUGUACUUGAAGUU | SEQ ID NO. 1806 | AACUUCAAGUACAUUGCAG |
| SEQ ID NO. 1120 | UGCAAUGUACUUGAAGUUA | SEQ ID NO. 1807 | UAACUUCAAGUACAUUGCA |
| SEQ ID NO. 1121 | GCAAUGUACUUGAAGUUAU | SEQ ID NO. 1808 | AUAACUUCAAGUACAUUGC |
| SEQ ID NO. 1122 | CAAUGUACUUGAAGUUAUU | SEQ ID NO. 1809 | AAUAACUUCAAGUACAUUG |
| SEQ ID NO. 1123 | AUGUACUUGAAGUUAUUAA | SEQ ID NO. 1810 | UUAAUAACUUCAAGUACAU |
| SEQ ID NO. 1124 | UGUACUUGAAGUUAUUAAA | SEQ ID NO. 1811 | UUUAAUAACUUCAAGUACA |
| SEQ ID NO. 1125 | ACUUGAAGUUAUUAAAGAU | SEQ ID NO. 1812 | AUCUUUAAUAACUUCAAGU |
| SEQ ID NO. 1126 | AAGUUAUUAAAGAUGGCUA | SEQ ID NO. 1813 | UAGCCAUCUUUAAUAACUU |
| SEQ ID NO. 1127 | AGUUAUUAAAGAUGGCUAU | SEQ ID NO. 1814 | AUAGCCAUCUUUAAUAACU |
| SEQ ID NO. 1128 | UAUUAAAGAUGGCUAUGAA | SEQ ID NO. 1815 | UUCAUAGCCAUCUUUAAUA |
| SEQ ID NO. 1129 | UUAAAGAUGGCUAUGAAAA | SEQ ID NO. 1816 | UUUUCAUAGCCAUCUUUAA |
| SEQ ID NO. 1130 | UAAAGAUGGCUAUGAAAAU | SEQ ID NO. 1817 | AUUUUCAUAGCCAUCUUUA |
| SEQ ID NO. 1131 | GGCGUCUGUGUGAUUUGUA | SEQ ID NO. 1818 | UACAAAUCACACAGACGCC |
| SEQ ID NO. 1132 | GCGUCUGUGUGAUUUGUAU | SEQ ID NO. 1819 | AUACAAAUCACACAGACGC |
| SEQ ID NO. 1133 | CGUCUGUGUGAUUUGUAUU | SEQ ID NO. 1820 | AAUACAAAUCACACAGACG |
| SEQ ID NO. 1134 | GUCUGUGUGAUUUGUAUUA | SEQ ID NO. 1821 | UAAUACAAAUCACACAGAC |
| SEQ ID NO. 1135 | CUGUGUGAUUUGUAUUAUA | SEQ ID NO. 1822 | UAUAAUACAAAUCACACAG |
| SEQ ID NO. 1136 | GUGUGAUUUGUAUUAUAUU | SEQ ID NO. 1823 | AAUAUAAUACAAAUCACAC |
| SEQ ID NO. 1137 | UGUGAUUUGUAUUAUAUUA | SEQ ID NO. 1824 | UAAUAUAAUACAAAUCACA |
| SEQ ID NO. 1138 | GUGAUUUGUAUUAUAUUAA | SEQ ID NO. 1825 | UUAAUAUAAUACAAAUCAC |
| SEQ ID NO. 1139 | UCCCGAACUAGAACUUGAA | SEQ ID NO. 1826 | UUCAAGUUCUAGUUCGGGA |

FIG. 2 Cont'd

| | | | |
|---|---|---|---|
| SEQ ID NO. 1140 | CCGAACUAGAACUUGAAGA | SEQ ID NO. 1827 | UCUUCAAGUUCUAGUUCGG |
| SEQ ID NO. 1141 | CGAACUAGAACUUGAAGAA | SEQ ID NO. 1828 | UUCUUCAAGUUCUAGUUCG |
| SEQ ID NO. 1142 | ACUAGAACUUGAAGAACUA | SEQ ID NO. 1829 | UAGUUCUUCAAGUUCUAGU |
| SEQ ID NO. 1143 | CUAGAACUUGAAGAACUAA | SEQ ID NO. 1830 | UUAGUUCUUCAAGUUCUAG |
| SEQ ID NO. 1144 | UAGAACUUGAAGAACUAAA | SEQ ID NO. 1831 | UUUAGUUCUUCAAGUUCUA |
| SEQ ID NO. 1145 | AGAACUUGAAGAACUAAAU | SEQ ID NO. 1832 | AUUUAGUUCUUCAAGUUCU |
| SEQ ID NO. 1146 | CUUGAAGAACUAAAUGCAA | SEQ ID NO. 1833 | UUGCAUUUAGUUCUUCAAG |
| SEQ ID NO. 1147 | UUGAAGAACUAAAUGCAAA | SEQ ID NO. 1834 | UUUGCAUUUAGUUCUUCAA |
| SEQ ID NO. 1148 | UGAAGAACUAAAUGCAAAA | SEQ ID NO. 1835 | UUUUGCAUUUAGUUCUUCA |
| SEQ ID NO. 1149 | GAAGAACUAAAUGCAAAAU | SEQ ID NO. 1836 | AUUUUGCAUUUAGUUCUUC |
| SEQ ID NO. 1150 | AGAACUAAAUGCAAAAUCA | SEQ ID NO. 1837 | UGAUUUUGCAUUUAGUUCU |
| SEQ ID NO. 1151 | ACCAGGACAGCCAAUACAA | SEQ ID NO. 1838 | UUGUAUUGGCUGUCCUGGU |
| SEQ ID NO. 1152 | CAGCCAAUACAAGUGGUUU | SEQ ID NO. 1839 | AAACCACUUGUAUUGGCUG |
| SEQ ID NO. 1153 | AGCCAAUACAAGUGGUUUA | SEQ ID NO. 1840 | UAAACCACUUGUAUUGGCU |
| SEQ ID NO. 1154 | GCCAAUACAAGUGGUUUAU | SEQ ID NO. 1841 | AUAAACCACUUGUAUUGGC |
| SEQ ID NO. 1155 | UCACAUGGUGUUUGAACUU | SEQ ID NO. 1842 | AAGUUCAAACACCAUGUGA |
| SEQ ID NO. 1156 | ACAUGGUGUUUGAACUUUU | SEQ ID NO. 1843 | AAAAGUUCAAACACCAUGU |
| SEQ ID NO. 1157 | UGGUGUUUGAACUUUUCAA | SEQ ID NO. 1844 | UUGAAAAGUUCAAACACCA |
| SEQ ID NO. 1158 | GGUGUUUGAACUUUUCAAG | SEQ ID NO. 1845 | CUUGAAAAGUUCAAACACC |
| SEQ ID NO. 1159 | UGUUUGAACUUUUCAAGAA | SEQ ID NO. 1846 | UUCUUGAAAAGUUCAAACA |
| SEQ ID NO. 1160 | GUUUGAACUUUUCAAGAAU | SEQ ID NO. 1847 | AUUCUUGAAAAGUUCAAAC |
| SEQ ID NO. 1161 | GAACUUUUCAAGAAUGCAA | SEQ ID NO. 1848 | UUGCAUUCUUGAAAAGUUC |
| SEQ ID NO. 1162 | AGCCACUAUGGAACACCAU | SEQ ID NO. 1849 | AUGGUGUUCCAUAGUGGCU |
| SEQ ID NO. 1163 | CUAUGGAACACCAUGCCAA | SEQ ID NO. 1850 | UUGGCAUGGUGUUCCAUAG |
| SEQ ID NO. 1164 | GGAACACCAUGCCAACAGA | SEQ ID NO. 1851 | UCUGUUGGCAUGGUGUUCC |
| SEQ ID NO. 1165 | CCAUGCCAACAGAGGUGUU | SEQ ID NO. 1852 | AACACCUCUGUUGGCAUGG |
| SEQ ID NO. 1166 | GUUCAUGUCACGCUGGGUA | SEQ ID NO. 1853 | UACCCAGCGUGACAUGAAC |
| SEQ ID NO. 1167 | CACGCUGGGUAAUGAGGAU | SEQ ID NO. 1854 | AUCCUCAUUACCCAGCGUG |
| SEQ ID NO. 1168 | GAGGAUUUGACUGUGAAGA | SEQ ID NO. 1855 | UCUUCACAGUCAAAUCCUC |
| SEQ ID NO. 1169 | AGGAUUUGACUGUGAAGAU | SEQ ID NO. 1856 | AUCUUCACAGUCAAAUCCU |
| SEQ ID NO. 1170 | CGAGGAGGUGGCGUUCCUU | SEQ ID NO. 1857 | AAGGAACGCCACCUCCUCG |
| SEQ ID NO. 1171 | UUUCUUUCAUUAUAUUUGC | SEQ ID NO. 1858 | GCAAAUAUAAUGAAAGAAA |
| SEQ ID NO. 1172 | UUCUUUCAUUAUAUUUGCC | SEQ ID NO. 1859 | GGCAAAUAUAAUGAAAGAA |
| SEQ ID NO. 1173 | AUAACUUCAAGUACAUUGC | SEQ ID NO. 1860 | GCAAUGUACUUGAAGUUAU |
| SEQ ID NO. 1174 | UUCUUCAAGUUCUAGUUCG | SEQ ID NO. 1861 | CGAACUAGAACUUGAAGAA |
| SEQ ID NO. 1175 | UUAAUAUAAUACAAAUCAC | SEQ ID NO. 1862 | GUGAUUUGUAUUAUAUUAA |
| SEQ ID NO. 1176 | UCUUCACAGUCAAAUCCUC | SEQ ID NO. 1863 | GAGGAUUUGACUGUGAAGA |
| SEQ ID NO. 1177 | UCAUCUUCACAGUCAAAUC | SEQ ID NO. 1864 | GAUUUGACUGUGAAGAUGA |

FIG. 2 Cont'd

| SEQ ID NO. 1178 | UCUUCAAGUUCUAGUUCGG | SEQ ID NO. 1865 | CCGAACUAGAACUUGAAGA |
|---|---|---|---|
| SEQ ID NO. 1179 | UAGUUCUUCAAGUUCUAGU | SEQ ID NO. 1866 | ACUAGAACUUGAAGAACUA |
| SEQ ID NO. 1180 | UUAGUUCUUCAAGUUCUAG | SEQ ID NO. 1867 | CUAGAACUUGAAGAACUAA |
| SEQ ID NO. 1181 | UAUCACAGUAUCUGUAAAG | SEQ ID NO. 1868 | CUUUACAGAUACUGUGAUA |
| SEQ ID NO. 1182 | UUGCAUUCUUGAAAAGUUC | SEQ ID NO. 1869 | GAACUUUCAAGAAUGCAA |
| SEQ ID NO. 1183 | UACAAAUCACACAGACGCC | SEQ ID NO. 1870 | GGCGUCUGUGUGAUUUGUA |
| SEQ ID NO. 1184 | AUACAAAUCACACAGACGC | SEQ ID NO. 1871 | GCGUCUGUGUGAUUUGUAU |
| SEQ ID NO. 1185 | UAAUACAAAUCACACAGAC | SEQ ID NO. 1872 | GUCUGUGUGAUUUGUAUUA |
| SEQ ID NO. 1186 | UUUAAUAACUUCAAGUACA | SEQ ID NO. 1873 | UGUACUUGAAGUUAUUAAA |
| SEQ ID NO. 1187 | UAACAUUCUAAUUGAAAUG | SEQ ID NO. 1874 | CAUUUCAAUUAGAAUGUUA |
| SEQ ID NO. 1188 | AUAAAUAGCUUUAGCAUCC | SEQ ID NO. 1875 | GGAUGCUAAAGCUAUUUAU |
| SEQ ID NO. 1189 | UUUCUGAUCCGUAUCACAG | SEQ ID NO. 1876 | CUGUGAUACGGAUCAGAAA |
| SEQ ID NO. 1190 | AAAGUACUGAACAUUCUGG | SEQ ID NO. 1877 | CCAGAAUGUUCAGUACUUU |
| SEQ ID NO. 1191 | UUAUAUUGCCAGUCUGAC | SEQ ID NO. 1878 | GUCAGACUGGCAAAUAUAA |
| SEQ ID NO. 1192 | UAUAAUACAAAUCACACAG | SEQ ID NO. 1879 | CUGUGUGAUUUGUAUUAUA |
| SEQ ID NO. 1193 | UACUGAACAUUCUGGCUGG | SEQ ID NO. 1880 | CCAGCCAGAAUGUUCAGUA |
| SEQ ID NO. 1194 | UUGUGUCGGUUUCUGAUCC | SEQ ID NO. 1881 | GGAUCAGAAACCGACACAA |
| SEQ ID NO. 1195 | UUUCCACCAAACAAUAAAG | SEQ ID NO. 1882 | CUUUAUUGUUUGGUGGAAA |
| SEQ ID NO. 1196 | AAGUACUGAACAUUCUGGC | SEQ ID NO. 1883 | GCCAGAAUGUUCAGUACUU |
| SEQ ID NO. 1197 | AACAUUCUAAUUGAAAUGC | SEQ ID NO. 1884 | GCAUUUCAAUUAGAAUGUU |
| SEQ ID NO. 1198 | UUCUGAUCCGUAUCACAGU | SEQ ID NO. 1885 | ACUGUGAUACGGAUCAGAA |
| SEQ ID NO. 1199 | UUAAAUCAAGAAGCUCCU | SEQ ID NO. 1886 | AGGAGCUUCUUGAUUUUAA |
| SEQ ID NO. 1200 | UUAAUAACUUCAAGUACAU | SEQ ID NO. 1887 | AUGUACUUGAAGUUAUUAA |
| SEQ ID NO. 1201 | AAUAUAAUACAAAUCACAC | SEQ ID NO. 1888 | GUGUGAUUUGUAUUAUAUU |
| SEQ ID NO. 1202 | UUUUGUCCUUAAAAUCAAG | SEQ ID NO. 1889 | CUUGAUUUUAAGGACAAAA |
| SEQ ID NO. 1203 | UUUGUCCUUAAAAUCAAGA | SEQ ID NO. 1890 | UCUUGAUUUUAAGGACAAA |
| SEQ ID NO. 1204 | UAGCAUUUUCAUAGCCAUC | SEQ ID NO. 1891 | GAUGGCUAUGAAAAUGCUA |
| SEQ ID NO. 1205 | UGAAGACUCUGGAUAUACC | SEQ ID NO. 1892 | GGUAUAUCCAGAGUCUUCA |
| SEQ ID NO. 1206 | UAGCUUUAGCAUCCUCAGC | SEQ ID NO. 1893 | GCUGAGGAUGCUAAAGCUA |
| SEQ ID NO. 1207 | UUCAUUAUUUGCCAGUC | SEQ ID NO. 1894 | GACUGGCAAAUAUAAUGAA |
| SEQ ID NO. 1208 | AAUGACAUCAUUGUGUCGG | SEQ ID NO. 1895 | CCGACACAAUGAUGUCAUU |
| SEQ ID NO. 1209 | UUGUAUUCAAUCACACCCU | SEQ ID NO. 1896 | AGGGUGUGAUUGAAUACAA |
| SEQ ID NO. 1210 | UAACUUCAAGUACAUUGCA | SEQ ID NO. 1897 | UGCAAUGUACUUGAAGUUA |
| SEQ ID NO. 1211 | UUCAAGUUCUAGUUCGGGA | SEQ ID NO. 1898 | UCCCGAACUAGAACUUGAA |
| SEQ ID NO. 1212 | UUCAAACACCAUGUGAUAG | SEQ ID NO. 1899 | CUAUCACAUGGUGUUUGAA |
| SEQ ID NO. 1213 | AUCUUCACAGUCAAAUCCU | SEQ ID NO. 1900 | AGGAUUUGACUGUGAAGAU |
| SEQ ID NO. 1214 | UAAAAUCAAGAAGCUCCUG | SEQ ID NO. 1901 | CAGGAGCUUCUUGAUUUUA |
| SEQ ID NO. 1215 | UAAUAUAAUACAAAUCACA | SEQ ID NO. 1902 | UGUGAUUUGUAUUAUAUUA |

FIG. 2 Cont'd

| | | | |
|---|---|---|---|
| SEQ ID NO. 1216 | UAGAAUCGAUCCAAAAAGU | SEQ ID NO. 1903 | ACUUUUUGGAUCGAUUCUA |
| SEQ ID NO. 1217 | AUCUUUAAUAACUUCAAGU | SEQ ID NO. 1904 | ACUUGAAGUUAUUAAAGAU |
| SEQ ID NO. 1218 | UCCUUGUAUUCAAUCACAC | SEQ ID NO. 1905 | GUGUGAUUGAAUACAAGGA |
| SEQ ID NO. 1219 | UUUCAUUAUAUUUGCCAGU | SEQ ID NO. 1906 | ACUGGCAAAUAUAAUGAAA |
| SEQ ID NO. 1220 | UAAAGAGUGCUGAUUGAGU | SEQ ID NO. 1907 | ACUCAAUCAGCACUCUUUA |
| SEQ ID NO. 1221 | UAUUCAAUCACACCCUGGG | SEQ ID NO. 1908 | CCCAGGGUGUGAUUGAAUA |
| SEQ ID NO. 1222 | UGAUCCGUAUCACAGUAUC | SEQ ID NO. 1909 | GAUACUGUGAUACGGAUCA |
| SEQ ID NO. 1223 | AAUAACUUCAAGUACAUUG | SEQ ID NO. 1910 | CAAUGUACUUGAAGUUAUU |
| SEQ ID NO. 1224 | AUAAACCACUUGUAUUGGC | SEQ ID NO. 1911 | GCCAAUACAAGUGGUUUAU |
| SEQ ID NO. 1225 | AUCACAGUAUCUGUAAAGU | SEQ ID NO. 1912 | ACUUUACAGAUACUGUGAU |
| SEQ ID NO. 1226 | AUUCUUGAAAAGUUCAAAC | SEQ ID NO. 1913 | GUUUGAACUUUUCAAGAAU |
| SEQ ID NO. 1227 | UUGCAUUUAGUUCUUCAAG | SEQ ID NO. 1914 | CUUGAAGAACUAAAUGCAA |
| SEQ ID NO. 1228 | UUCCACCAAACAAUAAAGA | SEQ ID NO. 1915 | UCUUUAUUGUUUGGUGGAA |
| SEQ ID NO. 1229 | AUCCUCAGCACUUUUGUCC | SEQ ID NO. 1916 | GGACAAAAGUGCUGAGGAU |
| SEQ ID NO. 1230 | UCAAAUCCUCAUUACCCAG | SEQ ID NO. 1917 | CUGGGUAAUGAGGAUUUGA |
| SEQ ID NO. 1231 | AACUUCAAGUACAUUGCAG | SEQ ID NO. 1918 | CUGCAAUGUACUUGAAGUU |
| SEQ ID NO. 1232 | AUGCGACUCAUGUAGAAUC | SEQ ID NO. 1919 | GAUUCUACAUGAGUCGCAU |
| SEQ ID NO. 1233 | AAAAGUACUGAACAUUCUG | SEQ ID NO. 1920 | CAGAAUGUUCAGUACUUUU |
| SEQ ID NO. 1234 | UCAUUGCAUUCUUGAAAAG | SEQ ID NO. 1921 | CUUUUCAAGAAUGCAAUGA |
| SEQ ID NO. 1235 | UUCUUGAAAAGUUCAAACA | SEQ ID NO. 1922 | UGUUUGAACUUUUCAAGAA |
| SEQ ID NO. 1236 | AUUUCUUUCAUUAUAUUUG | SEQ ID NO. 1923 | CAAAUAUAAUGAAAGAAAU |
| SEQ ID NO. 1237 | UUGAAAAGUUCAAACACCA | SEQ ID NO. 1924 | UGGUGUUUGAACUUUUCAA |
| SEQ ID NO. 1238 | AGUCAUAAAUAGCUUUAGC | SEQ ID NO. 1925 | GCUAAAGCUAUUUAUGACU |
| SEQ ID NO. 1239 | UAAAUAGCUUUAGCAUCCU | SEQ ID NO. 1926 | AGGAUGCUAAAGCUAUUUA |
| SEQ ID NO. 1240 | CUGUAAAGUCAUAAAUAGC | SEQ ID NO. 1927 | GCUAUUUAUGACUUUACAG |
| SEQ ID NO. 1241 | UUCUAAUUGAAAUGCGACU | SEQ ID NO. 1928 | AGUCGCAUUUCAAUUAGAA |
| SEQ ID NO. 1242 | AUUUAGUUCUUCAAGUUCU | SEQ ID NO. 1929 | AGAACUUGAAGAACUAAAU |
| SEQ ID NO. 1243 | UUUGUACCAAUUGAACGGA | SEQ ID NO. 1930 | UCCGUUCAAUUGGUACAAA |
| SEQ ID NO. 1244 | UGUAUUCAAUCACACCCUG | SEQ ID NO. 1931 | CAGGGUGUGAUUGAAUACA |
| SEQ ID NO. 1245 | UUUCAUAGCCAUCUUUAAU | SEQ ID NO. 1932 | AUUAAAGAUGGCUAUGAAA |
| SEQ ID NO. 1246 | AAUACAAAUCACACAGACG | SEQ ID NO. 1933 | CGUCUGUGAUUUGUAUU |
| SEQ ID NO. 1247 | UUUAGUUCUUCAAGUUCUA | SEQ ID NO. 1934 | UAGAACUUGAAGAACUAAA |
| SEQ ID NO. 1248 | AAAAGUACUGAACAUUCU | SEQ ID NO. 1935 | AGAAUGUUCAGUACUUUU |
| SEQ ID NO. 1249 | UAUAUUGCCAGUCUGACA | SEQ ID NO. 1936 | UGUCAGACUGGCAAAUAUA |
| SEQ ID NO. 1250 | AUAGCCAUCUUUAAUAACU | SEQ ID NO. 1937 | AGUUAUUAAAGAUGGCUAU |
| SEQ ID NO. 1251 | UCAAGAAGCUCCUGAAGAC | SEQ ID NO. 1938 | GUCUUCAGGAGCUUCUUGA |
| SEQ ID NO. 1252 | AUGGGAUGGUACAUAAACC | SEQ ID NO. 1939 | GGUUUAUGUACCAUCCCAU |
| SEQ ID NO. 1253 | AUAUUUGCCAGUCUGACAG | SEQ ID NO. 1940 | CUGUCAGACUGGCAAAUAU |

| | | | |
|---|---|---|---|
| SEQ ID NO. 1254 | UCUAAUUGAAAUGCGACUC | SEQ ID NO. 1941 | GAGUCGCAUUUCAAUUAGA |
| SEQ ID NO. 1255 | AUGACAUCAUUGUGUCGGU | SEQ ID NO. 1942 | ACCGACACAAUGAUGUCAU |
| SEQ ID NO. 1256 | UAAACCACUUGUAUUGGCU | SEQ ID NO. 1943 | AGCCAAUACAAGUGGUUUA |
| SEQ ID NO. 1257 | AUUCUAAUUGAAAUGCGAC | SEQ ID NO. 1944 | GUCGCAUUUCAAUUAGAAU |
| SEQ ID NO. 1258 | AAUCGAUCCAAAAAGUACU | SEQ ID NO. 1945 | AGUACUUUUUGGAUCGAUU |
| SEQ ID NO. 1259 | AAUCACACAGACGCCUAGC | SEQ ID NO. 1946 | GCUAGGCGUCUGUGUGAUU |
| SEQ ID NO. 1260 | AGUCAAAUCCUCAUUACCC | SEQ ID NO. 1947 | GGGUAAUGAGGAUUUGACU |
| SEQ ID NO. 1261 | AUCGAUCCAAAAAGUACUG | SEQ ID NO. 1948 | CAGUACUUUUUGGAUCGAU |
| SEQ ID NO. 1262 | AUUGUGUCGGUUUCUGAUC | SEQ ID NO. 1949 | GAUCAGAAACCGACACAAU |
| SEQ ID NO. 1263 | UCAAGUACAUUGCAGUUUG | SEQ ID NO. 1950 | CAAACUGCAAUGUACUUGA |
| SEQ ID NO. 1264 | AAAUAGCUUUAGCAUCCUC | SEQ ID NO. 1951 | GAGGAUGCUAAAGCUAUUU |
| SEQ ID NO. 1265 | AUUCAAUCACACCCUGGGC | SEQ ID NO. 1952 | GCCCAGGGUGUGAUUGAAU |
| SEQ ID NO. 1266 | AAGGAGACUUAUUUCUUUC | SEQ ID NO. 1953 | GAAAGAAAUAAGUCUCCUU |
| SEQ ID NO. 1267 | UGCAUUUAGUUCUUCAAGU | SEQ ID NO. 1954 | ACUUGAAGAACUAAAUGCA |
| SEQ ID NO. 1268 | UUGUACCAAUUGAACGGAU | SEQ ID NO. 1955 | AUCCGUUCAAUUGGUACAA |
| SEQ ID NO. 1269 | AUUGAAAUGCGACUCAUGU | SEQ ID NO. 1956 | ACAUGAGUCGCAUUUCAAU |
| SEQ ID NO. 1270 | AUAUAAUACAAAUCACACA | SEQ ID NO. 1957 | UGUGUGAUUUGUAUUAUAU |
| SEQ ID NO. 1271 | AUUUAUGCUUCCAAUGUGU | SEQ ID NO. 1958 | ACACAUUGGAAGCAUAAAU |
| SEQ ID NO. 1272 | AAAUCCUCAUUACCCAGCG | SEQ ID NO. 1959 | CGCUGGGUAAUGAGGAUUU |
| SEQ ID NO. 1273 | UUCCAAUGUGUUUUCGAUG | SEQ ID NO. 1960 | CAUCGAAAACACAUUGGAA |
| SEQ ID NO. 1274 | UUUUGCAUUUAGUUCUUCA | SEQ ID NO. 1961 | UGAAGAACUAAAUGCAAAA |
| SEQ ID NO. 1275 | UGUACCAAUUGAACGGAUG | SEQ ID NO. 1962 | CAUCCGUUCAAUUGGUACA |
| SEQ ID NO. 1276 | AAGAAGCUCCUGAAGACUC | SEQ ID NO. 1963 | GAGUCUUCAGGAGCUUCUU |
| SEQ ID NO. 1277 | AUCUGUAAAGUCAUAAAUA | SEQ ID NO. 1964 | UAUUUAUGACUUUACAGAU |
| SEQ ID NO. 1278 | UUCUAGUUCGGGAGAGUUA | SEQ ID NO. 1965 | UAACUCUCCCGAACUAGAA |
| SEQ ID NO. 1279 | AGACUCUGGAUAUACCAGC | SEQ ID NO. 1966 | GCUGGUAUAUCCAGAGUCU |
| SEQ ID NO. 1280 | AUAAUACAAAUCACACAGA | SEQ ID NO. 1967 | UCUGUGAUUUGUAUUAU |
| SEQ ID NO. 1281 | UUGUAUUGGCUGUCCUGGU | SEQ ID NO. 1968 | ACCAGGACAGCCAAUACAA |
| SEQ ID NO. 1282 | AAAAGUUCAAACACCAUGU | SEQ ID NO. 1969 | ACAUGGUGUUUGAACUUU |
| SEQ ID NO. 1283 | AAUCCUCAUUACCCAGCGU | SEQ ID NO. 1970 | ACGCUGGGUAAUGAGGAUU |
| SEQ ID NO. 1284 | ACAGUCAAAUCCUCAUUAC | SEQ ID NO. 1971 | GUAAUGAGGAUUUGACUGU |
| SEQ ID NO. 1285 | AUAGCUUUAGCAUCCUCAG | SEQ ID NO. 1972 | CUGAGGAUGCUAAAGCUAU |
| SEQ ID NO. 1286 | UUUGCCUUUUCCACCAAAC | SEQ ID NO. 1973 | GUUUGGUGGAAAAGGCAAA |
| SEQ ID NO. 1287 | CUUAAAAUCAAGAAGCUCC | SEQ ID NO. 1974 | GGAGCUUCUUGAUUUUAAG |
| SEQ ID NO. 1288 | AUCAUUGUGUCGGUUUCUG | SEQ ID NO. 1975 | CAGAAACCGACACAAUGAU |
| SEQ ID NO. 1289 | AUAAAGAGUGCUGAUUGAG | SEQ ID NO. 1976 | CUCAAUCAGCACUCUUUAU |
| SEQ ID NO. 1290 | CUUGAAAAGUUCAAACACC | SEQ ID NO. 1977 | GGUGUUUGAACUUUUCAAG |
| SEQ ID NO. 1291 | ACCAAACAAUAAAGAGUGC | SEQ ID NO. 1978 | GCACUCUUUAUUGUUUGGU |

FIG. 2 Cont'd

| | | | |
|---|---|---|---|
| SEQ ID NO. 1292 | UUCCUUUGCCUUUUCCACC | SEQ ID NO. 1979 | GGUGGAAAAGGCAAAGGAA |
| SEQ ID NO. 1293 | AAUUGAAAUGCGACUCAUG | SEQ ID NO. 1980 | CAUGAGUCGCAUUUCAAUU |
| SEQ ID NO. 1294 | CAAAUCCUCAUUACCCAGC | SEQ ID NO. 1981 | GCUGGGUAAUGAGGAUUUG |
| SEQ ID NO. 1295 | UGAGAAGAUUAUCUGGAAG | SEQ ID NO. 1982 | CUUCCAGAUAAUCUUCUCA |
| SEQ ID NO. 1296 | AUGCUUCCAAUGUGUUUUC | SEQ ID NO. 1983 | GAAAACACAUUGGAAGCAU |
| SEQ ID NO. 1297 | UUGAAAUGCGACUCAUGUA | SEQ ID NO. 1984 | UACAUGAGUCGCAUUUCAA |
| SEQ ID NO. 1298 | AAAGUUCAAACACCAUGUG | SEQ ID NO. 1985 | CACAUGGUGUUUGAACUUU |
| SEQ ID NO. 1299 | AAUUGAACGGAUGGUGUCC | SEQ ID NO. 1986 | GGACACCAUCCGUUCAAUU |
| SEQ ID NO. 1300 | AUUUUGCAUUUAGUUCUUC | SEQ ID NO. 1987 | GAAGAACUAAAUGCAAAAU |
| SEQ ID NO. 1301 | AUCCAAAAGUACUGAACA | SEQ ID NO. 1988 | UGUUCAGUACUUUUUGGAU |
| SEQ ID NO. 1302 | ACAUGAACUUGAAUAGGGG | SEQ ID NO. 1989 | CCCCUAUUCAAGUUCAUGU |
| SEQ ID NO. 1303 | UUGGAUUUAUGCUUCCAAU | SEQ ID NO. 1990 | AUUGGAAGCAUAAAUCCAA |
| SEQ ID NO. 1304 | AUUAUAUUUGCCAGUCUGA | SEQ ID NO. 1991 | UCAGACUGGCAAAUAUAAU |
| SEQ ID NO. 1305 | AAUCAAGAAGCUCCUGAAG | SEQ ID NO. 1992 | CUUCAGGAGCUUCUUGAUU |
| SEQ ID NO. 1306 | AAACACCUCUGUUGGCAUG | SEQ ID NO. 1993 | CAUGCCAACAGAGGUGUUU |
| SEQ ID NO. 1307 | AAAUCACACAGACGCCUAG | SEQ ID NO. 1994 | CUAGGCGUCUGUGUGAUUU |
| SEQ ID NO. 1308 | AAGUUCUAGUUCGGGAGAG | SEQ ID NO. 1995 | CUCUCCCGAACUAGAACUU |
| SEQ ID NO. 1309 | AAACAAUAAAGAGUGCUGA | SEQ ID NO. 1996 | UCAGCACUCUUUAUUGUUU |
| SEQ ID NO. 1310 | AAAAUCAAGAAGCUCCUGA | SEQ ID NO. 1997 | UCAGGAGCUUCUUGAUUUU |
| SEQ ID NO. 1311 | AAACCACUUGUAUUGGCUG | SEQ ID NO. 1998 | CAGCCAAUACAAGUGGUUU |
| SEQ ID NO. 1312 | AUGAACUUGAAUAGGGGGG | SEQ ID NO. 1999 | CCCCCCUAUUCAAGUUCAU |
| SEQ ID NO. 1313 | AUUACCCAGCGUGACAUGA | SEQ ID NO. 2000 | UCAUGUCACGCUGGGUAAU |
| SEQ ID NO. 1314 | ACAUCAUUGUGUCGGUUUC | SEQ ID NO. 2001 | GAAACCGACACAAUGAUGU |
| SEQ ID NO. 1315 | AAACACCAUGUGAUAGAGA | SEQ ID NO. 2002 | UCUCUAUCACAUGGUGUUU |
| SEQ ID NO. 1316 | CAUAAAUAGCUUUAGCAUC | SEQ ID NO. 2003 | GAUGCUAAAGCUAUUUAUG |
| SEQ ID NO. 1317 | UGUUUUCGAUGAGAUGGAC | SEQ ID NO. 2004 | GUCCAUCUCAUCGAAAACA |
| SEQ ID NO. 1318 | AGUUAAUAUAAUACAAAUC | SEQ ID NO. 2005 | GAUUUGUAUUAUAUUAACU |
| SEQ ID NO. 1319 | AUUGCAGUUUGGAUUUAUG | SEQ ID NO. 2006 | CAUAAAUCCAAACUGCAAU |
| SEQ ID NO. 1320 | UGAACAUUCUGGCUGGUGA | SEQ ID NO. 2007 | UCACCAGCCAGAAUGUUCA |
| SEQ ID NO. 1321 | AUCAAGAAGCUCCUGAAGA | SEQ ID NO. 2008 | UCUUCAGGAGCUUCUUGAU |
| SEQ ID NO. 1322 | ACAUUCUAAUUGAAAUGCG | SEQ ID NO. 2009 | CGCAUUUCAAUUAGAAUGU |
| SEQ ID NO. 1323 | UGCUUCCAAUGUGUUUUCG | SEQ ID NO. 2010 | CGAAAACACAUUGGAAGCA |
| SEQ ID NO. 1324 | AGCCAUCUUUAAUAACUUC | SEQ ID NO. 2011 | GAAGUUAUUAAAGAUGGCU |
| SEQ ID NO. 1325 | AAAGCUCUCCUUGUAUUCA | SEQ ID NO. 2012 | UGAAUACAAGGAGAGCUUU |
| SEQ ID NO. 1326 | AUUGAACGGAUGGUGUCCU | SEQ ID NO. 2013 | AGGACACCAUCCGUUCAAU |
| SEQ ID NO. 1327 | AUGUGUUUUCGAUGAGAUG | SEQ ID NO. 2014 | CAUCUCAUCGAAAACACAU |
| SEQ ID NO. 1328 | AACAAUAAAGAGUGCUGAU | SEQ ID NO. 2015 | AUCAGCACUCUUUAUUGUU |
| SEQ ID NO. 1329 | AAGUUCAAACACCAUGUGA | SEQ ID NO. 2016 | UCACAUGGUGUUUGAACUU |

FIG. 2 Cont'd

| | | | |
|---|---|---|---|
| SEQ ID NO. 1330 | UGGUGAUUUUGCAUUUAGU | SEQ ID NO. 2017 | ACUAAAUGCAAAAUCACCA |
| SEQ ID NO. 1331 | AGAGUGCUGAUUGAGUAAC | SEQ ID NO. 2018 | GUUACUCAAUCAGCACUCU |
| SEQ ID NO. 1332 | AAUAGCUUUAGCAUCCUCA | SEQ ID NO. 2019 | UGAGGAUGCUAAAGCUAUU |
| SEQ ID NO. 1333 | AACCACUUGUAUUGGCUGU | SEQ ID NO. 2020 | ACAGCCAAUACAAGUGGUU |
| SEQ ID NO. 1334 | UUGAAUAGGGGGGUAAACA | SEQ ID NO. 2021 | UGUUUACCCCCCUAUUCAA |
| SEQ ID NO. 1335 | AUAUACCAGCUUUGUACCA | SEQ ID NO. 2022 | UGGUACAAAGCUGGUAUAU |
| SEQ ID NO. 1336 | AUGUGAUAGAGAUGGGAUG | SEQ ID NO. 2023 | CAUCCCAUCUCUAUCACAU |
| SEQ ID NO. 1337 | AAAGUCAUAAAUAGCUUUA | SEQ ID NO. 2024 | UAAAGCUAUUUAUGACUUU |
| SEQ ID NO. 1338 | AAUAAAGAGUGCUGAUUGA | SEQ ID NO. 2025 | UCAAUCAGCACUCUUUAUU |
| SEQ ID NO. 1339 | GACAUGAACUUGAAUAGGG | SEQ ID NO. 2026 | CCCUAUUCAAGUUCAUGUC |
| SEQ ID NO. 1340 | ACAUAAACCACUUGUAUUG | SEQ ID NO. 2027 | CAAUACAAGUGGUUUAUGU |
| SEQ ID NO. 1341 | CAUAGCCAUCUUUAAUAAC | SEQ ID NO. 2028 | GUUAUUAAAGAUGGCUAUG |
| SEQ ID NO. 1342 | AAUGCGACUCAUGUAGAAU | SEQ ID NO. 2029 | AUUCUACAUGAGUCGCAUU |
| SEQ ID NO. 1343 | CAAGUACAUUGCAGUUUGG | SEQ ID NO. 2030 | CCAAACUGCAAUGUACUUG |
| SEQ ID NO. 1344 | AUUUCAUAGCCAUCUUUA | SEQ ID NO. 2031 | UAAAGAUGGCUAUGAAAAU |
| SEQ ID NO. 1345 | AGUUUGGAUUUAUGCUUCC | SEQ ID NO. 2032 | GGAAGCAUAAAUCCAAACU |
| SEQ ID NO. 1346 | CAUAAACCACUUGUAUUGG | SEQ ID NO. 2033 | CCAAUACAAGUGGUUUAUG |
| SEQ ID NO. 1347 | AACACCAUGUGAUAGAGAU | SEQ ID NO. 2034 | AUCUCUAUCACAUGGUGUU |
| SEQ ID NO. 1348 | ACACCAUGUGAUAGAGAUG | SEQ ID NO. 2035 | CAUCUCUAUCACAUGGUGU |
| SEQ ID NO. 1349 | AUGAGAUGGACUUCCUUUG | SEQ ID NO. 2036 | CAAAGGAAGUCCAUCUCAU |
| SEQ ID NO. 1350 | AGCUUUGUACCAAUUGAAC | SEQ ID NO. 2037 | GUUCAAUUGGUACAAAGCU |
| SEQ ID NO. 1351 | ACAGACGCCUAGCAUUUUC | SEQ ID NO. 2038 | GAAAAUGCUAGGCGUCUGU |
| SEQ ID NO. 1352 | AGUUCUAGUUCGGGAGAGU | SEQ ID NO. 2039 | ACUCUCCCGAACUAGAACU |
| SEQ ID NO. 1353 | AAAGAGUGCUGAUUGAGUA | SEQ ID NO. 2040 | UACUCAAUCAGCACUCUUU |
| SEQ ID NO. 1354 | ACCAUGUGAUAGAGAUGGG | SEQ ID NO. 2041 | CCCAUCUCUAUCACAUGGU |
| SEQ ID NO. 1355 | AUAGAGAUGGGAUGGUACA | SEQ ID NO. 2042 | UGUACCAUCCCAUCUCUAU |
| SEQ ID NO. 1356 | AAGAUUAUCUGGAAGGAGA | SEQ ID NO. 2043 | UCUCCUUCCAGAUAAUCUU |
| SEQ ID NO. 1357 | AGAUUAUCUGGAAGGAGAC | SEQ ID NO. 2044 | GUCUCCUUCCAGAUAAUCU |
| SEQ ID NO. 1358 | CACUUUUGUCCUUAAAAUC | SEQ ID NO. 2045 | GAUUUUAAGGACAAAAGUG |
| SEQ ID NO. 1359 | GAUAUACCAGCUUUGUACC | SEQ ID NO. 2046 | GGUACAAAGCUGGUAUAUC |
| SEQ ID NO. 1360 | AAGUACAUUGCAGUUUGGA | SEQ ID NO. 2047 | UCCAAACUGCAAUGUACUU |
| SEQ ID NO. 1361 | AACAUUCUGGCUGGUGACA | SEQ ID NO. 2048 | UGUCACCAGCCAGAAUGUU |
| SEQ ID NO. 1362 | GUAUUCAAUCACACCCUGG | SEQ ID NO. 2049 | CCAGGGUGUGAUUGAAUAC |
| SEQ ID NO. 1363 | AUCACACCCUGGGCCAUUG | SEQ ID NO. 2050 | CAAUGGCCCAGGGUGUGAU |
| SEQ ID NO. 1364 | AGCAUCCUCAGCACUUUUG | SEQ ID NO. 2051 | CAAAAGUGCUGAGGAUGCU |
| SEQ ID NO. 1365 | ACUUGUAUUGGCUGUCCUG | SEQ ID NO. 2052 | CAGGACAGCCAAUACAAGU |
| SEQ ID NO. 1366 | AAUGUGUUUUCGAUGAGAU | SEQ ID NO. 2053 | AUCUCAUCGAAAACACAUU |
| SEQ ID NO. 1367 | ACAUUCUGGCUGGUGACAG | SEQ ID NO. 2054 | CUGUCACCAGCCAGAAUGU |

FIG. 2 Cont'd

| SEQ ID NO. 1368 | CAAUUGAACGGAUGGUGUC | SEQ ID NO. 2055 | GACACCAUCCGUUCAAUUG |
|---|---|---|---|
| SEQ ID NO. 1369 | ACCAAUUGAACGGAUGGUG | SEQ ID NO. 2056 | CACCAUCCGUUCAAUUGGU |
| SEQ ID NO. 1370 | GAGAAGAUUAUCUGGAAGG | SEQ ID NO. 2057 | CCUUCCAGAUAAUCUUCUC |
| SEQ ID NO. 1371 | AGCUUUAGCAUCCUCAGCA | SEQ ID NO. 2058 | UGCUGAGGAUGCUAAAGCU |
| SEQ ID NO. 1372 | AGAAGAUUAUCUGGAAGGA | SEQ ID NO. 2059 | UCCUUCCAGAUAAUCUUCU |
| SEQ ID NO. 1373 | CUUGAAUAGGGGGGUAAAC | SEQ ID NO. 2060 | GUUUACCCCCCUAUUCAAG |
| SEQ ID NO. 1374 | GACUUCCUUUGCCUUUUCC | SEQ ID NO. 2061 | GGAAAAGGCAAAGGAAGUC |

FIG. 2 Cont'd

SEQUENCE LISTING

<160> NUMBER OF SEQ ID NOS: 2061

<210> SEQ ID NO 1
<211> LENGTH: 19
<212> TYPE: DNA
<213> ORGANISM: Homo sapiens

<400> SEQUENCE: 1
ctatcacatg gtgtttgaa                                                    19

<210> SEQ ID NO 2
<211> LENGTH: 19
<212> TYPE: DNA
<213> ORGANISM: Homo sapiens

<400> SEQUENCE: 2
caatacaagt ggtttatgt                                                    19

<210> SEQ ID NO 3
<211> LENGTH: 19
<212> TYPE: DNA
<213> ORGANISM: Homo sapiens

<400> SEQUENCE: 3
tctatcacat ggtgtttga                                                    19

<210> SEQ ID NO 4
<211> LENGTH: 19
<212> TYPE: DNA
<213> ORGANISM: Homo sapiens

<400> SEQUENCE: 4
ggcaaatata atgaaagaa                                                    19

<210> SEQ ID NO 5
<211> LENGTH: 19
<212> TYPE: DNA
<213> ORGANISM: Homo sapiens

<400> SEQUENCE: 5
tgttcagtac tttttggat                                                    19

<210> SEQ ID NO 6
<211> LENGTH: 19
<212> TYPE: DNA
<213> ORGANISM: Homo sapiens

<400> SEQUENCE: 6
attggaagca taaatccaa                                                    19

<210> SEQ ID NO 7
<211> LENGTH: 19
<212> TYPE: DNA
<213> ORGANISM: Homo sapiens

<400> SEQUENCE: 7
ccatcccatc tctatcaca                                                    19

<210> SEQ ID NO 8
<211> LENGTH: 19
<212> TYPE: DNA
<213> ORGANISM: Homo sapiens

<400> SEQUENCE: 8

| | |
|---|---|
| catcccatct ctatcacat | 19 |

<210> SEQ ID NO 9
<211> LENGTH: 19
<212> TYPE: DNA
<213> ORGANISM: Homo sapiens

<400> SEQUENCE: 9

| | |
|---|---|
| ggcaaatata atgaaagaa | 19 |

<210> SEQ ID NO 10
<211> LENGTH: 19
<212> TYPE: DNA
<213> ORGANISM: Homo sapiens

<400> SEQUENCE: 10

| | |
|---|---|
| gcaaatataa tgaaagaaa | 19 |

<210> SEQ ID NO 11
<211> LENGTH: 19
<212> TYPE: DNA
<213> ORGANISM: Homo sapiens

<400> SEQUENCE: 11

| | |
|---|---|
| caaatataat gaaagaaat | 19 |

<210> SEQ ID NO 12
<211> LENGTH: 19
<212> TYPE: DNA
<213> ORGANISM: Homo sapiens

<400> SEQUENCE: 12

| | |
|---|---|
| cattggaagc ataaatcca | 19 |

<210> SEQ ID NO 13
<211> LENGTH: 19
<212> TYPE: DNA
<213> ORGANISM: Homo sapiens

<400> SEQUENCE: 13

| | |
|---|---|
| caagtggttt atgtaccat | 19 |

<210> SEQ ID NO 14
<211> LENGTH: 19
<212> TYPE: DNA
<213> ORGANISM: Homo sapiens

<400> SEQUENCE: 14

| | |
|---|---|
| ggtttatgta ccatcccat | 19 |

<210> SEQ ID NO 15
<211> LENGTH: 19
<212> TYPE: DNA
<213> ORGANISM: Homo sapiens

<400> SEQUENCE: 15

| | |
|---|---|
| taccatccca tctctatca | 19 |

<210> SEQ ID NO 16
<211> LENGTH: 19
<212> TYPE: DNA
<213> ORGANISM: Homo sapiens

```
<400> SEQUENCE: 16
cccatctcta tcacatggt                                                19

<210> SEQ ID NO 17
<211> LENGTH: 19
<212> TYPE: DNA
<213> ORGANISM: Homo sapiens

<400> SEQUENCE: 17
catctctatc acatggtgt                                                19

<210> SEQ ID NO 18
<211> LENGTH: 19
<212> TYPE: DNA
<213> ORGANISM: Homo sapiens

<400> SEQUENCE: 18
gcaaatataa tgaaagaaa                                                19

<210> SEQ ID NO 19
<211> LENGTH: 19
<212> TYPE: DNA
<213> ORGANISM: Homo sapiens

<400> SEQUENCE: 19
caaatataat gaaagaaat                                                19

<210> SEQ ID NO 20
<211> LENGTH: 19
<212> TYPE: DNA
<213> ORGANISM: Homo sapiens

<400> SEQUENCE: 20
tggcaaatat aatgaaaga                                                19

<210> SEQ ID NO 21
<211> LENGTH: 19
<212> TYPE: DNA
<213> ORGANISM: Homo sapiens

<400> SEQUENCE: 21
ggggtggatc ctgtcacca                                                19

<210> SEQ ID NO 22
<211> LENGTH: 19
<212> TYPE: DNA
<213> ORGANISM: Homo sapiens

<400> SEQUENCE: 22
ttggaagcat aaatccaaa                                                19

<210> SEQ ID NO 23
<211> LENGTH: 19
<212> TYPE: DNA
<213> ORGANISM: Homo sapiens

<400> SEQUENCE: 23
aatacaagtg gtttatgta                                                19

<210> SEQ ID NO 24
<211> LENGTH: 19
<212> TYPE: DNA
<213> ORGANISM: Homo sapiens
```

```
<400> SEQUENCE: 24
ggtttatgta ccatcccat                                                      19

<210> SEQ ID NO 25
<211> LENGTH: 19
<212> TYPE: DNA
<213> ORGANISM: Homo sapiens

<400> SEQUENCE: 25
aaatataatg aaagaaata                                                      19

<210> SEQ ID NO 26
<211> LENGTH: 19
<212> TYPE: DNA
<213> ORGANISM: Homo sapiens

<400> SEQUENCE: 26
ggtacaaagc tggtatatc                                                      19

<210> SEQ ID NO 27
<211> LENGTH: 19
<212> TYPE: DNA
<213> ORGANISM: Homo sapiens

<400> SEQUENCE: 27
gctaaagcta tttatgact                                                      19

<210> SEQ ID NO 28
<211> LENGTH: 19
<212> TYPE: DNA
<213> ORGANISM: Homo sapiens

<400> SEQUENCE: 28
ctaaagctat ttatgactt                                                      19

<210> SEQ ID NO 29
<211> LENGTH: 19
<212> TYPE: DNA
<213> ORGANISM: Homo sapiens

<400> SEQUENCE: 29
taaagctatt tatgacttt                                                      19

<210> SEQ ID NO 30
<211> LENGTH: 19
<212> TYPE: DNA
<213> ORGANISM: Homo sapiens

<400> SEQUENCE: 30
aaagctattt atgacttta                                                      19

<210> SEQ ID NO 31
<211> LENGTH: 19
<212> TYPE: DNA
<213> ORGANISM: Homo sapiens

<400> SEQUENCE: 31
agctatttat gactttaca                                                      19

<210> SEQ ID NO 32
<211> LENGTH: 19
<212> TYPE: DNA
```

```
<213> ORGANISM: Homo sapiens

<400> SEQUENCE: 32
ctatttatga ctttacaga                                                19

<210> SEQ ID NO 33
<211> LENGTH: 19
<212> TYPE: DNA
<213> ORGANISM: Homo sapiens

<400> SEQUENCE: 33
atttatgact ttacagata                                                19

<210> SEQ ID NO 34
<211> LENGTH: 19
<212> TYPE: DNA
<213> ORGANISM: Homo sapiens

<400> SEQUENCE: 34
ttatgacttt acagatact                                                19

<210> SEQ ID NO 35
<211> LENGTH: 19
<212> TYPE: DNA
<213> ORGANISM: Homo sapiens

<400> SEQUENCE: 35
ctgtgatacg gatcagaaa                                                19

<210> SEQ ID NO 36
<211> LENGTH: 19
<212> TYPE: DNA
<213> ORGANISM: Homo sapiens

<400> SEQUENCE: 36
tcagaaaccg acacaatga                                                19

<210> SEQ ID NO 37
<211> LENGTH: 19
<212> TYPE: DNA
<213> ORGANISM: Homo sapiens

<400> SEQUENCE: 37
ccagaatgtt cagtactttt                                               19

<210> SEQ ID NO 38
<211> LENGTH: 19
<212> TYPE: DNA
<213> ORGANISM: Homo sapiens

<400> SEQUENCE: 38
cagaatgttc agtactttt                                                19

<210> SEQ ID NO 39
<211> LENGTH: 19
<212> TYPE: DNA
<213> ORGANISM: Homo sapiens

<400> SEQUENCE: 39
agaatgttca gtactttttt                                               19

<210> SEQ ID NO 40
<211> LENGTH: 19
```

```
<212> TYPE: DNA
<213> ORGANISM: Homo sapiens

<400> SEQUENCE: 40
gcatttcaat tagaatgtt                                                    19

<210> SEQ ID NO 41
<211> LENGTH: 19
<212> TYPE: DNA
<213> ORGANISM: Homo sapiens

<400> SEQUENCE: 41
catttcaatt agaatgtta                                                    19

<210> SEQ ID NO 42
<211> LENGTH: 19
<212> TYPE: DNA
<213> ORGANISM: Homo sapiens

<400> SEQUENCE: 42
caattagaat gttactcaa                                                    19

<210> SEQ ID NO 43
<211> LENGTH: 19
<212> TYPE: DNA
<213> ORGANISM: Homo sapiens

<400> SEQUENCE: 43
ttagaatgtt actcaatca                                                    19

<210> SEQ ID NO 44
<211> LENGTH: 19
<212> TYPE: DNA
<213> ORGANISM: Homo sapiens

<400> SEQUENCE: 44
actcaatcag cactcttta                                                    19

<210> SEQ ID NO 45
<211> LENGTH: 19
<212> TYPE: DNA
<213> ORGANISM: Homo sapiens

<400> SEQUENCE: 45
tcaatcagca ctctttatt                                                    19

<210> SEQ ID NO 46
<211> LENGTH: 19
<212> TYPE: DNA
<213> ORGANISM: Homo sapiens

<400> SEQUENCE: 46
catctcatcg aaaacacat                                                    19

<210> SEQ ID NO 47
<211> LENGTH: 19
<212> TYPE: DNA
<213> ORGANISM: Homo sapiens

<400> SEQUENCE: 47
aaacacattg gaagcataa                                                    19

<210> SEQ ID NO 48
```

```
<211> LENGTH: 19
<212> TYPE: DNA
<213> ORGANISM: Homo sapiens

<400> SEQUENCE: 48
aacacattgg aagcataaa                                                19

<210> SEQ ID NO 49
<211> LENGTH: 19
<212> TYPE: DNA
<213> ORGANISM: Homo sapiens

<400> SEQUENCE: 49
acacattgga agcataaat                                                19

<210> SEQ ID NO 50
<211> LENGTH: 19
<212> TYPE: DNA
<213> ORGANISM: Homo sapiens

<400> SEQUENCE: 50
gcaatgtact tgaagttat                                                19

<210> SEQ ID NO 51
<211> LENGTH: 19
<212> TYPE: DNA
<213> ORGANISM: Homo sapiens

<400> SEQUENCE: 51
caatgtactt gaagttatt                                                19

<210> SEQ ID NO 52
<211> LENGTH: 19
<212> TYPE: DNA
<213> ORGANISM: Homo sapiens

<400> SEQUENCE: 52
atgtacttga agttattaa                                                19

<210> SEQ ID NO 53
<211> LENGTH: 19
<212> TYPE: DNA
<213> ORGANISM: Homo sapiens

<400> SEQUENCE: 53
tgtacttgaa gttattaaa                                                19

<210> SEQ ID NO 54
<211> LENGTH: 19
<212> TYPE: DNA
<213> ORGANISM: Homo sapiens

<400> SEQUENCE: 54
tacttgaagt tattaaaga                                                19

<210> SEQ ID NO 55
<211> LENGTH: 18
<212> TYPE: DNA
<213> ORGANISM: Homo sapiens

<400> SEQUENCE: 55
ttaaagatgg ctatgaaa                                                 18
```

```
<210> SEQ ID NO 56
<211> LENGTH: 19
<212> TYPE: DNA
<213> ORGANISM: Homo sapiens

<400> SEQUENCE: 56
taaagatggc tatgaaaat                                              19

<210> SEQ ID NO 57
<211> LENGTH: 19
<212> TYPE: DNA
<213> ORGANISM: Homo sapiens

<400> SEQUENCE: 57
gtgtgatttg tattatatt                                              19

<210> SEQ ID NO 58
<211> LENGTH: 19
<212> TYPE: DNA
<213> ORGANISM: Homo sapiens

<400> SEQUENCE: 58
tgtgatttgt attatatta                                              19

<210> SEQ ID NO 59
<211> LENGTH: 19
<212> TYPE: DNA
<213> ORGANISM: Homo sapiens

<400> SEQUENCE: 59
gtgatttgta ttatattaa                                              19

<210> SEQ ID NO 60
<211> LENGTH: 19
<212> TYPE: DNA
<213> ORGANISM: Homo sapiens

<400> SEQUENCE: 60
gggtaatgag gatttgact                                              19

<210> SEQ ID NO 61
<211> LENGTH: 19
<212> TYPE: DNA
<213> ORGANISM: Homo sapiens

<400> SEQUENCE: 61
gatttgactg tgaagatga                                              19

<210> SEQ ID NO 62
<211> LENGTH: 19
<212> TYPE: DNA
<213> ORGANISM: Homo sapiens

<400> SEQUENCE: 62
gtcagactgg caaatataa                                              19

<210> SEQ ID NO 63
<211> LENGTH: 19
<212> TYPE: DNA
<213> ORGANISM: Homo sapiens

<400> SEQUENCE: 63
cgaactagaa cttgaagaa                                              19
```

```
<210> SEQ ID NO 64
<211> LENGTH: 19
<212> TYPE: DNA
<213> ORGANISM: Homo sapiens

<400> SEQUENCE: 64
actagaactt gaagaacta                                                19

<210> SEQ ID NO 65
<211> LENGTH: 19
<212> TYPE: DNA
<213> ORGANISM: Homo sapiens

<400> SEQUENCE: 65
ctagaacttg aagaactaa                                                19

<210> SEQ ID NO 66
<211> LENGTH: 19
<212> TYPE: DNA
<213> ORGANISM: Homo sapiens

<400> SEQUENCE: 66
agaacttgaa gaactaaat                                                19

<210> SEQ ID NO 67
<211> LENGTH: 19
<212> TYPE: DNA
<213> ORGANISM: Homo sapiens

<400> SEQUENCE: 67
cttgaagaac taatgcaa                                                 19

<210> SEQ ID NO 68
<211> LENGTH: 19
<212> TYPE: DNA
<213> ORGANISM: Homo sapiens

<400> SEQUENCE: 68
tgaagaacta aatgcaaaa                                                19

<210> SEQ ID NO 69
<211> LENGTH: 19
<212> TYPE: DNA
<213> ORGANISM: Homo sapiens

<400> SEQUENCE: 69
gaagaactaa atgcaaaat                                                19

<210> SEQ ID NO 70
<211> LENGTH: 19
<212> TYPE: DNA
<213> ORGANISM: Homo sapiens

<400> SEQUENCE: 70
agaactaaat gcaaaatca                                                19

<210> SEQ ID NO 71
<211> LENGTH: 19
<212> TYPE: DNA
<213> ORGANISM: Homo sapiens

<400> SEQUENCE: 71
gccaatacaa gtggtttat                                                19
```

<210> SEQ ID NO 72
<211> LENGTH: 19
<212> TYPE: DNA
<213> ORGANISM: Homo sapiens

<400> SEQUENCE: 72
gtgtttgaac ttttcaaga                                                  19

<210> SEQ ID NO 73
<211> LENGTH: 19
<212> TYPE: DNA
<213> ORGANISM: Homo sapiens

<400> SEQUENCE: 73
tgtttgaact tttcaagaa                                                  19

<210> SEQ ID NO 74
<211> LENGTH: 19
<212> TYPE: DNA
<213> ORGANISM: Homo sapiens

<400> SEQUENCE: 74
gtgtttaccc ccctattca                                                  19

<210> SEQ ID NO 75
<211> LENGTH: 19
<212> TYPE: DNA
<213> ORGANISM: Homo sapiens

<400> SEQUENCE: 75
tgtttacccc cctattcaa                                                  19

<210> SEQ ID NO 76
<211> LENGTH: 19
<212> TYPE: DNA
<213> ORGANISM: Homo sapiens

<400> SEQUENCE: 76
gggtaatgag gatttgact                                                  19

<210> SEQ ID NO 77
<211> LENGTH: 19
<212> TYPE: DNA
<213> ORGANISM: Homo sapiens

<400> SEQUENCE: 77
gatttgactg tgaagatga                                                  19

<210> SEQ ID NO 78
<211> LENGTH: 19
<212> TYPE: DNA
<213> ORGANISM: Homo sapiens

<400> SEQUENCE: 78
gtcagactgg caaatataa                                                  19

<210> SEQ ID NO 79
<211> LENGTH: 19
<212> TYPE: DNA
<213> ORGANISM: Homo sapiens

<400> SEQUENCE: 79
tcagactggc aaatataat                                          19

<210> SEQ ID NO 80
<211> LENGTH: 19
<212> TYPE: DNA
<213> ORGANISM: Homo sapiens

<400> SEQUENCE: 80
agactggcaa atataatga                                          19

<210> SEQ ID NO 81
<211> LENGTH: 19
<212> TYPE: DNA
<213> ORGANISM: Homo sapiens

<400> SEQUENCE: 81
gactggcaaa tataatgaa                                          19

<210> SEQ ID NO 82
<211> LENGTH: 19
<212> TYPE: DNA
<213> ORGANISM: Homo sapiens

<400> SEQUENCE: 82
actggcaaat ataatgaaa                                          19

<210> SEQ ID NO 83
<211> LENGTH: 19
<212> TYPE: DNA
<213> ORGANISM: Homo sapiens

<400> SEQUENCE: 83
tggcaaatat aatgaaaga                                          19

<210> SEQ ID NO 84
<211> LENGTH: 19
<212> TYPE: DNA
<213> ORGANISM: Homo sapiens

<400> SEQUENCE: 84
ggcaaatata atgaaagaa                                          19

<210> SEQ ID NO 85
<211> LENGTH: 19
<212> TYPE: DNA
<213> ORGANISM: Homo sapiens

<400> SEQUENCE: 85
gcaaatataa tgaaagaaa                                          19

<210> SEQ ID NO 86
<211> LENGTH: 19
<212> TYPE: DNA
<213> ORGANISM: Homo sapiens

<400> SEQUENCE: 86
caaatataat gaaagaaat                                          19

<210> SEQ ID NO 87
<211> LENGTH: 19
<212> TYPE: DNA
<213> ORGANISM: Homo sapiens

<400> SEQUENCE: 87
aaatataatg aaagaaata         19

<210> SEQ ID NO 88
<211> LENGTH: 19
<212> TYPE: DNA
<213> ORGANISM: Homo sapiens

<400> SEQUENCE: 88
gaaagaaata agtctcctt         19

<210> SEQ ID NO 89
<211> LENGTH: 19
<212> TYPE: DNA
<213> ORGANISM: Homo sapiens

<400> SEQUENCE: 89
agaaataagt ctccttcca         19

<210> SEQ ID NO 90
<211> LENGTH: 19
<212> TYPE: DNA
<213> ORGANISM: Homo sapiens

<400> SEQUENCE: 90
aaataagtct ccttccaga         19

<210> SEQ ID NO 91
<211> LENGTH: 19
<212> TYPE: DNA
<213> ORGANISM: Homo sapiens

<400> SEQUENCE: 91
ataagtctcc ttccagata         19

<210> SEQ ID NO 92
<211> LENGTH: 19
<212> TYPE: DNA
<213> ORGANISM: Homo sapiens

<400> SEQUENCE: 92
taagtctcct tccagataa         19

<210> SEQ ID NO 93
<211> LENGTH: 19
<212> TYPE: DNA
<213> ORGANISM: Homo sapiens

<400> SEQUENCE: 93
aagtctcctt ccagataat         19

<210> SEQ ID NO 94
<211> LENGTH: 19
<212> TYPE: DNA
<213> ORGANISM: Homo sapiens

<400> SEQUENCE: 94
gtctccttcc agataatct         19

<210> SEQ ID NO 95
<211> LENGTH: 19
<212> TYPE: DNA
<213> ORGANISM: Homo sapiens

```
<400> SEQUENCE: 95
cttccagata atcttctca                                          19

<210> SEQ ID NO 96
<211> LENGTH: 19
<212> TYPE: DNA
<213> ORGANISM: Homo sapiens

<400> SEQUENCE: 96
agataatctt ctcaggaca                                          19

<210> SEQ ID NO 97
<211> LENGTH: 19
<212> TYPE: DNA
<213> ORGANISM: Homo sapiens

<400> SEQUENCE: 97
tcaggacacc atccgttca                                          19

<210> SEQ ID NO 98
<211> LENGTH: 19
<212> TYPE: DNA
<213> ORGANISM: Homo sapiens

<400> SEQUENCE: 98
caggacacca tccgttcaa                                          19

<210> SEQ ID NO 99
<211> LENGTH: 19
<212> TYPE: DNA
<213> ORGANISM: Homo sapiens

<400> SEQUENCE: 99
aggacaccat ccgttcaat                                          19

<210> SEQ ID NO 100
<211> LENGTH: 19
<212> TYPE: DNA
<213> ORGANISM: Homo sapiens

<400> SEQUENCE: 100
ggacaccatc cgttcaatt                                          19

<210> SEQ ID NO 101
<211> LENGTH: 19
<212> TYPE: DNA
<213> ORGANISM: Homo sapiens

<400> SEQUENCE: 101
caccatccgt tcaattggt                                          19

<210> SEQ ID NO 102
<211> LENGTH: 19
<212> TYPE: DNA
<213> ORGANISM: Homo sapiens

<400> SEQUENCE: 102
accatccgtt caattggta                                          19

<210> SEQ ID NO 103
<211> LENGTH: 19
<212> TYPE: DNA
<213> ORGANISM: Homo sapiens
```

```
<400> SEQUENCE: 103
catccgttca attggtaca                                                 19

<210> SEQ ID NO 104
<211> LENGTH: 19
<212> TYPE: DNA
<213> ORGANISM: Homo sapiens

<400> SEQUENCE: 104
tccgttcaat tggtacaaa                                                 19

<210> SEQ ID NO 105
<211> LENGTH: 19
<212> TYPE: DNA
<213> ORGANISM: Homo sapiens

<400> SEQUENCE: 105
gttcaattgg tacaaagct                                                 19

<210> SEQ ID NO 106
<211> LENGTH: 19
<212> TYPE: DNA
<213> ORGANISM: Homo sapiens

<400> SEQUENCE: 106
ttggtacaaa gctggtata                                                 19

<210> SEQ ID NO 107
<211> LENGTH: 19
<212> TYPE: DNA
<213> ORGANISM: Homo sapiens

<400> SEQUENCE: 107
ggtacaaagc tggtatatc                                                 19

<210> SEQ ID NO 108
<211> LENGTH: 19
<212> TYPE: DNA
<213> ORGANISM: Homo sapiens

<400> SEQUENCE: 108
caaagctggt atatccaga                                                 19

<210> SEQ ID NO 109
<211> LENGTH: 19
<212> TYPE: DNA
<213> ORGANISM: Homo sapiens

<400> SEQUENCE: 109
gctggtatat ccagagtct                                                 19

<210> SEQ ID NO 110
<211> LENGTH: 19
<212> TYPE: DNA
<213> ORGANISM: Homo sapiens

<400> SEQUENCE: 110
ctggtatatc cagagtctt                                                 19

<210> SEQ ID NO 111
<211> LENGTH: 19
<212> TYPE: DNA
```

```
<213> ORGANISM: Homo sapiens

<400> SEQUENCE: 111
ggtatatcca gagtcttca                                                   19

<210> SEQ ID NO 112
<211> LENGTH: 19
<212> TYPE: DNA
<213> ORGANISM: Homo sapiens

<400> SEQUENCE: 112
ccagagtctt caggagctt                                                   19

<210> SEQ ID NO 113
<211> LENGTH: 19
<212> TYPE: DNA
<213> ORGANISM: Homo sapiens

<400> SEQUENCE: 113
gagtcttcag gagcttctt                                                   19

<210> SEQ ID NO 114
<211> LENGTH: 19
<212> TYPE: DNA
<213> ORGANISM: Homo sapiens

<400> SEQUENCE: 114
gtcttcagga gcttcttga                                                   19

<210> SEQ ID NO 115
<211> LENGTH: 19
<212> TYPE: DNA
<213> ORGANISM: Homo sapiens

<400> SEQUENCE: 115
cttcaggagc ttcttgatt                                                   19

<210> SEQ ID NO 116
<211> LENGTH: 19
<212> TYPE: DNA
<213> ORGANISM: Homo sapiens

<400> SEQUENCE: 116
ttcaggagct tcttgattt                                                   19

<210> SEQ ID NO 117
<211> LENGTH: 19
<212> TYPE: DNA
<213> ORGANISM: Homo sapiens

<400> SEQUENCE: 117
tcaggagctt cttgatttt                                                   19

<210> SEQ ID NO 118
<211> LENGTH: 19
<212> TYPE: DNA
<213> ORGANISM: Homo sapiens

<400> SEQUENCE: 118
caggagcttc ttgatttta                                                   19

<210> SEQ ID NO 119
<211> LENGTH: 19
```

```
<212> TYPE: DNA
<213> ORGANISM: Homo sapiens

<400> SEQUENCE: 119
aggagcttct tgattttaa                                                19

<210> SEQ ID NO 120
<211> LENGTH: 19
<212> TYPE: DNA
<213> ORGANISM: Homo sapiens

<400> SEQUENCE: 120
ggagcttctt gattttaag                                                19

<210> SEQ ID NO 121
<211> LENGTH: 19
<212> TYPE: DNA
<213> ORGANISM: Homo sapiens

<400> SEQUENCE: 121
cttcttgatt ttaaggaca                                                19

<210> SEQ ID NO 122
<211> LENGTH: 19
<212> TYPE: DNA
<213> ORGANISM: Homo sapiens

<400> SEQUENCE: 122
cttgatttta aggacaaaa                                                19

<210> SEQ ID NO 123
<211> LENGTH: 19
<212> TYPE: DNA
<213> ORGANISM: Homo sapiens

<400> SEQUENCE: 123
ggacaaaagt gctgaggat                                                19

<210> SEQ ID NO 124
<211> LENGTH: 19
<212> TYPE: DNA
<213> ORGANISM: Homo sapiens

<400> SEQUENCE: 124
aaagtgctga ggatgctaa                                                19

<210> SEQ ID NO 125
<211> LENGTH: 19
<212> TYPE: DNA
<213> ORGANISM: Homo sapiens

<400> SEQUENCE: 125
aagtgctgag gatgctaaa                                                19

<210> SEQ ID NO 126
<211> LENGTH: 19
<212> TYPE: DNA
<213> ORGANISM: Homo sapiens

<400> SEQUENCE: 126
gctgaggatg ctaaagcta                                                19

<210> SEQ ID NO 127
```

```
<211> LENGTH: 19
<212> TYPE: DNA
<213> ORGANISM: Homo sapiens

<400> SEQUENCE: 127
ctgaggatgc taaagctat                                                19

<210> SEQ ID NO 128
<211> LENGTH: 19
<212> TYPE: DNA
<213> ORGANISM: Homo sapiens

<400> SEQUENCE: 128
tgaggatgct aaagctatt                                                19

<210> SEQ ID NO 129
<211> LENGTH: 19
<212> TYPE: DNA
<213> ORGANISM: Homo sapiens

<400> SEQUENCE: 129
gaggatgcta aagctattt                                                19

<210> SEQ ID NO 130
<211> LENGTH: 19
<212> TYPE: DNA
<213> ORGANISM: Homo sapiens

<400> SEQUENCE: 130
aggatgctaa agctattta                                                19

<210> SEQ ID NO 131
<211> LENGTH: 19
<212> TYPE: DNA
<213> ORGANISM: Homo sapiens

<400> SEQUENCE: 131
ggatgctaaa gctatttat                                                19

<210> SEQ ID NO 132
<211> LENGTH: 19
<212> TYPE: DNA
<213> ORGANISM: Homo sapiens

<400> SEQUENCE: 132
gctaaagcta tttatgact                                                19

<210> SEQ ID NO 133
<211> LENGTH: 19
<212> TYPE: DNA
<213> ORGANISM: Homo sapiens

<400> SEQUENCE: 133
ctaaagctat ttatgactt                                                19

<210> SEQ ID NO 134
<211> LENGTH: 19
<212> TYPE: DNA
<213> ORGANISM: Homo sapiens

<400> SEQUENCE: 134
taaagctatt tatgacttt                                                19
```

```
<210> SEQ ID NO 135
<211> LENGTH: 19
<212> TYPE: DNA
<213> ORGANISM: Homo sapiens

<400> SEQUENCE: 135
taaagctatt tatgacttt                                                  19

<210> SEQ ID NO 136
<211> LENGTH: 19
<212> TYPE: DNA
<213> ORGANISM: Homo sapiens

<400> SEQUENCE: 136
agctatttat gactttaca                                                  19

<210> SEQ ID NO 137
<211> LENGTH: 19
<212> TYPE: DNA
<213> ORGANISM: Homo sapiens

<400> SEQUENCE: 137
ctatttatga ctttacaga                                                  19

<210> SEQ ID NO 138
<211> LENGTH: 19
<212> TYPE: DNA
<213> ORGANISM: Homo sapiens

<400> SEQUENCE: 138
atttatgact ttacagata                                                  19

<210> SEQ ID NO 139
<211> LENGTH: 19
<212> TYPE: DNA
<213> ORGANISM: Homo sapiens

<400> SEQUENCE: 139
ttatgacttt acagatact                                                  19

<210> SEQ ID NO 140
<211> LENGTH: 19
<212> TYPE: DNA
<213> ORGANISM: Homo sapiens

<400> SEQUENCE: 140
gactttacag atactgtga                                                  19

<210> SEQ ID NO 141
<211> LENGTH: 19
<212> TYPE: DNA
<213> ORGANISM: Homo sapiens

<400> SEQUENCE: 141
ctttacagat actgtgata                                                  19

<210> SEQ ID NO 142
<211> LENGTH: 19
<212> TYPE: DNA
<213> ORGANISM: Homo sapiens

<400> SEQUENCE: 142
cagatactgt gatacggat                                                  19
```

```
<210> SEQ ID NO 143
<211> LENGTH: 19
<212> TYPE: DNA
<213> ORGANISM: Homo sapiens

<400> SEQUENCE: 143
ctgtgatacg gatcagaaa                                               19

<210> SEQ ID NO 144
<211> LENGTH: 19
<212> TYPE: DNA
<213> ORGANISM: Homo sapiens

<400> SEQUENCE: 144
gatacggatc agaaaccga                                               19

<210> SEQ ID NO 145
<211> LENGTH: 19
<212> TYPE: DNA
<213> ORGANISM: Homo sapiens

<400> SEQUENCE: 145
cggatcagaa accgacaca                                               19

<210> SEQ ID NO 146
<211> LENGTH: 19
<212> TYPE: DNA
<213> ORGANISM: Homo sapiens

<400> SEQUENCE: 146
ggatcagaaa ccgacacaa                                               19

<210> SEQ ID NO 147
<211> LENGTH: 19
<212> TYPE: DNA
<213> ORGANISM: Homo sapiens

<400> SEQUENCE: 147
gatcagaaac cgacacaat                                               19

<210> SEQ ID NO 148
<211> LENGTH: 19
<212> TYPE: DNA
<213> ORGANISM: Homo sapiens

<400> SEQUENCE: 148
tcagaaaccg acacaatga                                               19

<210> SEQ ID NO 149
<211> LENGTH: 19
<212> TYPE: DNA
<213> ORGANISM: Homo sapiens

<400> SEQUENCE: 149
cagaaaccga cacaatgat                                               19

<210> SEQ ID NO 150
<211> LENGTH: 19
<212> TYPE: DNA
<213> ORGANISM: Homo sapiens

<400> SEQUENCE: 150
gaaaccgaca caatgatgt                                               19
```

<210> SEQ ID NO 151
<211> LENGTH: 19
<212> TYPE: DNA
<213> ORGANISM: Homo sapiens

<400> SEQUENCE: 151
ccgacacaat gatgtcatt                                                19

<210> SEQ ID NO 152
<211> LENGTH: 19
<212> TYPE: DNA
<213> ORGANISM: Homo sapiens

<400> SEQUENCE: 152
cacaatgatg tcattccca                                                19

<210> SEQ ID NO 153
<211> LENGTH: 19
<212> TYPE: DNA
<213> ORGANISM: Homo sapiens

<400> SEQUENCE: 153
caatgatgtc attcccaca                                                19

<210> SEQ ID NO 154
<211> LENGTH: 19
<212> TYPE: DNA
<213> ORGANISM: Homo sapiens

<400> SEQUENCE: 154
atgatgtcat tcccacaat                                                19

<210> SEQ ID NO 155
<211> LENGTH: 19
<212> TYPE: DNA
<213> ORGANISM: Homo sapiens

<400> SEQUENCE: 155
ccacaatggc ccagggtgt                                                19

<210> SEQ ID NO 156
<211> LENGTH: 19
<212> TYPE: DNA
<213> ORGANISM: Homo sapiens

<400> SEQUENCE: 156
caatggccca gggtgtgat                                                19

<210> SEQ ID NO 157
<211> LENGTH: 19
<212> TYPE: DNA
<213> ORGANISM: Homo sapiens

<400> SEQUENCE: 157
ggcccagggt gtgattgaa                                                19

<210> SEQ ID NO 158
<211> LENGTH: 19
<212> TYPE: DNA
<213> ORGANISM: Homo sapiens

<400> SEQUENCE: 158

```
gcccagggtg tgattgaat                                                19
```

<210> SEQ ID NO 159
<211> LENGTH: 19
<212> TYPE: DNA
<213> ORGANISM: Homo sapiens

<400> SEQUENCE: 159

```
cccagggtgt gattgaata                                                19
```

<210> SEQ ID NO 160
<211> LENGTH: 19
<212> TYPE: DNA
<213> ORGANISM: Homo sapiens

<400> SEQUENCE: 160

```
cagggtgtga ttgaataca                                                19
```

<210> SEQ ID NO 161
<211> LENGTH: 19
<212> TYPE: DNA
<213> ORGANISM: Homo sapiens

<400> SEQUENCE: 161

```
agggtgtgat tgaatacaa                                                19
```

<210> SEQ ID NO 162
<211> LENGTH: 19
<212> TYPE: DNA
<213> ORGANISM: Homo sapiens

<400> SEQUENCE: 162

```
gtgtgattga atacaagga                                                19
```

<210> SEQ ID NO 163
<211> LENGTH: 19
<212> TYPE: DNA
<213> ORGANISM: Homo sapiens

<400> SEQUENCE: 163

```
gtgattgaat acaaggaga                                                19
```

<210> SEQ ID NO 164
<211> LENGTH: 19
<212> TYPE: DNA
<213> ORGANISM: Homo sapiens

<400> SEQUENCE: 164

```
ggagagcttt ggggtggat                                                19
```

<210> SEQ ID NO 165
<211> LENGTH: 19
<212> TYPE: DNA
<213> ORGANISM: Homo sapiens

<400> SEQUENCE: 165

```
gctttggggt ggatcctgt                                                19
```

<210> SEQ ID NO 166
<211> LENGTH: 19
<212> TYPE: DNA
<213> ORGANISM: Homo sapiens

<400> SEQUENCE: 166 gggggtggatc ctgtcacca                                                19

<210> SEQ ID NO 167
<211> LENGTH: 19
<212> TYPE: DNA
<213> ORGANISM: Homo sapiens

<400> SEQUENCE: 167
ctgtcaccag ccagaatgt                                                 19

<210> SEQ ID NO 168
<211> LENGTH: 19
<212> TYPE: DNA
<213> ORGANISM: Homo sapiens

<400> SEQUENCE: 168
tcaccagcca gaatgttca                                                 19

<210> SEQ ID NO 169
<211> LENGTH: 19
<212> TYPE: DNA
<213> ORGANISM: Homo sapiens

<400> SEQUENCE: 169
ccagccagaa tgttcagta                                                 19

<210> SEQ ID NO 170
<211> LENGTH: 19
<212> TYPE: DNA
<213> ORGANISM: Homo sapiens

<400> SEQUENCE: 170
cagccagaat gttcagtac                                                 19

<210> SEQ ID NO 171
<211> LENGTH: 19
<212> TYPE: DNA
<213> ORGANISM: Homo sapiens

<400> SEQUENCE: 171
gccagaatgt tcagtactt                                                 19

<210> SEQ ID NO 172
<211> LENGTH: 19
<212> TYPE: DNA
<213> ORGANISM: Homo sapiens

<400> SEQUENCE: 172
ccagaatgtt cagtacttt                                                 19

<210> SEQ ID NO 173
<211> LENGTH: 19
<212> TYPE: DNA
<213> ORGANISM: Homo sapiens

<400> SEQUENCE: 173
cagaatgttc agtactttt                                                 19

<210> SEQ ID NO 174
<211> LENGTH: 19
<212> TYPE: DNA
<213> ORGANISM: Homo sapiens

<400> SEQUENCE: 174
agaatgttca gtactttt                                              19

<210> SEQ ID NO 175
<211> LENGTH: 19
<212> TYPE: DNA
<213> ORGANISM: Homo sapiens

<400> SEQUENCE: 175 tcagtactttt ttggatcga                                            19

<210> SEQ ID NO 176
<211> LENGTH: 19
<212> TYPE: DNA
<213> ORGANISM: Homo sapiens

<400> SEQUENCE: 176
cagtactttt tggatcgat                                             19

<210> SEQ ID NO 177
<211> LENGTH: 19
<212> TYPE: DNA
<213> ORGANISM: Homo sapiens

<400> SEQUENCE: 177
ttggatcgat tctacatga                                             19

<210> SEQ ID NO 178
<211> LENGTH: 19
<212> TYPE: DNA
<213> ORGANISM: Homo sapiens

<400> SEQUENCE: 178
ggatcgattc tacatgagt                                             19

<210> SEQ ID NO 179
<211> LENGTH: 19
<212> TYPE: DNA
<213> ORGANISM: Homo sapiens

<400> SEQUENCE: 179
ctacatgagt cgcatttca                                             19

<210> SEQ ID NO 180
<211> LENGTH: 19
<212> TYPE: DNA
<213> ORGANISM: Homo sapiens

<400> SEQUENCE: 180
tacatgagtc gcatttcaa                                             19

<210> SEQ ID NO 181
<211> LENGTH: 19
<212> TYPE: DNA
<213> ORGANISM: Homo sapiens

<400> SEQUENCE: 181
acatgagtcg catttcaat                                             19

<210> SEQ ID NO 182
<211> LENGTH: 19
<212> TYPE: DNA
<213> ORGANISM: Homo sapiens

```
<400> SEQUENCE: 182
catgagtcgc atttcaatt                                                    19

<210> SEQ ID NO 183
<211> LENGTH: 19
<212> TYPE: DNA
<213> ORGANISM: Homo sapiens

<400> SEQUENCE: 183
atgagtcgca tttcaatta                                                    19

<210> SEQ ID NO 184
<211> LENGTH: 19
<212> TYPE: DNA
<213> ORGANISM: Homo sapiens

<400> SEQUENCE: 184
tgagtcgcat ttcaattag                                                    19

<210> SEQ ID NO 185
<211> LENGTH: 19
<212> TYPE: DNA
<213> ORGANISM: Homo sapiens

<400> SEQUENCE: 185
gagtcgcatt tcaattaga                                                    19

<210> SEQ ID NO 186
<211> LENGTH: 19
<212> TYPE: DNA
<213> ORGANISM: Homo sapiens

<400> SEQUENCE: 186
agtcgcattt caattagaa                                                    19

<210> SEQ ID NO 187
<211> LENGTH: 19
<212> TYPE: DNA
<213> ORGANISM: Homo sapiens

<400> SEQUENCE: 187
gtcgcatttc aattagaat                                                    19

<210> SEQ ID NO 188
<211> LENGTH: 19
<212> TYPE: DNA
<213> ORGANISM: Homo sapiens

<400> SEQUENCE: 188
cgcatttcaa ttagaatgt                                                    19

<210> SEQ ID NO 189
<211> LENGTH: 19
<212> TYPE: DNA
<213> ORGANISM: Homo sapiens

<400> SEQUENCE: 189
gcatttcaat tagaatgtt                                                    19

<210> SEQ ID NO 190
<211> LENGTH: 19
<212> TYPE: DNA
```

```
<213> ORGANISM: Homo sapiens

<400> SEQUENCE: 190
catttcaatt agaatgtta                                                19

<210> SEQ ID NO 191
<211> LENGTH: 19
<212> TYPE: DNA
<213> ORGANISM: Homo sapiens

<400> SEQUENCE: 191
caattagaat gttactcaa                                                19

<210> SEQ ID NO 192
<211> LENGTH: 19
<212> TYPE: DNA
<213> ORGANISM: Homo sapiens

<400> SEQUENCE: 192
ttagaatgtt actcaatca                                                19

<210> SEQ ID NO 193
<211> LENGTH: 19
<212> TYPE: DNA
<213> ORGANISM: Homo sapiens

<400> SEQUENCE: 193
gaatgttact caatcagca                                                19

<210> SEQ ID NO 194
<211> LENGTH: 19
<212> TYPE: DNA
<213> ORGANISM: Homo sapiens

<400> SEQUENCE: 194
actcaatcag cactcttta                                                19

<210> SEQ ID NO 195
<211> LENGTH: 19
<212> TYPE: DNA
<213> ORGANISM: Homo sapiens

<400> SEQUENCE: 195
ctcaatcagc actctttat                                                19

<210> SEQ ID NO 196
<211> LENGTH: 19
<212> TYPE: DNA
<213> ORGANISM: Homo sapiens

<400> SEQUENCE: 196
tcaatcagca ctctttatt                                                19

<210> SEQ ID NO 197
<211> LENGTH: 19
<212> TYPE: DNA
<213> ORGANISM: Homo sapiens

<400> SEQUENCE: 197
tcagcactct ttattgttt                                                19

<210> SEQ ID NO 198
<211> LENGTH: 19
```

```
<212> TYPE: DNA
<213> ORGANISM: Homo sapiens

<400> SEQUENCE: 198
gcactcttta ttgtttggt                                              19

<210> SEQ ID NO 199
<211> LENGTH: 19
<212> TYPE: DNA
<213> ORGANISM: Homo sapiens

<400> SEQUENCE: 199
ctttattgtt tggtggaaa                                              19

<210> SEQ ID NO 200
<211> LENGTH: 19
<212> TYPE: DNA
<213> ORGANISM: Homo sapiens

<400> SEQUENCE: 200
tttattgttt ggtggaaaa                                              19

<210> SEQ ID NO 201
<211> LENGTH: 19
<212> TYPE: DNA
<213> ORGANISM: Homo sapiens

<400> SEQUENCE: 201
gtttggtgga aaggcaaa                                               19

<210> SEQ ID NO 202
<211> LENGTH: 19
<212> TYPE: DNA
<213> ORGANISM: Homo sapiens

<400> SEQUENCE: 202
ggtggaaaag gcaaaggaa                                              19

<210> SEQ ID NO 203
<211> LENGTH: 19
<212> TYPE: DNA
<213> ORGANISM: Homo sapiens

<400> SEQUENCE: 203
aggcaaagga agtccatct                                              19

<210> SEQ ID NO 204
<211> LENGTH: 19
<212> TYPE: DNA
<213> ORGANISM: Homo sapiens

<400> SEQUENCE: 204
ggcaaaggaa gtccatctc                                              19

<210> SEQ ID NO 205
<211> LENGTH: 19
<212> TYPE: DNA
<213> ORGANISM: Homo sapiens

<400> SEQUENCE: 205
gcaaaggaag tccatctca                                              19

<210> SEQ ID NO 206
```

```
<211> LENGTH: 19
<212> TYPE: DNA
<213> ORGANISM: Homo sapiens

<400> SEQUENCE: 206
caaaggaagt ccatctcat                                                      19

<210> SEQ ID NO 207
<211> LENGTH: 19
<212> TYPE: DNA
<213> ORGANISM: Homo sapiens

<400> SEQUENCE: 207
ggaagtccat ctcatcgaa                                                      19

<210> SEQ ID NO 208
<211> LENGTH: 19
<212> TYPE: DNA
<213> ORGANISM: Homo sapiens

<400> SEQUENCE: 208
gaagtccatc tcatcgaaa                                                      19

<210> SEQ ID NO 209
<211> LENGTH: 19
<212> TYPE: DNA
<213> ORGANISM: Homo sapiens

<400> SEQUENCE: 209
aagtccatct catcgaaaa                                                      19

<210> SEQ ID NO 210
<211> LENGTH: 19
<212> TYPE: DNA
<213> ORGANISM: Homo sapiens

<400> SEQUENCE: 210
gtccatctca tcgaaaaca                                                      19

<210> SEQ ID NO 211
<211> LENGTH: 19
<212> TYPE: DNA
<213> ORGANISM: Homo sapiens

<400> SEQUENCE: 211
ccatctcatc gaaaacaca                                                      19

<210> SEQ ID NO 212
<211> LENGTH: 19
<212> TYPE: DNA
<213> ORGANISM: Homo sapiens

<400> SEQUENCE: 212
catctcatcg aaaacacat                                                      19

<210> SEQ ID NO 213
<211> LENGTH: 19
<212> TYPE: DNA
<213> ORGANISM: Homo sapiens

<400> SEQUENCE: 213
atctcatcga aaacacatt                                                      19
```

```
<210> SEQ ID NO 214
<211> LENGTH: 19
<212> TYPE: DNA
<213> ORGANISM: Homo sapiens

<400> SEQUENCE: 214
tcatcgaaaa cacattgga                                                19

<210> SEQ ID NO 215
<211> LENGTH: 19
<212> TYPE: DNA
<213> ORGANISM: Homo sapiens

<400> SEQUENCE: 215
catcgaaaac acattggaa                                                19

<210> SEQ ID NO 216
<211> LENGTH: 19
<212> TYPE: DNA
<213> ORGANISM: Homo sapiens

<400> SEQUENCE: 216
cgaaaacaca ttggaagca                                                19

<210> SEQ ID NO 217
<211> LENGTH: 19
<212> TYPE: DNA
<213> ORGANISM: Homo sapiens

<400> SEQUENCE: 217
gaaaacacat tggaagcat                                                19

<210> SEQ ID NO 218
<211> LENGTH: 19
<212> TYPE: DNA
<213> ORGANISM: Homo sapiens

<400> SEQUENCE: 218
aaaacacatt ggaagcata                                                19

<210> SEQ ID NO 219
<211> LENGTH: 19
<212> TYPE: DNA
<213> ORGANISM: Homo sapiens

<400> SEQUENCE: 219
aaacacattg gaagcataa                                                19

<210> SEQ ID NO 220
<211> LENGTH: 19
<212> TYPE: DNA
<213> ORGANISM: Homo sapiens

<400> SEQUENCE: 220
aacacattgg aagcataaa                                                19

<210> SEQ ID NO 221
<211> LENGTH: 19
<212> TYPE: DNA
<213> ORGANISM: Homo sapiens

<400> SEQUENCE: 221
acacattgga agcataaat                                                19
```

```
<210> SEQ ID NO 222
<211> LENGTH: 19
<212> TYPE: DNA
<213> ORGANISM: Homo sapiens

<400> SEQUENCE: 222
cattggaagc ataaatcca                                               19

<210> SEQ ID NO 223
<211> LENGTH: 19
<212> TYPE: DNA
<213> ORGANISM: Homo sapiens

<400> SEQUENCE: 223
ggaagcataa atccaaact                                               19

<210> SEQ ID NO 224
<211> LENGTH: 19
<212> TYPE: DNA
<213> ORGANISM: Homo sapiens

<400> SEQUENCE: 224
gcataaatcc aaactgcaa                                               19

<210> SEQ ID NO 225
<211> LENGTH: 19
<212> TYPE: DNA
<213> ORGANISM: Homo sapiens

<400> SEQUENCE: 225
cataaatcca aactgcaat                                               19

<210> SEQ ID NO 226
<211> LENGTH: 19
<212> TYPE: DNA
<213> ORGANISM: Homo sapiens

<400> SEQUENCE: 226
aaatccaaac tgcaatgta                                               19

<210> SEQ ID NO 227
<211> LENGTH: 19
<212> TYPE: DNA
<213> ORGANISM: Homo sapiens

<400> SEQUENCE: 227
caaactgcaa tgtacttga                                               19

<210> SEQ ID NO 228
<211> LENGTH: 19
<212> TYPE: DNA
<213> ORGANISM: Homo sapiens

<400> SEQUENCE: 228
aaactgcaat gtacttgaa                                               19

<210> SEQ ID NO 229
<211> LENGTH: 19
<212> TYPE: DNA
<213> ORGANISM: Homo sapiens

<400> SEQUENCE: 229
ctgcaatgta cttgaagtt                                               19
```

<210> SEQ ID NO 230
<211> LENGTH: 19
<212> TYPE: DNA
<213> ORGANISM: Homo sapiens

<400> SEQUENCE: 230
gcaatgtact tgaagttat                                                19

<210> SEQ ID NO 231
<211> LENGTH: 19
<212> TYPE: DNA
<213> ORGANISM: Homo sapiens

<400> SEQUENCE: 231
caatgtactt gaagttatt                                                19

<210> SEQ ID NO 232
<211> LENGTH: 19
<212> TYPE: DNA
<213> ORGANISM: Homo sapiens

<400> SEQUENCE: 232
atgtacttga agttattaa                                                19

<210> SEQ ID NO 233
<211> LENGTH: 19
<212> TYPE: DNA
<213> ORGANISM: Homo sapiens

<400> SEQUENCE: 233
tgtacttgaa gttattaaa                                                19

<210> SEQ ID NO 234
<211> LENGTH: 19
<212> TYPE: DNA
<213> ORGANISM: Homo sapiens

<400> SEQUENCE: 234
tacttgaagt tattaaaga                                                19

<210> SEQ ID NO 235
<211> LENGTH: 19
<212> TYPE: DNA
<213> ORGANISM: Homo sapiens

<400> SEQUENCE: 235
tattaaagat ggctatgaa                                                19

<210> SEQ ID NO 236
<211> LENGTH: 19
<212> TYPE: DNA
<213> ORGANISM: Homo sapiens

<400> SEQUENCE: 236
ttaaagatgg ctatgaaaa                                                19

<210> SEQ ID NO 237
<211> LENGTH: 19
<212> TYPE: DNA
<213> ORGANISM: Homo sapiens

<400> SEQUENCE: 237

```
taaagatggc tatgaaaat                                                19

<210> SEQ ID NO 238
<211> LENGTH: 19
<212> TYPE: DNA
<213> ORGANISM: Homo sapiens

<400> SEQUENCE: 238
agatggctat gaaaatgct                                                19

<210> SEQ ID NO 239
<211> LENGTH: 19
<212> TYPE: DNA
<213> ORGANISM: Homo sapiens

<400> SEQUENCE: 239
gatggctatg aaaatgcta                                                19

<210> SEQ ID NO 240
<211> LENGTH: 19
<212> TYPE: DNA
<213> ORGANISM: Homo sapiens

<400> SEQUENCE: 240
gctaggcgtc tgtgtgatt                                                19

<210> SEQ ID NO 241
<211> LENGTH: 19
<212> TYPE: DNA
<213> ORGANISM: Homo sapiens

<400> SEQUENCE: 241
ctaggcgtct gtgtgattt                                                19

<210> SEQ ID NO 242
<211> LENGTH: 19
<212> TYPE: DNA
<213> ORGANISM: Homo sapiens

<400> SEQUENCE: 242
ggcgtctgtg tgatttgta                                                19

<210> SEQ ID NO 243
<211> LENGTH: 19
<212> TYPE: DNA
<213> ORGANISM: Homo sapiens

<400> SEQUENCE: 243
gcgtctgtgt gatttgtat                                                19

<210> SEQ ID NO 244
<211> LENGTH: 19
<212> TYPE: DNA
<213> ORGANISM: Homo sapiens

<400> SEQUENCE: 244
cgtctgtgtg atttgtatt                                                19

<210> SEQ ID NO 245
<211> LENGTH: 19
<212> TYPE: DNA
<213> ORGANISM: Homo sapiens

<400> SEQUENCE: 245
```

```
gtctgtgtga tttgtatta                                          19in

<210> SEQ ID NO 246
<211> LENGTH: 19
<212> TYPE: DNA
<213> ORGANISM: Homo sapiens

<400> SEQUENCE: 246
ctgtgtgatt tgtattata                                          19

<210> SEQ ID NO 247
<211> LENGTH: 19
<212> TYPE: DNA
<213> ORGANISM: Homo sapiens

<400> SEQUENCE: 247
tgtgtgattt gtattatat                                          19

<210> SEQ ID NO 248
<211> LENGTH: 19
<212> TYPE: DNA
<213> ORGANISM: Homo sapiens

<400> SEQUENCE: 248
gtgtgatttg tattatatt                                          19

<210> SEQ ID NO 249
<211> LENGTH: 19
<212> TYPE: DNA
<213> ORGANISM: Homo sapiens

<400> SEQUENCE: 249
tgtgatttgt attatatta                                          19

<210> SEQ ID NO 250
<211> LENGTH: 19
<212> TYPE: DNA
<213> ORGANISM: Homo sapiens

<400> SEQUENCE: 250
gtgatttgta ttatattaa                                          19

<210> SEQ ID NO 251
<211> LENGTH: 19
<212> TYPE: DNA
<213> ORGANISM: Homo sapiens

<400> SEQUENCE: 251
gatttgtatt atattaact                                          19

<210> SEQ ID NO 252
<211> LENGTH: 19
<212> TYPE: DNA
<213> ORGANISM: Homo sapiens

<400> SEQUENCE: 252
tattaactct cccgaacta                                          19

<210> SEQ ID NO 253
<211> LENGTH: 19
<212> TYPE: DNA
<213> ORGANISM: Homo sapiens
```

```
<400> SEQUENCE: 253
ttaactctcc cgaactaga                                              19

<210> SEQ ID NO 254
<211> LENGTH: 18
<212> TYPE: DNA
<213> ORGANISM: Homo sapiens

<400> SEQUENCE: 254
taactctccc gaactaga                                               18

<210> SEQ ID NO 255
<211> LENGTH: 19
<212> TYPE: DNA
<213> ORGANISM: Homo sapiens

<400> SEQUENCE: 255
ctctcccgaa ctagaactt                                              19

<210> SEQ ID NO 256
<211> LENGTH: 19
<212> TYPE: DNA
<213> ORGANISM: Homo sapiens

<400> SEQUENCE: 256
ctcccgaact agaacttga                                              19

<210> SEQ ID NO 257
<211> LENGTH: 19
<212> TYPE: DNA
<213> ORGANISM: Homo sapiens

<400> SEQUENCE: 257
tcccgaacta gaacttgaa                                              19

<210> SEQ ID NO 258
<211> LENGTH: 19
<212> TYPE: DNA
<213> ORGANISM: Homo sapiens

<400> SEQUENCE: 258
cccgaactag aacttgaag                                              19

<210> SEQ ID NO 259
<211> LENGTH: 19
<212> TYPE: DNA
<213> ORGANISM: Homo sapiens

<400> SEQUENCE: 259
ccgaactaga acttgaaga                                              19

<210> SEQ ID NO 260
<211> LENGTH: 19
<212> TYPE: DNA
<213> ORGANISM: Homo sapiens

<400> SEQUENCE: 260
cgaactagaa cttgaagaa                                              19

<210> SEQ ID NO 261
<211> LENGTH: 19
<212> TYPE: DNA
<213> ORGANISM: Homo sapiens
```

```
<400> SEQUENCE: 261
actagaactt gaagaacta                                              19

<210> SEQ ID NO 262
<211> LENGTH: 19
<212> TYPE: DNA
<213> ORGANISM: Homo sapiens

<400> SEQUENCE: 262
ctagaacttg aagaactaa                                              19

<210> SEQ ID NO 263
<211> LENGTH: 19
<212> TYPE: DNA
<213> ORGANISM: Homo sapiens

<400> SEQUENCE: 263
agaacttgaa gaactaaat                                              19

<210> SEQ ID NO 264
<211> LENGTH: 19
<212> TYPE: DNA
<213> ORGANISM: Homo sapiens

<400> SEQUENCE: 264
cttgaagaac taaatgcaa                                              19

<210> SEQ ID NO 265
<211> LENGTH: 19
<212> TYPE: DNA
<213> ORGANISM: Homo sapiens

<400> SEQUENCE: 265
tgaagaacta aatgcaaaa                                              19

<210> SEQ ID NO 266
<211> LENGTH: 19
<212> TYPE: DNA
<213> ORGANISM: Homo sapiens

<400> SEQUENCE: 266
gaagaactaa atgcaaaat                                              19

<210> SEQ ID NO 267
<211> LENGTH: 19
<212> TYPE: DNA
<213> ORGANISM: Homo sapiens

<400> SEQUENCE: 267
agaactaaat gcaaaatca                                              19

<210> SEQ ID NO 268
<211> LENGTH: 19
<212> TYPE: DNA
<213> ORGANISM: Homo sapiens

<400> SEQUENCE: 268
caccaggaca gccaataca                                              19

<210> SEQ ID NO 269
<211> LENGTH: 19
<212> TYPE: DNA
```

<213> ORGANISM: Homo sapiens

<400> SEQUENCE: 269
accaggacag ccaatacaa                                            19

<210> SEQ ID NO 270
<211> LENGTH: 19
<212> TYPE: DNA
<213> ORGANISM: Homo sapiens

<400> SEQUENCE: 270
caggacagcc aatacaagt                                            19

<210> SEQ ID NO 271
<211> LENGTH: 19
<212> TYPE: DNA
<213> ORGANISM: Homo sapiens

<400> SEQUENCE: 271
gacagccaat acaagtggt                                            19

<210> SEQ ID NO 272
<211> LENGTH: 19
<212> TYPE: DNA
<213> ORGANISM: Homo sapiens

<400> SEQUENCE: 272
cagccaatac aagtggttt                                            19

<210> SEQ ID NO 273
<211> LENGTH: 19
<212> TYPE: DNA
<213> ORGANISM: Homo sapiens

<400> SEQUENCE: 273
agccaataca agtggttta                                            19

<210> SEQ ID NO 274
<211> LENGTH: 19
<212> TYPE: DNA
<213> ORGANISM: Homo sapiens

<400> SEQUENCE: 274
gccaatacaa gtggtttat                                            19

<210> SEQ ID NO 275
<211> LENGTH: 19
<212> TYPE: DNA
<213> ORGANISM: Homo sapiens

<400> SEQUENCE: 275
caatacaagt ggtttatgt                                            19

<210> SEQ ID NO 276
<211> LENGTH: 19
<212> TYPE: DNA
<213> ORGANISM: Homo sapiens

<400> SEQUENCE: 276
acaagtggtt tatgtacca                                            19

<210> SEQ ID NO 277
<211> LENGTH: 19

<212> TYPE: DNA
<213> ORGANISM: Homo sapiens

<400> SEQUENCE: 277
tctatcacat ggtgtttga                                              19

<210> SEQ ID NO 278
<211> LENGTH: 19
<212> TYPE: DNA
<213> ORGANISM: Homo sapiens

<400> SEQUENCE: 278
ctatcacatg gtgtttgaa                                              19

<210> SEQ ID NO 279
<211> LENGTH: 19
<212> TYPE: DNA
<213> ORGANISM: Homo sapiens

<400> SEQUENCE: 279
tcacatggtg tttgaactt                                              19

<210> SEQ ID NO 280
<211> LENGTH: 19
<212> TYPE: DNA
<213> ORGANISM: Homo sapiens

<400> SEQUENCE: 280
cacatggtgt ttgaacttt                                              19

<210> SEQ ID NO 281
<211> LENGTH: 19
<212> TYPE: DNA
<213> ORGANISM: Homo sapiens

<400> SEQUENCE: 281
acatggtgtt tgaactttt                                              19

<210> SEQ ID NO 282
<211> LENGTH: 19
<212> TYPE: DNA
<213> ORGANISM: Homo sapiens

<400> SEQUENCE: 282
gtgtttgaac ttttcaaga                                              19

<210> SEQ ID NO 283
<211> LENGTH: 19
<212> TYPE: DNA
<213> ORGANISM: Homo sapiens

<400> SEQUENCE: 283
tgtttgaact tttcaagaa                                              19

<210> SEQ ID NO 284
<211> LENGTH: 19
<212> TYPE: DNA
<213> ORGANISM: Homo sapiens

<400> SEQUENCE: 284
gtttgaactt ttcaagaat                                              19

<210> SEQ ID NO 285

```
<211> LENGTH: 19
<212> TYPE: DNA
<213> ORGANISM: Homo sapiens

<400> SEQUENCE: 285
gaacttttca agaatgcaa                                               19

<210> SEQ ID NO 286
<211> LENGTH: 19
<212> TYPE: DNA
<213> ORGANISM: Homo sapiens

<400> SEQUENCE: 286
cttttcaaga atgcaatga                                               19

<210> SEQ ID NO 287
<211> LENGTH: 19
<212> TYPE: DNA
<213> ORGANISM: Homo sapiens

<400> SEQUENCE: 287
atgcaatgag agccactat                                               19

<210> SEQ ID NO 288
<211> LENGTH: 19
<212> TYPE: DNA
<213> ORGANISM: Homo sapiens

<400> SEQUENCE: 288
caatgagagc cactatgga                                               19

<210> SEQ ID NO 289
<211> LENGTH: 19
<212> TYPE: DNA
<213> ORGANISM: Homo sapiens

<400> SEQUENCE: 289
tgagagccac tatggaaca                                               19

<210> SEQ ID NO 290
<211> LENGTH: 19
<212> TYPE: DNA
<213> ORGANISM: Homo sapiens

<400> SEQUENCE: 290
gagccactat ggaacacca                                               19

<210> SEQ ID NO 291
<211> LENGTH: 19
<212> TYPE: DNA
<213> ORGANISM: Homo sapiens

<400> SEQUENCE: 291
ctatggaaca ccatgccaa                                               19

<210> SEQ ID NO 292
<211> LENGTH: 19
<212> TYPE: DNA
<213> ORGANISM: Homo sapiens

<400> SEQUENCE: 292
ggaacaccat gccaacaga                                               19
```

<210> SEQ ID NO 293
<211> LENGTH: 19
<212> TYPE: DNA
<213> ORGANISM: Homo sapiens

<400> SEQUENCE: 293
ccatgccaac agaggtgtt                                                    19

<210> SEQ ID NO 294
<211> LENGTH: 19
<212> TYPE: DNA
<213> ORGANISM: Homo sapiens

<400> SEQUENCE: 294
catgccaaca gaggtgttt                                                    19

<210> SEQ ID NO 295
<211> LENGTH: 19
<212> TYPE: DNA
<213> ORGANISM: Homo sapiens

<400> SEQUENCE: 295
atgccaacag aggtgttta                                                    19

<210> SEQ ID NO 296
<211> LENGTH: 19
<212> TYPE: DNA
<213> ORGANISM: Homo sapiens

<400> SEQUENCE: 296
agaggtgttt acccccta                                                     19

<210> SEQ ID NO 297
<211> LENGTH: 19
<212> TYPE: DNA
<213> ORGANISM: Homo sapiens

<400> SEQUENCE: 297
gaggtgttta cccccctat                                                    19

<210> SEQ ID NO 298
<211> LENGTH: 19
<212> TYPE: DNA
<213> ORGANISM: Homo sapiens

<400> SEQUENCE: 298
aggtgtttac cccctatt                                                     19

<210> SEQ ID NO 299
<211> LENGTH: 19
<212> TYPE: DNA
<213> ORGANISM: Homo sapiens

<400> SEQUENCE: 299
gtgtttaccc ccctattca                                                    19

<210> SEQ ID NO 300
<211> LENGTH: 19
<212> TYPE: DNA
<213> ORGANISM: Homo sapiens

<400> SEQUENCE: 300
tgtttacccc cctattcaa                                                    19

```
<210> SEQ ID NO 301
<211> LENGTH: 19
<212> TYPE: DNA
<213> ORGANISM: Homo sapiens

<400> SEQUENCE: 301 ttaccccct attcaagtt                                                19

<210> SEQ ID NO 302
<211> LENGTH: 19
<212> TYPE: DNA
<213> ORGANISM: Homo sapiens

<400> SEQUENCE: 302
acccccctat tcaagttca                                               19

<210> SEQ ID NO 303
<211> LENGTH: 19
<212> TYPE: DNA
<213> ORGANISM: Homo sapiens

<400> SEQUENCE: 303
cccccctatt caagttcat                                               19

<210> SEQ ID NO 304
<211> LENGTH: 19
<212> TYPE: DNA
<213> ORGANISM: Homo sapiens

<400> SEQUENCE: 304 ccccctattca agttcatgt                                              19

<210> SEQ ID NO 305
<211> LENGTH: 19
<212> TYPE: DNA
<213> ORGANISM: Homo sapiens

<400> SEQUENCE: 305
cctattcaag ttcatgtca                                               19

<210> SEQ ID NO 306
<211> LENGTH: 19
<212> TYPE: DNA
<213> ORGANISM: Homo sapiens

<400> SEQUENCE: 306
atgtcacgct gggtaatga                                               19

<210> SEQ ID NO 307
<211> LENGTH: 19
<212> TYPE: DNA
<213> ORGANISM: Homo sapiens

<400> SEQUENCE: 307
cacgctgggt aatgaggat                                               19

<210> SEQ ID NO 308
<211> LENGTH: 19
<212> TYPE: DNA
<213> ORGANISM: Homo sapiens

<400> SEQUENCE: 308
acgctgggta atgaggatt                                               19
```

```
<210> SEQ ID NO 309
<211> LENGTH: 19
<212> TYPE: DNA
<213> ORGANISM: Homo sapiens

<400> SEQUENCE: 309
cgctgggtaa tgaggattt                                                   19

<210> SEQ ID NO 310
<211> LENGTH: 19
<212> TYPE: DNA
<213> ORGANISM: Homo sapiens

<400> SEQUENCE: 310
ctgggtaatg aggatttga                                                   19

<210> SEQ ID NO 311
<211> LENGTH: 19
<212> TYPE: DNA
<213> ORGANISM: Homo sapiens

<400> SEQUENCE: 311
gggtaatgag gatttgact                                                   19

<210> SEQ ID NO 312
<211> LENGTH: 19
<212> TYPE: DNA
<213> ORGANISM: Homo sapiens

<400> SEQUENCE: 312
gtaatgagga tttgactgt                                                   19

<210> SEQ ID NO 313
<211> LENGTH: 19
<212> TYPE: DNA
<213> ORGANISM: Homo sapiens

<400> SEQUENCE: 313
aatgaggatt tgactgtga                                                   19

<210> SEQ ID NO 314
<211> LENGTH: 19
<212> TYPE: DNA
<213> ORGANISM: Homo sapiens

<400> SEQUENCE: 314
atgaggattt gactgtgaa                                                   19

<210> SEQ ID NO 315
<211> LENGTH: 19
<212> TYPE: DNA
<213> ORGANISM: Homo sapiens

<400> SEQUENCE: 315
gaggatttga ctgtgaaga                                                   19

<210> SEQ ID NO 316
<211> LENGTH: 19
<212> TYPE: DNA
<213> ORGANISM: Homo sapiens

<400> SEQUENCE: 316
```

```
gatttgactg tgaagatga                                          19

<210> SEQ ID NO 317
<211> LENGTH: 19
<212> TYPE: DNA
<213> ORGANISM: Homo sapiens

<400> SEQUENCE: 317
tgactgtgaa gatgagtga                                          19

<210> SEQ ID NO 318
<211> LENGTH: 19
<212> TYPE: DNA
<213> ORGANISM: Homo sapiens

<400> SEQUENCE: 318
gaagatgagt gaccgagga                                          19

<210> SEQ ID NO 319
<211> LENGTH: 19
<212> TYPE: DNA
<213> ORGANISM: Homo sapiens

<400> SEQUENCE: 319
gaccgaggag gtggcgttc                                          19

<210> SEQ ID NO 320
<211> LENGTH: 19
<212> TYPE: DNA
<213> ORGANISM: Homo sapiens

<400> SEQUENCE: 320
ccgaggaggt ggcgttcct                                          19

<210> SEQ ID NO 321
<211> LENGTH: 19
<212> TYPE: DNA
<213> ORGANISM: Homo sapiens

<400> SEQUENCE: 321
cgaggaggtg gcgttcctt                                          19

<210> SEQ ID NO 322
<211> LENGTH: 19
<212> TYPE: DNA
<213> ORGANISM: Homo sapiens

<400> SEQUENCE: 322
gaggaggtgg cgttccttt                                          19

<210> SEQ ID NO 323
<211> LENGTH: 19
<212> TYPE: DNA
<213> ORGANISM: Homo sapiens

<400> SEQUENCE: 323
ggaggtggcg ttcctttga                                          19

<210> SEQ ID NO 324
<211> LENGTH: 19
<212> TYPE: DNA
<213> ORGANISM: Homo sapiens

<400> SEQUENCE: 324
```
gcaatgtact tgaagttat 19

<210> SEQ ID NO 325
<211> LENGTH: 19
<212> TYPE: DNA
<213> ORGANISM: Homo sapiens

<400> SEQUENCE: 325
ggaagtccat ctcatcgaa 19

<210> SEQ ID NO 326
<211> LENGTH: 19
<212> TYPE: DNA
<213> ORGANISM: Homo sapiens

<400> SEQUENCE: 326
gctgaggatg ctaaagcta 19

<210> SEQ ID NO 327
<211> LENGTH: 19
<212> TYPE: DNA
<213> ORGANISM: Homo sapiens

<400> SEQUENCE: 327
catttcaatt agaatgtta 19

<210> SEQ ID NO 328
<211> LENGTH: 19
<212> TYPE: DNA
<213> ORGANISM: Homo sapiens

<400> SEQUENCE: 328
cgaactagaa cttgaagaa 19

<210> SEQ ID NO 329
<211> LENGTH: 19
<212> TYPE: DNA
<213> ORGANISM: Homo sapiens

<400> SEQUENCE: 329
gcataaatcc aaactgcaa 19

<210> SEQ ID NO 330
<211> LENGTH: 19
<212> TYPE: DNA
<213> ORGANISM: Homo sapiens

<400> SEQUENCE: 330
caatgtactt gaagttatt 19

<210> SEQ ID NO 331
<211> LENGTH: 19
<212> TYPE: DNA
<213> ORGANISM: Homo sapiens

<400> SEQUENCE: 331
ctgtgtgatt tgtattata 19

<210> SEQ ID NO 332
<211> LENGTH: 19
<212> TYPE: DNA
<213> ORGANISM: Homo sapiens

```
<400> SEQUENCE: 332
actagaactt gaagaacta                                               19

<210> SEQ ID NO 333
<211> LENGTH: 19
<212> TYPE: DNA
<213> ORGANISM: Homo sapiens

<400> SEQUENCE: 333
gaatgttact caatcagca                                               19

<210> SEQ ID NO 334
<211> LENGTH: 19
<212> TYPE: DNA
<213> ORGANISM: Homo sapiens

<400> SEQUENCE: 334
ggatgctaaa gctatttat                                               19

<210> SEQ ID NO 335
<211> LENGTH: 19
<212> TYPE: DNA
<213> ORGANISM: Homo sapiens

<400> SEQUENCE: 335
ctgtgatacg gatcagaaa                                               19

<210> SEQ ID NO 336
<211> LENGTH: 19
<212> TYPE: DNA
<213> ORGANISM: Homo sapiens

<400> SEQUENCE: 336
agggtgtgat tgaatacaa                                               19

<210> SEQ ID NO 337
<211> LENGTH: 19
<212> TYPE: DNA
<213> ORGANISM: Homo sapiens

<400> SEQUENCE: 337
cttgaagaac taaatgcaa                                               19

<210> SEQ ID NO 338
<211> LENGTH: 19
<212> TYPE: DNA
<213> ORGANISM: Homo sapiens

<400> SEQUENCE: 338
gtctgtgtga tttgtatta                                               19

<210> SEQ ID NO 339
<211> LENGTH: 19
<212> TYPE: DNA
<213> ORGANISM: Homo sapiens

<400> SEQUENCE: 339
gactttacag atactgtga                                               19

<210> SEQ ID NO 340
<211> LENGTH: 19
<212> TYPE: DNA
<213> ORGANISM: Homo sapiens
```

-continued

<400> SEQUENCE: 340
gcgtctgtgt gatttgtat                                        19

<210> SEQ ID NO 341
<211> LENGTH: 19
<212> TYPE: DNA
<213> ORGANISM: Homo sapiens

<400> SEQUENCE: 341
tgtgatttgt attatatta                                        19

<210> SEQ ID NO 342
<211> LENGTH: 19
<212> TYPE: DNA
<213> ORGANISM: Homo sapiens

<400> SEQUENCE: 342
tgtacttgaa gttattaaa                                        19

<210> SEQ ID NO 343
<211> LENGTH: 19
<212> TYPE: DNA
<213> ORGANISM: Homo sapiens

<400> SEQUENCE: 343
ctttacagat actgtgata                                        19

<210> SEQ ID NO 344
<211> LENGTH: 19
<212> TYPE: DNA
<213> ORGANISM: Homo sapiens

<400> SEQUENCE: 344
gatttgactg tgaagatga                                        19

<210> SEQ ID NO 345
<211> LENGTH: 19
<212> TYPE: DNA
<213> ORGANISM: Homo sapiens

<400> SEQUENCE: 345
cctattcaag ttcatgtca                                        19

<210> SEQ ID NO 346
<211> LENGTH: 19
<212> TYPE: DNA
<213> ORGANISM: Homo sapiens

<400> SEQUENCE: 346
caaatataat gaaagaaat                                        19

<210> SEQ ID NO 347
<211> LENGTH: 19
<212> TYPE: DNA
<213> ORGANISM: Homo sapiens

<400> SEQUENCE: 347
ctgtcagact ggcaaatat                                        19

<210> SEQ ID NO 348
<211> LENGTH: 19
<212> TYPE: DNA

```
<213> ORGANISM: Homo sapiens

<400> SEQUENCE: 348
tgtcagactg gcaaatata                                                  19

<210> SEQ ID NO 349
<211> LENGTH: 19
<212> TYPE: DNA
<213> ORGANISM: Homo sapiens

<400> SEQUENCE: 349
gtcagactgg caaatataa                                                  19

<210> SEQ ID NO 350
<211> LENGTH: 19
<212> TYPE: DNA
<213> ORGANISM: Homo sapiens

<400> SEQUENCE: 350
tcagactggc aaatataat                                                  19

<210> SEQ ID NO 351
<211> LENGTH: 19
<212> TYPE: DNA
<213> ORGANISM: Homo sapiens

<400> SEQUENCE: 351
gactggcaaa tataatgaa                                                  19

<210> SEQ ID NO 352
<211> LENGTH: 19
<212> TYPE: DNA
<213> ORGANISM: Homo sapiens

<400> SEQUENCE: 352
actggcaaat ataatgaaa                                                  19

<210> SEQ ID NO 353
<211> LENGTH: 19
<212> TYPE: DNA
<213> ORGANISM: Homo sapiens

<400> SEQUENCE: 353
ggcaaatata atgaaagaa                                                  19

<210> SEQ ID NO 354
<211> LENGTH: 19
<212> TYPE: DNA
<213> ORGANISM: Homo sapiens

<400> SEQUENCE: 354
gcaaatataa tgaaagaaa                                                  19

<210> SEQ ID NO 355
<211> LENGTH: 19
<212> TYPE: DNA
<213> ORGANISM: Homo sapiens

<400> SEQUENCE: 355
caaatataat gaaagaaat                                                  19

<210> SEQ ID NO 356
<211> LENGTH: 19
```

```
<212> TYPE: DNA
<213> ORGANISM: Homo sapiens

<400> SEQUENCE: 356
aaatataatg aaagaaata                                                19

<210> SEQ ID NO 357
<211> LENGTH: 19
<212> TYPE: DNA
<213> ORGANISM: Homo sapiens

<400> SEQUENCE: 357
aatataatga aagaaataa                                                19

<210> SEQ ID NO 358
<211> LENGTH: 19
<212> TYPE: DNA
<213> ORGANISM: Homo sapiens

<400> SEQUENCE: 358
gaaagaaata agtctcctt                                                19

<210> SEQ ID NO 359
<211> LENGTH: 19
<212> TYPE: DNA
<213> ORGANISM: Homo sapiens

<400> SEQUENCE: 359
cagataatct tctcaggac                                                19

<210> SEQ ID NO 360
<211> LENGTH: 19
<212> TYPE: DNA
<213> ORGANISM: Homo sapiens

<400> SEQUENCE: 360
ggacaccatc cgttcaatt                                                19

<210> SEQ ID NO 361
<211> LENGTH: 19
<212> TYPE: DNA
<213> ORGANISM: Homo sapiens

<400> SEQUENCE: 361
accatccgtt caattggta                                                19

<210> SEQ ID NO 362
<211> LENGTH: 19
<212> TYPE: DNA
<213> ORGANISM: Homo sapiens

<400> SEQUENCE: 362
tccgttcaat tggtacaaa                                                19

<210> SEQ ID NO 363
<211> LENGTH: 19
<212> TYPE: DNA
<213> ORGANISM: Homo sapiens

<400> SEQUENCE: 363
ccagagtctt caggagctt                                                19

<210> SEQ ID NO 364
```

```
<211> LENGTH: 19
<212> TYPE: DNA
<213> ORGANISM: Homo sapiens

<400> SEQUENCE: 364
tcaggagctt cttgatttt                                               19

<210> SEQ ID NO 365
<211> LENGTH: 19
<212> TYPE: DNA
<213> ORGANISM: Homo sapiens

<400> SEQUENCE: 365
caggagcttc ttgatttta                                               19

<210> SEQ ID NO 366
<211> LENGTH: 19
<212> TYPE: DNA
<213> ORGANISM: Homo sapiens

<400> SEQUENCE: 366
aggagcttct tgattttaa                                               19

<210> SEQ ID NO 367
<211> LENGTH: 19
<212> TYPE: DNA
<213> ORGANISM: Homo sapiens

<400> SEQUENCE: 367
ggagcttctt gattttaag                                               19

<210> SEQ ID NO 368
<211> LENGTH: 19
<212> TYPE: DNA
<213> ORGANISM: Homo sapiens

<400> SEQUENCE: 368
tcttgatttt aaggacaaa                                               19

<210> SEQ ID NO 369
<211> LENGTH: 19
<212> TYPE: DNA
<213> ORGANISM: Homo sapiens

<400> SEQUENCE: 369
cttgatttta aggacaaaa                                               19

<210> SEQ ID NO 370
<211> LENGTH: 19
<212> TYPE: DNA
<213> ORGANISM: Homo sapiens

<400> SEQUENCE: 370
ggacaaaagt gctgaggat                                               19

<210> SEQ ID NO 371
<211> LENGTH: 19
<212> TYPE: DNA
<213> ORGANISM: Homo sapiens

<400> SEQUENCE: 371
gctgaggatg ctaaagcta                                               19
```

```
<210> SEQ ID NO 372
<211> LENGTH: 19
<212> TYPE: DNA
<213> ORGANISM: Homo sapiens

<400> SEQUENCE: 372
ctgaggatgc taaagctat                                                19

<210> SEQ ID NO 373
<211> LENGTH: 19
<212> TYPE: DNA
<213> ORGANISM: Homo sapiens

<400> SEQUENCE: 373
tgaggatgct aaagctatt                                                19

<210> SEQ ID NO 374
<211> LENGTH: 19
<212> TYPE: DNA
<213> ORGANISM: Homo sapiens

<400> SEQUENCE: 374
aggatgctaa agctattta                                                19

<210> SEQ ID NO 375
<211> LENGTH: 19
<212> TYPE: DNA
<213> ORGANISM: Homo sapiens

<400> SEQUENCE: 375
ggatgctaaa gctatttat                                                19

<210> SEQ ID NO 376
<211> LENGTH: 19
<212> TYPE: DNA
<213> ORGANISM: Homo sapiens

<400> SEQUENCE: 376
aaagctattt atgacttta                                                19

<210> SEQ ID NO 377
<211> LENGTH: 19
<212> TYPE: DNA
<213> ORGANISM: Homo sapiens

<400> SEQUENCE: 377
atttatgact ttacagata                                                19

<210> SEQ ID NO 378
<211> LENGTH: 19
<212> TYPE: DNA
<213> ORGANISM: Homo sapiens

<400> SEQUENCE: 378
ctttacagat actgtgata                                                19

<210> SEQ ID NO 379
<211> LENGTH: 19
<212> TYPE: DNA
<213> ORGANISM: Homo sapiens

<400> SEQUENCE: 379
cagatactgt gatacggat                                                19
```

```
<210> SEQ ID NO 380
<211> LENGTH: 19
<212> TYPE: DNA
<213> ORGANISM: Homo sapiens

<400> SEQUENCE: 380
actgtgatac ggatcagaa                                                  19

<210> SEQ ID NO 381
<211> LENGTH: 19
<212> TYPE: DNA
<213> ORGANISM: Homo sapiens

<400> SEQUENCE: 381
ctgtgatacg gatcagaaa                                                  19

<210> SEQ ID NO 382
<211> LENGTH: 19
<212> TYPE: DNA
<213> ORGANISM: Homo sapiens

<400> SEQUENCE: 382
ggatcagaaa ccgacacaa                                                  19

<210> SEQ ID NO 383
<211> LENGTH: 19
<212> TYPE: DNA
<213> ORGANISM: Homo sapiens

<400> SEQUENCE: 383
gatcagaaac cgacacaat                                                  19

<210> SEQ ID NO 384
<211> LENGTH: 19
<212> TYPE: DNA
<213> ORGANISM: Homo sapiens

<400> SEQUENCE: 384
cagaaaccga cacaatgat                                                  19

<210> SEQ ID NO 385
<211> LENGTH: 19
<212> TYPE: DNA
<213> ORGANISM: Homo sapiens

<400> SEQUENCE: 385
accgacacaa tgatgtcat                                                  19

<210> SEQ ID NO 386
<211> LENGTH: 19
<212> TYPE: DNA
<213> ORGANISM: Homo sapiens

<400> SEQUENCE: 386
ccgacacaat gatgtcatt                                                  19

<210> SEQ ID NO 387
<211> LENGTH: 19
<212> TYPE: DNA
<213> ORGANISM: Homo sapiens

<400> SEQUENCE: 387
ggcccagggt gtgattgaa                                                  19
```

<210> SEQ ID NO 388
<211> LENGTH: 19
<212> TYPE: DNA
<213> ORGANISM: Homo sapiens

<400> SEQUENCE: 388
gcccagggtg tgattgaat                                                19

<210> SEQ ID NO 389
<211> LENGTH: 19
<212> TYPE: DNA
<213> ORGANISM: Homo sapiens

<400> SEQUENCE: 389
cccagggtgt gattgaata                                                19

<210> SEQ ID NO 390
<211> LENGTH: 19
<212> TYPE: DNA
<213> ORGANISM: Homo sapiens

<400> SEQUENCE: 390
agggtgtgat tgaatacaa                                                19

<210> SEQ ID NO 391
<211> LENGTH: 19
<212> TYPE: DNA
<213> ORGANISM: Homo sapiens

<400> SEQUENCE: 391
gggtgtgatt gaatacaag                                                19

<210> SEQ ID NO 392
<211> LENGTH: 19
<212> TYPE: DNA
<213> ORGANISM: Homo sapiens

<400> SEQUENCE: 392
gtgtgattga atacaagga                                                19

<210> SEQ ID NO 393
<211> LENGTH: 19
<212> TYPE: DNA
<213> ORGANISM: Homo sapiens

<400> SEQUENCE: 393
gtgattgaat acaaggaga                                                19

<210> SEQ ID NO 394
<211> LENGTH: 19
<212> TYPE: DNA
<213> ORGANISM: Homo sapiens

<400> SEQUENCE: 394
tgaatacaag gagagcttt                                                19

<210> SEQ ID NO 395
<211> LENGTH: 19
<212> TYPE: DNA
<213> ORGANISM: Homo sapiens

<400> SEQUENCE: 395

```
ggagagcttt ggggtggat                                              19

<210> SEQ ID NO 396
<211> LENGTH: 19
<212> TYPE: DNA
<213> ORGANISM: Homo sapiens

<400> SEQUENCE: 396
ccagccagaa tgttcagta                                              19

<210> SEQ ID NO 397
<211> LENGTH: 19
<212> TYPE: DNA
<213> ORGANISM: Homo sapiens

<400> SEQUENCE: 397
gccagaatgt tcagtactt                                              19

<210> SEQ ID NO 398
<211> LENGTH: 19
<212> TYPE: DNA
<213> ORGANISM: Homo sapiens

<400> SEQUENCE: 398
ccagaatgtt cagtacttt                                              19

<210> SEQ ID NO 399
<211> LENGTH: 19
<212> TYPE: DNA
<213> ORGANISM: Homo sapiens

<400> SEQUENCE: 399
cagaatgttc agtactttt                                              19

<210> SEQ ID NO 400
<211> LENGTH: 19
<212> TYPE: DNA
<213> ORGANISM: Homo sapiens

<400> SEQUENCE: 400
agaatgttca gtacttttt                                              19

<210> SEQ ID NO 401
<211> LENGTH: 19
<212> TYPE: DNA
<213> ORGANISM: Homo sapiens

<400> SEQUENCE: 401 agtactttt ggatcgatt                                               19

<210> SEQ ID NO 402
<211> LENGTH: 19
<212> TYPE: DNA
<213> ORGANISM: Homo sapiens

<400> SEQUENCE: 402 acttttgga tcgattcta                                               19

<210> SEQ ID NO 403
<211> LENGTH: 19
<212> TYPE: DNA
<213> ORGANISM: Homo sapiens

<400> SEQUENCE: 403
```

-continued gattctacat gagtcgcat 19

<210> SEQ ID NO 404
<211> LENGTH: 19
<212> TYPE: DNA
<213> ORGANISM: Homo sapiens

<400> SEQUENCE: 404
acatgagtcg catttcaat 19

<210> SEQ ID NO 405
<211> LENGTH: 19
<212> TYPE: DNA
<213> ORGANISM: Homo sapiens

<400> SEQUENCE: 405
catgagtcgc atttcaatt 19

<210> SEQ ID NO 406
<211> LENGTH: 19
<212> TYPE: DNA
<213> ORGANISM: Homo sapiens

<400> SEQUENCE: 406
agtcgcattt caattagaa 19

<210> SEQ ID NO 407
<211> LENGTH: 19
<212> TYPE: DNA
<213> ORGANISM: Homo sapiens

<400> SEQUENCE: 407
gtcgcatttc aattagaat 19

<210> SEQ ID NO 408
<211> LENGTH: 19
<212> TYPE: DNA
<213> ORGANISM: Homo sapiens

<400> SEQUENCE: 408
gcatttcaat tagaatgtt 19

<210> SEQ ID NO 409
<211> LENGTH: 19
<212> TYPE: DNA
<213> ORGANISM: Homo sapiens

<400> SEQUENCE: 409
catttcaatt agaatgtta 19

<210> SEQ ID NO 410
<211> LENGTH: 19
<212> TYPE: DNA
<213> ORGANISM: Homo sapiens

<400> SEQUENCE: 410
caattagaat gttactcaa 19

<210> SEQ ID NO 411
<211> LENGTH: 19
<212> TYPE: DNA
<213> ORGANISM: Homo sapiens

```
<400> SEQUENCE: 411
gaatgttact caatcagca                                              19

<210> SEQ ID NO 412
<211> LENGTH: 19
<212> TYPE: DNA
<213> ORGANISM: Homo sapiens

<400> SEQUENCE: 412
actcaatcag cactcttta                                              19

<210> SEQ ID NO 413
<211> LENGTH: 19
<212> TYPE: DNA
<213> ORGANISM: Homo sapiens

<400> SEQUENCE: 413
ctttattgtt tggtggaaa                                              19

<210> SEQ ID NO 414
<211> LENGTH: 19
<212> TYPE: DNA
<213> ORGANISM: Homo sapiens

<400> SEQUENCE: 414
gtttggtgga aaggcaaa                                               19

<210> SEQ ID NO 415
<211> LENGTH: 19
<212> TYPE: DNA
<213> ORGANISM: Homo sapiens

<400> SEQUENCE: 415
ggtggaaaag gcaaaggaa                                              19

<210> SEQ ID NO 416
<211> LENGTH: 19
<212> TYPE: DNA
<213> ORGANISM: Homo sapiens

<400> SEQUENCE: 416
gtggaaaagg caaaggaag                                              19

<210> SEQ ID NO 417
<211> LENGTH: 19
<212> TYPE: DNA
<213> ORGANISM: Homo sapiens

<400> SEQUENCE: 417
tggaaaaggc aaaggaagt                                              19

<210> SEQ ID NO 418
<211> LENGTH: 19
<212> TYPE: DNA
<213> ORGANISM: Homo sapiens

<400> SEQUENCE: 418
caaaggaagt ccatctcat                                              19

<210> SEQ ID NO 419
<211> LENGTH: 19
<212> TYPE: DNA
<213> ORGANISM: Homo sapiens
```

```
<400> SEQUENCE: 419
ggaagtccat ctcatcgaa                                                19

<210> SEQ ID NO 420
<211> LENGTH: 19
<212> TYPE: DNA
<213> ORGANISM: Homo sapiens

<400> SEQUENCE: 420
gaagtccatc tcatcgaaa                                                19

<210> SEQ ID NO 421
<211> LENGTH: 19
<212> TYPE: DNA
<213> ORGANISM: Homo sapiens

<400> SEQUENCE: 421
ccatctcatc gaaaacaca                                                19

<210> SEQ ID NO 422
<211> LENGTH: 19
<212> TYPE: DNA
<213> ORGANISM: Homo sapiens

<400> SEQUENCE: 422
catctcatcg aaaacacat                                                19

<210> SEQ ID NO 423
<211> LENGTH: 19
<212> TYPE: DNA
<213> ORGANISM: Homo sapiens

<400> SEQUENCE: 423
catcgaaaac acattggaa                                                19

<210> SEQ ID NO 424
<211> LENGTH: 19
<212> TYPE: DNA
<213> ORGANISM: Homo sapiens

<400> SEQUENCE: 424
gaaaacacat tggaagcat                                                19

<210> SEQ ID NO 425
<211> LENGTH: 19
<212> TYPE: DNA
<213> ORGANISM: Homo sapiens

<400> SEQUENCE: 425
aaaacacatt ggaagcata                                                19

<210> SEQ ID NO 426
<211> LENGTH: 19
<212> TYPE: DNA
<213> ORGANISM: Homo sapiens

<400> SEQUENCE: 426
aacacattgg aagcataaa                                                19

<210> SEQ ID NO 427
<211> LENGTH: 19
<212> TYPE: DNA
```

```
<213> ORGANISM: Homo sapiens

<400> SEQUENCE: 427
acacattgga agcataaat                                                 19

<210> SEQ ID NO 428
<211> LENGTH: 19
<212> TYPE: DNA
<213> ORGANISM: Homo sapiens

<400> SEQUENCE: 428
gcataaatcc aaactgcaa                                                 19

<210> SEQ ID NO 429
<211> LENGTH: 19
<212> TYPE: DNA
<213> ORGANISM: Homo sapiens

<400> SEQUENCE: 429
cataaatcca aactgcaat                                                 19

<210> SEQ ID NO 430
<211> LENGTH: 19
<212> TYPE: DNA
<213> ORGANISM: Homo sapiens

<400> SEQUENCE: 430
aaatccaaac tgcaatgta                                                 19

<210> SEQ ID NO 431
<211> LENGTH: 19
<212> TYPE: DNA
<213> ORGANISM: Homo sapiens

<400> SEQUENCE: 431
tccaaactgc aatgtactt                                                 19

<210> SEQ ID NO 432
<211> LENGTH: 19
<212> TYPE: DNA
<213> ORGANISM: Homo sapiens

<400> SEQUENCE: 432
ctgcaatgta cttgaagtt                                                 19

<210> SEQ ID NO 433
<211> LENGTH: 19
<212> TYPE: DNA
<213> ORGANISM: Homo sapiens

<400> SEQUENCE: 433
tgcaatgtac ttgaagtta                                                 19

<210> SEQ ID NO 434
<211> LENGTH: 19
<212> TYPE: DNA
<213> ORGANISM: Homo sapiens

<400> SEQUENCE: 434
gcaatgtact tgaagttat                                                 19

<210> SEQ ID NO 435
<211> LENGTH: 19
```

```
<212> TYPE: DNA
<213> ORGANISM: Homo sapiens

<400> SEQUENCE: 435
caatgtactt gaagttatt                                                19

<210> SEQ ID NO 436
<211> LENGTH: 19
<212> TYPE: DNA
<213> ORGANISM: Homo sapiens

<400> SEQUENCE: 436
atgtacttga agttattaa                                                19

<210> SEQ ID NO 437
<211> LENGTH: 19
<212> TYPE: DNA
<213> ORGANISM: Homo sapiens

<400> SEQUENCE: 437
tgtacttgaa gttattaaa                                                19

<210> SEQ ID NO 438
<211> LENGTH: 19
<212> TYPE: DNA
<213> ORGANISM: Homo sapiens

<400> SEQUENCE: 438
acttgaagtt attaaagat                                                19

<210> SEQ ID NO 439
<211> LENGTH: 19
<212> TYPE: DNA
<213> ORGANISM: Homo sapiens

<400> SEQUENCE: 439
aagttattaa agatggcta                                                19

<210> SEQ ID NO 440
<211> LENGTH: 19
<212> TYPE: DNA
<213> ORGANISM: Homo sapiens

<400> SEQUENCE: 440
agttattaaa gatggctat                                                19

<210> SEQ ID NO 441
<211> LENGTH: 19
<212> TYPE: DNA
<213> ORGANISM: Homo sapiens

<400> SEQUENCE: 441
tattaaagat ggctatgaa                                                19

<210> SEQ ID NO 442
<211> LENGTH: 17
<212> TYPE: DNA
<213> ORGANISM: Homo sapiens

<400> SEQUENCE: 442
aaagatggct atgaaaa                                                  17

<210> SEQ ID NO 443
```

```
<211> LENGTH: 19
<212> TYPE: DNA
<213> ORGANISM: Homo sapiens

<400> SEQUENCE: 443
taaagatggc tatgaaaat                                           19

<210> SEQ ID NO 444
<211> LENGTH: 19
<212> TYPE: DNA
<213> ORGANISM: Homo sapiens

<400> SEQUENCE: 444
ggcgtctgtg tgatttgta                                           19

<210> SEQ ID NO 445
<211> LENGTH: 19
<212> TYPE: DNA
<213> ORGANISM: Homo sapiens

<400> SEQUENCE: 445
gcgtctgtgt gatttgtat                                           19

<210> SEQ ID NO 446
<211> LENGTH: 19
<212> TYPE: DNA
<213> ORGANISM: Homo sapiens

<400> SEQUENCE: 446
cgtctgtgtg atttgtatt                                           19

<210> SEQ ID NO 447
<211> LENGTH: 19
<212> TYPE: DNA
<213> ORGANISM: Homo sapiens

<400> SEQUENCE: 447
gtctgtgtga tttgtatta                                           19

<210> SEQ ID NO 448
<211> LENGTH: 19
<212> TYPE: DNA
<213> ORGANISM: Homo sapiens

<400> SEQUENCE: 448
ctgtgtgatt tgtattata                                           19

<210> SEQ ID NO 449
<211> LENGTH: 19
<212> TYPE: DNA
<213> ORGANISM: Homo sapiens

<400> SEQUENCE: 449
gtgtgatttg tattatatt                                           19

<210> SEQ ID NO 450
<211> LENGTH: 19
<212> TYPE: DNA
<213> ORGANISM: Homo sapiens

<400> SEQUENCE: 450
tgtgatttgt attatatta                                           19
```

```
<210> SEQ ID NO 451
<211> LENGTH: 19
<212> TYPE: DNA
<213> ORGANISM: Homo sapiens

<400> SEQUENCE: 451
gtgatttgta ttatattaa                                            19

<210> SEQ ID NO 452
<211> LENGTH: 19
<212> TYPE: DNA
<213> ORGANISM: Homo sapiens

<400> SEQUENCE: 452
tcccgaacta gaacttgaa                                            19

<210> SEQ ID NO 453
<211> LENGTH: 19
<212> TYPE: DNA
<213> ORGANISM: Homo sapiens

<400> SEQUENCE: 453
ccgaactaga acttgaaga                                            19

<210> SEQ ID NO 454
<211> LENGTH: 19
<212> TYPE: DNA
<213> ORGANISM: Homo sapiens

<400> SEQUENCE: 454
cgaactagaa cttgaagaa                                            19

<210> SEQ ID NO 455
<211> LENGTH: 19
<212> TYPE: DNA
<213> ORGANISM: Homo sapiens

<400> SEQUENCE: 455
actagaactt gaagaacta                                            19

<210> SEQ ID NO 456
<211> LENGTH: 19
<212> TYPE: DNA
<213> ORGANISM: Homo sapiens

<400> SEQUENCE: 456
ctagaacttg aagaactaa                                            19

<210> SEQ ID NO 457
<211> LENGTH: 19
<212> TYPE: RNA
<213> ORGANISM: Homo sapiens

<400> SEQUENCE: 457
uagaacuuga agaacuaaa                                            19

<210> SEQ ID NO 458
<211> LENGTH: 19
<212> TYPE: DNA
<213> ORGANISM: Homo sapiens

<400> SEQUENCE: 458
agaacttgaa gaactaaat                                            19
```

```
<210> SEQ ID NO 459
<211> LENGTH: 19
<212> TYPE: DNA
<213> ORGANISM: Homo sapiens

<400> SEQUENCE: 459
cttgaagaac taaatgcaa                                                19

<210> SEQ ID NO 460
<211> LENGTH: 17
<212> TYPE: DNA
<213> ORGANISM: Homo sapiens

<400> SEQUENCE: 460
gaagaactaa atgcaaa                                                  17

<210> SEQ ID NO 461
<211> LENGTH: 19
<212> TYPE: DNA
<213> ORGANISM: Homo sapiens

<400> SEQUENCE: 461
tgaagaacta aatgcaaaa                                                19

<210> SEQ ID NO 462
<211> LENGTH: 19
<212> TYPE: DNA
<213> ORGANISM: Homo sapiens

<400> SEQUENCE: 462
gaagaactaa atgcaaaat                                                19

<210> SEQ ID NO 463
<211> LENGTH: 19
<212> TYPE: DNA
<213> ORGANISM: Homo sapiens

<400> SEQUENCE: 463
agaactaaat gcaaaatca                                                19

<210> SEQ ID NO 464
<211> LENGTH: 19
<212> TYPE: DNA
<213> ORGANISM: Homo sapiens

<400> SEQUENCE: 464
accaggacag ccaatacaa                                                19

<210> SEQ ID NO 465
<211> LENGTH: 19
<212> TYPE: DNA
<213> ORGANISM: Homo sapiens

<400> SEQUENCE: 465
cagccaatac aagtggttt                                                19

<210> SEQ ID NO 466
<211> LENGTH: 19
<212> TYPE: DNA
<213> ORGANISM: Homo sapiens

<400> SEQUENCE: 466
agccaataca agtggttta                                                19
```

<210> SEQ ID NO 467
<211> LENGTH: 19
<212> TYPE: DNA
<213> ORGANISM: Homo sapiens

<400> SEQUENCE: 467
gccaatacaa gtggtttat                                              19

<210> SEQ ID NO 468
<211> LENGTH: 19
<212> TYPE: DNA
<213> ORGANISM: Homo sapiens

<400> SEQUENCE: 468
tcacatggtg tttgaactt                                              19

<210> SEQ ID NO 469
<211> LENGTH: 19
<212> TYPE: DNA
<213> ORGANISM: Homo sapiens

<400> SEQUENCE: 469
acatggtgtt tgaactttt                                              19

<210> SEQ ID NO 470
<211> LENGTH: 19
<212> TYPE: DNA
<213> ORGANISM: Homo sapiens

<400> SEQUENCE: 470
tggtgtttga acttttcaa                                              19

<210> SEQ ID NO 471
<211> LENGTH: 19
<212> TYPE: DNA
<213> ORGANISM: Homo sapiens

<400> SEQUENCE: 471
ggtgtttgaa cttttcaag                                              19

<210> SEQ ID NO 472
<211> LENGTH: 19
<212> TYPE: DNA
<213> ORGANISM: Homo sapiens

<400> SEQUENCE: 472
tgtttgaact tttcaagaa                                              19

<210> SEQ ID NO 473
<211> LENGTH: 19
<212> TYPE: DNA
<213> ORGANISM: Homo sapiens

<400> SEQUENCE: 473
gtttgaactt ttcaagaat                                              19

<210> SEQ ID NO 474
<211> LENGTH: 19
<212> TYPE: DNA
<213> ORGANISM: Homo sapiens

<400> SEQUENCE: 474

```
gaacttttca agaatgcaa                                              19

<210> SEQ ID NO 475
<211> LENGTH: 19
<212> TYPE: DNA
<213> ORGANISM: Homo sapiens

<400> SEQUENCE: 475
agccactatg gaacaccat                                              19

<210> SEQ ID NO 476
<211> LENGTH: 19
<212> TYPE: DNA
<213> ORGANISM: Homo sapiens

<400> SEQUENCE: 476
ctatggaaca ccatgccaa                                              19

<210> SEQ ID NO 477
<211> LENGTH: 19
<212> TYPE: DNA
<213> ORGANISM: Homo sapiens

<400> SEQUENCE: 477
ggaacaccat gccaacaga                                              19

<210> SEQ ID NO 478
<211> LENGTH: 19
<212> TYPE: DNA
<213> ORGANISM: Homo sapiens

<400> SEQUENCE: 478
ccatgccaac agaggtgtt                                              19

<210> SEQ ID NO 479
<211> LENGTH: 19
<212> TYPE: DNA
<213> ORGANISM: Homo sapiens

<400> SEQUENCE: 479
gttcatgtca cgctgggta                                              19

<210> SEQ ID NO 480
<211> LENGTH: 19
<212> TYPE: DNA
<213> ORGANISM: Homo sapiens

<400> SEQUENCE: 480
cacgctgggt aatgaggat                                              19

<210> SEQ ID NO 481
<211> LENGTH: 19
<212> TYPE: DNA
<213> ORGANISM: Homo sapiens

<400> SEQUENCE: 481
gaggatttga ctgtgaaga                                              19

<210> SEQ ID NO 482
<211> LENGTH: 19
<212> TYPE: DNA
<213> ORGANISM: Homo sapiens

<400> SEQUENCE: 482
```
aggatttgac tgtgaagat			19

<210> SEQ ID NO 483
<211> LENGTH: 19
<212> TYPE: DNA
<213> ORGANISM: Homo sapiens

<400> SEQUENCE: 483
cgaggaggtg gcgttcctt			19

<210> SEQ ID NO 484
<211> LENGTH: 19
<212> TYPE: DNA
<213> ORGANISM: Homo sapiens

<400> SEQUENCE: 484
tttctttcat tatatttgc			19

<210> SEQ ID NO 485
<211> LENGTH: 19
<212> TYPE: DNA
<213> ORGANISM: Homo sapiens

<400> SEQUENCE: 485
ttctttcatt atatttgcc			19

<210> SEQ ID NO 486
<211> LENGTH: 19
<212> TYPE: DNA
<213> ORGANISM: Homo sapiens

<400> SEQUENCE: 486
ataacttcaa gtacattgc			19

<210> SEQ ID NO 487
<211> LENGTH: 19
<212> TYPE: DNA
<213> ORGANISM: Homo sapiens

<400> SEQUENCE: 487
ttcttcaagt tctagttcg			19

<210> SEQ ID NO 488
<211> LENGTH: 19
<212> TYPE: DNA
<213> ORGANISM: Homo sapiens

<400> SEQUENCE: 488
ttaatataat acaaatcac			19

<210> SEQ ID NO 489
<211> LENGTH: 19
<212> TYPE: DNA
<213> ORGANISM: Homo sapiens

<400> SEQUENCE: 489
tcttcacagt caaatcctc			19

<210> SEQ ID NO 490
<211> LENGTH: 19
<212> TYPE: DNA
<213> ORGANISM: Homo sapiens

<400> SEQUENCE: 490
tcatcttcac agtcaaatc                                                19

<210> SEQ ID NO 491
<211> LENGTH: 19
<212> TYPE: DNA
<213> ORGANISM: Homo sapiens

<400> SEQUENCE: 491
tcttcaagtt ctagttcgg                                                19

<210> SEQ ID NO 492
<211> LENGTH: 19
<212> TYPE: DNA
<213> ORGANISM: Homo sapiens

<400> SEQUENCE: 492
tagttcttca agttctagt                                                19

<210> SEQ ID NO 493
<211> LENGTH: 19
<212> TYPE: DNA
<213> ORGANISM: Homo sapiens

<400> SEQUENCE: 493
ttagttcttc aagttctag                                                19

<210> SEQ ID NO 494
<211> LENGTH: 19
<212> TYPE: DNA
<213> ORGANISM: Homo sapiens

<400> SEQUENCE: 494
tatcacagta tctgtaaag                                                19

<210> SEQ ID NO 495
<211> LENGTH: 19
<212> TYPE: DNA
<213> ORGANISM: Homo sapiens

<400> SEQUENCE: 495
ttgcattctt gaaaagttc                                                19

<210> SEQ ID NO 496
<211> LENGTH: 19
<212> TYPE: DNA
<213> ORGANISM: Homo sapiens

<400> SEQUENCE: 496
tacaaatcac acagacgcc                                                19

<210> SEQ ID NO 497
<211> LENGTH: 19
<212> TYPE: DNA
<213> ORGANISM: Homo sapiens

<400> SEQUENCE: 497
atacaaatca cacagacgc                                                19

<210> SEQ ID NO 498
<211> LENGTH: 19
<212> TYPE: DNA
<213> ORGANISM: Homo sapiens

```
<400> SEQUENCE: 498
taatacaaat cacacagac                                           19

<210> SEQ ID NO 499
<211> LENGTH: 19
<212> TYPE: DNA
<213> ORGANISM: Homo sapiens

<400> SEQUENCE: 499
tttaataact tcaagtaca                                           19

<210> SEQ ID NO 500
<211> LENGTH: 19
<212> TYPE: DNA
<213> ORGANISM: Homo sapiens

<400> SEQUENCE: 500
taacattcta attgaaatg                                           19

<210> SEQ ID NO 501
<211> LENGTH: 19
<212> TYPE: DNA
<213> ORGANISM: Homo sapiens

<400> SEQUENCE: 501
ataaatagct ttagcatcc                                           19

<210> SEQ ID NO 502
<211> LENGTH: 19
<212> TYPE: DNA
<213> ORGANISM: Homo sapiens

<400> SEQUENCE: 502
tttctgatcc gtatcacag                                           19

<210> SEQ ID NO 503
<211> LENGTH: 19
<212> TYPE: DNA
<213> ORGANISM: Homo sapiens

<400> SEQUENCE: 503
aaagtactga acattctgg                                           19

<210> SEQ ID NO 504
<211> LENGTH: 19
<212> TYPE: DNA
<213> ORGANISM: Homo sapiens

<400> SEQUENCE: 504
ttatatttgc cagtctgac                                           19

<210> SEQ ID NO 505
<211> LENGTH: 19
<212> TYPE: DNA
<213> ORGANISM: Homo sapiens

<400> SEQUENCE: 505
tataatacaa atcacacag                                           19

<210> SEQ ID NO 506
<211> LENGTH: 19
<212> TYPE: DNA
```

```
<213> ORGANISM: Homo sapiens

<400> SEQUENCE: 506
tactgaacat tctggctgg                                                    19

<210> SEQ ID NO 507
<211> LENGTH: 19
<212> TYPE: DNA
<213> ORGANISM: Homo sapiens

<400> SEQUENCE: 507
ttgtgtcggt ttctgatcc                                                    19

<210> SEQ ID NO 508
<211> LENGTH: 19
<212> TYPE: DNA
<213> ORGANISM: Homo sapiens

<400> SEQUENCE: 508
tttccaccaa acaataaag                                                    19

<210> SEQ ID NO 509
<211> LENGTH: 19
<212> TYPE: DNA
<213> ORGANISM: Homo sapiens

<400> SEQUENCE: 509
aagtactgaa cattctggc                                                    19

<210> SEQ ID NO 510
<211> LENGTH: 19
<212> TYPE: DNA
<213> ORGANISM: Homo sapiens

<400> SEQUENCE: 510
aacattctaa ttgaaatgc                                                    19

<210> SEQ ID NO 511
<211> LENGTH: 19
<212> TYPE: DNA
<213> ORGANISM: Homo sapiens

<400> SEQUENCE: 511
ttctgatccg tatcacagt                                                    19

<210> SEQ ID NO 512
<211> LENGTH: 19
<212> TYPE: DNA
<213> ORGANISM: Homo sapiens

<400> SEQUENCE: 512
ttaaaatcaa gaagctcct                                                    19

<210> SEQ ID NO 513
<211> LENGTH: 19
<212> TYPE: DNA
<213> ORGANISM: Homo sapiens

<400> SEQUENCE: 513
ttaataactt caagtacat                                                    19

<210> SEQ ID NO 514
<211> LENGTH: 19
```

```
<212> TYPE: DNA
<213> ORGANISM: Homo sapiens

<400> SEQUENCE: 514
aatataatac aaatcacac                                                19

<210> SEQ ID NO 515
<211> LENGTH: 19
<212> TYPE: DNA
<213> ORGANISM: Homo sapiens

<400> SEQUENCE: 515
ttttgtcctt aaaatcaag                                                19

<210> SEQ ID NO 516
<211> LENGTH: 19
<212> TYPE: DNA
<213> ORGANISM: Homo sapiens

<400> SEQUENCE: 516
tttgtcctta aaatcaaga                                                19

<210> SEQ ID NO 517
<211> LENGTH: 19
<212> TYPE: DNA
<213> ORGANISM: Homo sapiens

<400> SEQUENCE: 517
tagcattttc atagccatc                                                19

<210> SEQ ID NO 518
<211> LENGTH: 19
<212> TYPE: DNA
<213> ORGANISM: Homo sapiens

<400> SEQUENCE: 518
tgaagactct ggatatacc                                                19

<210> SEQ ID NO 519
<211> LENGTH: 19
<212> TYPE: DNA
<213> ORGANISM: Homo sapiens

<400> SEQUENCE: 519
tagctttagc atcctcagc                                                19

<210> SEQ ID NO 520
<211> LENGTH: 19
<212> TYPE: DNA
<213> ORGANISM: Homo sapiens

<400> SEQUENCE: 520
ttcattatat ttgccagtc                                                19

<210> SEQ ID NO 521
<211> LENGTH: 19
<212> TYPE: DNA
<213> ORGANISM: Homo sapiens

<400> SEQUENCE: 521
aatgacatca ttgtgtcgg                                                19

<210> SEQ ID NO 522
```

-continued

<210> SEQ ID NO 522
<211> LENGTH: 19
<212> TYPE: DNA
<213> ORGANISM: Homo sapiens

<400> SEQUENCE: 522
ttgtattcaa tcacaccct                                               19

<210> SEQ ID NO 523
<211> LENGTH: 19
<212> TYPE: DNA
<213> ORGANISM: Homo sapiens

<400> SEQUENCE: 523
taacttcaag tacattgca                                               19

<210> SEQ ID NO 524
<211> LENGTH: 19
<212> TYPE: DNA
<213> ORGANISM: Homo sapiens

<400> SEQUENCE: 524
ttcaagttct agttcggga                                               19

<210> SEQ ID NO 525
<211> LENGTH: 19
<212> TYPE: DNA
<213> ORGANISM: Homo sapiens

<400> SEQUENCE: 525
ttcaaacacc atgtgatag                                               19

<210> SEQ ID NO 526
<211> LENGTH: 19
<212> TYPE: DNA
<213> ORGANISM: Homo sapiens

<400> SEQUENCE: 526
atcttcacag tcaaatcct                                               19

<210> SEQ ID NO 527
<211> LENGTH: 19
<212> TYPE: DNA
<213> ORGANISM: Homo sapiens

<400> SEQUENCE: 527
taaaatcaag aagctcctg                                               19

<210> SEQ ID NO 528
<211> LENGTH: 19
<212> TYPE: DNA
<213> ORGANISM: Homo sapiens

<400> SEQUENCE: 528
taatataata caaatcaca                                               19

<210> SEQ ID NO 529
<211> LENGTH: 19
<212> TYPE: DNA
<213> ORGANISM: Homo sapiens

<400> SEQUENCE: 529
tagaatcgat ccaaaaagt                                               19

-continued

```
<210> SEQ ID NO 530
<211> LENGTH: 19
<212> TYPE: DNA
<213> ORGANISM: Homo sapiens

<400> SEQUENCE: 530
atctttaata acttcaagt                                                19

<210> SEQ ID NO 531
<211> LENGTH: 19
<212> TYPE: DNA
<213> ORGANISM: Homo sapiens

<400> SEQUENCE: 531
tccttgtatt caatcacac                                                19

<210> SEQ ID NO 532
<211> LENGTH: 19
<212> TYPE: DNA
<213> ORGANISM: Homo sapiens

<400> SEQUENCE: 532
tttcattata tttgccagt                                                19

<210> SEQ ID NO 533
<211> LENGTH: 19
<212> TYPE: DNA
<213> ORGANISM: Homo sapiens

<400> SEQUENCE: 533
taaagagtgc tgattgagt                                                19

<210> SEQ ID NO 534
<211> LENGTH: 19
<212> TYPE: DNA
<213> ORGANISM: Homo sapiens

<400> SEQUENCE: 534
tattcaatca caccctggg                                                19

<210> SEQ ID NO 535
<211> LENGTH: 19
<212> TYPE: DNA
<213> ORGANISM: Homo sapiens

<400> SEQUENCE: 535
tgatccgtat cacagtatc                                                19

<210> SEQ ID NO 536
<211> LENGTH: 19
<212> TYPE: DNA
<213> ORGANISM: Homo sapiens

<400> SEQUENCE: 536
aataacttca agtacattg                                                19

<210> SEQ ID NO 537
<211> LENGTH: 19
<212> TYPE: DNA
<213> ORGANISM: Homo sapiens

<400> SEQUENCE: 537
ataaaccact tgtattggc                                                19
```

```
<210> SEQ ID NO 538
<211> LENGTH: 19
<212> TYPE: DNA
<213> ORGANISM: Homo sapiens

<400> SEQUENCE: 538
atcacagtat ctgtaaagt                                                    19

<210> SEQ ID NO 539
<211> LENGTH: 19
<212> TYPE: DNA
<213> ORGANISM: Homo sapiens

<400> SEQUENCE: 539
attcttgaaa agttcaaac                                                    19

<210> SEQ ID NO 540
<211> LENGTH: 19
<212> TYPE: DNA
<213> ORGANISM: Homo sapiens

<400> SEQUENCE: 540
ttgcatttag ttcttcaag                                                    19

<210> SEQ ID NO 541
<211> LENGTH: 19
<212> TYPE: DNA
<213> ORGANISM: Homo sapiens

<400> SEQUENCE: 541
ttccaccaaa caataaaga                                                    19

<210> SEQ ID NO 542
<211> LENGTH: 19
<212> TYPE: DNA
<213> ORGANISM: Homo sapiens

<400> SEQUENCE: 542
atcctcagca cttttgtcc                                                    19

<210> SEQ ID NO 543
<211> LENGTH: 19
<212> TYPE: DNA
<213> ORGANISM: Homo sapiens

<400> SEQUENCE: 543
tcaaatcctc attacccag                                                    19

<210> SEQ ID NO 544
<211> LENGTH: 19
<212> TYPE: DNA
<213> ORGANISM: Homo sapiens

<400> SEQUENCE: 544
aacttcaagt acattgcag                                                    19

<210> SEQ ID NO 545
<211> LENGTH: 19
<212> TYPE: DNA
<213> ORGANISM: Homo sapiens

<400> SEQUENCE: 545
atgcgactca tgtagaatc                                                    19
```

<210> SEQ ID NO 546
<211> LENGTH: 19
<212> TYPE: DNA
<213> ORGANISM: Homo sapiens

<400> SEQUENCE: 546
aaaagtactg aacattctg                                                19

<210> SEQ ID NO 547
<211> LENGTH: 19
<212> TYPE: DNA
<213> ORGANISM: Homo sapiens

<400> SEQUENCE: 547
tcattgcatt cttgaaaag                                                19

<210> SEQ ID NO 548
<211> LENGTH: 19
<212> TYPE: DNA
<213> ORGANISM: Homo sapiens

<400> SEQUENCE: 548
ttcttgaaaa gttcaaaca                                                19

<210> SEQ ID NO 549
<211> LENGTH: 19
<212> TYPE: DNA
<213> ORGANISM: Homo sapiens

<400> SEQUENCE: 549
atttctttca ttatatttg                                                19

<210> SEQ ID NO 550
<211> LENGTH: 19
<212> TYPE: DNA
<213> ORGANISM: Homo sapiens

<400> SEQUENCE: 550
ttgaaaagtt caaacacca                                                19

<210> SEQ ID NO 551
<211> LENGTH: 19
<212> TYPE: DNA
<213> ORGANISM: Homo sapiens

<400> SEQUENCE: 551
agtcataaat agctttagc                                                19

<210> SEQ ID NO 552
<211> LENGTH: 19
<212> TYPE: DNA
<213> ORGANISM: Homo sapiens

<400> SEQUENCE: 552
taaatagctt tagcatcct                                                19

<210> SEQ ID NO 553
<211> LENGTH: 19
<212> TYPE: DNA
<213> ORGANISM: Homo sapiens

<400> SEQUENCE: 553
ctgtaaagtc ataaatagc                                                19

<210> SEQ ID NO 554
<211> LENGTH: 19
<212> TYPE: DNA
<213> ORGANISM: Homo sapiens

<400> SEQUENCE: 554
ttctaattga aatgcgact                                                19

<210> SEQ ID NO 555
<211> LENGTH: 19
<212> TYPE: DNA
<213> ORGANISM: Homo sapiens

<400> SEQUENCE: 555
atttagttct tcaagttct                                                19

<210> SEQ ID NO 556
<211> LENGTH: 19
<212> TYPE: DNA
<213> ORGANISM: Homo sapiens

<400> SEQUENCE: 556
tttgtaccaa ttgaacgga                                                19

<210> SEQ ID NO 557
<211> LENGTH: 19
<212> TYPE: DNA
<213> ORGANISM: Homo sapiens

<400> SEQUENCE: 557
tgtattcaat cacaccctg                                                19

<210> SEQ ID NO 558
<211> LENGTH: 19
<212> TYPE: DNA
<213> ORGANISM: Homo sapiens

<400> SEQUENCE: 558
tttcatagcc atctttaat                                                19

<210> SEQ ID NO 559
<211> LENGTH: 19
<212> TYPE: DNA
<213> ORGANISM: Homo sapiens

<400> SEQUENCE: 559
aatacaaatc acacagacg                                                19

<210> SEQ ID NO 560
<211> LENGTH: 19
<212> TYPE: DNA
<213> ORGANISM: Homo sapiens

<400> SEQUENCE: 560
tttagttctt caagttcta                                                19

<210> SEQ ID NO 561
<211> LENGTH: 19
<212> TYPE: DNA
<213> ORGANISM: Homo sapiens

<400> SEQUENCE: 561
aaaaagtact gaacattct                                                19

<210> SEQ ID NO 562
<211> LENGTH: 19
<212> TYPE: DNA
<213> ORGANISM: Homo sapiens

<400> SEQUENCE: 562
tatatttgcc agtctgaca                                                19

<210> SEQ ID NO 563
<211> LENGTH: 19
<212> TYPE: DNA
<213> ORGANISM: Homo sapiens

<400> SEQUENCE: 563
atagccatct ttaataact                                                19

<210> SEQ ID NO 564
<211> LENGTH: 19
<212> TYPE: DNA
<213> ORGANISM: Homo sapiens

<400> SEQUENCE: 564
tcaagaagct cctgaagac                                                19

<210> SEQ ID NO 565
<211> LENGTH: 19
<212> TYPE: DNA
<213> ORGANISM: Homo sapiens

<400> SEQUENCE: 565
atgggatggt acataaacc                                                19

<210> SEQ ID NO 566
<211> LENGTH: 19
<212> TYPE: DNA
<213> ORGANISM: Homo sapiens

<400> SEQUENCE: 566
atatttgcca gtctgacag                                                19

<210> SEQ ID NO 567
<211> LENGTH: 19
<212> TYPE: DNA
<213> ORGANISM: Homo sapiens

<400> SEQUENCE: 567
tctaattgaa atgcgactc                                                19

<210> SEQ ID NO 568
<211> LENGTH: 19
<212> TYPE: DNA
<213> ORGANISM: Homo sapiens

<400> SEQUENCE: 568
atgacatcat tgtgtcggt                                                19

<210> SEQ ID NO 569
<211> LENGTH: 19
<212> TYPE: DNA
<213> ORGANISM: Homo sapiens

```
<400> SEQUENCE: 569
taaaccactt gtattggct                                                  19

<210> SEQ ID NO 570
<211> LENGTH: 19
<212> TYPE: DNA
<213> ORGANISM: Homo sapiens

<400> SEQUENCE: 570
attctaattg aaatgcgac                                                  19

<210> SEQ ID NO 571
<211> LENGTH: 19
<212> TYPE: DNA
<213> ORGANISM: Homo sapiens

<400> SEQUENCE: 571
aatcgatcca aaaagtact                                                  19

<210> SEQ ID NO 572
<211> LENGTH: 19
<212> TYPE: DNA
<213> ORGANISM: Homo sapiens

<400> SEQUENCE: 572
aatcacacag acgcctagc                                                  19

<210> SEQ ID NO 573
<211> LENGTH: 19
<212> TYPE: DNA
<213> ORGANISM: Homo sapiens

<400> SEQUENCE: 573
agtcaaatcc tcattaccc                                                  19

<210> SEQ ID NO 574
<211> LENGTH: 19
<212> TYPE: DNA
<213> ORGANISM: Homo sapiens

<400> SEQUENCE: 574
atcgatccaa aaagtactg                                                  19

<210> SEQ ID NO 575
<211> LENGTH: 19
<212> TYPE: DNA
<213> ORGANISM: Homo sapiens

<400> SEQUENCE: 575
attgtgtcgg tttctgatc                                                  19

<210> SEQ ID NO 576
<211> LENGTH: 19
<212> TYPE: DNA
<213> ORGANISM: Homo sapiens

<400> SEQUENCE: 576
tcaagtacat tgcagtttg                                                  19

<210> SEQ ID NO 577
<211> LENGTH: 19
<212> TYPE: DNA
<213> ORGANISM: Homo sapiens
```

```
<400> SEQUENCE: 577
aaatagcttt agcatcctc                                                19

<210> SEQ ID NO 578
<211> LENGTH: 19
<212> TYPE: DNA
<213> ORGANISM: Homo sapiens

<400> SEQUENCE: 578
attcaatcac accctgggc                                                19

<210> SEQ ID NO 579
<211> LENGTH: 19
<212> TYPE: DNA
<213> ORGANISM: Homo sapiens

<400> SEQUENCE: 579
aaggagactt atttctttc                                                19

<210> SEQ ID NO 580
<211> LENGTH: 19
<212> TYPE: DNA
<213> ORGANISM: Homo sapiens

<400> SEQUENCE: 580
tgcatttagt tcttcaagt                                                19

<210> SEQ ID NO 581
<211> LENGTH: 19
<212> TYPE: DNA
<213> ORGANISM: Homo sapiens

<400> SEQUENCE: 581
ttgtaccaat tgaacggat                                                19

<210> SEQ ID NO 582
<211> LENGTH: 19
<212> TYPE: DNA
<213> ORGANISM: Homo sapiens

<400> SEQUENCE: 582
attgaaatgc gactcatgt                                                19

<210> SEQ ID NO 583
<211> LENGTH: 19
<212> TYPE: DNA
<213> ORGANISM: Homo sapiens

<400> SEQUENCE: 583
atataataca aatcacaca                                                19

<210> SEQ ID NO 584
<211> LENGTH: 19
<212> TYPE: DNA
<213> ORGANISM: Homo sapiens

<400> SEQUENCE: 584
atttatgctt ccaatgtgt                                                19

<210> SEQ ID NO 585
<211> LENGTH: 19
<212> TYPE: DNA
```

```
<213> ORGANISM: Homo sapiens

<400> SEQUENCE: 585
aaatcctcat tacccagcg                                               19

<210> SEQ ID NO 586
<211> LENGTH: 19
<212> TYPE: DNA
<213> ORGANISM: Homo sapiens

<400> SEQUENCE: 586
ttccaatgtg ttttcgatg                                               19

<210> SEQ ID NO 587
<211> LENGTH: 19
<212> TYPE: DNA
<213> ORGANISM: Homo sapiens

<400> SEQUENCE: 587
ttttgcattt agttcttca                                               19

<210> SEQ ID NO 588
<211> LENGTH: 19
<212> TYPE: DNA
<213> ORGANISM: Homo sapiens

<400> SEQUENCE: 588
tgtaccaatt gaacggatg                                               19

<210> SEQ ID NO 589
<211> LENGTH: 19
<212> TYPE: DNA
<213> ORGANISM: Homo sapiens

<400> SEQUENCE: 589
aagaagctcc tgaagactc                                               19

<210> SEQ ID NO 590
<211> LENGTH: 19
<212> TYPE: DNA
<213> ORGANISM: Homo sapiens

<400> SEQUENCE: 590
atctgtaaag tcataaata                                               19

<210> SEQ ID NO 591
<211> LENGTH: 19
<212> TYPE: DNA
<213> ORGANISM: Homo sapiens

<400> SEQUENCE: 591
ttctagttcg ggagagtta                                               19

<210> SEQ ID NO 592
<211> LENGTH: 19
<212> TYPE: DNA
<213> ORGANISM: Homo sapiens

<400> SEQUENCE: 592
agactctgga tataccagc                                               19

<210> SEQ ID NO 593
<211> LENGTH: 19
```

<212> TYPE: DNA
<213> ORGANISM: Homo sapiens

<400> SEQUENCE: 593
ataatacaaa tcacacaga                                                19

<210> SEQ ID NO 594
<211> LENGTH: 19
<212> TYPE: DNA
<213> ORGANISM: Homo sapiens

<400> SEQUENCE: 594
ttgtattggc tgtcctggt                                                19

<210> SEQ ID NO 595
<211> LENGTH: 19
<212> TYPE: DNA
<213> ORGANISM: Homo sapiens

<400> SEQUENCE: 595
aaaagttcaa acaccatgt                                                19

<210> SEQ ID NO 596
<211> LENGTH: 19
<212> TYPE: DNA
<213> ORGANISM: Homo sapiens

<400> SEQUENCE: 596
aatcctcatt acccagcgt                                                19

<210> SEQ ID NO 597
<211> LENGTH: 19
<212> TYPE: DNA
<213> ORGANISM: Homo sapiens

<400> SEQUENCE: 597
acagtcaaat cctcattac                                                19

<210> SEQ ID NO 598
<211> LENGTH: 19
<212> TYPE: DNA
<213> ORGANISM: Homo sapiens

<400> SEQUENCE: 598
atagctttag catcctcag                                                19

<210> SEQ ID NO 599
<211> LENGTH: 19
<212> TYPE: DNA
<213> ORGANISM: Homo sapiens

<400> SEQUENCE: 599
tttgcctttt ccaccaaac                                                19

<210> SEQ ID NO 600
<211> LENGTH: 19
<212> TYPE: DNA
<213> ORGANISM: Homo sapiens

<400> SEQUENCE: 600
cttaaaatca agaagctcc                                                19

<210> SEQ ID NO 601

```
<211> LENGTH: 19
<212> TYPE: DNA
<213> ORGANISM: Homo sapiens

<400> SEQUENCE: 601
atcattgtgt cggtttctg                                               19

<210> SEQ ID NO 602
<211> LENGTH: 19
<212> TYPE: DNA
<213> ORGANISM: Homo sapiens

<400> SEQUENCE: 602
ataaagagtg ctgattgag                                               19

<210> SEQ ID NO 603
<211> LENGTH: 19
<212> TYPE: DNA
<213> ORGANISM: Homo sapiens

<400> SEQUENCE: 603
cttgaaaagt tcaaacacc                                               19

<210> SEQ ID NO 604
<211> LENGTH: 19
<212> TYPE: DNA
<213> ORGANISM: Homo sapiens

<400> SEQUENCE: 604
accaaacaat aaagagtgc                                               19

<210> SEQ ID NO 605
<211> LENGTH: 19
<212> TYPE: DNA
<213> ORGANISM: Homo sapiens

<400> SEQUENCE: 605
ttcctttgcc ttttccacc                                               19

<210> SEQ ID NO 606
<211> LENGTH: 19
<212> TYPE: DNA
<213> ORGANISM: Homo sapiens

<400> SEQUENCE: 606
aattgaaatg cgactcatg                                               19

<210> SEQ ID NO 607
<211> LENGTH: 19
<212> TYPE: DNA
<213> ORGANISM: Homo sapiens

<400> SEQUENCE: 607
caaatcctca ttacccagc                                               19

<210> SEQ ID NO 608
<211> LENGTH: 19
<212> TYPE: DNA
<213> ORGANISM: Homo sapiens

<400> SEQUENCE: 608
tgagaagatt atctggaag                                               19
```

-continued

```
<210> SEQ ID NO 609
<211> LENGTH: 19
<212> TYPE: DNA
<213> ORGANISM: Homo sapiens

<400> SEQUENCE: 609
atgcttccaa tgtgttttc                                                19

<210> SEQ ID NO 610
<211> LENGTH: 19
<212> TYPE: DNA
<213> ORGANISM: Homo sapiens

<400> SEQUENCE: 610
ttgaaatgcg actcatgta                                                19

<210> SEQ ID NO 611
<211> LENGTH: 19
<212> TYPE: DNA
<213> ORGANISM: Homo sapiens

<400> SEQUENCE: 611
aaagttcaaa caccatgtg                                                19

<210> SEQ ID NO 612
<211> LENGTH: 19
<212> TYPE: DNA
<213> ORGANISM: Homo sapiens

<400> SEQUENCE: 612
aattgaacgg atggtgtcc                                                19

<210> SEQ ID NO 613
<211> LENGTH: 19
<212> TYPE: DNA
<213> ORGANISM: Homo sapiens

<400> SEQUENCE: 613
attttgcatt tagttcttc                                                19

<210> SEQ ID NO 614
<211> LENGTH: 19
<212> TYPE: DNA
<213> ORGANISM: Homo sapiens

<400> SEQUENCE: 614
atccaaaaag tactgaaca                                                19

<210> SEQ ID NO 615
<211> LENGTH: 19
<212> TYPE: DNA
<213> ORGANISM: Homo sapiens

<400> SEQUENCE: 615
acatgaactt gaatagggg                                                19

<210> SEQ ID NO 616
<211> LENGTH: 19
<212> TYPE: DNA
<213> ORGANISM: Homo sapiens

<400> SEQUENCE: 616
ttggatttat gcttccaat                                                19
```

<210> SEQ ID NO 617
<211> LENGTH: 19
<212> TYPE: DNA
<213> ORGANISM: Homo sapiens

<400> SEQUENCE: 617
attatatttg ccagtctga                                            19

<210> SEQ ID NO 618
<211> LENGTH: 19
<212> TYPE: DNA
<213> ORGANISM: Homo sapiens

<400> SEQUENCE: 618
aatcaagaag ctcctgaag                                            19

<210> SEQ ID NO 619
<211> LENGTH: 19
<212> TYPE: DNA
<213> ORGANISM: Homo sapiens

<400> SEQUENCE: 619
aaacacctct gttggcatg                                            19

<210> SEQ ID NO 620
<211> LENGTH: 19
<212> TYPE: DNA
<213> ORGANISM: Homo sapiens

<400> SEQUENCE: 620
aaatcacaca gacgcctag                                            19

<210> SEQ ID NO 621
<211> LENGTH: 19
<212> TYPE: DNA
<213> ORGANISM: Homo sapiens

<400> SEQUENCE: 621
aagttctagt tcgggagag                                            19

<210> SEQ ID NO 622
<211> LENGTH: 19
<212> TYPE: DNA
<213> ORGANISM: Homo sapiens

<400> SEQUENCE: 622
aaacaataaa gagtgctga                                            19

<210> SEQ ID NO 623
<211> LENGTH: 19
<212> TYPE: DNA
<213> ORGANISM: Homo sapiens

<400> SEQUENCE: 623
aaaatcaaga agctcctga                                            19

<210> SEQ ID NO 624
<211> LENGTH: 19
<212> TYPE: DNA
<213> ORGANISM: Homo sapiens

<400> SEQUENCE: 624
aaaccacttg tattggctg                                            19

```
<210> SEQ ID NO 625
<211> LENGTH: 19
<212> TYPE: DNA
<213> ORGANISM: Homo sapiens

<400> SEQUENCE: 625
atgaacttga ataggggg                                                19

<210> SEQ ID NO 626
<211> LENGTH: 19
<212> TYPE: DNA
<213> ORGANISM: Homo sapiens

<400> SEQUENCE: 626
attacccagc gtgacatga                                               19

<210> SEQ ID NO 627
<211> LENGTH: 19
<212> TYPE: DNA
<213> ORGANISM: Homo sapiens

<400> SEQUENCE: 627
acatcattgt gtcggtttc                                               19

<210> SEQ ID NO 628
<211> LENGTH: 19
<212> TYPE: DNA
<213> ORGANISM: Homo sapiens

<400> SEQUENCE: 628
aaacaccatg tgatagaga                                               19

<210> SEQ ID NO 629
<211> LENGTH: 19
<212> TYPE: DNA
<213> ORGANISM: Homo sapiens

<400> SEQUENCE: 629
cataaatagc tttagcatc                                               19

<210> SEQ ID NO 630
<211> LENGTH: 19
<212> TYPE: DNA
<213> ORGANISM: Homo sapiens

<400> SEQUENCE: 630
tgttttcgat gagatggac                                               19

<210> SEQ ID NO 631
<211> LENGTH: 19
<212> TYPE: DNA
<213> ORGANISM: Homo sapiens

<400> SEQUENCE: 631
agttaatata atacaaatc                                               19

<210> SEQ ID NO 632
<211> LENGTH: 19
<212> TYPE: DNA
<213> ORGANISM: Homo sapiens

<400> SEQUENCE: 632
```
attgcagttt ggatttatg 19

<210> SEQ ID NO 633
<211> LENGTH: 19
<212> TYPE: DNA
<213> ORGANISM: Homo sapiens

<400> SEQUENCE: 633
tgaacattct ggctggtga 19

<210> SEQ ID NO 634
<211> LENGTH: 19
<212> TYPE: DNA
<213> ORGANISM: Homo sapiens

<400> SEQUENCE: 634
atcaagaagc tcctgaaga 19

<210> SEQ ID NO 635
<211> LENGTH: 19
<212> TYPE: DNA
<213> ORGANISM: Homo sapiens

<400> SEQUENCE: 635
acattctaat tgaaatgcg 19

<210> SEQ ID NO 636
<211> LENGTH: 19
<212> TYPE: DNA
<213> ORGANISM: Homo sapiens

<400> SEQUENCE: 636
tgcttccaat gtgttttcg 19

<210> SEQ ID NO 637
<211> LENGTH: 19
<212> TYPE: DNA
<213> ORGANISM: Homo sapiens

<400> SEQUENCE: 637
agccatcttt aataacttc 19

<210> SEQ ID NO 638
<211> LENGTH: 19
<212> TYPE: DNA
<213> ORGANISM: Homo sapiens

<400> SEQUENCE: 638
aaagctctcc ttgtattca 19

<210> SEQ ID NO 639
<211> LENGTH: 19
<212> TYPE: DNA
<213> ORGANISM: Homo sapiens

<400> SEQUENCE: 639
attgaacgga tggtgtcct 19

<210> SEQ ID NO 640
<211> LENGTH: 19
<212> TYPE: DNA
<213> ORGANISM: Homo sapiens

<400> SEQUENCE: 640

| | |
|---|---|
| atgtgttttc gatgagatg | 19 |

<210> SEQ ID NO 641
<211> LENGTH: 19
<212> TYPE: DNA
<213> ORGANISM: Homo sapiens

<400> SEQUENCE: 641

| | |
|---|---|
| aacaataaag agtgctgat | 19 |

<210> SEQ ID NO 642
<211> LENGTH: 19
<212> TYPE: DNA
<213> ORGANISM: Homo sapiens

<400> SEQUENCE: 642

| | |
|---|---|
| aagttcaaac accatgtga | 19 |

<210> SEQ ID NO 643
<211> LENGTH: 19
<212> TYPE: DNA
<213> ORGANISM: Homo sapiens

<400> SEQUENCE: 643

| | |
|---|---|
| tggtgatttt gcatttagt | 19 |

<210> SEQ ID NO 644
<211> LENGTH: 19
<212> TYPE: DNA
<213> ORGANISM: Homo sapiens

<400> SEQUENCE: 644

| | |
|---|---|
| agagtgctga ttgagtaac | 19 |

<210> SEQ ID NO 645
<211> LENGTH: 19
<212> TYPE: DNA
<213> ORGANISM: Homo sapiens

<400> SEQUENCE: 645

| | |
|---|---|
| aatagcttta gcatcctca | 19 |

<210> SEQ ID NO 646
<211> LENGTH: 19
<212> TYPE: DNA
<213> ORGANISM: Homo sapiens

<400> SEQUENCE: 646

| | |
|---|---|
| aaccacttgt attggctgt | 19 |

<210> SEQ ID NO 647
<211> LENGTH: 19
<212> TYPE: DNA
<213> ORGANISM: Homo sapiens

<400> SEQUENCE: 647

| | |
|---|---|
| ttgaataggg gggtaaaca | 19 |

<210> SEQ ID NO 648
<211> LENGTH: 19
<212> TYPE: DNA
<213> ORGANISM: Homo sapiens

```
<400> SEQUENCE: 648
atataccagc tttgtacca                                                   19

<210> SEQ ID NO 649
<211> LENGTH: 19
<212> TYPE: DNA
<213> ORGANISM: Homo sapiens

<400> SEQUENCE: 649
atgtgataga gatgggatg                                                   19

<210> SEQ ID NO 650
<211> LENGTH: 19
<212> TYPE: DNA
<213> ORGANISM: Homo sapiens

<400> SEQUENCE: 650
aaagtcataa atagcttta                                                   19

<210> SEQ ID NO 651
<211> LENGTH: 19
<212> TYPE: DNA
<213> ORGANISM: Homo sapiens

<400> SEQUENCE: 651
aataaagagt gctgattga                                                   19

<210> SEQ ID NO 652
<211> LENGTH: 19
<212> TYPE: DNA
<213> ORGANISM: Homo sapiens

<400> SEQUENCE: 652
gacatgaact tgaataggg                                                   19

<210> SEQ ID NO 653
<211> LENGTH: 19
<212> TYPE: DNA
<213> ORGANISM: Homo sapiens

<400> SEQUENCE: 653
acataaacca cttgtattg                                                   19

<210> SEQ ID NO 654
<211> LENGTH: 19
<212> TYPE: DNA
<213> ORGANISM: Homo sapiens

<400> SEQUENCE: 654
catagccatc tttaataac                                                   19

<210> SEQ ID NO 655
<211> LENGTH: 19
<212> TYPE: DNA
<213> ORGANISM: Homo sapiens

<400> SEQUENCE: 655
aatgcgactc atgtagaat                                                   19

<210> SEQ ID NO 656
<211> LENGTH: 19
<212> TYPE: DNA
<213> ORGANISM: Homo sapiens
```

```
<400> SEQUENCE: 656
caagtacatt gcagtttgg                                              19

<210> SEQ ID NO 657
<211> LENGTH: 19
<212> TYPE: DNA
<213> ORGANISM: Homo sapiens

<400> SEQUENCE: 657
attttcatag ccatcttta                                              19

<210> SEQ ID NO 658
<211> LENGTH: 19
<212> TYPE: DNA
<213> ORGANISM: Homo sapiens

<400> SEQUENCE: 658
agtttggatt tatgcttcc                                              19

<210> SEQ ID NO 659
<211> LENGTH: 19
<212> TYPE: DNA
<213> ORGANISM: Homo sapiens

<400> SEQUENCE: 659
cataaaccac ttgtattgg                                              19

<210> SEQ ID NO 660
<211> LENGTH: 19
<212> TYPE: DNA
<213> ORGANISM: Homo sapiens

<400> SEQUENCE: 660
aacaccatgt gatagagat                                              19

<210> SEQ ID NO 661
<211> LENGTH: 19
<212> TYPE: DNA
<213> ORGANISM: Homo sapiens

<400> SEQUENCE: 661
acaccatgtg atagagatg                                              19

<210> SEQ ID NO 662
<211> LENGTH: 19
<212> TYPE: DNA
<213> ORGANISM: Homo sapiens

<400> SEQUENCE: 662
atgagatgga cttcctttg                                              19

<210> SEQ ID NO 663
<211> LENGTH: 19
<212> TYPE: DNA
<213> ORGANISM: Homo sapiens

<400> SEQUENCE: 663
agctttgtac caattgaac                                              19

<210> SEQ ID NO 664
<211> LENGTH: 19
<212> TYPE: DNA
```

```
<213> ORGANISM: Homo sapiens

<400> SEQUENCE: 664
acagacgcct agcattttc                                                19

<210> SEQ ID NO 665
<211> LENGTH: 19
<212> TYPE: DNA
<213> ORGANISM: Homo sapiens

<400> SEQUENCE: 665
agttctagtt cgggagagt                                                19

<210> SEQ ID NO 666
<211> LENGTH: 19
<212> TYPE: DNA
<213> ORGANISM: Homo sapiens

<400> SEQUENCE: 666
aaagagtgct gattgagta                                                19

<210> SEQ ID NO 667
<211> LENGTH: 19
<212> TYPE: DNA
<213> ORGANISM: Homo sapiens

<400> SEQUENCE: 667
accatgtgat agagatggg                                                19

<210> SEQ ID NO 668
<211> LENGTH: 19
<212> TYPE: DNA
<213> ORGANISM: Homo sapiens

<400> SEQUENCE: 668
atagagatgg gatggtaca                                                19

<210> SEQ ID NO 669
<211> LENGTH: 19
<212> TYPE: DNA
<213> ORGANISM: Homo sapiens

<400> SEQUENCE: 669
aagattatct ggaaggaga                                                19

<210> SEQ ID NO 670
<211> LENGTH: 19
<212> TYPE: DNA
<213> ORGANISM: Homo sapiens

<400> SEQUENCE: 670
agattatctg gaaggagac                                                19

<210> SEQ ID NO 671
<211> LENGTH: 19
<212> TYPE: DNA
<213> ORGANISM: Homo sapiens

<400> SEQUENCE: 671
cacttttgtc cttaaaatc                                                19

<210> SEQ ID NO 672
<211> LENGTH: 19
```

```
<212> TYPE: DNA
<213> ORGANISM: Homo sapiens

<400> SEQUENCE: 672
gatataccag ctttgtacc                                              19

<210> SEQ ID NO 673
<211> LENGTH: 19
<212> TYPE: DNA
<213> ORGANISM: Homo sapiens

<400> SEQUENCE: 673
aagtacattg cagtttgga                                              19

<210> SEQ ID NO 674
<211> LENGTH: 19
<212> TYPE: DNA
<213> ORGANISM: Homo sapiens

<400> SEQUENCE: 674
aacattctgg ctggtgaca                                              19

<210> SEQ ID NO 675
<211> LENGTH: 19
<212> TYPE: DNA
<213> ORGANISM: Homo sapiens

<400> SEQUENCE: 675
gtattcaatc acaccctgg                                              19

<210> SEQ ID NO 676
<211> LENGTH: 19
<212> TYPE: DNA
<213> ORGANISM: Homo sapiens

<400> SEQUENCE: 676
atcacaccct gggccattg                                              19

<210> SEQ ID NO 677
<211> LENGTH: 19
<212> TYPE: DNA
<213> ORGANISM: Homo sapiens

<400> SEQUENCE: 677
agcatcctca gcacttttg                                              19

<210> SEQ ID NO 678
<211> LENGTH: 19
<212> TYPE: DNA
<213> ORGANISM: Homo sapiens

<400> SEQUENCE: 678
acttgtattg gctgtcctg                                              19

<210> SEQ ID NO 679
<211> LENGTH: 19
<212> TYPE: DNA
<213> ORGANISM: Homo sapiens

<400> SEQUENCE: 679
aatgtgtttt cgatgagat                                              19

<210> SEQ ID NO 680
```

```
<211> LENGTH: 19
<212> TYPE: DNA
<213> ORGANISM: Homo sapiens

<400> SEQUENCE: 680
acattctggc tggtgacag                                                19

<210> SEQ ID NO 681
<211> LENGTH: 19
<212> TYPE: DNA
<213> ORGANISM: Homo sapiens

<400> SEQUENCE: 681
caattgaacg gatggtgtc                                                19

<210> SEQ ID NO 682
<211> LENGTH: 19
<212> TYPE: DNA
<213> ORGANISM: Homo sapiens

<400> SEQUENCE: 682
accaattgaa cggatggtg                                                19

<210> SEQ ID NO 683
<211> LENGTH: 19
<212> TYPE: DNA
<213> ORGANISM: Homo sapiens

<400> SEQUENCE: 683
gagaagatta tctggaagg                                                19

<210> SEQ ID NO 684
<211> LENGTH: 19
<212> TYPE: DNA
<213> ORGANISM: Homo sapiens

<400> SEQUENCE: 684
agctttagca tcctcagca                                                19

<210> SEQ ID NO 685
<211> LENGTH: 19
<212> TYPE: DNA
<213> ORGANISM: Homo sapiens

<400> SEQUENCE: 685
agaagattat ctggaagga                                                19

<210> SEQ ID NO 686
<211> LENGTH: 19
<212> TYPE: DNA
<213> ORGANISM: Homo sapiens

<400> SEQUENCE: 686
cttgaatagg ggggtaaac                                                19

<210> SEQ ID NO 687
<211> LENGTH: 19
<212> TYPE: DNA
<213> ORGANISM: Homo sapiens

<400> SEQUENCE: 687
gacttccttt gcctttcc                                                 19
```

```
<210> SEQ ID NO 688
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 688
cuaucacaug guguuugaa                                                19

<210> SEQ ID NO 689
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 689
caauacaagu gguuuaugu                                                19

<210> SEQ ID NO 690
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 690
ucuaucacau gguguuuga                                                19

<210> SEQ ID NO 691
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 691
ggcaaauaua augaaagaa                                                19

<210> SEQ ID NO 692
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 692
uguucaguac uuuuuggau                                                19

<210> SEQ ID NO 693
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 693
auuggaagca uaaauccaa                                                    19

<210> SEQ ID NO 694
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 694
ccaucccauc ucuaucaca                                                    19

<210> SEQ ID NO 695
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 695
caucccaucu cuaucacau                                                    19

<210> SEQ ID NO 696
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 696
ggcaaauaua augaaagaa                                                    19

<210> SEQ ID NO 697
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 697
gcaaauauaa ugaaagaaa                                                    19

<210> SEQ ID NO 698
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: PDK1 siRNA

<400> SEQUENCE: 698
caaauauaau gaaagaaau                    19

<210> SEQ ID NO 699
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 699
cauuggaagc auaaaucca                    19

<210> SEQ ID NO 700
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 700
caagugguuu auguaccau                    19

<210> SEQ ID NO 701
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 701
gguuuaugua ccaucccau                    19

<210> SEQ ID NO 702
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 702
uaccauccca ucucuauca                    19

<210> SEQ ID NO 703
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 703
cccaucucua ucacauggu                                          19

<210> SEQ ID NO 704
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 704
caucucuauc acauggugu                                          19

<210> SEQ ID NO 705
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 705
gcaaauauaa ugaaagaaa                                          19

<210> SEQ ID NO 706
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 706
caaatataat gaaagaaat                                          19

<210> SEQ ID NO 707
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 707
tggcaaatat aatgaaaga                                          19

<210> SEQ ID NO 708
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 708
ggggtggatc ctgtcacca                                          19

<210> SEQ ID NO 709

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 709
ttggaagcat aaatccaaa                                                      19

<210> SEQ ID NO 710
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 710
aatacaagtg gtttatgta                                                      19

<210> SEQ ID NO 711
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 711
ggtttatgta ccatcccat                                                      19

<210> SEQ ID NO 712
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 712
aaauauaaug aaagaaaua                                                      19

<210> SEQ ID NO 713
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 713
gguacaaagc ugguauauc                                                      19

<210> SEQ ID NO 714
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: PDK1 siRNA

<400> SEQUENCE: 714
gcuaaagcua uuuaugacu                                                    19

<210> SEQ ID NO 715
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 715
cuaaagcuau uuaugacuu                                                    19

<210> SEQ ID NO 716
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 716
uaaagcuauu uaugacuuu                                                    19

<210> SEQ ID NO 717
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 717
aaagcuauuu augacuuua                                                    19

<210> SEQ ID NO 718
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 718
agcuauuuau gacuuuaca                                                    19

<210> SEQ ID NO 719
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

-continued

<400> SEQUENCE: 719
cuauuuauga cuuuacaga                                                19

<210> SEQ ID NO 720
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 720
auuuaugacu uuacagaua                                                19

<210> SEQ ID NO 721
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 721
uuaugacuuu acagauacu                                                19

<210> SEQ ID NO 722
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 722
cugugauacg gaucagaaa                                                19

<210> SEQ ID NO 723
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 723
ucagaaaccg acacaauga                                                19

<210> SEQ ID NO 724
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 724
ccagaauguu caguacuuu                                                19

```
<210> SEQ ID NO 725
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 725
cagaauguuc aguacuuuu                                                19

<210> SEQ ID NO 726
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 726
agaauguuca guacuuuuu                                                19

<210> SEQ ID NO 727
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 727
gcauuucaau uagaauguu                                                19

<210> SEQ ID NO 728
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 728
cauuucaauu agaauguua                                                19

<210> SEQ ID NO 729
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 729
caauuagaau guuacucaa                                                19

<210> SEQ ID NO 730
<211> LENGTH: 19
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 730
uuagaauguu acucaauca                                                    19

<210> SEQ ID NO 731
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 731
acucaaucag cacucuuua                                                    19

<210> SEQ ID NO 732
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 732
ucaaucagca cucuuuauu                                                    19

<210> SEQ ID NO 733
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 733
caucucaucg aaaacacau                                                    19

<210> SEQ ID NO 734
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 734
aaacacauug gaagcauaa                                                    19

<210> SEQ ID NO 735
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued

```
      oligonucleotide
<220> FEATURE:
<223> OTHER INFORMATION: PDK1 siRNA

<400> SEQUENCE: 735
aacacauugg aagcauaaa                                                  19

<210> SEQ ID NO 736
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 736
acacauugga agcauaaau                                                  19

<210> SEQ ID NO 737
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 737
gcaauguacu ugaaguuau                                                  19

<210> SEQ ID NO 738
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 738
caauguacuu gaaguuauu                                                  19

<210> SEQ ID NO 739
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 739
auguacuuga aguuauuaa                                                  19

<210> SEQ ID NO 740
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 740
uguacuugaa guuauuaaa                                             19

<210> SEQ ID NO 741
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 741
uacuugaagu uauuaaga                                              19

<210> SEQ ID NO 742
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 742
uuaaagaugg cuaugaaaa                                             19

<210> SEQ ID NO 743
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 743
uaaagauggc uaugaaaau                                             19

<210> SEQ ID NO 744
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 744
gugugauuug uauuauauu                                             19

<210> SEQ ID NO 745
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 745
ugugauuugu auuauauua                                             19
```

```
<210> SEQ ID NO 746
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 746
gugauuugua uuauauuaa                                                19

<210> SEQ ID NO 747
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 747
gauuuguauu auauuaacu                                                19

<210> SEQ ID NO 748
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 748
uuaacucucc cgaacuaga                                                19

<210> SEQ ID NO 749
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 749
ccgaacuaga acuugaaga                                                19

<210> SEQ ID NO 750
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 750
cgaacuagaa cuugaagaa                                                19

<210> SEQ ID NO 751
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 751
acuagaacuu gaagaacua                                                19

<210> SEQ ID NO 752
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 752
cuagaacuug aagaacuaa                                                19

<210> SEQ ID NO 753
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 753
agaacuugaa gaacuaaau                                                19

<210> SEQ ID NO 754
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 754
cuugaagaac uaaaugcaa                                                19

<210> SEQ ID NO 755
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 755
ugaagaacua aaugcaaaa                                                19

<210> SEQ ID NO 756
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: PDK1 siRNA

<400> SEQUENCE: 756
gaagaacuaa augcaaaau                                                  19

<210> SEQ ID NO 757
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 757
agaacuaaau gcaaaauca                                                  19

<210> SEQ ID NO 758
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 758
gccaauacaa gugguuuau                                                  19

<210> SEQ ID NO 759
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 759
guguuugaac uuuucaaga                                                  19

<210> SEQ ID NO 760
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 760
uguuugaacu uuucaagaa                                                  19

<210> SEQ ID NO 761
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 761
```
guguuuaccc cccuauuca                    19

<210> SEQ ID NO 762
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 762
uguuuacccc ccuauucaa                    19

<210> SEQ ID NO 763
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 763
ggguaaugag gauuugacu                    19

<210> SEQ ID NO 764
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 764
gauuugacug ugaagauga                    19

<210> SEQ ID NO 765
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 765
gucagacugg caaauauaa                    19

<210> SEQ ID NO 766
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 766
ucagacuggc aaauauaau                    19

```
<210> SEQ ID NO 767
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 767
agacuggcaa auauaauga                                               19

<210> SEQ ID NO 768
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 768
gacuggcaaa uauaaugaa                                               19

<210> SEQ ID NO 769
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 769
acuggcaaau auaaugaaa                                               19

<210> SEQ ID NO 770
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 770
uggcaaauau aaugaaaga                                               19

<210> SEQ ID NO 771
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 771
ggcaaauaua augaaagaa                                               19

<210> SEQ ID NO 772
<211> LENGTH: 19
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 772
gcaaauauaa ugaaagaaa                                                     19

<210> SEQ ID NO 773
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 773
caaauauaau gaaagaaau                                                     19

<210> SEQ ID NO 774
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 774
aaauauaaug aaagaaaua                                                     19

<210> SEQ ID NO 775
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 775
gaaagaaaua agucuccuu                                                     19

<210> SEQ ID NO 776
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 776
agaaauaagu cuccuucca                                                     19

<210> SEQ ID NO 777
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: PDK1 siRNA

<400> SEQUENCE: 777
aaauaagucu ccuuccaga                                                    19

<210> SEQ ID NO 778
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 778
auaagucucc uuccagaua                                                    19

<210> SEQ ID NO 779
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 779
uaagucuccu uccagauaa                                                    19

<210> SEQ ID NO 780
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 780
aagucuccuu ccagauaau                                                    19

<210> SEQ ID NO 781
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 781
gucuccuucc agauaaucu                                                    19

<210> SEQ ID NO 782
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 782
```
cuuccagaua aucuucuca                                            19

<210> SEQ ID NO 783
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 783
agauaaucuu cucaggaca                                            19

<210> SEQ ID NO 784
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 784
ucaggacacc auccguuca                                            19

<210> SEQ ID NO 785
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 785
caggacacca uccguucaa                                            19

<210> SEQ ID NO 786
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 786
aggacaccau ccguucaau                                            19

<210> SEQ ID NO 787
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 787
ggacaccauc cguucaauu                                            19

<210> SEQ ID NO 788

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 788
caccauccgu ucaauuggu                                                 19

<210> SEQ ID NO 789
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 789
accauccguu caauuggua                                                 19

<210> SEQ ID NO 790
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 790
cauccguuca auugguaca                                                 19

<210> SEQ ID NO 791
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 791
uccguucaau ugguacaaa                                                 19

<210> SEQ ID NO 792
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 792
guucaauugg uacaaagcu                                                 19

<210> SEQ ID NO 793
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: PDK1 siRNA

<400> SEQUENCE: 793
uugguacaaa gcugguaua                                                  19

<210> SEQ ID NO 794
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 794
gguacaaagc ugguauauc                                                  19

<210> SEQ ID NO 795
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 795
caaagcuggu auaccaga                                                   19

<210> SEQ ID NO 796
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 796
gcugguauau ccagagucu                                                  19

<210> SEQ ID NO 797
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 797
cugguauauc cagagucuu                                                  19

<210> SEQ ID NO 798
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

-continued

<400> SEQUENCE: 798
gguauaucca gagucuuca                                          19

<210> SEQ ID NO 799
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 799
ccagagucuu caggagcuu                                          19

<210> SEQ ID NO 800
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 800
gagucuucag gagcuucuu                                          19

<210> SEQ ID NO 801
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 801 gcuucagga gcuucuuga                                           19

<210> SEQ ID NO 802
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 802
cuucaggagc uucuugauu                                          19

<210> SEQ ID NO 803
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 803
uucaggagcu ucuugauuu                                          19

```
<210> SEQ ID NO 804
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 804
ucaggagcuu cuugauuuu                                               19

<210> SEQ ID NO 805
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 805
caggagcuuc uugauuuua                                               19

<210> SEQ ID NO 806
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 806
aggagcuucu ugauuuaa                                                19

<210> SEQ ID NO 807
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 807
ggagcuucuu gauuuaag                                                19

<210> SEQ ID NO 808
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 808
cuucuugauu uuaaggaca                                               19

<210> SEQ ID NO 809
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 809
cuugauuuua aggacaaaa                                                       19

<210> SEQ ID NO 810
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 810
ggacaaaagu gcugaggau                                                       19

<210> SEQ ID NO 811
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 811
aaagugcuga ggaugcuaa                                                       19

<210> SEQ ID NO 812
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 812
aagugcugag gaugcuaaa                                                       19

<210> SEQ ID NO 813
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 813
gcugaggaug cuaaagcua                                                       19

<210> SEQ ID NO 814
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: PDK1 siRNA

<400> SEQUENCE: 814
cugaggaugc uaaagcuau                                              19

<210> SEQ ID NO 815
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 815
ugaggaugcu aaagcuauu                                              19

<210> SEQ ID NO 816
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 816
gaggaugcua aagcuauuu                                              19

<210> SEQ ID NO 817
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 817
aggaugcuaa agcuauuua                                              19

<210> SEQ ID NO 818
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 818
ggaugcuaaa gcuauuuau                                              19

<210> SEQ ID NO 819
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 819
gcuaaagcua uuuaugacu                                                    19

<210> SEQ ID NO 820
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 820
cuaaagcuau uuaugacuu                                                    19

<210> SEQ ID NO 821
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 821
uaaagcuauu uaugacuuu                                                    19

<210> SEQ ID NO 822
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 822
aaagcuauuu augacuuua                                                    19

<210> SEQ ID NO 823
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 823
agcuauuuau gacuuuaca                                                    19

<210> SEQ ID NO 824
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 824
cuauuuauga cuuuacaga                                                    19
```

-continued

<210> SEQ ID NO 825
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 825
auuuaugacu uuacagaua                                                  19

<210> SEQ ID NO 826
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 826
uuaugacuuu acagauacu                                                  19

<210> SEQ ID NO 827
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 827
gacuuuacag auacuguga                                                  19

<210> SEQ ID NO 828
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 828
cuuuacagau acugugaua                                                  19

<210> SEQ ID NO 829
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 829
cagauacugu gauacggau                                                  19

<210> SEQ ID NO 830
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 830
cugugauacg gaucagaaa                                                       19

<210> SEQ ID NO 831
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 831
gauacggauc agaaaccga                                                       19

<210> SEQ ID NO 832
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 832
cggaucagaa accgacaca                                                       19

<210> SEQ ID NO 833
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 833
ggaucagaaa ccgacacaa                                                       19

<210> SEQ ID NO 834
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 834
gaucagaaac cgacacaau                                                       19

<210> SEQ ID NO 835
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: PDK1 siRNA

<400> SEQUENCE: 835
ucagaaaccg acacaauga                                          19

<210> SEQ ID NO 836
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 836
cagaaaccga cacaaugau                                          19

<210> SEQ ID NO 837
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 837
gaaaccgaca caaugaugu                                          19

<210> SEQ ID NO 838
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 838
ccgacacaau gaugucauu                                          19

<210> SEQ ID NO 839
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 839
cacaaugaug ucauccca                                           19

<210> SEQ ID NO 840
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 840
```

-continued caaugauguc auucccaca					19

<210> SEQ ID NO 841
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 841
augaugucau ucccacaau					19

<210> SEQ ID NO 842
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 842
ccacaauggc ccaggguguu					19

<210> SEQ ID NO 843
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 843
caauggccca ggguguagau					19

<210> SEQ ID NO 844
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 844
ggcccagggu gugauugaa					19

<210> SEQ ID NO 845
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 845
gcccagggug ugauugaau					19

```
<210> SEQ ID NO 846
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 846
cccagggugu gauugaaua                                              19

<210> SEQ ID NO 847
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 847
caggguguga uugaauaca                                              19

<210> SEQ ID NO 848
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 848
agggugugau ugaauacaa                                              19

<210> SEQ ID NO 849
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 849
gugugauuga auacaagga                                              19

<210> SEQ ID NO 850
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 850
gugauugaau acaaggaga                                              19

<210> SEQ ID NO 851
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 851
ggagagcuuu gggguggau                                                        19

<210> SEQ ID NO 852
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 852
gcuuuggggu ggauccugu                                                        19

<210> SEQ ID NO 853
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 853 ggggguggauc cugucacca                                                       19

<210> SEQ ID NO 854
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 854
cugucaccag ccagaaugu                                                        19

<210> SEQ ID NO 855
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 855
ucaccagcca gaauguuca                                                        19

<210> SEQ ID NO 856
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: PDK1 siRNA

<400> SEQUENCE: 856
ccagccagaa uguucagua                                            19

<210> SEQ ID NO 857
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 857
cagccagaau guucaguac                                            19

<210> SEQ ID NO 858
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 858
gccagaaugu ucaguacuu                                            19

<210> SEQ ID NO 859
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 859
ccagaauguu caguacuuu                                            19

<210> SEQ ID NO 860
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 860
cagaauguuc aguacuuuu                                            19

<210> SEQ ID NO 861
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 861
```
agaauguuca guacuuuuu 19

<210> SEQ ID NO 862
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 862
ucaguacuuu uuggaucga 19

<210> SEQ ID NO 863
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 863
caguacuuuu uggaucgau 19

<210> SEQ ID NO 864
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 864
uuggaucgau ucuacauga 19

<210> SEQ ID NO 865
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 865
ggaucgauuc uacaugagu 19

<210> SEQ ID NO 866
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 866
cuacaugagu cgcauuuca 19

<210> SEQ ID NO 867

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 867
uacaugaguc gcauuucaa                                                   19

<210> SEQ ID NO 868
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 868
acaugagucg cauuucaau                                                   19

<210> SEQ ID NO 869
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 869
caugagucgc auuucaauu                                                   19

<210> SEQ ID NO 870
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 870
augagucgca uuucaauua                                                   19

<210> SEQ ID NO 871
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 871
ugagucgcau uucaauuag                                                   19

<210> SEQ ID NO 872
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: PDK1 siRNA

<400> SEQUENCE: 872
gagucgcauu ucaauuaga                                                    19

<210> SEQ ID NO 873
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 873
agucgcauuu caauuagaa                                                    19

<210> SEQ ID NO 874
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 874
gucgcauuuc aauuagaau                                                    19

<210> SEQ ID NO 875
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 875
cgcauuucaa uuagaaugu                                                    19

<210> SEQ ID NO 876
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 876
gcauuucaau uagaauguu                                                    19

<210> SEQ ID NO 877
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 877
cauuucaauu agaauguua                                               19

<210> SEQ ID NO 878
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 878
caauuagaau guuacucaa                                               19

<210> SEQ ID NO 879
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 879
uuagaauguu acucaauca                                               19

<210> SEQ ID NO 880
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 880
gaauguuacu caaucagca                                               19

<210> SEQ ID NO 881
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 881
acucaaucag cacucuuua                                               19

<210> SEQ ID NO 882
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 882
cucaaucagc acucuuuau                                               19
```

<210> SEQ ID NO 883
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 883
ucaaucagca cucuuuauu                                              19

<210> SEQ ID NO 884
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 884
ucagcacucu uuauuguuu                                              19

<210> SEQ ID NO 885
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 885
gcacucuuua uuguuuggu                                              19

<210> SEQ ID NO 886
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 886
cuuuauuguu ugguggaaa                                              19

<210> SEQ ID NO 887
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 887
uuuauuguuu gguggaaaa                                              19

<210> SEQ ID NO 888
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 888 guuggugga aaaggcaaa                                                  19

<210> SEQ ID NO 889
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 889
gguggaaaag gcaaaggaa                                                 19

<210> SEQ ID NO 890
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 890
aggcaaagga aguccaucu                                                 19

<210> SEQ ID NO 891
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 891
ggcaaaggaa guccaucuc                                                 19

<210> SEQ ID NO 892
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 892
gcaaaggaag uccaucuca                                                 19

<210> SEQ ID NO 893
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: PDK1 siRNA

<400> SEQUENCE: 893
caaaggaagu ccaucucau                                            19

<210> SEQ ID NO 894
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 894
ggaaguccau cucaucgaa                                            19

<210> SEQ ID NO 895
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 895
gaaguccauc ucaucgaaa                                            19

<210> SEQ ID NO 896
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 896
aaguccaucu caucgaaaa                                            19

<210> SEQ ID NO 897
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 897
guccaucuca ucgaaaaca                                            19

<210> SEQ ID NO 898
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 898
ccaucucauc gaaaacaca                                                    19

<210> SEQ ID NO 899
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 899
caucucaucg aaaacacau                                                    19

<210> SEQ ID NO 900
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 900
aucucaucga aaacacauu                                                    19

<210> SEQ ID NO 901
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 901
ucaucgaaaa cacauugga                                                    19

<210> SEQ ID NO 902
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 902
caucgaaaac acauuggaa                                                    19

<210> SEQ ID NO 903
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 903
cgaaaacaca uuggaagca                                                    19
```

<210> SEQ ID NO 904
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 904
gaaaacacau uggaagcau                                                19

<210> SEQ ID NO 905
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 905
aaaacacauu ggaagcaua                                                19

<210> SEQ ID NO 906
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 906
aaacacauug gaagcauaa                                                19

<210> SEQ ID NO 907
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 907
aacacauugg aagcauaaa                                                19

<210> SEQ ID NO 908
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 908
acacauugga agcauaaau                                                19

<210> SEQ ID NO 909
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 909
cauuggaagc auaaaucca                                            19

<210> SEQ ID NO 910
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 910
ggaagcauaa auccaaacu                                            19

<210> SEQ ID NO 911
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 911
gcauaaaucc aaacugcaa                                            19

<210> SEQ ID NO 912
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 912
cauaaaucca aacugcaau                                            19

<210> SEQ ID NO 913
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 913
aaauccaaac ugcaaugua                                            19

<210> SEQ ID NO 914
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: PDK1 siRNA

<400> SEQUENCE: 914
caaacugcaa uguacuuga                                               19

<210> SEQ ID NO 915
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 915
aaacugcaau guacuugaa                                               19

<210> SEQ ID NO 916
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 916
cugcaaugua cuugaaguu                                               19

<210> SEQ ID NO 917
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 917
gcaauguacu ugaaguuau                                               19

<210> SEQ ID NO 918
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 918
caauguacuu gaaguuauu                                               19

<210> SEQ ID NO 919
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 919
```
auguacuuga aguuauuaa                                          19

<210> SEQ ID NO 920
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 920
uguacuugaa guuauuaaa                                          19

<210> SEQ ID NO 921
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 921
uacuugaagu uauuaaga                                           19

<210> SEQ ID NO 922
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 922
uauuaaagau ggcuaugaa                                          19

<210> SEQ ID NO 923
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 923
uuaaagaugg cuaugaaaa                                          19

<210> SEQ ID NO 924
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 924
uaaagauggc uaugaaaau                                          19

```
<210> SEQ ID NO 925
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 925
agauggcuau gaaaaugcu                                                  19

<210> SEQ ID NO 926
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 926
gauggcuaug aaaaugcua                                                  19

<210> SEQ ID NO 927
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 927
gcuaggcguc ugugugauu                                                  19

<210> SEQ ID NO 928
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 928
cuaggcgucu gugugauuu                                                  19

<210> SEQ ID NO 929
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 929
ggcgucugug ugauuugua                                                  19

<210> SEQ ID NO 930
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 930
gcgucugugu gauuuguau                                                       19

<210> SEQ ID NO 931
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 931
cgucugugug auuuguauu                                                       19

<210> SEQ ID NO 932
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 932
gucuguguga uuuguauua                                                       19

<210> SEQ ID NO 933
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 933
cugugugauu uguauuaua                                                       19

<210> SEQ ID NO 934
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 934
ugugugauuu guauuauau                                                       19

<210> SEQ ID NO 935
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

-continued

<223> OTHER INFORMATION: PDK1 siRNA

<400> SEQUENCE: 935
gugugauuug uauuauauu                                                        19

<210> SEQ ID NO 936
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 936
ugugauuugu auuauauua                                                        19

<210> SEQ ID NO 937
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 937
gugauuugua uuauauuaa                                                        19

<210> SEQ ID NO 938
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 938
gauuuguauu auauuaacu                                                        19

<210> SEQ ID NO 939
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 939
uauuaacucu cccgaacua                                                        19

<210> SEQ ID NO 940
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 940
uuaacucucc cgaacuaga                                            19

<210> SEQ ID NO 941
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 941
uaacucuccc gaacuagaa                                            19

<210> SEQ ID NO 942
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 942
cucucccgaa cuagaacuu                                            19

<210> SEQ ID NO 943
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 943
cucccgaacu agaacuuga                                            19

<210> SEQ ID NO 944
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 944
ucccgaacua gaacuugaa                                            19

<210> SEQ ID NO 945
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 945
cccgaacuag aacuugaag                                            19

<210> SEQ ID NO 946

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 946
ccgaacuaga acugaaga                                                       19

<210> SEQ ID NO 947
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 947
cgaacuagaa cuugaagaa                                                      19

<210> SEQ ID NO 948
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 948
acuagaacuu gaagaacua                                                      19

<210> SEQ ID NO 949
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 949
cuagaacuug aagaacuaa                                                      19

<210> SEQ ID NO 950
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 950
agaacuugaa gaacuaaau                                                      19

<210> SEQ ID NO 951
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: PDK1 siRNA

<400> SEQUENCE: 951
cuugaagaac uaaaugcaa                                                19

<210> SEQ ID NO 952
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 952
ugaagaacua aaugcaaaa                                                19

<210> SEQ ID NO 953
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 953
gaagaacuaa augcaaaau                                                19

<210> SEQ ID NO 954
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 954
agaacuaaau gcaaaauca                                                19

<210> SEQ ID NO 955
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 955
caccaggaca gccaauaca                                                19

<210> SEQ ID NO 956
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 956
accaggacag ccaauacaa                                               19

<210> SEQ ID NO 957
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 957
caggacagcc aauacaagu                                               19

<210> SEQ ID NO 958
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 958
gacagccaau acaaguggu                                               19

<210> SEQ ID NO 959
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 959
cagccaauac aagugguuu                                               19

<210> SEQ ID NO 960
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 960
agccaauaca agugguuua                                               19

<210> SEQ ID NO 961
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 961
gccaauacaa gugguuuau                                               19
```

<210> SEQ ID NO 962
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 962 caaucaagu gguuuaugu                                                   19

<210> SEQ ID NO 963
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 963
acaagugguu uauguacca                                                  19

<210> SEQ ID NO 964
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 964
ucuaucacau gguguuuga                                                  19

<210> SEQ ID NO 965
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 965
cuaucacaug guguuugaa                                                  19

<210> SEQ ID NO 966
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 966
ucacauggug uuugaacuu                                                  19

<210> SEQ ID NO 967
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 967
cacauggugu uugaacuuu                                                   19

<210> SEQ ID NO 968
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 968
acaugguguu ugaacuuuu                                                   19

<210> SEQ ID NO 969
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 969
guguuugaac uuucaaga                                                    19

<210> SEQ ID NO 970
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 970
uguuugaacu uuucaagaa                                                   19

<210> SEQ ID NO 971
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 971 guugaacuu uucaagaau                                                    19

<210> SEQ ID NO 972
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: PDK1 siRNA

<400> SEQUENCE: 972
gaacuuuuca agaaugcaa                                            19

<210> SEQ ID NO 973
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 973
cuuuucaaga augcaauga                                            19

<210> SEQ ID NO 974
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 974
augcaaugag agccacuau                                            19

<210> SEQ ID NO 975
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 975
caaugagagc cacuaugga                                            19

<210> SEQ ID NO 976
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 976
ugagagccac uauggaaca                                            19

<210> SEQ ID NO 977
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 977
gagccacuau ggaacacca                                                  19

<210> SEQ ID NO 978
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 978
cuauggaaca ccaugccaa                                                  19

<210> SEQ ID NO 979
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 979
ggaacaccau gccaacaga                                                  19

<210> SEQ ID NO 980
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 980
ccaugccaac agagguguu                                                  19

<210> SEQ ID NO 981
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 981
caugccaaca gagguguuu                                                  19

<210> SEQ ID NO 982
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 982
augccaacag agguguuua                                                  19
```

```
<210> SEQ ID NO 983
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 983
agagguguuu accccccua                                                19

<210> SEQ ID NO 984
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 984
gagguguuua cccccccuau                                               19

<210> SEQ ID NO 985
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 985
agguguuuac ccccccuauu                                               19

<210> SEQ ID NO 986
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 986
guguuuaccc cccuauuca                                                19

<210> SEQ ID NO 987
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 987
uguuuacccc ccuauucaa                                                19

<210> SEQ ID NO 988
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 988 uuacccccu auucaaguu                                                        19

<210> SEQ ID NO 989
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 989 acccccuau ucaaguuca                                                        19

<210> SEQ ID NO 990
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 990 cccccuauu caaguucau                                                        19

<210> SEQ ID NO 991
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 991
ccccuauuca aguucaugu                                                       19

<210> SEQ ID NO 992
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 992
ccuauucaag uucauguca                                                       19

<210> SEQ ID NO 993
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: PDK1 siRNA

<400> SEQUENCE: 993
augucacgcu ggguaauga                                              19

<210> SEQ ID NO 994
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 994
cacgcugggu aaugaggau                                              19

<210> SEQ ID NO 995
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 995
acgcugggua augaggauu                                              19

<210> SEQ ID NO 996
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 996
cgcuggguaa ugaggauuu                                              19

<210> SEQ ID NO 997
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 997
cuggguaaug aggauuuga                                              19

<210> SEQ ID NO 998
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 998
ggguaaugag gauuugacu                                                    19

<210> SEQ ID NO 999
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 999
guaaugagga uuugacugu                                                    19

<210> SEQ ID NO 1000
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1000
aaugaggauu ugacuguga                                                    19

<210> SEQ ID NO 1001
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1001
augaggauuu gacugugaa                                                    19

<210> SEQ ID NO 1002
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1002
gaggauuuga cugugaaga                                                    19

<210> SEQ ID NO 1003
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1003
gauuugacug ugaagauga                                                    19

```
<210> SEQ ID NO 1004
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1004
ugacugugaa gaugaguga                                                  19

<210> SEQ ID NO 1005
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1005
gaagaugagu gaccgagga                                                  19

<210> SEQ ID NO 1006
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1006
gaccgaggag guggcguuc                                                  19

<210> SEQ ID NO 1007
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1007
ccgaggaggu ggcguuccu                                                  19

<210> SEQ ID NO 1008
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1008
cgaggaggug gcguuccuu                                                  19

<210> SEQ ID NO 1009
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1009
gaggaggugg cguccuuu                                                   19

<210> SEQ ID NO 1010
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1010
ggagguggcg uuccuuuga                                                  19

<210> SEQ ID NO 1011
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1011
gcaauguacu ugaaguuau                                                  19

<210> SEQ ID NO 1012
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1012
ggaaguccau cucaucgaa                                                  19

<210> SEQ ID NO 1013
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1013
gcugaggaug cuaaagcua                                                  19

<210> SEQ ID NO 1014
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: PDK1 siRNA

<400> SEQUENCE: 1014
cauuucaauu agaauguua                                                  19

<210> SEQ ID NO 1015
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1015
cgaacuagaa cuugaagaa                                                  19

<210> SEQ ID NO 1016
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1016
gcauaaaucc aaacugcaa                                                  19

<210> SEQ ID NO 1017
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1017
caauguacuu gaaguuauu                                                  19

<210> SEQ ID NO 1018
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1018
cugugugauu uguauuaua                                                  19

<210> SEQ ID NO 1019
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1019
```

```
acuagaacuu gaagaacua                                        19

<210> SEQ ID NO 1020
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1020
gaauguuacu caaucagca                                        19

<210> SEQ ID NO 1021
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1021
ggaugcuaaa gcuauuuau                                        19

<210> SEQ ID NO 1022
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1022
cugugauacg gaucagaaa                                        19

<210> SEQ ID NO 1023
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1023
agggugugau ugaauacaa                                        19

<210> SEQ ID NO 1024
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1024
cuugaagaac uaaaugcaa                                        19

<210> SEQ ID NO 1025
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1025
gucuguguga uuuguauua                                              19

<210> SEQ ID NO 1026
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1026
gacuuuacag auacuguga                                              19

<210> SEQ ID NO 1027
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1027
gcgucugugu gauuuguau                                              19

<210> SEQ ID NO 1028
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1028
ugugauuugu auuauauua                                              19

<210> SEQ ID NO 1029
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1029
uguacuugaa guuauuaaa                                              19

<210> SEQ ID NO 1030
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: PDK1 siRNA

<400> SEQUENCE: 1030
cuuuacagau acugugaua                                                      19

<210> SEQ ID NO 1031
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1031
gauuugacug ugaagauga                                                      19

<210> SEQ ID NO 1032
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1032
ccuauucaag uucauguca                                                      19

<210> SEQ ID NO 1033
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1033
caaauauaau gaaagaaau                                                      19

<210> SEQ ID NO 1034
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1034
cugucagacu ggcaaauau                                                      19

<210> SEQ ID NO 1035
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

<400> SEQUENCE: 1035
ugucagacug gcaaauaua                                            19

<210> SEQ ID NO 1036
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1036
gucagacugg caaauauaa                                            19

<210> SEQ ID NO 1037
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1037
ucagacuggc aaauauaau                                            19

<210> SEQ ID NO 1038
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1038
gacuggcaaa uauaaugaa                                            19

<210> SEQ ID NO 1039
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1039
acuggcaaau auaaugaaa                                            19

<210> SEQ ID NO 1040
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1040
ggcaaauaua augaaagaa                                            19

<210> SEQ ID NO 1041
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 1041
gcaaauauaa ugaaagaaa                                               19

<210> SEQ ID NO 1042
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 1042
caaauauaau gaaagaaau                                               19

<210> SEQ ID NO 1043
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 1043
aaauauaaug aaagaaaua                                               19

<210> SEQ ID NO 1044
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 1044
aauauaauga agaaauaa                                                19

<210> SEQ ID NO 1045
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: PDK1 siRNA

<400> SEQUENCE: 1045
gaaagaaaua agucccuu                                                19

<210> SEQ ID NO 1046
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1046
cagauaaucu ucucaggac                                                   19

<210> SEQ ID NO 1047
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1047
ggacaccauc cguucaauu                                                   19

<210> SEQ ID NO 1048
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1048
accauccguu caauuggua                                                   19

<210> SEQ ID NO 1049
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1049
uccguucaau ugguacaaa                                                   19

<210> SEQ ID NO 1050
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1050
ccagagucuu caggagcuu                                                   19

<210> SEQ ID NO 1051
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: PDK1 siRNA

<400> SEQUENCE: 1051
ucaggagcuu cuugauuuu                                              19

<210> SEQ ID NO 1052
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1052
caggagcuuc uugauuuua                                              19

<210> SEQ ID NO 1053
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1053
aggagcuucu ugauuuuaa                                              19

<210> SEQ ID NO 1054
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1054
ggagcuucuu gauuuuaag                                              19

<210> SEQ ID NO 1055
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1055
ucuugauuuu aaggacaaa                                              19

<210> SEQ ID NO 1056
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 1056
cuugauuuua aggacaaaa                                              19

<210> SEQ ID NO 1057
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1057
ggacaaaagu gcugaggau                                              19

<210> SEQ ID NO 1058
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1058
gcugaggaug cuaaagcua                                              19

<210> SEQ ID NO 1059
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1059
cugaggaugc uaaagcuau                                              19

<210> SEQ ID NO 1060
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1060
ugaggaugcu aaagcuauu                                              19

<210> SEQ ID NO 1061
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1061
aggaugcuaa agcuauuua                                              19
```

```
<210> SEQ ID NO 1062
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1062
ggaugcuaaa gcuauuuau                                                    19

<210> SEQ ID NO 1063
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1063
aaagcuauuu augacuuua                                                    19

<210> SEQ ID NO 1064
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1064
auuuaugacu uuacagaua                                                    19

<210> SEQ ID NO 1065
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1065
cuuuacagau acugugaua                                                    19

<210> SEQ ID NO 1066
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1066
cagauacugu gauacggau                                                    19

<210> SEQ ID NO 1067
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1067
acugugauac ggaucagaa                                                 19

<210> SEQ ID NO 1068
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1068
cugugauacg gaucagaaa                                                 19

<210> SEQ ID NO 1069
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1069
ggaucagaaa ccgacacaa                                                 19

<210> SEQ ID NO 1070
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1070
gaucagaaac cgacacaau                                                 19

<210> SEQ ID NO 1071
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1071
cagaaaccga cacaaugau                                                 19

<210> SEQ ID NO 1072
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: PDK1 siRNA

<400> SEQUENCE: 1072
accgacacaa ugaugucau                                            19

<210> SEQ ID NO 1073
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1073
ccgacacaau gaugucauu                                            19

<210> SEQ ID NO 1074
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1074
ggcccagggu gugauugaa                                            19

<210> SEQ ID NO 1075
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1075
gcccagggug ugauugaau                                            19

<210> SEQ ID NO 1076
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1076
cccagggugu gauugaaua                                            19

<210> SEQ ID NO 1077
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1077
```
agggugugau ugaauacaa        19

<210> SEQ ID NO 1078
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1078
gggugugauu gaauacaag        19

<210> SEQ ID NO 1079
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1079
gugugauuga auacaagga        19

<210> SEQ ID NO 1080
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1080
gugauugaau acaaggaga        19

<210> SEQ ID NO 1081
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1081
ugaauacaag gagagcuuu        19

<210> SEQ ID NO 1082
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1082
ggagagcuuu gggguggau        19

```
<210> SEQ ID NO 1083
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1083
ccagccagaa uguucagua                                                  19

<210> SEQ ID NO 1084
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1084
gccagaaugu ucaguacuu                                                  19

<210> SEQ ID NO 1085
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1085
ccagaauguu caguacuuu                                                  19

<210> SEQ ID NO 1086
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1086
cagaauguuc aguacuuuu                                                  19

<210> SEQ ID NO 1087
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1087
agaauguuca guacuuuuu                                                  19

<210> SEQ ID NO 1088
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1088
aguacuuuuu ggaucgauu                                                  19

<210> SEQ ID NO 1089
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1089 acuuuugga ucgauucua                                                   19

<210> SEQ ID NO 1090
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1090
gauucuacau gagucgcau                                                  19

<210> SEQ ID NO 1091
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1091
acaugagucg cauuucaau                                                  19

<210> SEQ ID NO 1092
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1092
caugagucgc auuucaauu                                                  19

<210> SEQ ID NO 1093
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: PDK1 siRNA

<400> SEQUENCE: 1093
agucgcauuu caauuagaa                                          19

<210> SEQ ID NO 1094
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1094
gucgcauuuc aauuagaau                                          19

<210> SEQ ID NO 1095
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1095
gcauuucaau uagaauguu                                          19

<210> SEQ ID NO 1096
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1096
cauuucaauu agaauguua                                          19

<210> SEQ ID NO 1097
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1097
caauuagaau guuacucaa                                          19

<210> SEQ ID NO 1098
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1098

```
gaauguuacu caaucagca                                              19

<210> SEQ ID NO 1099
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1099
acucaaucag cacucuuua                                              19

<210> SEQ ID NO 1100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1100
cuuuauuguu ugguggaaa                                              19

<210> SEQ ID NO 1101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1101
guuuggugga aaaggcaaa                                              19

<210> SEQ ID NO 1102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1102
gguggaaaag gcaaaggaa                                              19

<210> SEQ ID NO 1103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1103
guggaaaagg caaaggaag                                              19

<210> SEQ ID NO 1104
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1104
uggaaaaggc aaaggaagu                                                    19

<210> SEQ ID NO 1105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1105
caaaggaagu ccaucucau                                                    19

<210> SEQ ID NO 1106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1106
ggaaguccau cucaucgaa                                                    19

<210> SEQ ID NO 1107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1107
gaaguccauc ucaucgaaa                                                    19

<210> SEQ ID NO 1108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1108
ccaucucauc gaaaacaca                                                    19

<210> SEQ ID NO 1109
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: PDK1 siRNA

<400> SEQUENCE: 1109
caucucaucg aaaacacau                                              19

<210> SEQ ID NO 1110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1110
caucgaaaac acauuggaa                                              19

<210> SEQ ID NO 1111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1111
gaaaacacau uggaagcau                                              19

<210> SEQ ID NO 1112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1112
aaaacacauu ggaagcaua                                              19

<210> SEQ ID NO 1113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1113
aacacauugg aagcauaaa                                              19

<210> SEQ ID NO 1114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1114
acacauugga agcauaaau                                                    19

<210> SEQ ID NO 1115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1115
gcauaaaucc aaacugcaa                                                    19

<210> SEQ ID NO 1116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1116
cauaaaucca aacugcaau                                                    19

<210> SEQ ID NO 1117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1117
aaauccaaac ugcaaugua                                                    19

<210> SEQ ID NO 1118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1118
uccaaacugc aauguacuu                                                    19

<210> SEQ ID NO 1119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1119
cugcaaugua cuugaaguu                                                    19

<210> SEQ ID NO 1120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1120
ugcaauguac uugaaguua                                              19

<210> SEQ ID NO 1121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1121
gcaauguacu ugaaguuau                                              19

<210> SEQ ID NO 1122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1122
caauguacuu gaaguuauu                                              19

<210> SEQ ID NO 1123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1123
auguacuuga aguuauuaa                                              19

<210> SEQ ID NO 1124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1124
uguacuugaa guuauuaaa                                              19

<210> SEQ ID NO 1125
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1125
acuugaaguu auuaaagau                                                 19

<210> SEQ ID NO 1126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1126
aaguuauuaa agauggcua                                                 19

<210> SEQ ID NO 1127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1127
aguuauuaaa gauggcuau                                                 19

<210> SEQ ID NO 1128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1128
uauuaaagau ggcuaugaa                                                 19

<210> SEQ ID NO 1129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1129
uuaaagaugg cuaugaaaa                                                 19

<210> SEQ ID NO 1130
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: PDK1 siRNA

<400> SEQUENCE: 1130
uaaagauggc uaugaaaau                                                  19

<210> SEQ ID NO 1131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1131
ggcgucugug ugauuugua                                                  19

<210> SEQ ID NO 1132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1132
gcgucugugu gauuuguau                                                  19

<210> SEQ ID NO 1133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1133
cgucugugug auuuguauu                                                  19

<210> SEQ ID NO 1134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1134
gucuguguga uuuguauua                                                  19

<210> SEQ ID NO 1135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 1135
cugugugauu uguauuaua                                              19

<210> SEQ ID NO 1136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1136
gugugauuug uauuauauu                                              19

<210> SEQ ID NO 1137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1137
ugugauuugu auuauauua                                              19

<210> SEQ ID NO 1138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1138
gugauuugua uuauauuaa                                              19

<210> SEQ ID NO 1139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1139
ucccgaacua gaacuugaa                                              19

<210> SEQ ID NO 1140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1140
ccgaacuaga acuugaaga                                              19
```

<210> SEQ ID NO 1141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1141
cgaacuagaa cuugaagaa                                              19

<210> SEQ ID NO 1142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1142
acuagaacuu gaagaacua                                              19

<210> SEQ ID NO 1143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1143
cuagaacuug aagaacuaa                                              19

<210> SEQ ID NO 1144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1144
uagaacuuga agaacuaaa                                              19

<210> SEQ ID NO 1145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1145
agaacuugaa gaacuaaau                                              19

<210> SEQ ID NO 1146
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1146
cuugaagaac uaaaugcaa                                                       19

<210> SEQ ID NO 1147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1147
uugaagaacu aaaugcaaa                                                       19

<210> SEQ ID NO 1148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1148
ugaagaacua aaugcaaaa                                                       19

<210> SEQ ID NO 1149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1149
gaagaacuaa augcaaaau                                                       19

<210> SEQ ID NO 1150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1150
agaacuaaau gcaaaauca                                                       19

<210> SEQ ID NO 1151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: PDK1 siRNA

<400> SEQUENCE: 1151
accaggacag ccaauacaa                                                19

<210> SEQ ID NO 1152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1152
cagccaauac aaguggquuu                                               19

<210> SEQ ID NO 1153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1153
agccaauaca agugguuua                                                19

<210> SEQ ID NO 1154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1154
gccaauacaa gugguuuau                                                19

<210> SEQ ID NO 1155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1155
ucacauggug uuugaacuu                                                19

<210> SEQ ID NO 1156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1156
```

```
acauggiguu ugaacuuuu                                              19

<210> SEQ ID NO 1157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1157
ugguguuuga acuuuucaa                                              19

<210> SEQ ID NO 1158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1158
gguguuugaa cuuuucaag                                              19

<210> SEQ ID NO 1159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1159
uguuugaacu uuucaagaa                                              19

<210> SEQ ID NO 1160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1160 guugaacuu uucaagaau                                               19

<210> SEQ ID NO 1161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1161
gaacuuuuca agaaugcaa                                              19
```

```
<210> SEQ ID NO 1162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1162
agccacuaug gaacaccau                                                  19

<210> SEQ ID NO 1163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1163
cuauggaaca ccaugccaa                                                  19

<210> SEQ ID NO 1164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1164
ggaacaccau gccaacaga                                                  19

<210> SEQ ID NO 1165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1165
ccaugccaac agagguguu                                                  19

<210> SEQ ID NO 1166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1166
guucauguca cgcugggua                                                  19

<210> SEQ ID NO 1167
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1167
cacgcugggu aaugaggau                                                        19

<210> SEQ ID NO 1168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1168
gaggauuuga cugugaaga                                                        19

<210> SEQ ID NO 1169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1169
aggauuugac ugugaagau                                                        19

<210> SEQ ID NO 1170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1170
cgaggaggug gcguuccuu                                                        19

<210> SEQ ID NO 1171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1171
uuucuuucau uauauuugc                                                        19

<210> SEQ ID NO 1172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: PDK1 siRNA

<400> SEQUENCE: 1172
uucuuucauu auauugcc                                                19

<210> SEQ ID NO 1173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1173
auaacuucaa guacauugc                                               19

<210> SEQ ID NO 1174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1174
uucuucaagu ucuaguucg                                               19

<210> SEQ ID NO 1175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1175
uuaauauaau acaaaucac                                               19

<210> SEQ ID NO 1176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1176
ucuucacagu caaauccuc                                               19

<210> SEQ ID NO 1177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1177
```

```
ucaucuucac agucaaauc                                          19

<210> SEQ ID NO 1178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1178
ucuucaaguu cuaguucgg                                          19

<210> SEQ ID NO 1179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1179
uaguucuuca aguucuagu                                          19

<210> SEQ ID NO 1180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1180
uuaguucuuc aaguucuag                                          19

<210> SEQ ID NO 1181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1181
uaucacagua ucuguaaag                                          19

<210> SEQ ID NO 1182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1182
uugcauucuu gaaaaguuc                                          19

<210> SEQ ID NO 1183
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1183
uacaaaucac acagacgcc                                                19

<210> SEQ ID NO 1184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1184
auacaaauca cacagacgc                                                19

<210> SEQ ID NO 1185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1185
uaauacaaau cacacagac                                                19

<210> SEQ ID NO 1186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1186
uuuaauaacu ucaaguaca                                                19

<210> SEQ ID NO 1187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1187
uaacauucua auugaaaug                                                19

<210> SEQ ID NO 1188
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: PDK1 siRNA

<400> SEQUENCE: 1188
auaaauagcu uuagcaucc                                                      19

<210> SEQ ID NO 1189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1189
uuucugaucc guaucacag                                                      19

<210> SEQ ID NO 1190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1190
aaaguacuga acauucugg                                                      19

<210> SEQ ID NO 1191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1191
uuauauuugc cagucugac                                                      19

<210> SEQ ID NO 1192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1192
uauaauacaa aucacacag                                                      19

<210> SEQ ID NO 1193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 1193
uacugaacau ucuggcugg                                                   19

<210> SEQ ID NO 1194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1194
uugugucggu uucugaucc                                                   19

<210> SEQ ID NO 1195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1195
uuuccaccaa acaauaaag                                                   19

<210> SEQ ID NO 1196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1196
aaguacugaa cauucuggc                                                   19

<210> SEQ ID NO 1197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1197
aacauucuaa uugaaaugc                                                   19

<210> SEQ ID NO 1198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1198
uucugauccg uaucacagu                                                   19
```

<210> SEQ ID NO 1199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1199
uuaaaaucaa gaagcuccu                                              19

<210> SEQ ID NO 1200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1200
uuaauaacuu caaguacau                                              19

<210> SEQ ID NO 1201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1201
aauauaauac aaaucacac                                              19

<210> SEQ ID NO 1202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1202
uuuuguccuu aaaaucaag                                              19

<210> SEQ ID NO 1203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1203
uuuguccuua aaaucaaga                                              19

<210> SEQ ID NO 1204
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1204
uagcauuuuc auagccauc                                              19

<210> SEQ ID NO 1205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1205
ugaagacucu ggauauacc                                              19

<210> SEQ ID NO 1206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1206
uagcuuuagc auccucagc                                              19

<210> SEQ ID NO 1207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1207
uucauuauau uugccaguc                                              19

<210> SEQ ID NO 1208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1208
aaugacauca uugugucgg                                              19

<210> SEQ ID NO 1209
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: PDK1 siRNA

<400> SEQUENCE: 1209
uuguauucaa ucacacccu                                                    19

<210> SEQ ID NO 1210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1210
uaacuucaag uacauugca                                                    19

<210> SEQ ID NO 1211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1211
uucaaguucu aguucggga                                                    19

<210> SEQ ID NO 1212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1212
uucaaacacc augugauag                                                    19

<210> SEQ ID NO 1213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1213
aucuucacag ucaaauccu                                                    19

<210> SEQ ID NO 1214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1214
uaaaaucaag aagcuccug    19

<210> SEQ ID NO 1215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1215
uaauauaaua caaaucaca    19

<210> SEQ ID NO 1216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1216
uagaaucgau ccaaaaagu    19

<210> SEQ ID NO 1217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1217
aucuuuaaua acuucaagu    19

<210> SEQ ID NO 1218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1218
uccuuguauu caaucacac    19

<210> SEQ ID NO 1219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1219
uuucauuaua uuugccagu    19

```
<210> SEQ ID NO 1220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1220
uaaagagugc ugauugagu                                               19

<210> SEQ ID NO 1221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1221
uauucaauca cacccuggg                                               19

<210> SEQ ID NO 1222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1222
ugauccguau cacaguauc                                               19

<210> SEQ ID NO 1223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1223
aauaacuuca aguacauug                                               19

<210> SEQ ID NO 1224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1224
auaaaccacu uguauuggc                                               19

<210> SEQ ID NO 1225
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1225
aucacaguau cuguaaagu                                                  19

<210> SEQ ID NO 1226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1226
auucuugaaa aguucaaac                                                  19

<210> SEQ ID NO 1227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1227
uugcauuuag uucuucaag                                                  19

<210> SEQ ID NO 1228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1228
uuccaccaaa caauaaaga                                                  19

<210> SEQ ID NO 1229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1229
auccucagca cuuuugucc                                                  19

<210> SEQ ID NO 1230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: PDK1 siRNA

<400> SEQUENCE: 1230
ucaaauccuc auuacccag                                              19

<210> SEQ ID NO 1231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1231
aacuucaagu acauugcag                                              19

<210> SEQ ID NO 1232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1232
augcgacuca uguagaauc                                              19

<210> SEQ ID NO 1233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1233
aaaaguacug aacauucug                                              19

<210> SEQ ID NO 1234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1234
ucauugcauu cuugaaaag                                              19

<210> SEQ ID NO 1235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1235
uucuugaaaa guucaaaca                                        19

<210> SEQ ID NO 1236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1236
auuucuuuca uuauauuug                                        19

<210> SEQ ID NO 1237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1237
uugaaaaguu caaacacca                                        19

<210> SEQ ID NO 1238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1238
agucauaaau agcuuuagc                                        19

<210> SEQ ID NO 1239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1239
uaaauagcuu uagcauccu                                        19

<210> SEQ ID NO 1240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1240
cuguaaaguc auaaauagc                                        19

<210> SEQ ID NO 1241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1241
uucuaauuga aaugcgacu                                              19

<210> SEQ ID NO 1242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1242
auuuaguucu ucaaguucu                                              19

<210> SEQ ID NO 1243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1243
uuuguaccaa uugaacgga                                              19

<210> SEQ ID NO 1244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1244
uguauucaau cacacccug                                              19

<210> SEQ ID NO 1245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1245
uuucauagcc aucuuuaau                                              19

<210> SEQ ID NO 1246
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1246
aauacaaauc acacagacg                                                   19

<210> SEQ ID NO 1247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1247
uuuaguucuu caaguucua                                                   19

<210> SEQ ID NO 1248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1248
aaaaaguacu gaacauucu                                                   19

<210> SEQ ID NO 1249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1249
uauauuugcc agucugaca                                                   19

<210> SEQ ID NO 1250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1250
auagccaucu uuaauaacu                                                   19

<210> SEQ ID NO 1251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: PDK1 siRNA

<400> SEQUENCE: 1251
ucaagaagcu ccugaagac                                              19

<210> SEQ ID NO 1252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1252
augggauggu acauaaacc                                              19

<210> SEQ ID NO 1253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1253
auauuugcca gucugacag                                              19

<210> SEQ ID NO 1254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1254
ucuaauugaa augcgacuc                                              19

<210> SEQ ID NO 1255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1255
augacaucau ugugucggu                                              19

<210> SEQ ID NO 1256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1256
```
uaaaccacuu guauuggcu					19

<210> SEQ ID NO 1257
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: PDK1 siRNA

<400> SEQUENCE: 1257
auucuaauug aaaugcgac					19

<210> SEQ ID NO 1258
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: PDK1 siRNA

<400> SEQUENCE: 1258
aaucgaucca aaaaguacu					19

<210> SEQ ID NO 1259
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: PDK1 siRNA

<400> SEQUENCE: 1259
aaucacacag acgccuagc					19

<210> SEQ ID NO 1260
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: PDK1 siRNA

<400> SEQUENCE: 1260
agucaaaucc ucauuaccc					19

<210> SEQ ID NO 1261
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: PDK1 siRNA

<400> SEQUENCE: 1261
aucgauccaa aaaguacug					19

<210> SEQ ID NO 1262

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1262
auugugucgg uuucugauc                                                  19

<210> SEQ ID NO 1263
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1263
ucaaguacau ugcaguuug                                                  19

<210> SEQ ID NO 1264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1264
aaauagcuuu agcauccuc                                                  19

<210> SEQ ID NO 1265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1265
auucaaucac acccugggc                                                  19

<210> SEQ ID NO 1266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1266
aaggagacuu auuucuuuc                                                  19

<210> SEQ ID NO 1267
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: PDK1 siRNA

<400> SEQUENCE: 1267
ugcauuuagu ucuucaagu                                                    19

<210> SEQ ID NO 1268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1268
uuguaccaau ugaacggau                                                    19

<210> SEQ ID NO 1269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1269
auugaaaugc gacucaugu                                                    19

<210> SEQ ID NO 1270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1270
auauaauaca aaucacaca                                                    19

<210> SEQ ID NO 1271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1271
auuuaugcuu ccaaugugu                                                    19

<210> SEQ ID NO 1272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1272
aaauccucau uacccagcg                                                    19

<210> SEQ ID NO 1273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1273
uuccaaugug uuuucgaug                                                    19

<210> SEQ ID NO 1274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1274
uuuugcauuu aguucuuca                                                    19

<210> SEQ ID NO 1275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1275
uguaccaauu gaacggaug                                                    19

<210> SEQ ID NO 1276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1276
aagaagcucc ugaagacuc                                                    19

<210> SEQ ID NO 1277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1277
aucuguaaag ucauaaaua                                                    19

```
<210> SEQ ID NO 1278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1278
uucuaguucg ggagaguua                                               19

<210> SEQ ID NO 1279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1279
agacucugga uauaccagc                                               19

<210> SEQ ID NO 1280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1280 auaaucaaa ucacacaga                                                19

<210> SEQ ID NO 1281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1281
uuguauuggc uguccuggu                                               19

<210> SEQ ID NO 1282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1282
aaaaguucaa acaccaugu                                               19

<210> SEQ ID NO 1283
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1283
aauccucauu acccagcgu                                                    19

<210> SEQ ID NO 1284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1284
acagucaaau ccucauuac                                                    19

<210> SEQ ID NO 1285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1285
auagcuuuag cauccucag                                                    19

<210> SEQ ID NO 1286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1286
uuugccuuuu ccaccaaac                                                    19

<210> SEQ ID NO 1287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1287
cuuaaaauca agaagcucc                                                    19

<210> SEQ ID NO 1288
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: PDK1 siRNA

<400> SEQUENCE: 1288
aucauugugu cgguuucug                                              19

<210> SEQ ID NO 1289
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1289
auaaagagug cugauugag                                              19

<210> SEQ ID NO 1290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1290
cuugaaaagu ucaaacacc                                              19

<210> SEQ ID NO 1291
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1291
accaaacaau aaagagugc                                              19

<210> SEQ ID NO 1292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1292
uuccuuugcc uuuuccacc                                              19

<210> SEQ ID NO 1293
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 1293
aauugaaaug cgacucaug                                              19

<210> SEQ ID NO 1294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1294
caaauccuca uuacccagc                                              19

<210> SEQ ID NO 1295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1295
ugagaagauu aucuggaag                                              19

<210> SEQ ID NO 1296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1296
augcuuccaa uguguuuuc                                              19

<210> SEQ ID NO 1297
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1297
uugaaaugcg acucaugua                                              19

<210> SEQ ID NO 1298
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1298
aaaguucaaa caccaugug                                              19
```

```
<210> SEQ ID NO 1299
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1299
aauugaacgg auggugucc                                                    19

<210> SEQ ID NO 1300
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1300
auuuugcauu uaguucuuc                                                    19

<210> SEQ ID NO 1301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1301
auccaaaaag uacugaaca                                                    19

<210> SEQ ID NO 1302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1302
acaugaacuu gaauagggg                                                    19

<210> SEQ ID NO 1303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1303
uuggauuuau gcuuccaau                                                    19

<210> SEQ ID NO 1304
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1304
auuauauuug ccagucuga                                                    19

<210> SEQ ID NO 1305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1305
aaucaagaag cuccugaag                                                    19

<210> SEQ ID NO 1306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1306
aaacaccucu guuggcaug                                                    19

<210> SEQ ID NO 1307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1307
aaaucacaca gacgccuag                                                    19

<210> SEQ ID NO 1308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1308
aaguucuagu ucgggagag                                                    19

<210> SEQ ID NO 1309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: PDK1 siRNA

<400> SEQUENCE: 1309
aaacaauaaa gagugcuga                                                19

<210> SEQ ID NO 1310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1310
aaaaucaaga agcuccuga                                                19

<210> SEQ ID NO 1311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1311
aaaccacuug uauuggcug                                                19

<210> SEQ ID NO 1312
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1312
augaacuuga auagggggg                                                19

<210> SEQ ID NO 1313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1313
auuacccagc gugacauga                                                19

<210> SEQ ID NO 1314
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1314
```

```
acaucauugu gucgguuuc                                                19

<210> SEQ ID NO 1315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1315
aaacaccaug ugauagaga                                                19

<210> SEQ ID NO 1316
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1316
cauaaauagc uuuagcauc                                                19

<210> SEQ ID NO 1317
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1317
uguuuucgau gagauggac                                                19

<210> SEQ ID NO 1318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1318
aguuaauaua auacaaauc                                                19

<210> SEQ ID NO 1319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1319
auugcaguuu ggauuuaug                                                19
```

```
<210> SEQ ID NO 1320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1320
ugaacauucu ggcugguga                                              19

<210> SEQ ID NO 1321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1321
aucaagaagc uccugaaga                                              19

<210> SEQ ID NO 1322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1322
acauucuaau ugaaaugcg                                              19

<210> SEQ ID NO 1323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1323
ugcuuccaau guguuuucg                                              19

<210> SEQ ID NO 1324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1324
agccaucuuu aauaacuuc                                              19

<210> SEQ ID NO 1325
<211> LENGTH: 19
<212> TYPE: RNA
<213> ORGANISM: Artificial Sequence
```

```
-continued

<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1325
aaagcucucc uuguauuca                                              19

<210> SEQ ID NO 1326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1326
auugaacgga ugguguccu                                              19

<210> SEQ ID NO 1327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1327
auguguuuuc gaugagaug                                              19

<210> SEQ ID NO 1328
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1328
aacaauaaag agugcugau                                              19

<210> SEQ ID NO 1329
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1329
aaguucaaac accauguga                                              19

<210> SEQ ID NO 1330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: PDK1 siRNA

<400> SEQUENCE: 1330
uggugauuuu gcauuuagu                                                  19

<210> SEQ ID NO 1331
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1331
agagugcuga uugaguaac                                                  19

<210> SEQ ID NO 1332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1332
aauagcuuua gcauccuca                                                  19

<210> SEQ ID NO 1333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1333
aaccacuugu auuggcugu                                                  19

<210> SEQ ID NO 1334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1334
uugaauaggg ggguaaaca                                                  19

<210> SEQ ID NO 1335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1335
```
auauaccagc uuuguacca                                                19

<210> SEQ ID NO 1336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1336
augugauaga gauggaug                                                 19

<210> SEQ ID NO 1337
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1337
aaagucauaa auagcuuua                                                19

<210> SEQ ID NO 1338
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1338
aauaaagagu gcugauuga                                                19

<210> SEQ ID NO 1339
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1339
gacaugaacu ugaauaggg                                                19

<210> SEQ ID NO 1340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1340
acauaaacca cuuguauug                                                19

<210> SEQ ID NO 1341

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1341
cauagccauc uuuaauaac                                                19

<210> SEQ ID NO 1342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1342
aaugcgacuc auguagaau                                                19

<210> SEQ ID NO 1343
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1343
caaguacauu gcaguuugg                                                19

<210> SEQ ID NO 1344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1344
auuuucauag ccaucuuua                                                19

<210> SEQ ID NO 1345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1345
aguuuggauu uaugcuucc                                                19

<210> SEQ ID NO 1346
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: PDK1 siRNA

<400> SEQUENCE: 1346
cauaaaccac uuguauugg                                                19

<210> SEQ ID NO 1347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1347
aacaccaugu gauagagau                                                19

<210> SEQ ID NO 1348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1348
acaccaugug auagagaug                                                19

<210> SEQ ID NO 1349
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1349
augagaugga cuuccuuug                                                19

<210> SEQ ID NO 1350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1350
agcuuuguac caauugaac                                                19

<210> SEQ ID NO 1351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

<400> SEQUENCE: 1351
acagacgccu agcauuuuc                                    19

<210> SEQ ID NO 1352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1352
aguucuaguu cgggagagu                                    19

<210> SEQ ID NO 1353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1353
aaagagugcu gauugagua                                    19

<210> SEQ ID NO 1354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1354
accaugugau agagaugggg                                   19

<210> SEQ ID NO 1355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1355
auagagaugg gaugguaca                                    19

<210> SEQ ID NO 1356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1356
aagauuaucu ggaaggaga                                    19

<210> SEQ ID NO 1357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1357
agauuaucug gaaggagac                                              19

<210> SEQ ID NO 1358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1358 cacuuuguc cuuaaaauc                                               19

<210> SEQ ID NO 1359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1359
gauauaccag cuuuguacc                                              19

<210> SEQ ID NO 1360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1360
aaguacauug caguuugga                                              19

<210> SEQ ID NO 1361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1361
aacauucugg cuggugaca                                              19

<210> SEQ ID NO 1362
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1362
guauucaauc acacccugg                                                 19

<210> SEQ ID NO 1363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1363
aucacacccu gggccauug                                                 19

<210> SEQ ID NO 1364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1364
agcauccuca gcacuuuug                                                 19

<210> SEQ ID NO 1365
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1365
acuuguauug gcuguccug                                                 19

<210> SEQ ID NO 1366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1366
aauguguuuu cgaugagau                                                 19

<210> SEQ ID NO 1367
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
    oligonucleotide
<220> FEATURE:
<223> OTHER INFORMATION: PDK1 siRNA

<400> SEQUENCE: 1367
acauucuggc uggugacag                                                    19

<210> SEQ ID NO 1368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1368
caauugaacg gaugguguc                                                    19

<210> SEQ ID NO 1369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1369
accaauugaa cggauggug                                                    19

<210> SEQ ID NO 1370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1370
gagaagauua ucuggaagg                                                    19

<210> SEQ ID NO 1371
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1371
agcuuuagca uccucagca                                                    19

<210> SEQ ID NO 1372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA
```

```
<400> SEQUENCE: 1372
agaagauuau cuggaagga                                              19

<210> SEQ ID NO 1373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1373
cuugaauagg gggguaaac                                              19

<210> SEQ ID NO 1374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PDK1 siRNA

<400> SEQUENCE: 1374
gacuuccuuu gccuuuucc                                              19

<210> SEQ ID NO 1375
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1375
uucaaacacc augugauag                                              19

<210> SEQ ID NO 1376
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1376
acauaaacca cuuguauug                                              19

<210> SEQ ID NO 1377
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1377
ucaaacacca ugugauaga                                              19

<210> SEQ ID NO 1378
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1378
uucuuucauu auauugcc                                                    19

<210> SEQ ID NO 1379
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1379
auccaaaaag uacugaaca                                                   19

<210> SEQ ID NO 1380
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1380
uuggauuuau gcuuccaau                                                   19

<210> SEQ ID NO 1381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1381
ugugauagag augggaugg                                                   19

<210> SEQ ID NO 1382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1382
augugauaga gaugggaug                                                   19

<210> SEQ ID NO 1383
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1383
uucuuucauu auauugcc                                                    19

<210> SEQ ID NO 1384
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 1384
uuucuuucau uauauuugc                                              19

<210> SEQ ID NO 1385
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1385
auuucuuuca uuauauuug                                              19

<210> SEQ ID NO 1386
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1386
uggauuuaug cuuccaaug                                              19

<210> SEQ ID NO 1387
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1387
augguacaua aaccacuug                                              19

<210> SEQ ID NO 1388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1388
augggauggu acauaaacc                                              19

<210> SEQ ID NO 1389
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1389
ugauagagau gggauggua                                              19

<210> SEQ ID NO 1390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1390
accaugugau agagauggg						19

<210> SEQ ID NO 1391
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1391
acaccaugug auagagaug						19

<210> SEQ ID NO 1392
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1392
uuucuuucau uauauuugc						19

<210> SEQ ID NO 1393
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1393
atttctttca ttatatttg						19

<210> SEQ ID NO 1394
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1394
tctttcatta tatttgcca						19

<210> SEQ ID NO 1395
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1395
tggtgacagg atccacccc						19

<210> SEQ ID NO 1396
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1396
tttggattta tgcttccaa                                                19

<210> SEQ ID NO 1397
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1397
tacataaacc acttgtatt                                                19

<210> SEQ ID NO 1398
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1398
atgggatggt acataaacc                                                19

<210> SEQ ID NO 1399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1399
uauuucuuuc auuauauuu                                                19

<210> SEQ ID NO 1400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1400
gauauaccag cuuuguacc                                                19

<210> SEQ ID NO 1401
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1401
agucauaaau agcuuuagc                                                19

<210> SEQ ID NO 1402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1402
aagucauaaa uagcuuuag                                                19

<210> SEQ ID NO 1403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1403
aaagucauaa auagcuuua                                                19

<210> SEQ ID NO 1404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1404
uaaagucaua aauagcuuu                                                19

<210> SEQ ID NO 1405
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1405
uguaaaguca uaaauagcu                                                19

<210> SEQ ID NO 1406
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1406
ucuguaaagu cauaaauag                                                19

<210> SEQ ID NO 1407
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1407
uaucuguaaa gucauaaau                                                19

<210> SEQ ID NO 1408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1408

-continued aguaucugua aagucauaa					19

<210> SEQ ID NO 1409
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1409
uuucugaucc guaucacag					19

<210> SEQ ID NO 1410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1410
ucauuguguc gguuucuga					19

<210> SEQ ID NO 1411
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1411
aaaguacuga acauucugg					19

<210> SEQ ID NO 1412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1412
aaaaguacug aacauucug					19

<210> SEQ ID NO 1413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1413
aaaaaguacu gaacauucu					19

<210> SEQ ID NO 1414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1414
aacauucuaa uugaaaugc					19

<210> SEQ ID NO 1415
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1415
uaacauucua auugaaaug                                                19

<210> SEQ ID NO 1416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1416
uugaguaaca uucuaauug                                                19

<210> SEQ ID NO 1417
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1417
ugauugagua acauucuaa                                                19

<210> SEQ ID NO 1418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1418
uaaagagugc ugauugagu                                                19

<210> SEQ ID NO 1419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1419
aauaaagagu gcugauuga                                                19

<210> SEQ ID NO 1420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1420 auguguuuc gaugagaug                                                 19

```
<210> SEQ ID NO 1421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1421
uuaugcuucc aauguguuu                                                      19

<210> SEQ ID NO 1422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1422
uuuaugcuuc caauguguu                                                      19

<210> SEQ ID NO 1423
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1423
auuuaugcuu ccaaugugu                                                      19

<210> SEQ ID NO 1424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1424
auaacuucaa guacauugc                                                      19

<210> SEQ ID NO 1425
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1425
aauaacuuca aguacauug                                                      19

<210> SEQ ID NO 1426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1426
uuaauaacuu caaguacau                                                      19
```

```
<210> SEQ ID NO 1427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1427
uuuaauaacu ucaaguaca                                                19

<210> SEQ ID NO 1428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1428
ucuuuaauaa cuucaagua                                                19

<210> SEQ ID NO 1429
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1429
uuuucauagc caucuuuaa                                                19

<210> SEQ ID NO 1430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1430
auuuucauag ccaucuuua                                                19

<210> SEQ ID NO 1431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1431
aauauaauac aaaucacac                                                19

<210> SEQ ID NO 1432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1432
uaauauaaua caaaucaca                                                19

<210> SEQ ID NO 1433
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1433
uuaauauaau acaaucac                                                   19

<210> SEQ ID NO 1434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1434
aguuaauaua auacaaauc                                                  19

<210> SEQ ID NO 1435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1435
ucuaguucgg gagaguuaa                                                  19

<210> SEQ ID NO 1436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1436
ucuucaaguu cuaguucgg                                                  19

<210> SEQ ID NO 1437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1437
uucuucaagu ucuaguucg                                                  19

<210> SEQ ID NO 1438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1438
uaguucuuca aguucuagu                                                  19

<210> SEQ ID NO 1439
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1439
uuaguucuuc aaguucuag                                                       19

<210> SEQ ID NO 1440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1440
auuuaguucu ucaaguucu                                                       19

<210> SEQ ID NO 1441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1441
uugcauuuag uucuucaag                                                       19

<210> SEQ ID NO 1442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1442
uuuugcauuu aguucuuca                                                       19

<210> SEQ ID NO 1443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1443
auuuugcauu uaguucuuc                                                       19

<210> SEQ ID NO 1444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1444
ugauuuugca uuuaguucu                                                       19

<210> SEQ ID NO 1445
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1445
auaaaccacu uguauuggc                                                  19

<210> SEQ ID NO 1446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1446
ucuugaaaag uucaaacac                                                  19

<210> SEQ ID NO 1447
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1447
uucuugaaaa guucaaaca                                                  19

<210> SEQ ID NO 1448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1448
ugaauagggg gguaaacac                                                  19

<210> SEQ ID NO 1449
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1449
uugaauaggg ggguaaaca                                                  19

<210> SEQ ID NO 1450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1450
agucaaaucc ucauuaccc                                                  19

<210> SEQ ID NO 1451
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1451
ucaucuucac agucaaauc                                                      19

<210> SEQ ID NO 1452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1452
uuauauuugc cagucugac                                                      19

<210> SEQ ID NO 1453
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1453
auuauauuug ccagucuga                                                      19

<210> SEQ ID NO 1454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1454
ucauuauauu ugccagucu                                                      19

<210> SEQ ID NO 1455
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1455
uucauuauau uugccaguc                                                      19

<210> SEQ ID NO 1456
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1456
uuucauuaua uuugccagu                                                      19

<210> SEQ ID NO 1457
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1457
ucuuucauua uauuugcca                                                 19

<210> SEQ ID NO 1458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1458
uucuuucauu auauuugcc                                                 19

<210> SEQ ID NO 1459
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1459
uuucuuucau uauauuugc                                                 19

<210> SEQ ID NO 1460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1460
auuucuuuca uuauauuug                                                 19

<210> SEQ ID NO 1461
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1461
uauuucuuuc auuauauuu                                                 19

<210> SEQ ID NO 1462
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1462
aaggagacuu auuucuuuc                                                 19

<210> SEQ ID NO 1463
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1463
uggaaggaga cuuauuucu                                                19

<210> SEQ ID NO 1464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1464
ucuggaagga gacuuauuu                                                19

<210> SEQ ID NO 1465
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1465
uaucuggaag gagacuuau                                                19

<210> SEQ ID NO 1466
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1466
uuaucuggaa ggagacuua                                                19

<210> SEQ ID NO 1467
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1467
auuaucugga aggagacuu                                                19

<210> SEQ ID NO 1468
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1468
agauuaucug gaaggagac                                                19

<210> SEQ ID NO 1469
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1469
ugagaagauu aucuggaag                                                19

<210> SEQ ID NO 1470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1470
uguccugaga agauuaucu                                                19

<210> SEQ ID NO 1471
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1471
ugaacggaug guguccuga                                                19

<210> SEQ ID NO 1472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1472
uugaacggau gguguccug                                                19

<210> SEQ ID NO 1473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1473
auugaacgga uggugnccu                                                19

<210> SEQ ID NO 1474
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1474
aauugaacgg augguqucc                                                19

<210> SEQ ID NO 1475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1475
accaauugaa cggauggug                                                  19

<210> SEQ ID NO 1476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1476
uaccaauuga acggauggu                                                  19

<210> SEQ ID NO 1477
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1477
uguaccaauu gaacggaug                                                  19

<210> SEQ ID NO 1478
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1478
uuuguaccaa uugaacgga                                                  19

<210> SEQ ID NO 1479
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1479
agcuuuguac caauugaac                                                  19

<210> SEQ ID NO 1480
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1480
uauaccagcu uuguaccaa                                                  19

<210> SEQ ID NO 1481
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1481
```
gauauaccag cuuuguacc                                              19

<210> SEQ ID NO 1482
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1482
ucuggauaua ccagcuuug                                              19

<210> SEQ ID NO 1483
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1483
agacucugga uauaccagc                                              19

<210> SEQ ID NO 1484
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1484
aagacucugg auauaccag                                              19

<210> SEQ ID NO 1485
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1485
ugaagacucu ggauauacc                                              19

<210> SEQ ID NO 1486
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1486
aagcuccuga agacucugg                                              19

<210> SEQ ID NO 1487
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1487

-continued aagaagcucc ugaagacuc                                             19

<210> SEQ ID NO 1488
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1488
ucaagaagcu ccugaagac                                             19

<210> SEQ ID NO 1489
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1489
aaucaagaag cuccugaag                                             19

<210> SEQ ID NO 1490
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1490
aaaucaagaa gcuccugaa                                             19

<210> SEQ ID NO 1491
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1491
aaaaucaaga agcuccuga                                             19

<210> SEQ ID NO 1492
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1492
uaaaaucaag aagcuccug                                             19

<210> SEQ ID NO 1493
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1493
uuaaaaucaa gaagcuccu                                             19

<210> SEQ ID NO 1494
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1494
cuuaaaauca agaagcucc                                                19

<210> SEQ ID NO 1495
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1495
uguccuuaaa aucaagaag                                                19

<210> SEQ ID NO 1496
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1496
uuuuguccuu aaaaucaag                                                19

<210> SEQ ID NO 1497
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1497
auccucagca cuuuugucc                                                19

<210> SEQ ID NO 1498
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1498
uuagcauccu cagcacuuu                                                19

<210> SEQ ID NO 1499
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1499
uuuagcaucc ucagcacuu                                                19

```
<210> SEQ ID NO 1500
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1500
uagcuuuagc auccucagc                                                    19

<210> SEQ ID NO 1501
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1501
auagcuuuag cauccucag                                                    19

<210> SEQ ID NO 1502
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1502
aauagcuuua gcauccuca                                                    19

<210> SEQ ID NO 1503
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1503
aaauagcuuu agcauccuc                                                    19

<210> SEQ ID NO 1504
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1504
uaaauagcuu uagcauccu                                                    19

<210> SEQ ID NO 1505
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1505
auaaauagcu uuagcaucc                                                    19
```

```
<210> SEQ ID NO 1506
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1506
agucauaaau agcuuuagc                                                  19

<210> SEQ ID NO 1507
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1507
aagucauaaa uagcuuuag                                                  19

<210> SEQ ID NO 1508
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1508
aaagucauaa auagcuuua                                                  19

<210> SEQ ID NO 1509
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1509
uaaagucaua aauagcuuu                                                  19

<210> SEQ ID NO 1510
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1510
uguaaaguca uaaauagcu                                                  19

<210> SEQ ID NO 1511
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1511
ucuguaaagu cauaaauag                                                  19

<210> SEQ ID NO 1512
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1512
uaucuguaaa gucauaaau                                                 19

<210> SEQ ID NO 1513
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1513
aguaucugua aagucauaa                                                 19

<210> SEQ ID NO 1514
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1514
ucacaguauc uguaaaguc                                                 19

<210> SEQ ID NO 1515
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1515
uaucacagua ucuguaaag                                                 19

<210> SEQ ID NO 1516
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1516
auccguauca caguaucug                                                 19

<210> SEQ ID NO 1517
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1517
uuucugaucc guaucacag                                                 19

<210> SEQ ID NO 1518
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1518
ucgguuucug auccguauc                                                      19

<210> SEQ ID NO 1519
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1519
ugugucgguu ucugauccg                                                      19

<210> SEQ ID NO 1520
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1520
uugugucggu uucugaucc                                                      19

<210> SEQ ID NO 1521
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1521 auugucgg uuucugauc                                                        19

<210> SEQ ID NO 1522
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1522
ucauuguguc gguuucuga                                                      19

<210> SEQ ID NO 1523
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1523
aucauugugu cgguuucug                                                      19

<210> SEQ ID NO 1524
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1524
acaucauugu gucgguuuc                                                  19

<210> SEQ ID NO 1525
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1525
aaugacauca uugugucgg                                                  19

<210> SEQ ID NO 1526
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1526
ugggaaugac aucauugug                                                  19

<210> SEQ ID NO 1527
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1527 uguggaaug acaucauug                                                   19

<210> SEQ ID NO 1528
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1528 auuguggaa ugacaucau                                                   19

<210> SEQ ID NO 1529
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1529
acacccuggg ccauugugg                                                  19

<210> SEQ ID NO 1530
<211> LENGTH: 19
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1530
aucacacccu gggccauug                                                    19

<210> SEQ ID NO 1531
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1531
uucaaucaca cccugggcc                                                    19

<210> SEQ ID NO 1532
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1532
auucaaucac acccugggc                                                    19

<210> SEQ ID NO 1533
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1533
uauucaauca cacccuggg                                                    19

<210> SEQ ID NO 1534
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1534
uguauucaau cacacccug                                                    19

<210> SEQ ID NO 1535
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1535
uuguauucaa ucacacccu                                                    19

<210> SEQ ID NO 1536
<211> LENGTH: 19
<212> TYPE: RNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 1536
uccuuguauu caaucacac                                                    19

<210> SEQ ID NO 1537
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1537
ucuccuugua uucaaucac                                                    19

<210> SEQ ID NO 1538
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1538
auccacccca aagcucucc                                                    19

<210> SEQ ID NO 1539
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1539
acaggaucca ccccaaagc                                                    19

<210> SEQ ID NO 1540
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1540
uggugacagg auccacccc                                                    19

<210> SEQ ID NO 1541
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1541
acauucuggc uggugacag                                                    19

<210> SEQ ID NO 1542
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1542
ugaacauucu ggcugguga                                              19

<210> SEQ ID NO 1543
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1543
uacugaacau ucuggcugg                                              19

<210> SEQ ID NO 1544
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1544
guacugaaca uucuggcug                                              19

<210> SEQ ID NO 1545
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1545
aaguacugaa cauucuggc                                              19

<210> SEQ ID NO 1546
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1546
aaaguacuga acauucugg                                              19

<210> SEQ ID NO 1547
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1547
aaaaguacug aacauucug                                              19

<210> SEQ ID NO 1548
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1548
aaaaaguacu gaacauucu                                           19

<210> SEQ ID NO 1549
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1549
ucgauccaaa aaguacuga                                           19

<210> SEQ ID NO 1550
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1550
aucgauccaa aaaguacug                                           19

<210> SEQ ID NO 1551
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1551
ucauguagaa ucgauccaa                                           19

<210> SEQ ID NO 1552
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1552
acucauguag aaucgaucc                                           19

<210> SEQ ID NO 1553
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1553
ugaaaugcga cucauguag                                           19

<210> SEQ ID NO 1554
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1554
uugaaaugcg acucaugua                                                    19

<210> SEQ ID NO 1555
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1555
auugaaaugc gacucaugu                                                    19

<210> SEQ ID NO 1556
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1556
aauugaaaug cgacucaug                                                    19

<210> SEQ ID NO 1557
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1557
uaauugaaau gcgacucau                                                    19

<210> SEQ ID NO 1558
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1558
cuaauugaaa ugcgacuca                                                    19

<210> SEQ ID NO 1559
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1559
ucuaauugaa augcgacuc                                                    19

<210> SEQ ID NO 1560
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1560
```
uucuaauuga aaugcgacu						19

<210> SEQ ID NO 1561
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1561
auucuaauug aaaugcgac						19

<210> SEQ ID NO 1562
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1562
acauucuaau ugaaaugcg						19

<210> SEQ ID NO 1563
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1563
aacauucuaa uugaaaugc						19

<210> SEQ ID NO 1564
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1564
uaacauucua auugaaaug						19

<210> SEQ ID NO 1565
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1565
uugaguaaca uucuaauug						19

<210> SEQ ID NO 1566
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1566
ugauugagua acauucuaa						19

<210> SEQ ID NO 1567
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1567
ugcugauuga guaacauuc						19

<210> SEQ ID NO 1568
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1568
uaaagagugc ugauugagu						19

<210> SEQ ID NO 1569
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1569
auaaagagug cugauugag						19

<210> SEQ ID NO 1570
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1570
aauaaagagu gcugauuga						19

<210> SEQ ID NO 1571
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1571
aaacaauaaa gagugcuga						19

<210> SEQ ID NO 1572
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1572
accaaacaau aaagagugc						19

<210> SEQ ID NO 1573
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1573
uuuccaccaa acaauaaag                                                19

<210> SEQ ID NO 1574
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1574
uuuuccacca aacaauaaa                                                19

<210> SEQ ID NO 1575
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1575
uuugccuuuu ccaccaaac                                                19

<210> SEQ ID NO 1576
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1576
uuccuuugcc uuuuccacc                                                19

<210> SEQ ID NO 1577
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1577
agauggacuu ccuuugccu                                                19

<210> SEQ ID NO 1578
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1578
gagauggacu uccuuugcc                                                19

```
<210> SEQ ID NO 1579
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1579
ugagauggac uuccuuugc                                                    19

<210> SEQ ID NO 1580
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1580
augagaugga cuuccuuug                                                    19

<210> SEQ ID NO 1581
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1581
uucgaugaga uggacuucc                                                    19

<210> SEQ ID NO 1582
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1582
uuucgaugag auggacuuc                                                    19

<210> SEQ ID NO 1583
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1583
uuuucgauga gauggacuu                                                    19

<210> SEQ ID NO 1584
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1584
uguuuucgau gagauggac                                                    19
```

```
<210> SEQ ID NO 1585
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1585
uguguuuucg augagaugg                                                   19

<210> SEQ ID NO 1586
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1586 auguguuuc gaugagaug                                                    19

<210> SEQ ID NO 1587
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1587
aauguguuuu cgaugagau                                                   19

<210> SEQ ID NO 1588
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1588
uccaaugugu uuucgauga                                                   19

<210> SEQ ID NO 1589
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1589
uuccaaugug uuuucgaug                                                   19

<210> SEQ ID NO 1590
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1590
ugcuuccaau uguuuucg                                                    19

<210> SEQ ID NO 1591
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1591
augcuuccaa uguguuuc                                                  19

<210> SEQ ID NO 1592
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1592
uaugcuucca auguguuuu                                                 19

<210> SEQ ID NO 1593
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1593
uuaugcuucc aauguguuu                                                 19

<210> SEQ ID NO 1594
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1594
uuuaugcuuc caauguguu                                                 19

<210> SEQ ID NO 1595
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1595
auuuaugcuu ccaaugugu                                                 19

<210> SEQ ID NO 1596
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1596
uggauuuaug cuuccaaug                                                 19

<210> SEQ ID NO 1597
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1597
aguuuggauu uaugcuucc                                             19

<210> SEQ ID NO 1598
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1598
uugcaguuug gauuuaugc                                             19

<210> SEQ ID NO 1599
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1599
auugcaguuu ggauuuaug                                             19

<210> SEQ ID NO 1600
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1600
uacauugcag uuuggauuu                                             19

<210> SEQ ID NO 1601
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1601
ucaaguacau ugcaguuug                                             19

<210> SEQ ID NO 1602
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1602
uucaaguaca uugcaguuu                                             19

<210> SEQ ID NO 1603
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1603
aacuucaagu acauugcag                                                19

<210> SEQ ID NO 1604
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1604
auaacuucaa guacauugc                                                19

<210> SEQ ID NO 1605
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1605
aauaacuuca aguacauug                                                19

<210> SEQ ID NO 1606
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1606
uuaauaacuu caaguacauu                                               20

<210> SEQ ID NO 1607
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1607
uuuaauaacu ucaaguaca                                                19

<210> SEQ ID NO 1608
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1608
ucuuuaauaa cuucaagua                                                19

<210> SEQ ID NO 1609
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1609
uucauagcca ucuuuaaua                                                       19

<210> SEQ ID NO 1610
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1610 uuucauagc caucuuuaa                                                        19

<210> SEQ ID NO 1611
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1611 auuucauag ccaucuuua                                                        19

<210> SEQ ID NO 1612
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1612
agcauuuuca uagccaucu                                                       19

<210> SEQ ID NO 1613
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1613
uagcauuuuc auagccauc                                                       19

<210> SEQ ID NO 1614
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1614
aaucacacag acgccuagc                                                       19

<210> SEQ ID NO 1615
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1615
aaaucacaca gacgccuag                                                      19

<210> SEQ ID NO 1616
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1616
uacaaaucac acagacgcc                                                      19

<210> SEQ ID NO 1617
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1617
auacaaauca cacagacgc                                                      19

<210> SEQ ID NO 1618
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1618
aauacaaauc acacagacg                                                      19

<210> SEQ ID NO 1619
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1619
uaauacaaau cacacagac                                                      19

<210> SEQ ID NO 1620
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1620
uauaauacaa aucacacag                                                      19

<210> SEQ ID NO 1621
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 1621
auauaauaca aaucacaca                                                    19

<210> SEQ ID NO 1622
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1622
aauauaauac aaaucacac                                                    19

<210> SEQ ID NO 1623
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1623
uaauauaaua caaaucaca                                                    19

<210> SEQ ID NO 1624
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1624
uuaauauaau acaaaucac                                                    19

<210> SEQ ID NO 1625
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1625
aguuaauaua auacaaauc                                                    19

<210> SEQ ID NO 1626
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1626
uaguucggga gaguuaaua                                                    19

<210> SEQ ID NO 1627
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1627
ucuaguucgg gagaguuaa                                                     19

<210> SEQ ID NO 1628
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1628
uucuaguucg ggagaguua                                                     19

<210> SEQ ID NO 1629
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1629
aaguucuagu ucgggagag                                                     19

<210> SEQ ID NO 1630
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1630
ucaaguucua guucgggag                                                     19

<210> SEQ ID NO 1631
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1631
uucaaguucu aguucggga                                                     19

<210> SEQ ID NO 1632
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1632
cuucaaguuc uaguucggg                                                     19

<210> SEQ ID NO 1633
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1633
ucuucaaguu cuaguucgg                                                    19

<210> SEQ ID NO 1634
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1634
uucuucaagu ucuaguucg                                                    19

<210> SEQ ID NO 1635
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1635
uaguucuuca aguucuagu                                                    19

<210> SEQ ID NO 1636
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1636
uuaguucuuc aaguucuag                                                    19

<210> SEQ ID NO 1637
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1637
auuuaguucu ucaaguucu                                                    19

<210> SEQ ID NO 1638
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1638
uugcauuuag uucuucaag                                                    19

<210> SEQ ID NO 1639
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1639
```
uuuugcauuu aguucuuca                                                19

<210> SEQ ID NO 1640
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1640
auuuugcauu uaguucuuc                                                19

<210> SEQ ID NO 1641
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1641
ugauuuugca uuuaguucu                                                19

<210> SEQ ID NO 1642
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1642
uguauuggcu guccuggug                                                19

<210> SEQ ID NO 1643
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1643
uuguauuggc uguccuggu                                                19

<210> SEQ ID NO 1644
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1644
acuuguauug gcuguccug                                                19

<210> SEQ ID NO 1645
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1645

```
accacuugua uuggcuguc                                              19

<210> SEQ ID NO 1646
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1646
aaaccacuug uauuggcug                                              19

<210> SEQ ID NO 1647
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1647
uaaaccacuu guauuggcu                                              19

<210> SEQ ID NO 1648
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1648
auaaaccacu uguauuggc                                              19

<210> SEQ ID NO 1649
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1649
acauaaacca cuuguauug                                              19

<210> SEQ ID NO 1650
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1650
ugguacauaa accacuugu                                              19

<210> SEQ ID NO 1651
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1651
ucaaacacca cugugauaga                                             19
```

<210> SEQ ID NO 1652
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1652
uucaaacacc augugauag                                                19

<210> SEQ ID NO 1653
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1653
aaguucaaac accauguga                                                19

<210> SEQ ID NO 1654
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1654
aaaguucaaa caccaugug                                                19

<210> SEQ ID NO 1655
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1655
aaaaguucaa acaccaugu                                                19

<210> SEQ ID NO 1656
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1656
ucuugaaaag uucaaacac                                                19

<210> SEQ ID NO 1657
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1657
uucuugaaaa guucaaaca                                                19

```
<210> SEQ ID NO 1658
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1658
auucuugaaa aguucaaac                                                   19

<210> SEQ ID NO 1659
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1659
uugcauucuu gaaaaguuc                                                   19

<210> SEQ ID NO 1660
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1660
ucauugcauu cuugaaaag                                                   19

<210> SEQ ID NO 1661
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1661
auaguggcuc ucauugcau                                                   19

<210> SEQ ID NO 1662
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1662
uccauagugg cucucauug                                                   19

<210> SEQ ID NO 1663
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1663
uguuccauag uggcucuca                                                   19
```

<210> SEQ ID NO 1664
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1664
ugguguucca uaguggcuc					19

<210> SEQ ID NO 1665
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1665
uuggcauggu guuccauag					19

<210> SEQ ID NO 1666
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1666
ucuguuggca ugguguucc					19

<210> SEQ ID NO 1667
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1667
aacaccucug uuggcaugg					19

<210> SEQ ID NO 1668
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1668
aaacaccucu guuggcaug					19

<210> SEQ ID NO 1669
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1669
uaaacaccuc guuggcau					19

<210> SEQ ID NO 1670

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1670 uagggggua aacaccucu                                                   19

<210> SEQ ID NO 1671
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1671 auaggggu aaacaccuc                                                    19

<210> SEQ ID NO 1672
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1672 aauaggggg uaaacaccu                                                   19

<210> SEQ ID NO 1673
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1673
ugaauagggg gguaaacac                                                  19

<210> SEQ ID NO 1674
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1674
uugaauaggg ggguaaaca                                                  19

<210> SEQ ID NO 1675
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1675
aacuugaaua gggggguaa                                                  19

<210> SEQ ID NO 1676
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1676
ugaacuugaa uagggggu                                                      19

<210> SEQ ID NO 1677
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1677
augaacuuga auaggggg                                                      19

<210> SEQ ID NO 1678
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1678
acaugaacuu gaauagggg                                                     19

<210> SEQ ID NO 1679
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1679
ugacaugaac uugaauagg                                                     19

<210> SEQ ID NO 1680
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1680
ucauuaccca gcgugacau                                                     19

<210> SEQ ID NO 1681
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1681
auccucauua cccagcgug                                                     19

<210> SEQ ID NO 1682
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1682
aauccucauu acccagcgu                                                        19

<210> SEQ ID NO 1683
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1683
aaauccucau uacccagcg                                                        19

<210> SEQ ID NO 1684
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1684
ucaaauccuc auuacccag                                                        19

<210> SEQ ID NO 1685
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1685
agucaaaucc ucauuaccc                                                        19

<210> SEQ ID NO 1686
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1686
acagucaaau ccucauuac                                                        19

<210> SEQ ID NO 1687
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1687
ucacagucaa auccucauu                                                        19

<210> SEQ ID NO 1688
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1688
uucacaguca aauccucau                                                     19

<210> SEQ ID NO 1689
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1689
ucuucacagu caaauccuc                                                     19

<210> SEQ ID NO 1690
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1690
ucaucuucac agucaaauc                                                     19

<210> SEQ ID NO 1691
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1691
ucacucaucu ucacaguca                                                     19

<210> SEQ ID NO 1692
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1692
uccucgguca cucaucuuc                                                     19

<210> SEQ ID NO 1693
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1693
gaacgccacc uccucgguc                                                     19

<210> SEQ ID NO 1694
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1694
aggaacgcca ccuccucgg                                              19

<210> SEQ ID NO 1695
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1695
aaggaacgcc accuccucg                                              19

<210> SEQ ID NO 1696
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1696
aaaggaacgc caccuccuc                                              19

<210> SEQ ID NO 1697
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1697
ucaaaggaac gccaccucc                                              19

<210> SEQ ID NO 1698
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1698
auaacuucaa guacauugc                                              19

<210> SEQ ID NO 1699
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1699
uucgaugaga uggacuucc                                              19

<210> SEQ ID NO 1700
<211> LENGTH: 19
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 1700
uagcuuuagc auccucagc				19

<210> SEQ ID NO 1701
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1701
uaacauucua auugaaaug				19

<210> SEQ ID NO 1702
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1702
uucuucaagu ucuaguucg				19

<210> SEQ ID NO 1703
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1703
uugcaguuug gauuuaugc				19

<210> SEQ ID NO 1704
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1704
aauaacuuca aguacauug				19

<210> SEQ ID NO 1705
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1705
uauaauacaa aucacacag				19

<210> SEQ ID NO 1706
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1706
uaguucuuca aguucuagu					19

<210> SEQ ID NO 1707
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1707
ugcugauuga guaacauuc					19

<210> SEQ ID NO 1708
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1708
auaaauagcu uuagcaucc					19

<210> SEQ ID NO 1709
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1709
uuucugaucc guaucacag					19

<210> SEQ ID NO 1710
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1710
uuguauucaa ucacacccu					19

<210> SEQ ID NO 1711
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1711
uugcauuuag uucuucaag					19

<210> SEQ ID NO 1712
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1712
uaauacaaau cacacagac                                                    19

<210> SEQ ID NO 1713
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1713
ucacaguauc uguaaaguc                                                    19

<210> SEQ ID NO 1714
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1714
auacaaauca cacagacgc                                                    19

<210> SEQ ID NO 1715
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1715
uaauauaaua caaaucaca                                                    19

<210> SEQ ID NO 1716
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1716
uuuaauaacu ucaaguaca                                                    19

<210> SEQ ID NO 1717
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1717
uaucacagua ucuguaaag                                                    19

<210> SEQ ID NO 1718
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1718
``` ucaucuuac agucaaauc					19

<210> SEQ ID NO 1719
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1719
ugacaugaac uugaauagg					19

<210> SEQ ID NO 1720
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1720
auuucuuuca uuauauuug					19

<210> SEQ ID NO 1721
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1721
auauuugcca gucugacag					19

<210> SEQ ID NO 1722
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1722
uauauuugcc agucugaca					19

<210> SEQ ID NO 1723
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1723
uuauauuugc cagucugac					19

<210> SEQ ID NO 1724
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1724
auuauauuug ccagucuga                                                19

<210> SEQ ID NO 1725
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1725
uucauuauau uugccaguc                                                19

<210> SEQ ID NO 1726
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1726
uuucauuaua uuugccagu                                                19

<210> SEQ ID NO 1727
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1727
uucuuucauu auauuugcc                                                19

<210> SEQ ID NO 1728
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1728
uuucuuucau uauauuugc                                                19

<210> SEQ ID NO 1729
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1729
auuucuuuca uuauauuug                                                19

<210> SEQ ID NO 1730
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1730
uauuucuuuc auuauauuu                                                19

<210> SEQ ID NO 1731
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1731
uuauuucuuu cauuauauu                                              19

<210> SEQ ID NO 1732
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1732
aaggagacuu auuucuuuc                                              19

<210> SEQ ID NO 1733
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1733
guccugagaa gauuaucug                                              19

<210> SEQ ID NO 1734
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1734
aauugaacgg augguucc                                               19

<210> SEQ ID NO 1735
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1735
uaccaauuga acggauggu                                              19

<210> SEQ ID NO 1736
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1736
uuuguaccaa uugaacgga                                              19

<210> SEQ ID NO 1737
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1737
aagcuccuga agacucugg                                                19

<210> SEQ ID NO 1738
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1738
aaaaucaaga agcuccuga                                                19

<210> SEQ ID NO 1739
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1739
uaaaaucaag aagcuccug                                                19

<210> SEQ ID NO 1740
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1740
uuaaaaucaa gaagcuccu                                                19

<210> SEQ ID NO 1741
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1741
cuuaaaauca agaagcucc                                                19

<210> SEQ ID NO 1742
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1742
uuuguccuua aaaucaaga                                                19

```
<210> SEQ ID NO 1743
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1743 uuuugccuu aaaaucaag                                                 19

<210> SEQ ID NO 1744
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1744
auccucagca cuuuugucc                                                19

<210> SEQ ID NO 1745
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1745
uagcuuuagc auccucagc                                                19

<210> SEQ ID NO 1746
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1746
auagcuuuag cauccucag                                                19

<210> SEQ ID NO 1747
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1747
aauagcuuua gcauccuca                                                19

<210> SEQ ID NO 1748
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1748
uaaauagcuu uagcauccu                                                19

<210> SEQ ID NO 1749
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1749
auaaauagcu uuagcaucc                                                      19

<210> SEQ ID NO 1750
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1750
uaaagucaua aauagcuuu                                                      19

<210> SEQ ID NO 1751
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1751
uaucuguaaa gucauaaau                                                      19

<210> SEQ ID NO 1752
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1752
uaucacagua ucuguaaag                                                      19

<210> SEQ ID NO 1753
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1753
auccguauca caguaucug                                                      19

<210> SEQ ID NO 1754
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1754
uucugauccg uaucacagu                                                      19

<210> SEQ ID NO 1755
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1755
uuucugaucc guaucacag                                                19

<210> SEQ ID NO 1756
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1756
uugugucggu uucugaucc                                                19

<210> SEQ ID NO 1757
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1757
auugugucgg uuucugauc                                                19

<210> SEQ ID NO 1758
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1758
aucauugugu cgguuucug                                                19

<210> SEQ ID NO 1759
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1759
augacaucau ugugucggu                                                19

<210> SEQ ID NO 1760
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1760
aaugacauca uugugucgg                                                19

<210> SEQ ID NO 1761
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1761
uucaaucaca cccugggcc                                                      19

<210> SEQ ID NO 1762
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1762
auucaaucac acccugggc                                                      19

<210> SEQ ID NO 1763
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1763
uauucaauca cacccuggg                                                      19

<210> SEQ ID NO 1764
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1764
uuguauucaa ucacacccu                                                      19

<210> SEQ ID NO 1765
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1765
cuuguauuca aucacaccc                                                      19

<210> SEQ ID NO 1766
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1766
uccuuguauu caaucacac                                                      19

<210> SEQ ID NO 1767
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1767
ucuccuugua uucaaucac                                              19

<210> SEQ ID NO 1768
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1768
aaagcucucc uuguauuca                                              19

<210> SEQ ID NO 1769
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1769
auccacccca aagcucucc                                              19

<210> SEQ ID NO 1770
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1770
uacugaacau ucuggcugg                                              19

<210> SEQ ID NO 1771
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1771
aaguacugaa cauucuggc                                              19

<210> SEQ ID NO 1772
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1772
aaaguacuga acauucugg                                              19

<210> SEQ ID NO 1773
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1773
aaaaguacug aacauucug                                                  19

<210> SEQ ID NO 1774
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1774
aaaaaguacu gaacauucu                                                  19

<210> SEQ ID NO 1775
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1775
aaucgaucca aaaaguacu                                                  19

<210> SEQ ID NO 1776
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1776
uagaaucgau ccaaaaagu                                                  19

<210> SEQ ID NO 1777
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1777
augcgacuca uguagaauc                                                  19

<210> SEQ ID NO 1778
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1778
auugaaaugc gacucaugu                                                  19

<210> SEQ ID NO 1779
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1779
aauugaaaug cgacucaug                                                    19

<210> SEQ ID NO 1780
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1780
uucuaauuga aaugcgacu                                                    19

<210> SEQ ID NO 1781
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1781
auucuaauug aaaugcgac                                                    19

<210> SEQ ID NO 1782
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1782
aacauucuaa uugaaaugc                                                    19

<210> SEQ ID NO 1783
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1783
uaacauucua auugaaaug                                                    19

<210> SEQ ID NO 1784
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1784
uugaguaaca uucuaauug                                                    19

<210> SEQ ID NO 1785
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1785
ugcugauuga guaacauuc                                                19

<210> SEQ ID NO 1786
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1786
uaaagagugc ugauugagu                                                19

<210> SEQ ID NO 1787
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1787
uuuccaccaa acaauaaag                                                19

<210> SEQ ID NO 1788
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1788
uuugccuuuu ccaccaaac                                                19

<210> SEQ ID NO 1789
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1789
uuccuuugcc uuuuccacc                                                19

<210> SEQ ID NO 1790
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1790
cuuccuuugc cuuuuccac                                                19

<210> SEQ ID NO 1791
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1791
acuuccuuug ccuuuucca                                                    19

<210> SEQ ID NO 1792
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1792
augagaugga cuuccuuug                                                    19

<210> SEQ ID NO 1793
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1793
uucgaugaga uggacuucc                                                    19

<210> SEQ ID NO 1794
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1794
uuucgaugag auggacuuc                                                    19

<210> SEQ ID NO 1795
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1795
uguguuuucg augagaugg                                                    19

<210> SEQ ID NO 1796
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1796
auguguuuuc gaugagaug                                                    19

<210> SEQ ID NO 1797
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1797
```
uuccaaugug uuuucgaug                            19

<210> SEQ ID NO 1798
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1798
augcuuccaa uguguuuuc                            19

<210> SEQ ID NO 1799
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1799
uaugcuucca auguguuuu                            19

<210> SEQ ID NO 1800
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1800
uuuaugcuuc caauguguu                            19

<210> SEQ ID NO 1801
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1801
auuuaugcuu ccaaugugu                            19

<210> SEQ ID NO 1802
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1802
uugcaguuug gauuuaugc                            19

<210> SEQ ID NO 1803
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1803

-continued auugcaguuu ggauuuaug                                                    19

<210> SEQ ID NO 1804
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1804
uacauugcag uuuggauuu                                                    19

<210> SEQ ID NO 1805
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1805
aaguacauug caguuugga                                                    19

<210> SEQ ID NO 1806
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1806
aacuucaagu acauugcag                                                    19

<210> SEQ ID NO 1807
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1807
uaacuucaag uacauugca                                                    19

<210> SEQ ID NO 1808
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1808
auaacuucaa guacauugc                                                    19

<210> SEQ ID NO 1809
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1809
aauaacuuca aguacauug                                                    19

<210> SEQ ID NO 1810
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1810
uuaauaacuu caaguacau                                                19

<210> SEQ ID NO 1811
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1811
uuuaauaacu ucaaguaca                                                19

<210> SEQ ID NO 1812
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1812
aucuuuaaua acuucaagu                                                19

<210> SEQ ID NO 1813
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1813
uagccaucuu uaauaacuu                                                19

<210> SEQ ID NO 1814
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1814
auagccaucu uuaauaacu                                                19

<210> SEQ ID NO 1815
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1815
uucauagcca ucuuuaaua                                                19

<210> SEQ ID NO 1816
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1816
uuuucauagc caucuuuaa                                                    19

<210> SEQ ID NO 1817
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1817
auuuucauag ccaucuuua                                                    19

<210> SEQ ID NO 1818
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1818
uacaaaucac acagacgcc                                                    19

<210> SEQ ID NO 1819
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1819
auacaaauca cacagacgc                                                    19

<210> SEQ ID NO 1820
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1820
aauacaaauc acacagacg                                                    19

<210> SEQ ID NO 1821
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1821
uaauacaaau cacacagac                                                    19

```
<210> SEQ ID NO 1822
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1822
uauaauacaa aucacacag                                                      19

<210> SEQ ID NO 1823
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1823
aauauaauac aaaucacac                                                      19

<210> SEQ ID NO 1824
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1824
uaauauaaua caaaucaca                                                      19

<210> SEQ ID NO 1825
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1825
uuaauauaau acaaaucac                                                      19

<210> SEQ ID NO 1826
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1826
uucaaguucu aguucggga                                                      19

<210> SEQ ID NO 1827
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1827
ucuucaaguu cuaguucgg                                                      19

<210> SEQ ID NO 1828
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1828
uucuucaagu ucuaguucg                                                  19

<210> SEQ ID NO 1829
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1829
uaguucuuca aguucuagu                                                  19

<210> SEQ ID NO 1830
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1830
uuaguucuuc aaguucuag                                                  19

<210> SEQ ID NO 1831
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1831
uuuaguucuu caaguucua                                                  19

<210> SEQ ID NO 1832
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1832
auuuaguucu ucaaguucu                                                  19

<210> SEQ ID NO 1833
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1833
uugcauuuag uucuucaag                                                  19

<210> SEQ ID NO 1834
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1834
uuugcauuua guucuucaa                                                    19

<210> SEQ ID NO 1835
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1835
uuuugcauuu aguucuuca                                                    19

<210> SEQ ID NO 1836
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1836
auuuugcauu uaguucuuc                                                    19

<210> SEQ ID NO 1837
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1837
ugauuuugca uuuaguucu                                                    19

<210> SEQ ID NO 1838
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1838
uuguauuggc uguccuggu                                                    19

<210> SEQ ID NO 1839
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1839
aaaccacuug uauuggcug                                                    19

<210> SEQ ID NO 1840
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 1840
uaaaccacuu guauuggcu                                                    19

<210> SEQ ID NO 1841
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1841
auaaaccacu uguauuggc                                                    19

<210> SEQ ID NO 1842
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1842
aaguucaaac accauguga                                                    19

<210> SEQ ID NO 1843
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1843
aaaaguucaa acaccaugu                                                    19

<210> SEQ ID NO 1844
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1844
uugaaaaguu caaacacca                                                    19

<210> SEQ ID NO 1845
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1845
cuugaaaagu ucaaacacc                                                    19

<210> SEQ ID NO 1846
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1846
uucuugaaaa guucaaaca                                                    19

<210> SEQ ID NO 1847
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1847
auucuugaaa aguucaaac                                                    19

<210> SEQ ID NO 1848
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1848
uugcauucuu gaaaaguuc                                                    19

<210> SEQ ID NO 1849
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1849
augguguucc auaguggcu                                                    19

<210> SEQ ID NO 1850
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1850
uuggcauggu guccauag                                                     19

<210> SEQ ID NO 1851
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1851
ucuguuggca ugguguucc                                                    19

<210> SEQ ID NO 1852
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1852
aacaccucug uuggcaugg                                              19

<210> SEQ ID NO 1853
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1853
uacccagcgu gacaugaac                                              19

<210> SEQ ID NO 1854
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1854
auccucauua cccagcgug                                              19

<210> SEQ ID NO 1855
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1855
ucuucacagu caaauccuc                                              19

<210> SEQ ID NO 1856
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1856
aucuucacag ucaaauccu                                              19

<210> SEQ ID NO 1857
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1857
aaggaacgcc accuccucg                                              19

<210> SEQ ID NO 1858
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1858
gcaaauauaa ugaaagaaa                                                        19

<210> SEQ ID NO 1859
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1859
ggcaaauaua augaaagaa                                                        19

<210> SEQ ID NO 1860
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1860 gcauguacu ugaaguuau                                                         19

<210> SEQ ID NO 1861
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1861
cgaacuagaa cuugaagaa                                                        19

<210> SEQ ID NO 1862
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1862
gugauuugua uuauauuaa                                                        19

<210> SEQ ID NO 1863
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1863
gaggauuuga cugugaaga                                                        19

<210> SEQ ID NO 1864
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1864
gauuugacug ugaagauga                                                    19

<210> SEQ ID NO 1865
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1865
ccgaacuaga acuugaaga                                                    19

<210> SEQ ID NO 1866
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1866
acuagaacuu gaagaacua                                                    19

<210> SEQ ID NO 1867
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1867
cuagaacuug aagaacuaa                                                    19

<210> SEQ ID NO 1868
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1868
cuuuacagau acugugaua                                                    19

<210> SEQ ID NO 1869
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1869
gaacuuuuca agaaugcaa                                                    19

<210> SEQ ID NO 1870
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1870
ggcgucugug ugauuugua                                                        19

<210> SEQ ID NO 1871
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1871
gcgucugugu gauuuguau                                                        19

<210> SEQ ID NO 1872
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1872
gucuguguga uuuguauua                                                        19

<210> SEQ ID NO 1873
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1873
uguacuugaa guuauuaaa                                                        19

<210> SEQ ID NO 1874
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1874
cauuucaauu agaauguua                                                        19

<210> SEQ ID NO 1875
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1875
ggaugcuaaa gcuauuuau                                                        19

<210> SEQ ID NO 1876
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1876
cugugauacg gaucagaaa                                        19

<210> SEQ ID NO 1877
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1877
ccagaauguu caguacuuu                                        19

<210> SEQ ID NO 1878
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1878
gucagacugg caaauauaa                                        19

<210> SEQ ID NO 1879
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1879
cugugugauu uguauuaua                                        19

<210> SEQ ID NO 1880
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1880
ccagccagaa uguucagua                                        19

<210> SEQ ID NO 1881
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1881
ggaucagaaa ccgacacaa                                        19

<210> SEQ ID NO 1882
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1882

-continued cuuuauuguu uggug gaaa                                              19

<210> SEQ ID NO 1883
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1883
gccagaaugu ucaguacuu                                               19

<210> SEQ ID NO 1884
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1884
gcauuucaau uagaauguu                                               19

<210> SEQ ID NO 1885
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1885
acugugauac ggaucagaa                                               19

<210> SEQ ID NO 1886
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1886
aggagcuucu ugauuuuaa                                               19

<210> SEQ ID NO 1887
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1887
auguacuuga aguuauuaa                                               19

<210> SEQ ID NO 1888
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1888
gugugauuug uauuauauu                                               19

<210> SEQ ID NO 1889
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1889
cuugauuuua aggacaaaa                                                19

<210> SEQ ID NO 1890
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1890
ucuugauuuu aaggacaaa                                                19

<210> SEQ ID NO 1891
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1891
gauggcuaug aaaaugcua                                                19

<210> SEQ ID NO 1892
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1892
gguauaucca gagucuuca                                                19

<210> SEQ ID NO 1893
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1893
gcugaggaug cuaaagcua                                                19

<210> SEQ ID NO 1894
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1894
gacuggcaaa uauaaugaa                                                19

```
<210> SEQ ID NO 1895
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1895
ccgacacaau gaugucauu                                                   19

<210> SEQ ID NO 1896
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1896
agggugugau ugaauacaa                                                   19

<210> SEQ ID NO 1897
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1897
ugcaauguac uugaaguua                                                   19

<210> SEQ ID NO 1898
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1898
ucccgaacua gaacuugaa                                                   19

<210> SEQ ID NO 1899
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1899
cuaucacaug guguuugaa                                                   19

<210> SEQ ID NO 1900
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1900
aggauuugac ugugaagau                                                   19
```

```
<210> SEQ ID NO 1901
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1901
caggagcuuc uugauuuua                                                    19

<210> SEQ ID NO 1902
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1902
ugugauuugu auuauauua                                                    19

<210> SEQ ID NO 1903
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1903
acuuuuugga ucgauucua                                                    19

<210> SEQ ID NO 1904
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1904
acuugaaguu auuaaagau                                                    19

<210> SEQ ID NO 1905
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1905
gugugauuga auacaagga                                                    19

<210> SEQ ID NO 1906
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1906
acuggcaaau auaaugaaa                                                    19

<210> SEQ ID NO 1907
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1907
acucaaucag cacucuuua                                                    19

<210> SEQ ID NO 1908
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1908 cccaggugu gauugaaua                                                     19

<210> SEQ ID NO 1909
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1909
gauacuguga uacggauca                                                    19

<210> SEQ ID NO 1910
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1910
caauguacuu gaaguuauu                                                    19

<210> SEQ ID NO 1911
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1911
gccaauacaa gugguuuau                                                    19

<210> SEQ ID NO 1912
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1912
acuuuacaga uacgugau                                                     19

<210> SEQ ID NO 1913
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1913 guugaacuu uucaagaau                                                   19

<210> SEQ ID NO 1914
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1914
cuugaagaac uaaaugcaa                                                  19

<210> SEQ ID NO 1915
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1915
ucuuuauugu uugguggaa                                                  19

<210> SEQ ID NO 1916
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1916
ggacaaaagu gcugaggau                                                  19

<210> SEQ ID NO 1917
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1917
cuggguaaug aggauuuga                                                  19

<210> SEQ ID NO 1918
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1918
cugcaaugua cuugaaguu                                                  19

<210> SEQ ID NO 1919
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1919
gauucuacau gagucgcau                                                   19

<210> SEQ ID NO 1920
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1920
cagaauguuc aguacuuuu                                                   19

<210> SEQ ID NO 1921
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1921
cuuuucaaga augcaauga                                                   19

<210> SEQ ID NO 1922
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1922
uguuugaacu uuucaagaa                                                   19

<210> SEQ ID NO 1923
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1923
caaauauaau gaaagaaau                                                   19

<210> SEQ ID NO 1924
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1924
ugguguuuga acuuuucaa                                                   19

<210> SEQ ID NO 1925
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1925
gcuaaagcua uuuaugacu                                                  19

<210> SEQ ID NO 1926
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1926
aggaugcuaa agcuauuua                                                  19

<210> SEQ ID NO 1927
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1927
gcuauuuaug acuuuacag                                                  19

<210> SEQ ID NO 1928
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1928
agucgcauuu caauuagaa                                                  19

<210> SEQ ID NO 1929
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1929
agaacuugaa gaacuaaau                                                  19

<210> SEQ ID NO 1930
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1930
uccguucaau ugguacaaa                                                  19

<210> SEQ ID NO 1931
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1931 cagggugüga uugaauaca                                                        19

<210> SEQ ID NO 1932
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1932
auuaaagaug gcuaugaaa                                                        19

<210> SEQ ID NO 1933
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1933
cgucugugug auuuguauu                                                        19

<210> SEQ ID NO 1934
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1934
uagaacuuga agaacuaaa                                                        19

<210> SEQ ID NO 1935
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1935
agaauguuca guacuuuuu                                                        19

<210> SEQ ID NO 1936
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1936
ugucagacug gcaaauaua                                                        19

<210> SEQ ID NO 1937
<211> LENGTH: 19
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 1937
aguuauuaaa gauggcuau                                              19

<210> SEQ ID NO 1938
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1938
gucuucagga gcuucuuga                                              19

<210> SEQ ID NO 1939
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1939
gguuuaugua ccaucccau                                              19

<210> SEQ ID NO 1940
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1940
cugucagacu ggcaaauau                                              19

<210> SEQ ID NO 1941
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1941
gagucgcauu ucaauuaga                                              19

<210> SEQ ID NO 1942
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1942
accgacacaa ugaugucau                                              19

<210> SEQ ID NO 1943
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1943
agccaauaca agugguuua                    19

<210> SEQ ID NO 1944
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1944
gucgcauuuc aauuagaau                    19

<210> SEQ ID NO 1945
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1945
aguacuuuuu ggaucgauu                    19

<210> SEQ ID NO 1946
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1946
gcuaggcguc ugugugauu                    19

<210> SEQ ID NO 1947
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1947
ggguaaugag gauuugacu                    19

<210> SEQ ID NO 1948
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1948
caguacuuuu uggaucgau                    19

<210> SEQ ID NO 1949
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1949
gaucagaaac cgacacaau                                                    19

<210> SEQ ID NO 1950
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1950
caaacugcaa uguacuuga                                                    19

<210> SEQ ID NO 1951
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1951
gaggaugcua aagcuauuu                                                    19

<210> SEQ ID NO 1952
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1952
gcccagggug ugauugaau                                                    19

<210> SEQ ID NO 1953
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1953
gaaagaaaua agucuccuu                                                    19

<210> SEQ ID NO 1954
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1954
acuugaagaa cuaaaugca                                                    19

<210> SEQ ID NO 1955
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1955
```
auccguucaa uugguacaa                                                19

<210> SEQ ID NO 1956
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1956
acaugagucg cauuucaau                                                19

<210> SEQ ID NO 1957
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1957
ugugugauuu guauuauau                                                19

<210> SEQ ID NO 1958
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1958
acacauugga agcauaaau                                                19

<210> SEQ ID NO 1959
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1959
cgcuggguaa ugaggauuu                                                19

<210> SEQ ID NO 1960
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1960
caucgaaaac acauuggaa                                                19

<210> SEQ ID NO 1961
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1961
ugaagaacua aaugcaaaa         19

<210> SEQ ID NO 1962
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1962
cauccguuca auugguaca         19

<210> SEQ ID NO 1963
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1963
gagucuucag gagcuucuu         19

<210> SEQ ID NO 1964
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1964
uauuuaugac uuuacagau         19

<210> SEQ ID NO 1965
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1965
uaacucuccc gaacuagaa         19

<210> SEQ ID NO 1966
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1966
gcugguauau ccagagucu         19

<210> SEQ ID NO 1967
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1967
ucugugugau uuguauuau         19

<210> SEQ ID NO 1968
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1968
accaggacag ccaauacaa                                                19

<210> SEQ ID NO 1969
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1969
acaugguguu ugaacuuuu                                                19

<210> SEQ ID NO 1970
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1970
acgcugggua augaggauu                                                19

<210> SEQ ID NO 1971
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1971
guaaugagga uuugacugu                                                19

<210> SEQ ID NO 1972
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1972
cugaggaugc uaaagcuau                                                19

<210> SEQ ID NO 1973
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1973
guuuggugga aaaggcaaa                                                19

<210> SEQ ID NO 1974
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1974
ggagcuucuu gauuuaag                                              19

<210> SEQ ID NO 1975
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1975
cagaaaccga cacaaugau                                             19

<210> SEQ ID NO 1976
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1976
cucaaucagc acucuuuau                                             19

<210> SEQ ID NO 1977
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1977
gguguuugaa cuuuucaag                                             19

<210> SEQ ID NO 1978
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1978
gcacucuuua uuguuuggu                                             19

<210> SEQ ID NO 1979
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1979
gguggaaaag gcaaaggaa                                             19

```
<210> SEQ ID NO 1980
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1980
caugagucgc auucaauu                                                       19

<210> SEQ ID NO 1981
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1981
gcuggguaau gaggauuug                                                      19

<210> SEQ ID NO 1982
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1982
cuuccagaua aucuucuca                                                      19

<210> SEQ ID NO 1983
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1983
gaaaacacau uggaagcau                                                      19

<210> SEQ ID NO 1984
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1984
uacaugaguc gcauuucaa                                                      19

<210> SEQ ID NO 1985
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1985
cacauggugu uugaacuuu                                                      19

<210> SEQ ID NO 1986
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1986
ggacaccauc cguucaauu                                                  19

<210> SEQ ID NO 1987
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1987
gaagaacuaa augcaaaau                                                  19

<210> SEQ ID NO 1988
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1988
uguucaguac uuuuuggau                                                  19

<210> SEQ ID NO 1989
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1989
ccccuauuca aguucaugu                                                  19

<210> SEQ ID NO 1990
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1990
auuggaagca uaaauccaa                                                  19

<210> SEQ ID NO 1991
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1991
ucagacuggc aaauauaau                                                  19

<210> SEQ ID NO 1992
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1992
cuucaggagc uucuugauu                                                19

<210> SEQ ID NO 1993
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1993
caugccaaca gagguguuu                                                19

<210> SEQ ID NO 1994
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1994
cuaggcgucu gugugauuu                                                19

<210> SEQ ID NO 1995
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1995
cucucccgaa cuagaacuu                                                19

<210> SEQ ID NO 1996
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1996
ucagcacucu uuauuguuu                                                19

<210> SEQ ID NO 1997
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1997
ucaggagcuu cuugauuuu                                                19

<210> SEQ ID NO 1998
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1998
cagccaauac aagugguuu                                                   19

<210> SEQ ID NO 1999
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1999 cccccuauu caaguucau                                                    19

<210> SEQ ID NO 2000
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2000
ucaugucacg cuggguaau                                                   19

<210> SEQ ID NO 2001
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2001
gaaaccgaca caaugaugu                                                   19

<210> SEQ ID NO 2002
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2002
ucucuaucac augguguuu                                                   19

<210> SEQ ID NO 2003
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2003
gaugcuaaag cuauuuaug                                                   19

<210> SEQ ID NO 2004
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 2004
guccaucuca ucgaaaaca                                                  19

<210> SEQ ID NO 2005
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2005
gauuuguauu auauuaacu                                                  19

<210> SEQ ID NO 2006
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2006
cauaaaucca aacugcaau                                                  19

<210> SEQ ID NO 2007
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2007
ucaccagcca gaauguuca                                                  19

<210> SEQ ID NO 2008
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2008
ucuucaggag cuucuugau                                                  19

<210> SEQ ID NO 2009
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2009
cgcauuucaa uuagaaugu                                                  19

<210> SEQ ID NO 2010
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 2010
cgaaaacaca uuggaagca                                                     19

<210> SEQ ID NO 2011
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2011 gaaguauua aagauggcu                                                      19

<210> SEQ ID NO 2012
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2012
ugaauacaag gagagcuuu                                                     19

<210> SEQ ID NO 2013
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2013
aggacaccau ccguucaau                                                     19

<210> SEQ ID NO 2014
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2014
caucucaucg aaaacacau                                                     19

<210> SEQ ID NO 2015
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2015
aucagcacuc uuuauuguu                                                     19

<210> SEQ ID NO 2016
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 2016
ucacauggug uuugaacuu                                                      19

<210> SEQ ID NO 2017
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2017
acuaaaugca aaaucacca                                                      19

<210> SEQ ID NO 2018
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2018
guuacucaau cagcacucu                                                      19

<210> SEQ ID NO 2019
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2019
ugaggaugcu aaagcuauu                                                      19

<210> SEQ ID NO 2020
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2020
acagccaaua caagugguu                                                      19

<210> SEQ ID NO 2021
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2021
uguuuacccc ccuauucaa                                                      19

<210> SEQ ID NO 2022
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 2022
ugguacaaag cugguauau                                              19

<210> SEQ ID NO 2023
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2023
caucccaucu cuaucacau                                              19

<210> SEQ ID NO 2024
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2024
uaaagcuauu uaugacuuu                                              19

<210> SEQ ID NO 2025
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2025
ucaaucagca cucuuuauu                                              19

<210> SEQ ID NO 2026
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2026
cccuauucaa guucauguc                                              19

<210> SEQ ID NO 2027
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2027
caauacaagu gguuuaugu                                              19

<210> SEQ ID NO 2028
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 2028
guuauuaaag auggcuaug                                                19

<210> SEQ ID NO 2029
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2029
auucuacaug agucgcauu                                                19

<210> SEQ ID NO 2030
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2030
ccaaacugca auguacuug                                                19

<210> SEQ ID NO 2031
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2031
uaaagauggc uaugaaaau                                                19

<210> SEQ ID NO 2032
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2032
ggaagcauaa auccaaacu                                                19

<210> SEQ ID NO 2033
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2033
ccaauacaag ugguuuaug                                                19

<210> SEQ ID NO 2034
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2034
```
aucucuauca cauggucuu                                              19

<210> SEQ ID NO 2035
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2035
caucucuauc acauggugu                                              19

<210> SEQ ID NO 2036
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2036
caaaggaagu ccaucucau                                              19

<210> SEQ ID NO 2037
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2037
guucaauugg uacaaagcu                                              19

<210> SEQ ID NO 2038
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2038
gaaaaugcua ggcgucugu                                              19

<210> SEQ ID NO 2039
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2039 acucuccga acuagaacu                                               19

<210> SEQ ID NO 2040
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2040

-continued uacucaauca gcacucuuu                                        19

<210> SEQ ID NO 2041
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2041
cccaucucua ucacauggu                                        19

<210> SEQ ID NO 2042
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2042
uguaccaucc caucucuau                                        19

<210> SEQ ID NO 2043
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2043
ucuccuucca gauaaucuu                                        19

<210> SEQ ID NO 2044
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2044
gucuccuucc agauaaucu                                        19

<210> SEQ ID NO 2045
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2045
gauuuuaagg acaaaagug                                        19

<210> SEQ ID NO 2046
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2046
gguacaaagc ugguauauc                                        19

<210> SEQ ID NO 2047
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2047
uccaaacugc aauguacuu                                              19

<210> SEQ ID NO 2048
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2048
ugucaccagc cagaauguu                                              19

<210> SEQ ID NO 2049
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2049
ccagggugug auugaauac                                              19

<210> SEQ ID NO 2050
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2050
caauggccca gggugugau                                              19

<210> SEQ ID NO 2051
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2051
caaaagugcu gaggaugcu                                              19

<210> SEQ ID NO 2052
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2052
caggacagcc aauacaagu                                              19

<210> SEQ ID NO 2053
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2053
aucucaucga aaacacauu                                                 19

<210> SEQ ID NO 2054
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2054
cugucaccag ccagaaugu                                                 19

<210> SEQ ID NO 2055
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2055
gacaccaucc guucaauug                                                 19

<210> SEQ ID NO 2056
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2056
caccauccgu ucaauuggu                                                 19

<210> SEQ ID NO 2057
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2057
ccuuccagau aaucuucuc                                                 19

<210> SEQ ID NO 2058
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2058
ugcugaggau gcuaaagcu                                                 19

-continued

```
<210> SEQ ID NO 2059
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2059
uccuuccaga uaaucuucu                                                      19

<210> SEQ ID NO 2060
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2060 guuuacccc cuauucaag                                                       19

<210> SEQ ID NO 2061
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2061
ggaaaaggca aaggaaguc                                                      19
```

SIRNA AND THEIR USE IN METHODS AND COMPOSITIONS FOR INHIBITING THE EXPRESSION OF THE PDK1 GENE

SEQUENCE LISTING

The instant application contains a Sequence Listing which has been submitted electronically in ASCII format and is hereby incorporated by reference in its entirety. Said ASCII copy, created on Nov. 6, 2017, is named 14262_105019_SL.txt and is 446,775 bytes in size.

FIELD OF THE INVENTION

The present invention relates to the field of siRNA products and their use in methods and compositions for the treatment and/or prevention of eye conditions, and more particularly for the treatment and/or prevention of eye conditions such as conjunctivitis and/or ocular allergy, related to high levels of expression and or activity of PDK1.

BACKGROUND OF THE INVENTION

RNA interference (RNAi) is a naturally occurring post-transcriptional regulatory mechanism present in most eukaryotic cells that uses small double stranded RNA (dsRNA) molecules to direct homology-dependent gene silencing. Its discovery by Fire and Mello in the worm *C. elegans* {Fire, 1998} was awarded the Nobel Prize in 2006. Shortly after its first description, RNAi was also shown to occur in mammalian cells, not through long dsRNAs but by means of double-stranded small interfering RNAs (siRNAs) 21 nucleotides long {Elbashir, 2001}.

The process of RNA interference is thought to be an evolutionarily-conserved cellular defence mechanism used to prevent the expression of foreign genes and is commonly shared by diverse phyla and flora, where it is called post-transcriptional gene silencing. Since the discovery of the RNAi mechanism there has been an explosion of research to uncover new compounds that can selectively alter gene expression as a new way to treat human disease by addressing targets that are otherwise "undruggable" with traditional pharmaceutical approaches involving small molecules or proteins.

According to current knowledge, the mechanism of RNAi is initiated when long double stranded RNAs are processed by an RNase III-like protein known as Dicer. The protein Dicer typically contains an N-terminal RNA helicase domain, an RNA-binding so-called Piwi/Argonaute/Zwille (PAZ) domain, two RNase III domains and a double-stranded RNA binding domain (dsRBD) {Collins, 2005} and its activity leads to the processing of the long double stranded RNAs into 21-24 nucleotide double stranded siRNAs with 2 base 3' overhangs and a 5' phosphate and 3' hydroxyl group. The resulting siRNA duplexes are then incorporated into the effector complex known as RNA-induced silencing complex (RISC), where the antisense or guide strand of the siRNA guides RISC to recognize and cleave target mRNA sequences {Elbashir, 2001} upon adenosine-triphosphate (ATP)-dependent unwinding of the double-stranded siRNA molecule through an RNA helicase activity {Nykanen, 2001}. The catalytic activity of RISC, which leads to mRNA degradation, is mediated by the endonuclease Argonaute 2 (AGO2) {Liu, 2004; Song, 2004}. AGO2 belongs to the highly conserved Argonaute family of proteins. Argonaute proteins are ~100 KDa highly basic proteins that contain two common domains, namely PIWI and PAZ domains {Cerutti, 2000}. The PIWI domain is crucial for the interaction with Dicer and contains the nuclease activity responsible for the cleavage of mRNAs {Song, 2004}. AGO2 uses one strand of the siRNA duplex as a guide to find messenger RNAs containing complementary sequences and cleaves the phosphodiester backbone between bases 10 and 11 relative to the guide strand's 5' end {Elbashir, 2001}. An important step during the activation of RISC is the cleavage of the sense or passenger strand by AGO2, removing this strand from the complex {Rand, 2005}. Crystallography studies analyzing the interaction between the siRNA guide strand and the PIWI domain reveal that it is only nucleotides 2 to 8 that constitute a "seed sequence" that directs target mRNA recognition by RISC, and that a mismatch of a single nucleotide in this sequence may drastically affect silencing capability of the molecule {Doench 2004; Lewis, 2003}. Once the mRNA has been cleaved, due to the presence of unprotected RNA ends in the fragments the mRNA is further cleaved and degraded by intracellular nucleases and will no longer be translated into proteins {Orban, 2005} while RISC will be recycled for subsequent rounds {Hutvagner, 2002}. This constitutes a catalytic process leading to the selective reduction of specific mRNA molecules and the corresponding proteins. It is possible to exploit this native mechanism for gene silencing with the purpose of regulating any gene(s) of choice by directly delivering siRNA effectors into the cells or tissues, where they will activate RISC and produce a potent and specific silencing of the targeted mRNA. RNAi has been applied in biomedical research such as treatment for HIV, viral hepatitis, cardiovascular and cerebrovascular diseases, metabolic disease, neurodegenerative disorders and cancer {Angaji S A et al 2010}.

Many studies have been published describing the ideal features a siRNA should have to achieve maximum effectiveness, regarding length, structure, chemical composition, and sequence. Initial parameters for siRNA design were set out by Tuschl and co-workers in WO02/44321, although many subsequent studies, algorithms and/or improvements have been published since then. siRNA selection approaches have become more sophisticated as mechanistic details have emerged, in addition further analysis of existing and new data can provide additional insights into further refinement of these approaches {Walton S P et al 2010}. Alternatively, several recent studies reported the design and analysis of novel RNAi-triggering structures distinct from the classical 19+2 siRNA structure and which do not conform to the key features of classical siRNA in terms of overhang, length, or symmetry, discussing the flexibility of the RNAi machinery in mammalian cells {Chang C I et al 2011}.

Also, a lot of effort has been put into enhancing siRNA stability as this is perceived as one of the main obstacles for therapy based on siRNA, given the ubiquitous nature of RNAses in biological fluids. Another inherent problem of siRNA molecules is their immunogenicity, whereby siRNAs have been found to induce unspecific activation of the innate immune system. The knockdown of unintended genes (mRNAs) is a well-known side effect of siRNA-mediated gene silencing. It is caused as a result of partial complementarity between the siRNA and mRNAs other than the intended target and causes off-target effects (OTEs) from genes having sequence complementarity to either siRNA strand. One of the main strategies followed for stability enhancement and OTE reduction has been the use of modified nucleotides such as 2'-O-methyl nucleotides, 2'-amino nucleotides, or nucleotides containing 2'-0 or 4'-C methylene bridges. Also, the modification of the ribonucleotide backbone connecting adjacent nucleotides has been described, mainly by the introduction of phosphorothioate modified nucleotides. It seems that enhanced stability and/or reduction of immunogenicity are often inversely proportional to efficacy {Parrish, 2000}, and only a certain number, positions and/or combinations of modified nucleotides may result in a stable and/or non-immunogenic silencing compound. As this is an important hurdle for siRNA-based treatments, different studies have been published which describe certain modification patterns showing good results, examples of such include EP1527176, WO2008/050329, WO2008/104978 or WO2009/044392, although many more may be found in the literature {Sanghvi Y S. 2011; Deleavey et al 2012}.

Allergic diseases are characterized by an overreaction of the human immune system to a foreign protein substance ("allergen") that is eaten, breathed into the lungs, injected or touched. Allergies have a genetic component. If only one parent has allergies of any type, chances are 1 in 3 that each child will have an allergy. If both parents have allergies, it is much more likely (7 in 10) that their children will have allergies. There are no cures for allergies; however they can be managed with proper prevention and treatment.

About 30% of people worldwide suffer from allergic symptoms and 40-80% of them have symptoms in the eyes {Key B. 2001}. Allergic diseases affecting the eyes or ocular allergies constitute a heterogenic group of diseases with a very broad spectrum of clinical manifestations. An ocular allergy usually occurs when the conjunctiva (membrane covering the eye and the lining of the eyelid) reacts to an allergen. An ocular allergy can happen independently or in conjunction with other allergy symptoms (such as rhinitis or asthma).

Basic and clinical research has provided a better understanding of the cells, mediators, and immunologic events which occur in ocular allergy. The eye, particularly the conjunctiva, has a relatively large number of mast cells. When allergens are present they can bind to immunoglobulin, IgE, in the FcεRI receptors on the surface of these mast cells and trigger their activation and release of mediators of allergy (a process known as degranulation). Degranulation releases mast cell components, including histamine, prostaglandins, tryptase and leukotrienes, into the environment outside the mast cell. Through a variety of mechanisms these components produce the signs and symptoms of the ocular allergy. The activation of the mast cells of the allergic inflammation is frequently designated as an acute phase response or early phase of the ocular allergy. The acute phase response can progress to a late phase response characterized by recruitment of inflammatory cells to the site of the allergic inflammation, for example as an influx of eosinophils and neutrophils into the conjunctiva.

Ocular allergy represents one of the most common conditions encountered by allergist and ophthalmologists. Ocular allergy is usually associated with the following symptoms and signs: conjunctivitis, blepharitis, blepharoconjuntivitis or keratoconjunctivitis. The eye becomes red and itchy and there occurs lacrimation and slight discharge. Severe cases may also show eye burning sensation, pain and photophobia.

Allergic diseases affecting the eyes include mild forms such as seasonal allergic conjunctivitis (SAC) and perennial allergic conjunctivitis (PAC); and more severe manifestations such as vernal keratoconjunctivitis (VKC); atopic keratoconjunctivitis (AKC) and giant papillary conjunctivitis (GPC). The latter ones can be associated with complications such as corneal damage and may cause vision loss.

SAC and PAC are commonly IgE-mast cell mediated hypersensitivity reaction to external allergens; whereas AKC and VKC are characterized by chronic inflammation involving several immune cell types. SAC and PAC allergens, with the help of antigen presenting cells (APCs), trigger a Th2-predominant immune response that induces B cells to release IgE. Activation of the allergic response usually involves infiltration and degranulation of mast cells.

SAC is the most common allergic disease in the eye, usually caused by allergens like airborne pollen, dust, and animal dander. The signs and symptoms usually occur during the spring and summer, and generally abate during the winter months. Itching, redness and swelling of the conjunctiva are the most characteristic symptoms, but also tearing, burning sensation, and photophobia. In most cases, SAC is not serious. However, it may be very disturbing to patients because it can affect their quality of life and can have significant socioeconomic impact {Kari O. and Saari K M 2010}.

PAC is the second most common allergic disease in the eye, usually caused by animals and mites. The symptoms and signs are much the same as in SAC, the difference is the specific allergens to which the patient is allergic and that PAC can occur throughout the year with exposure to perennial allergens. PAC affects all age groups but mostly young and middle-aged people of both sexes. In addition, PAC is often connected to dry eye syndrome.

SAC and PAC are the most common forms of ocular allergies. Estimates vary, but these types of allergy are said to affect at least 15-20% of the general population. SAC and PAC are often underdiagnosed and consequently undertreated. In SAC and PAC allergen induced local release of IgE prompts degranulation of mast cells in Ca2+ dependent mechanism. IgE-activated mast cells liberate preformed inflammatory mediators such as histamine and leukotriene 4 that are the first mediators of the allergic response. These mediators attract eosinophils that infiltrate the region amplifying the allergic response.

VKC is a relatively rare chronic allergic inflammation of the ocular surface that mainly affects children and young adolescents. Main symptoms are itching, redness, swelling, discharge and photophobia. The most characteristic sign is giant papillae in the upper tarsal conjunctiva.

AKC is a bilateral chronic inflammatory disease of the ocular surface and eyelid. The most characteristic sign are eczematous lesions on the eyelid which are itchy. It is not unusual for AKC patients to have cataract surgery at a young age {Kari O. and Saari K M 2010}.

GPC is an inflammatory disease characterized by papillary hypertrophy of the superior tarsal conjunctiva. GPC is caused by inert substances rather than allergens. When these irritative stimuli are removed the conjunctival papillary changes resolve. Protein deposits on the surface of the contact lens could become antigenic and stimulate the production of IgE {La Rosa M. et al 2013}.

Current treatments for ocular allergy include non-pharmacologic and pharmacologic strategies. Avoidance of the antigen is the primary behavioural modification for all types of ocular allergies. Artificial tear substitutes provide a barrier function and help to improve the first-line defence at the level of the conjunctiva mucosa. When non-pharmacologic strategies do not provide adequate symptom relief, pharmacologic treatments may be applied.

The mainstay of the management of ocular allergy involves the use of anti-allergic therapeutic agents such as antihistamine, dual-action or combination treatments and mast cell stabilizers. Topical antihistamines (such as Emedastine and Levocabastine) competitively and reversibly block histamine receptors and relieve itching and redness, but only for a short time. Antihistamines do not affect other proinflammatory mediators which remain inhibited. A limited duration of action necessitates frequent dosing and topical antihistamines may be irritating to the eye, especially with prolonged use.

Combination treatments using decongestants (such as oxymetazoline, tetrahydrozoline, and naphazonline) in combination with antihistamines act as vasoconstrictors but are known to sting or burn on instillation. Other adverse events include mydriasis and rebound hyperemia, rendering these combination treatments more suitable for short-term relief. In addition, these drugs are not recommended for use in patients with narrow-angle glaucoma. Mast cell stabilizers (such as cromoglycate, lodoxamide, nedocromil) have a mechanism of action that is unclear. They do not relieve existing symptoms and can be used only on a prophylactic basis to prevent mast cell degranulation with subsequent exposure to the allergen. They require a loading period during which they must be applied before the antigen exposure {La Rosa M. et al 2013}.

When the above mentioned anti-allergic drugs do not allow adequate control of the allergic inflammatory process, anti-inflammatory agents are used. Corticosteroids remain among the most potent pharmacologic agents used in the more severe variants of ocular allergy {La Rosa M. et al 2013}. However, steroidal drugs can have side effects that threaten the overall health of the patient. Chronic administration of corticosteroids can lead to drug-induced osteoporosis by suppressing intestinal calcium absorption and inhibiting bone formation. Other adverse side effects of chronic administration of corticosteroids include hypertension, hyperglycemia, hyperlipidemia (increased levels of triglycerides) and hypercholesterolemia (increased levels of cholesterol) because of the effects of these drugs on the body metabolic processes. It is also known that certain corticosteroids have a greater potential for elevating intraocular pressure ("IOP") than other compounds in this class. For example, it is known that prednisolone, which is a very potent ocular anti-inflammatory agent, has a greater tendency to elevate IOP than fluorometholone, which has moderate ocular anti-inflammatory activity. It is also known that the risk of IOP elevations associated with the topical ophthalmic use of corticosteroids increases over time. In other words, the chronic (i.e., long-term) use of these agents increases the risk of significant IOP elevations. Therefore, corticosteroids may not be appropriate for the long-term treatment of ocular allergies. In addition, chronic use of corticosteroids is contraindicated due to an increased risk for the development of cataracts and glaucoma {Ono S J, and Abelson M B, 2005}.

Allergy immunotherapy is useful in reducing the response to allergens, but its role in allergic conjunctivitis has not been proven. The main objective of this treatment is to induce clinical tolerance to the specific allergen. The therapy is administered subcutaneously in progressively increasing doses to remain below the threshold of a clinical reaction. Sublingual immunotherapy (SLIT) is considered an alternative to subcutaneous allergy immunotherapy and is administered orally under the tongue, but long-term results with SLIT are not yet available. Most of the trials with this form of therapy have been for allergic rhinitis. In general, immune responses to allergen administration are not predictive of the effectiveness of the therapy and the therapy itself can produce systemic reactions, the incidence and severity of which vary dependent of the type of allergen administered {La Rosa M. et al 2013}.

In addition, the majority of newer ophthalmic anti-allergic agents have limited durations of action and twice daily dosing is required. A topical preparation with a longer duration of action would be advantageous because it may be instilled once daily. Thus, new therapies that can offer advantages in areas such as efficacy and duration of action, while offering similar safety profiles than traditional ophthalmic anti-allergic agents, are needed.

RNA interference-based therapies have been pointed out as having the potential to satisfy unmet needs in allergy treatment {Popescu F D. 2005}. It has been demonstrated that systemic administration of CD40 siRNA in mice sensitized with an allergen is capable of attenuating nasal allergic symptoms through inhibition of dendritic cell and B cell functions and generation of regulatory T cells {Suzuki M. et al 2009}. In addition, siRNA-based allergen-specific therapy for allergic rhinitis has also been developed by using CD40-silenced and allergen-pulsed dendritic cells {Suzuki M et al 2010}.

Initiation of the allergy reaction starts with the binding of the allergen to the IgE molecules in the FcεRI receptors of mast cells. The activation of FcεRI triggers a change in the mast cell allowing entrance of calcium form the extracellular compartment. Entrance of Ca2+ into mast cells activates phosphatidylinositol-3-kinase (PI3K). Activation of the PI3K pathway includes activation of phosphoinositide-dependent kinase (PDK1) which in turn phosphorylates downstream targets of PI3K such as PKB/Akt, SGK and PKC. These kinases are responsible for the activation of calcium channels to mobilize intracellular calcium stores and activate mast cell degranulation {Shumilina E, et al 2010}.

PDK1 is also known as PDPK1 or PDHK1. The structure of PDK1 can be divided into two domains; the kinase or catalytic domain and the Pleckstrin homology domain (PH domain). PH domain is a protein domain of approximately 120 amino acids that occurs in a wide range of proteins involved in intracellular signalling or as constituents of the cytoskeleton. The kinase domain has three ligand binding sites; the substrate binding site, the ATP binding site, and the docking site (also known as PIF pocket). PDK1 is constitutively active and it is found at the cytoplasm and the mitochondrial matrix.

EP1513947 (MEDICAL RES COUNCIL) describes a method for selecting or designing a compound for modulating the activity of PDK1.

US2009/0275570 (ASTRAZENECA AB) describes compounds possessing PDK1 inhibitory activity for the treatment of cancer.

SUMMARY OF THE INVENTION

The present invention provides improved products for reducing PDK1 expression and consequent ocular inflammation in ocular allergies. The advantage of treating ocular allergies with siRNA products versus traditional anti-allergic therapeutic agents and allergy immunotherapeutic drugs is that treatments based on siRNA will have a longer-lasting effect. This result is due to the fact that once the effector molecule is no longer present, the cell will have to synthesise new proteins from scratch; whereas traditional treatments would leave the levels of said protein intact.

Ocular allergies appear to be on the rise worldwide. Particularly in industrialized nations, environmental pollution is widely considered a major contributor to the heightened sensitivity of allergic individuals. In addition to worsening emissions pollution, studies have also pointed to a global increase in airborne allergens. Still another consideration is that residents of poorer countries are less likely to seek treatment for ocular allergies, a factor which may keep the reported incidence of the disease artificially low in underdeveloped countries.

Asthma and Allergy Foundation in America (AAFA) indicated that the US annual cost of allergies is estimated to be nearly $14.5 billion. They estimated 50 million Americans suffer from all types of allergies (1 in 5 Americans) including indoor/outdoor, food & drug, latex, insect, skin and eye allergies. US allergy prevalence overall has been increasing since the early 1980s across all age, sex and racial groups.

Despite geographic peculiarities, physicians from around the world find common ground in their criteria for choosing an appropriate treatment course. These criteria include efficacy, safety, and convenience of dosing and comfort of administration for the patient, according to specialists from several countries. Therefore, with an increasing number of patients complaining of a range of ocular allergic symptoms worldwide, finding the optimal treatment is every day both more complex and more interesting.

DESCRIPTION OF THE DRAWINGS

FIG. 1: shows short fragments of the target gene sequence PDK1 chosen as the target sequences of the siRNAs of the present invention.

FIG. 2: shows oligonucleotide sequences for siRNA molecules of the present invention targeting PDK1 encompassed by the present invention. The SEQ ID NOs given in the Figure refer to the sense (5'->3') strand; typically siRNAs will be administered as dsRNAs, so will include both the sense strand and its complement antisense strand. SEQ ID NO. 688 to SEQ ID NO. 1374 are siRNAs targeting SEQ ID NO. 1 to SEQ ID NO. 687, respectively. Generally, an siRNA will include the sense and antisense strand, and may also include 3' dinucleotide overhangs (for example, dTdT). However, this is not essential.

DETAILED DESCRIPTION OF THE INVENTION

Figure 3:
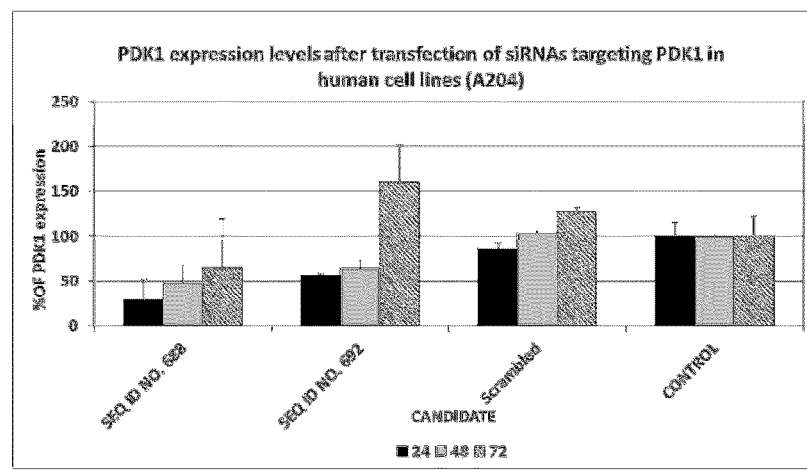
FIG. 3: in vitro PDK1 expression levels after transfection of siRNAs targeting PDK1 in human cell line A204.

In a first aspect, the present invention relates to the provision of a siRNA molecule for use as a medicament, preferably in the treatment and/or prevention of an eye condition characterised by increased expression and/or activity of PDK1, wherein said molecule specifically targets a sequence selected from the group consisting of: SEQ ID NO. 1-SEQ ID NO. 687 and reduces expression of the PDK1 gene when introduced in a cell. Preferably the target sequence is selected from the group consisting of SEQ ID NO. 1-SEQ ID NO. 24, more preferably the group consisting of SEQ ID NO. 1-SEQ ID NO. 6, and even more preferably the target sequence comprises or consists of SEQ ID NO. 1.

A gene is "targeted" by a siRNA according to the present invention when, for example, the siRNA molecule selectively decreases or inhibits the expression of the gene. The phrase "selectively decrease or inhibit" as used herein encompasses siRNAs that affect expression of one gene, in this case PDK1. Alternatively, a siRNA targets a gene when (one strand of) the siRNA hybridizes under stringent conditions to the gene transcript, i.e. its mRNA. Hybridizing "under stringent conditions" means annealing to the target mRNA region under standard conditions, e.g., high temperature and/or low salt content which tend to disfavour hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387-389. Nucleic acid sequences cited herein are written in a 5' to 3' direction unless indicated otherwise. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases these bases may appear as "dT" to differentiate deoxyribonucleotides present in a chain of ribonucleotides.

The target sequence as defined above is described as a target DNA sequence as used for definition of transcript variants in databases used for the purposes of designing siRNAs, whereas the specific compounds to be used will be RNA sequences defined as such.

An expert in the field can access any target gene sequence through public data bases. For example, the GenBank Accession Number corresponding to human PDK1 mRNA is NM_001261816 (Gene ID: 5170). Homologous GenBank Accession Number corresponding to mouse PDK1 mRNA is NM_001080773 (Gene ID: 18607). Furthermore, ENSEMBL (MBL-EBI/Wellcome Trust Sanger Institute) has the following PDK1 human and mouse Accession Numbers: ENSG00000140992 and ENSMUSG00000024122, respectively.

The GenBank Accession Numbers corresponding to three PDK1 transcripts produced by alternative splicing are: NP_001248745.1 (Accession Numbers: NM_001261816.1, GI:387849238), NP_002604.1 (Accession Numbers: NM_002613.4, GI:387849236), and NP_112558.2 (Accession Numbers: NM_031268.5, GI:387849237). Furthermore, ENSEMBL (MBL-EBI/Wellcome Trust Sanger Institute) has 10 further PDK1 public transcripts published: ENSP00000344220, ENSP00000455492, ENSP00000395357, ENSP00000268673, ENSP00000455025, ENSP00000455684, ENSP00000373876, ENSP00000455551, ENSP00000455438, and ENSP00000346895.

Said preferred target region identified by the present invention comprises or consists of at least one sequence selected from the group consisting of SEQ ID NO. 1-SEQ ID NO. 687.

In a preferred embodiment, said preferred target region comprises or consists of at least one sequence selected from the group consisting of SEQ ID NO. 1-SEQ ID NO. 24. SEQ ID NO. 1 presents 100% homology between the following species: *Homo sapiens, Mus musculus, Canis lupus familiaris,* and *Rattus norvegicus.* SEQ ID NO. 2-SEQ ID NO. 6 present 100% homology between the following species: *Homo sapiens, Mus musculus,* and *Canis lupus familiaris.*

In another preferred embodiment, said preferred target region comprises or consists of at least one sequence selected from the group consisting of SEQ ID NO. 1-SEQ ID NO. 6.

In the RNAi field, when in vitro studies demonstrated that a human siRNA is not able to induce knock down of the animal model gene, a surrogate compound (animal-active analogue) is synthetized in order to analyze the efficacy of the siRNA in the relevant animal model. This surrogate is designed against the same region as the human siRNA, thus the two siRNAs have the same sequence except for a few nucleotides, depending on the homology between the human and the rabbit target gene. This approach has been widely used for development of other oligonucleotides, specifically for toxicology studies {Kornbrust D. et al. 2013}.

In a more preferred embodiment, said preferred target region invention comprises or consists of SEQ ID NO. 1 (5'-CTATCACATGGTGTTTGAA-3').

Consequently, a siRNA according to the aspects of the present invention will preferably comprise a double stranded RNA molecule, whose antisense strand will comprise an RNA sequence substantially complementary to at least one sequence selected from the group consisting of SEQ ID NO. 1-SEQ ID NO. 687, and whose sense strand will comprise an RNA sequence complementary to the antisense strand, wherein both strands are hybridised by standard base pairing between nucleotides. More preferably, a siRNA according to aspects of the present invention will preferably comprise a double stranded RNA molecule, whose antisense strand will comprise an RNA sequence substantially complementary to selected from the group consisting of SEQ ID NO. 1-SEQ ID NO. 6, and even more preferably consisting of SEQ ID NO. 1.

Within the meaning of the present invention "substantially complementary" to a target mRNA sequence, may also be understood as "substantially identical" to said target sequence. "Identity" as is known by one of ordinary skill in the art, is the degree of sequence relatedness between nucleotide sequences as determined by matching the order and identity of nucleotides between sequences. In one embodiment the antisense strand of an siRNA having 85%, 86%, 87%, 88%, 89%, 90%, 91%, 92%, 93%, 94%, 95%, 96%, 97%, 98% or 99% complementarity, to the target mRNA sequence are considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule. In a preferred embodiment, the antisense siRNA strand is 100% complementary to the target mRNA sequence, and the sense strand is 100% complementary to the antisense strand over the double stranded portion of the siRNA. The siRNA may also include unpaired overhangs, for example, 3' dinucleotide overhangs, preferably dTdT.

In a preferred embodiment, said eye condition identified by the present invention is an ocular allergy and/or ocular conjunctivitis. More preferably, said eye condition is selected from seasonal allergic conjunctivitis, perennial allergic conjunctivitis, vernal keratoconjunctivitis, atopic keratoconjunctivitis, giant papillary conjunctivitis, dry eye syndrome and combinations thereof.

As is known from the state of the art, many different structures have been proposed to achieve RNA interference. Generally these double stranded molecules are from about 19 to about 25 nucleotides in length, and include blunt-ended structures as well as those with overhangs. Overhangs have been described to be advantageous and may be present on the 5' ends or on the 3' ends of either strand as they reduce recognition by RNAses and imitate Dicer's natural substrate. Some authors recommend including overhangs on both 3' ends of the molecules, whereas others consider one overhang to be sufficient. Others have described the use of blunt-ended structures with specific modification patterns (EP 1527176, WO 2005/062937, WO 2008/104978, EP 2322617, EP 2348133, US 2013/0130377, and many others).

Overhangs may be comprised of between 1 and 5 nucleotides; typically overhangs are made up of dinucleotides. Classical molecules used in the field, comprise a 19 nucleotide double stranded molecule which further comprises 3' dinucleotide overhangs preferably comprising deoxynucleotides as taught in initial studies by Tuschl (WO02/44321). These overhangs are said to further enhance resistance to nuclease (RNase) degradation. Later, Kim et al 2005 describe that 21-mer products (containing dinucleotide overhangs) are necessary for loading onto RISC. Further, Bramsen et al. 2009 describe the introduction of possible destabilizing modifications to the overhangs to further increase silencing efficiency.

As such, a preferred embodiment of the various aspects of the present invention refers to siRNA molecules targeting at least one sequence selected from the group consisting of SEQ ID NO. 1-SEQ ID NO. 687 which comprise at least one overhang. More preferably, said siRNA molecules target at least one sequence selected from the group consisting of SEQ ID NO. 1-SEQ ID NO. 6, and even more preferably consisting of SEQ ID NO. 1. Where the invention relates to an siRNA molecule targeting at least one sequence selected from SEQ ID NO. 1 to SEQ ID NO. 687, the siRNA will include an antisense strand of equivalent length and complementary to the target, and a sense strand of equivalent length and complementary to the antisense strand. The antisense and sense strands may further include additional bases which are not complementary to the other strand or the target, and/or which are not paired in the double stranded portion of the siRNA. For example, SEQ ID NO 1 is a 19 nucleotide sequence; the siRNA may include a 19 bp double stranded region over this portion of sequence identity, and dinucleotide overhangs A preferred embodiment of the various aspects of the present invention refers to siRNA molecules targeting at least one sequence selected from the group consisting of SEQ ID NO. 1-SEQ ID NO. 687, wherein each strand of the double-stranded siRNA molecules is about 18 to about 28 or more (e.g., about 18, 19, 20, 21, 22, 23, 24, 25, 26, 27, or 28 or more) nucleotides long.

Another preferred embodiment of the various aspects of the present invention refers to siRNA molecules of 18-28 nucleotides long or more and comprising a nucleotide sequence selected from the group consisting of SEQ ID NO. 688-SEQ ID NO. 1374. More preferably, the double-stranded siRNA molecules are at least 19 nucleotides long and selected from the group consisting of SEQ ID NO. 688-SEQ ID NO. 1374.

Another alternative embodiment of the various aspects of the present invention provides blunt-ended molecules.

Further, a preferred embodiment of the present invention relates to an siRNA comprising or consisting of a 19 nucleotide double-stranded structure targeting at least one sequence selected from the group consisting of SEQ ID NO. 1-SEQ ID NO. 687. More preferably, the siRNA comprising or consisting of a 19 nucleotide double-stranded structure targeting at least one sequence selected from the group consisting of SEQ ID NO. 1-SEQ ID NO. 6, and even more preferably consisting of SEQ ID NO. 1.

A particular embodiment of the present invention relates to a 19 nucleotide double-stranded blunt-ended siRNA targeted against at least one sequence selected from the group consisting of SEQ ID NO. 1-SEQ ID NO. 687. More preferably, the siRNA is targeted against at least one sequence selected from the group consisting of SEQ ID NO. 1-SEQ ID NO. 6, and even more preferably consisting of SEQ ID NO. 1. In a further particular embodiment this compound comprises or consists of at least one sequence selected from the group consisting of SEQ ID NO. 688-SEQ ID NO. 1374. In a further preferred embodiment, the antisense strand of this siRNA is at least 80%, preferably at least 90%, complementary to at least one sequence selected from the group consisting of SEQ ID NO. 688-SEQ ID NO. 1374.

In a preferred embodiment, this compound comprises or consists of at least one sequence selected from the group consisting of SEQ ID NO. 688-SEQ ID NO. 693.

In a more preferred embodiment, this compound comprises or consists of SEQ ID NO. 688 (5'-CUAUCACAUG-GUGUUUGAA-3'), corresponding to sense strand of our referenced compound named SYL116021.

Furthermore, as described in the section termed background of the art, an important issue with siRNA molecules is their instability in biological fluids due to the ubiquitous nature of RNAses. Consequently, the use of many different chemical modifications to nucleotides has been described with the purpose of enhancing compound stability.

Another inherent problem of siRNA molecules is their immunogenicity, whereby siRNAs have been found to induce unspecific activation of the innate immune system, including up-regulation of certain cytokines, e.g. type I and/or type II interferon as well as IL-12, IL-6 and/or TNF-alpha production.

The origin of these effects is thought to be activation of Toll-like receptors such as TLR7, TLR8 and/or TLR3 by siRNA.

Both of these effects, recognition by RNases and immunogenicity, have also been described to be sequence-dependent.

Some of the chemical modifications which enhance compound stability by decreasing susceptibility to RNAses are also able to reduce induction of immune recognition of subsequent response. However, insertion of chemically modified nucleotides in a siRNA may also result in decreased silencing efficacy as described in the previous section, and hence must be approached with caution.

Consequently, in a preferred embodiment of the various aspects of the present invention, the siRNA further comprises at least one nucleotide with a chemical modification.

Preferred chemical modifications which enhance stability and reduce immunogenic effects include 2'-O-methyl nucleotides, 2'-fluoro nucleotides, 2'-amino nucleotides, 2'-deoxy nucleotides, or nucleotides containing 2'-O or 4'-C methylene bridges. Others preferred chemical modifications for exonuclease protection include ExoEndoLight (EEL): modification of all pyrimidines in the sense strand to 2'-O-methyl residues, and modifications of all pyrimidines in a 5'-UA-3' or 5'-CA-3' motif in the antisense strand. In addition, position 1 of the sense strand can also be changed to 2'-O-methyl, preventing 5'-phosphorylation of the sense strand and thus increasing specificity of the siRNA by further inactivating the sense strand. In addition, the sense strand can also include a 2'-O-methyl modification in position 14, because 2'-O-Me at this position further inactivates the sense strand and therefore increases specificity of the siRNAs. Others preferred chemical modifications for exonuclease protection include Methyl-Fluoro (MEF): exo protection alternating 2'-fluoro and 2'-O-methyl modifications starting (5'-end) with a 2'-F on the sense strand and starting with 2'-O-Me on the antisense strand. In addition, position 1 of the sense strand can also be changed to 2'-O-Me and position 1 of the antisense strand to 2'-F (as this can efficiently be 5'-phosphorylated). Also, modification of the ribonucleotide backbone connecting adjacent nucleotides can also be made by the introduction of phosphorothioate modified nucleotides. A further preferred chemical modification within the meaning of the present invention relates to the substitution of uracyl ribonucleotides with deoxythymidine (deoxyribonucleotides). In another preferred embodiment of the present invention, the at least one chemically modified nucleotide is on the sense strand, on the antisense strand or on both strands of the siRNA.

siRNA molecules as described above may be delivered to the cell interior in their native structure using methods known in the art. For example, when studying in vitro gene silencing, these compounds are administered using standard transfection reagents. To achieve effects in vivo these compounds may also be administered naked or using delivery enhancing agents such as for example liposomes, conjugation with a specific moiety, etc. although many different alternatives are known in the art, and are used differently depending on the desired target site within the body.

Alternatively, siRNA molecules of the various aspects of the invention can be expressed within cells from eukaryotic promoters. Recombinant vectors capable of expressing the siRNA molecules can be delivered and persist in target cells. Alternatively, vectors can be used that provide for transient expression of nucleic acid molecules. Such vectors can be repeatedly administered as necessary. Once expressed, the siRNA molecule interacts with the target mRNA and generates an RNA interfering response. The siRNA molecules produced in this manner are often termed shRNA (short hairpin RNA), as their sense and antisense strands are joined by a small loop of nucleotides. Delivery of siRNA molecule expressing vectors can be systemic, such as by intravenous or intra-muscular administration, by administration to target cells ex-planted from a subject followed by reintroduction into the subject, or by any other means that would allow for introduction into the desired target cell.

A further aspect of the invention relates to the use of siRNA targeting at least one sequence selected from the group consisting of SEQ ID NO. 1-SEQ ID NO. 687 in the preparation of a medicament for use in a method of treatment of an eye condition characterised by increased expression and/or activity of PDK1. More preferably, said at least one sequence is selected from the group consisting of SEQ ID NO. 1-SEQ ID NO. 6, and even more preferably said at least one sequence consists of SEQ ID NO. 1. The method comprises inhibiting expression of PDK1 in a patient. The term inhibition is used to indicate a decrease or downregulation of expression or activity. Preferably, the eye condition is an ocular allergy and/or conjunctivitis. In one embodiment, the eye condition is selected from the group comprising seasonal allergic conjunctivitis, perennial allergic conjunctivitis, vernal keratoconjunctivitis, atopic keratoconjunctivitis, giant papillary conjunctivitis, dry eye syndrome and combinations thereof.

Also provided is a method of treatment of an eye condition characterised by increased expression and/or activity of PDK1. The method comprises inhibiting expression of PDK1 in a patient. The method may comprise administering siRNA targeting at least one sequence selected from the group consisting of SEQ ID NO. 1-SEQ ID NO. 687 More preferably, said at least one sequence is selected from the group consisting of SEQ ID NO. 1-SEQ ID NO. 6, and even more preferably said at least one sequence consists of SEQ ID NO. 1.

In some countries, the combination of chronic allergic conjunctivitis and dry eye syndrome is quite common. The increasing dry eye problem is due to common artificial climatization, indoor and outdoor pollutants and to other unknown reasons. Patients with dry eye syndrome are more prone to suffer from ocular allergies since the tear film is an important barrier in preventing allergens from coming into contact with mast cells.

Therapeutic treatment with siRNAs directed against PDK1 mRNA is expected to be beneficial over small molecule topical ocular drops by increasing the length of time that effect is observed, thereby allowing less frequent dosing and greater patient compliance. This is especially important in cases such as ocular allergies, comprising but not limited to vernal keratoconjunctivitis, atopic keratoconjunctivitis, and giant papillary conjunctivitis, as they are often chronic conditions. In addition, siRNA-based treatments allow the use of so called "undruggable targets" such as intracellular proteins like PDK1 as therapeutic targets.

Bearing in mind the preparation of such a medicament, the siRNA of the various aspects of the present invention may be formulated as a pharmaceutical composition. Preferably, the compositions and formulations of said siRNAs may be administered topically to the organ of interest. In an even more preferred embodiment they may be formulated for topical administration to the eye, preferably to the corneal surface of the eye. Application to the corneal surface may, for example be in the form of eye drops, a gel, lotion, cream or ocular inserts. Other administration forms to the eye may include injection into the eye.

A further preferred embodiment of the various aspects of the present invention relates to an siRNA specifically targeting at least one sequence selected from the group consisting of SEQ ID NO. 1-SEQ ID NO. 687 as described in the preceding paragraphs, for use as a medicament for the treatment of an eye condition characterised by increased expression and/or activity of PDK1. More preferably, said at least one sequence is selected from the group consisting of SEQ ID NO. 1-SEQ ID NO. 6, and even more preferably said at least one sequence consists of SEQ ID NO. 1. As described above, it may be an siRNA comprising or consisting of a 19 nucleotide double-stranded structure targeting at least one sequence selected from the group consisting of SEQ ID NO. 1-SEQ ID NO. 687. This siRNA may be blunt-ended. Preferably, the siRNA comprises or consists of at least one sequence selected from the group consisting of SEQ ID NO. 688-SEQ ID NO. 1374.

Within the context of the present invention, to "specifically target" a sequence the siRNA of the invention preferably comprises at least the same seed sequence. Thus, any sequence according to the invention that specifically targets at least one sequence selected from the group consisting of SEQ ID NO. 1-SEQ ID NO. 687 is preferably identical in positions 2-8 of the antisense strand. More preferably, said at least one sequence is selected from the group consisting of SEQ ID NO. 1-SEQ ID NO. 6, and even more preferably said at least one sequence consists of SEQ ID NO. 1.

Notwithstanding the above, the siRNAs of the various aspects of the present invention may be used to silence PDK1 expression in tissues other than the eye. Consequently, said siRNAs should be formulated accordingly.

For example, a siRNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In one embodiment of the present invention, the siRNA molecule is delivered through a cell-specific siRNA carrier that combines components of the hepatitis B virus and liposomes. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. The preferred compositions of the invention are aqueous solutions, specifically saline solutions such as phosphate-buffered saline (PBS) with a pH range of about 7.0 to about 7.4, preferably with a pH of 7.2+0.5.

A siRNA molecule of the invention may be complexed with membrane disruptive agents and/or a cationic lipid or helper lipid molecule.

Delivery systems which may be used with the invention include, for example, aqueous and non-aqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e. g., fatty acids, fatty acid esters, fatty alcohols and amino acids), and hydrophilic polymers (e. g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) a disease state. The pharmaceutically effective dose generally depends on the type of disease, the composition used, the route of administration, the type of mammal being treated, the physical characteristics of the specific mammal under consideration, concurrent medication, and other factors that those skilled in the medical arts will recognize.

A therapeutically effective amount may also refer to the amount of a siRNA sufficient to delay or minimize the onset of an eye disorder associated with ocular allergy. A therapeutically effective amount may also refer to the amount of the therapeutic agent that provides a therapeutic benefit in the treatment or management of an eye disorder associated with ocular allergy. Further, a therapeutically effective amount with respect to a siRNA of the invention means that amount of therapeutic agent alone, or in combination with other therapies, that provides a therapeutic benefit in the treatment or management of an eye disorder associated with ocular allergy. Used in connection with an amount of a siRNA of the invention, the term can encompass an amount that improves overall therapy, reduces or avoids unwanted effects, or enhances the therapeutic efficacy of or synergizes with another therapeutic agent.

A therapeutic benefit in the treatment or management of an eye disorder such as ocular allergy is the sustained decrease in allergic symptoms. Given that siRNA will decrease the levels of PDK1 within the cell, once the treatment stops the cell must re-synthesise new proteins. As such therapies based on siRNA treatments will have a more sustained effect. This is considered a significant enhancement of the therapeutic efficacy.

An additional benefit of using siRNA is the minimum probability of side effects or acute toxicity issues derived from its presence in systemic circulation, often associated with different eyedrop-based treatments. This is due to the fact that when the compound enters the bloodstream, it will be rapidly degraded by RNAses present in the blood.

On the other hand, the fact that the siRNA molecule can be marketed in single dose vials means addition of antimicrobial preservatives to the formulation can be avoided. Preservatives are present in the majority of formulations on the market today. These preservatives can produce intolerance in some patients, making it necessary to stop the treatment. Both issues are especially important when bearing in mind that conditions such as ocular allergies, comprising but not limited to vernal keratoconjunctivitis, atopic keratoconjunctivitis, giant papillary conjunctivitis, toxic conjunctivitis (or toxic follicular conjunctivitis) and contact allergy, are often chronic and therefore so is the treatment.

One of the preferred administration routes is topical, by instillation directly to the eye, preferably using eye drops. As described above, therapeutic treatment with siRNAs directed against PDK1 mRNA is expected to be beneficial over small molecule topical ocular drops by increasing the length of time that the effect is observed, thereby allowing less frequent dosing and greater patient compliance.

However, as explained above, administration routes other than directly to the eye can also be used. The precise dosage and administration schedule to be employed in the formulation will also depend on the route of administration. A skilled person would understand that the precise dosage and administration schedule to be employed also depends on the seriousness of the disorder, and should be decided according to the judgment of the practitioner and each patient's circumstances. It is also understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The formulations or siRNA of the invention and described herein can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agent. The pharmaceutical compositions or siRNA of the invention and described herein can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

In preferred embodiments, the compositions of the invention are formulated in a solution, preferably a buffered saline solution such as PBS, or a gel for topical administration to the eye, such as, for example, in the form of eyedrops. In such embodiments, the formulations may be cationic emulsions and/or contain biopolymers including, but not limited to, poly(lactide-co-glycolide), carbopol, hialuronic acid and polyacrylic acid.

The nucleic acid molecules of the invention can also be administered in the form of suppositories, e. g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

As such, a further preferred embodiment of the present invention relates to a pharmaceutical composition wherein said composition comprises at least an siRNA targeting at least one sequence selected from the group consisting of SEQ ID NO. 1-SEQ ID NO. 687, as has been described in the preceding paragraphs. More preferably, said at least one sequence is selected from the group consisting of SEQ ID NO. 1-SEQ ID NO. 6, and even more preferably said at least one sequence consists of SEQ ID NO. 1.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

As used herein the terms "ocular allergy" refers to an allergic disorder of the ocular surface caused by increased expression and/or activity of PDK1. It may also be called allergic conjunctivitis". Ocular allergy includes a wide variety of pathological conditions including but not limited to: seasonal allergic conjunctivitis (SAC), perennial allergic conjunctivitis (PAC), vernal keratoconjunctivitis (VKC), atopic keratoconjunctivitis (AKC), and giant papillary conjunctivitis (GPC).

As used herein the terms "conjunctivitis" refers to an inflammation of the conjunctiva. It is also called pink eye or madras eye in India. It is commonly due to an infection (usually viral, but sometimes bacterial) or an allergic reaction.

"Clinical symptoms" of ocular allergy include but are not limited to ocular itching, ocular redness, swelling of the eyelids, chemosis, tearing, and nasal inflammation, nasal congestion, rhinorrhea, nasal pruritis and ear/palate pruritis, and sneezing. It is preferred that the present invention treats or prevents at least two clinical symptoms, more preferably at least three, even more preferably more than four.

The term "patient," as used herein, refers to animals, including mammals, preferably humans.

As used herein the term "allergen" refers to any antigenic substance in the environment that is capable of producing immediate hypersensitivity (allergy). The list of known allergens includes plant pollens, spores of mold, animal dander, house dust, foods, feathers, dyes, soaps, detergents, cosmetics, plastics, and drugs. Allergens can enter the body by being inhaled, swallowed, touched, or injected. Airborne allergens are allergens that are light enough to be carried through air currents, for example but not limited to, pollen or spores.

The term "allergic conjunctivitis" in the present invention is understood as inflammation of the conjunctiva caused by an allergic reaction. The conjunctiva is a thin membrane that covers the eye. When an allergen irritates the conjunctiva, common symptoms that occur in the eye include: redness (mainly due to vasodilation of the peripheral small blood vessels), ocular itching, eyelid swelling, increased lacrimation, photophobia, watery discharge, and foreign body sensation (with pain). Symptoms are usually worse for patients when the weather is warm and dry, whereas cooler temperatures and rain tend to assuage symptoms.

The term "blepharitis" in the present invention is understood as a chronic inflammation of the eyelid.

The term "blepharoconjunctivitis" in the present invention is understood as the simultaneous occurrence of two separate eye conditions: blepharitis and conjunctivitis. Blepharitis affects the outer eyelids, while conjunctivitis occurs in the conjunctiva.

The term "keratoconjunctivitis" in the present invention is understood as the inflammation of the cornea and conjunctiva.

The invention is further described in the following non-limiting examples.

EXAMPLES

0. Materials

Mouse PDK1 Probe: Taqman Gene Expression Assay Mm00554306_m1.
18S Endogenous control: Taqman Gene Expression Assay. Hs99999901_s1.
Multiscribe Reverse Transcriptase 50U/ml (Applied Biosystems P/N 4311235).
RNAse inhibitor 20U/µl (Applied Biosystems P/N N8080119).
TaqMan 2× Universal Master Mix.
Non Radioactive Cell Proliferation Assay kit (Promega, Mannheim, Germany).
Human mast cells (HMC-1).
Ionomycin calcium salt 1 mM in DMSO (from Sigma Life Science Ref#I3909-1 ml).
Annexin-V detection kit Life Technologies (Ref: V13241).

1. In Vitro Analysis 1.1 PDK1 Expression Levels after Transfection of siRNAs of the Present Invention in Different Cell Lines.

Figure 4:
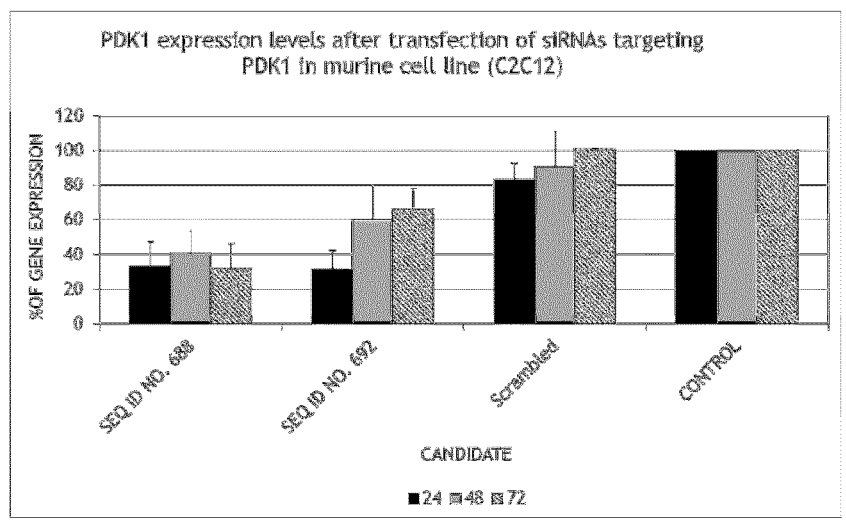
FIG. 4: in vitro PDK1 expression levels after transfection of siRNAs targeting PDK1 in murine cell line C2C12.

In order to demonstrate the silencing effect of the siRNAs of the present invention, in vitro PDK1 expression levels were measured after transfection of a selection of siRNAs of the present invention in different cell lines. Human A204 and murine C2C12 cells were transfected with 100 nM of SEQ ID NO. 688 and SEQ ID NO. 692 (both 19 bp blunt ended dsRNA structures) with Transit TKO and Lipofectamine 2000 respectively as transfection agents. All transfections were performed following standard manufacturer's instructions. In the same transfection a scrambled siRNA sequence was used as a control of the specificity of interference. Cell pellets were collected at 24, 48, and 72 hours after transfection experiment and processed to evaluate possible variations in mRNA levels as a consequence of siRNA mechanism of action. RNA levels were quantified by real-time PCR using a relative quantitation method, the Comparative Threshold 2-44 CT method {Livak and Schmittgen, 2001}. All real time quantitative PCR experiments were performed in triplicate and repeated in three independent experiments. Mean and standard deviation were calculated. As FIG. 3 shows SEQ ID NO. 688 reduced significantly PDK1 mRNA levels approximately 50% in A204 cells and 70% in C2C12 cells. For SEQ ID NO. 688 PDK1 mRNA levels are not completely recovered at 72 hours (FIG. 3). SEQ ID NO. 692 also reduces PDK1 gene expression levels both in A204 cells (50%) and C2C12 cells (40-50%). For SEQ ID NO. 692, PDK1 gene expression levels are completely recovered at 72 hours (FIG. 4).

1.2 Cellular Viability of Different Cell Lines after Transfection with a siRNA of the Present Invention.

Figure 5:
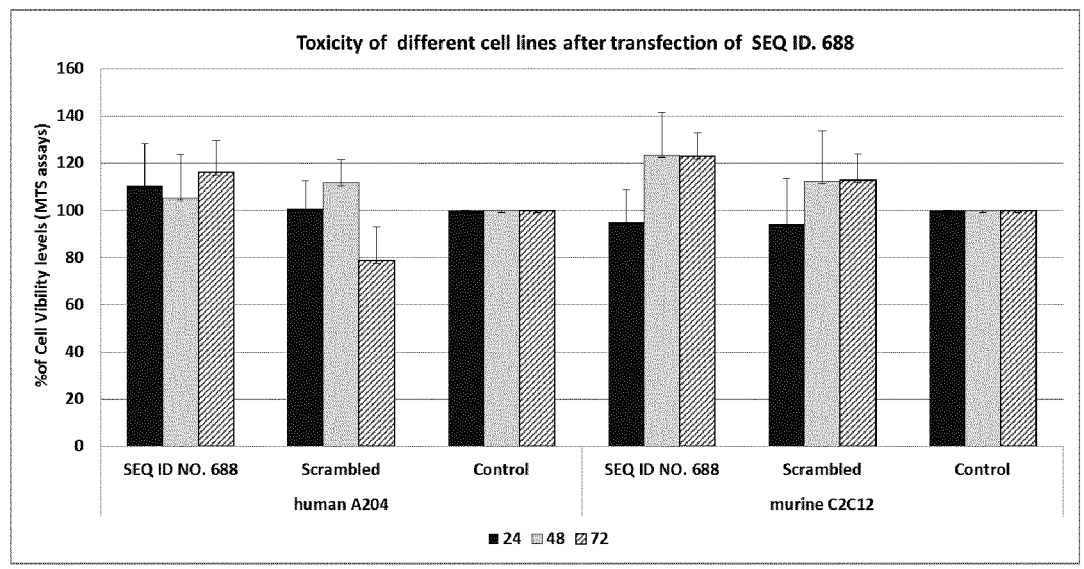
FIG. 5: in vitro toxicity of different cell lines after transfection of SEQ ID NO. 688.

In order to demonstrate the cellular viability of the siRNAs of the present invention, in vitro toxicity levels were measured after transfection of a specific siRNA of the present invention in different cell lines. Human A204 and murine C2C12 and J744A.1 cells were transfected with 100 nM of SEQ ID NO. 688 (19 bp blunt ended dsRNA structure), with Transit TKO and Lipofectamine 2000 respectively as transfection agents. All transfections were performed following standard manufacturer's instructions. In the same transfection a scrambled siRNA sequence was used as a control of the specificity of interference. Cell pellets were collected at 24, 48, and 72 hours after transfection experiment and processed to evaluate possible variations cell viability levels as a consequence of siRNA transfection. Cell viability was measured using CellTiter 96® Aqueous Non-Radiactive Cell. Proliferation Assay from Promega. This method is based on capacity of living cells (dehydrogenase enzymes) to reduce the MTS tetrazolium compound into formazan product as measured by the amount of 490 nm absorbance. Mean and standard deviation were calculated. As FIG. 5 shows no changes in cell viability levels siRNA were found for SEQ ID NO. 688 comparing to control and scrambled siRNA. SEQ ID NO. 688 is not toxic and it is safe.

1.3 Induced Degranulation in Human Macrophages HMC-1 Cells after Transfection of a siRNA of the Present Invention.

Figure 6:
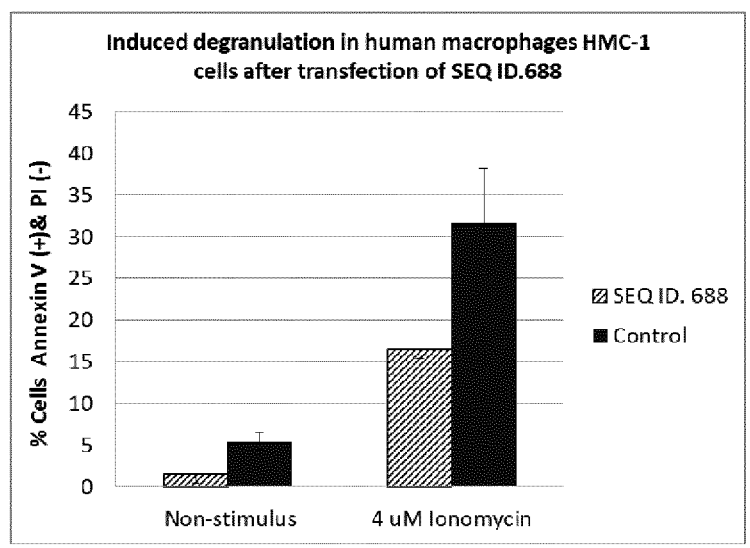
FIG. 6: in vitro induced degranulation in human macrophages HMC-1 cells after transfection of SEQ ID NO. 688.
Figure 7:
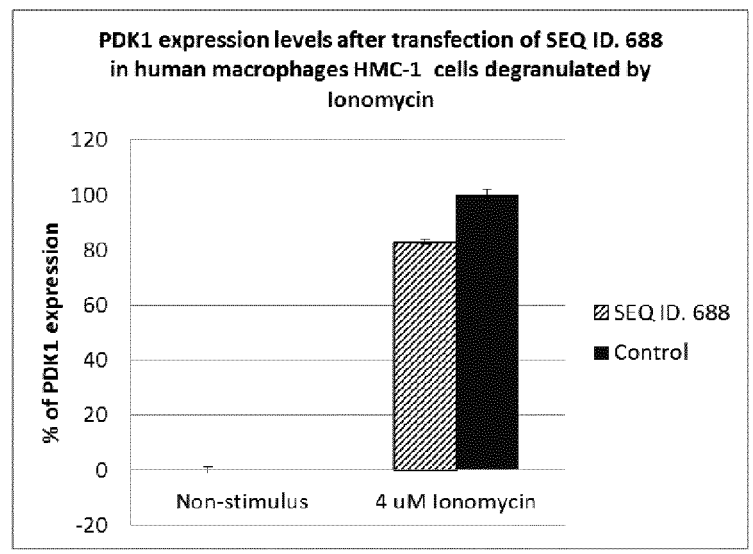
FIG. 7: in vitro PDK1 expression levels after transfection of SEQ ID NO. 688 in human macrophages HMC-1 cells degranulated by Ionomycin.

The aim of degranulation assays was to knockdown the expression PDK1 transfecting a siRNA of the present invention, specifically SEQ ID NO. 688 (19 bp blunt ended dsRNA structure), to evaluate the rate of degranulation from human mast cell line (HMC-1) as an allergic response index. Degranulation was successfully induced using a calcium ionophore, Ionomycin, at 4 µM concentration. Annexin-V binding methodology was use as parameter to evaluate degranulation processes as it was described in Demo and collaborators work (Demo et al, 1999). Gene silencing experiments with SEQ ID NO. 688 showed a strong reduction (approximately 50%) on annexin-V binding on the surface of cells transfected with SEQ ID NO. 688 at Ionomycin (4 µM) concentration. These results showed how SEQ ID NO. 688 administration could prevent mast degranulation (FIG. 6). In parallel to degranulation assays detection of PDK1 mRNA levels were determined, 24 hours after transfection experiments by real-time PCR using a relative quantitation method, the Comparative Threshold 2-ΔΔ CT method {Livak and Schmittgen, 2001}. As FIG. 7 shows, a reduction of 20% of PDK1 mRNA levels was found in human HMC-1 mast cells. Taking into account these results, it is demonstrated that a reduction of PDK1 mRNA levels after transfection of SEQ ID NO. 688 could prevent human mast degranulation.

2. In Vivo Analysis

The objective of these examples was to analyze the efficacy of the siRNAs of the present invention, designed to silence expression of PDK1. Specifically, siRNA with SEQ ID NO. 688 (19 bp blunt ended dsRNA structure, SYL116021) was analyzed to reduce symptoms associated with ocular allergies in a mouse model of ocular allergy induced by ragweed pollen.

Ragweeds are flowering plants in the genus *Ambrosia* in the sunflower family Asteraceae. Ragweed pollen is highly allergenic, generally considered the greatest aeroallergen of all airborne pollens and the prime cause of hay fever worldwide. The National Institute of Environmental Health Science (NIEHS) indicates that ragweed and other weeds such as curly dock, lambs quarters, pigweed, plantain, sheep sorrel and sagebrush are some of the most prolific producers of pollen allergens around the world. This pollen is commonly used in animal models for studying allergic conjunctivitis {Bacsi A et al 2005}.

The aim of this analysis was to determine if down regulation of PDK1 by ocular instillation of compounds of the present invention, specifically SEQ ID NO. 688 (SYL116021) alleviates the symptoms caused by ragweed pollen-induced ocular allergy in mice.

We have analysed whether PDK1 is expressed in the mouse eye and if its expression is up-regulated in response to ragweed pollen-induced ocular allergy. We have also assessed the effect of silencing the expression of PDK1 using locally applied SEQ ID NO. 688 (SYL116021) on allergy response in the above mentioned mouse model. For this purpose the following parameters have been analyzed:

Clinical signs in response to allergy induction: typical ocular signs of allergic conjunctivitis include itching, eyelid swelling, conjunctival swelling (chemosis), and mucus deposition. Mucus associated to ocular allergies is profuse, stringy and even sticky. Alterations to the conjunctiva usually cause the bulbar conjunctiva to take on a "glassy" appearance and the colouring of the palpebral conjunctiva is more pink than red with a frequently milky appearance.

Number of local mast cells: minutes after allergic stimulation conjunctival mast cells degranulate; the release of inflammatory mediators attracts more mast cells that migrate from deeper layers of the conjunctiva.

Local infiltration of eosinophils: infiltration of inflammatory cells to the conjunctiva occurs hours after allergen exposure and is part of the late response to allergens. Although several different types of cells migrate to the conjunctiva the main type are eosinophils.

Expression changes in molecular biomarkers related to allergy.

PDK1: Mast cells function is strictly regulated through changes of ion channel activity and several signaling pathways. Activation of mast cells in response to allergens causes changes in membrane permeability to ions. Entrance of Ca2+ to the cells activates phosphatidylinositol 3 kinase (PI3K). Activation of the PI3K pathway includes activation of phospho-inositide-dependent kinase (PDK1) which in turn phosphorylates downstream targets of PI3K such as PKB/Akt, SGK and PKC. These kinases are responsible for the activation of calcium channels to mobilize intracellular calcium stores and activate mast cell degranulation {Shumilina E, et al. 2010}.

2.1 Methods
A. Animals and Animal Procedures
2.1.1 Test System Characterisation

TABLE 1

Test system characterisation

| | |
|---|---|
| Species: | Mouse |
| Strain: | BALB-C |
| Sex: | Female |
| Colour: | White |
| Rationale for selection of species/strain: | This strain has been previously been established as a good model for ocular allergies {Bacsi A. et al 2005}. |
| Approx. age of the animals at the beginning of the study: | 8-10 weeks |

A further advantage of the siRNAs of the present invention is that SEQ ID NO. 1-SEQ ID NO. 24 correspond to highly conserved regions of the PDK1 gene, throughout different animal sequences. In fact, these sequences are identical between human and mouse, making this animal model especially suitable for the study of for ocular allergies.

2.1.2 Induction of Allergy

Allergic conjunctivitis was induced by immunizing the animals with a mixture of 50 µg ragweed (Rw) pollen in 0.25 ml alum by intraperitoneal injection on day 1. The immunization solution was prepared immediately prior to administration and was protected from light at all times. Ten days after immunization 1.25 mg of Rw pollen was topically instilled into each eye. Administrations were performed in a dose volume of 5 µL/eye. This procedure was adapted from a standard preexisting published protocol known to an expert in the field and validated prior to assessing the efficacy of the siRNAs {Magone M. T. et al 1998}.

2.1.3 Test Item Administration

Figure 8:
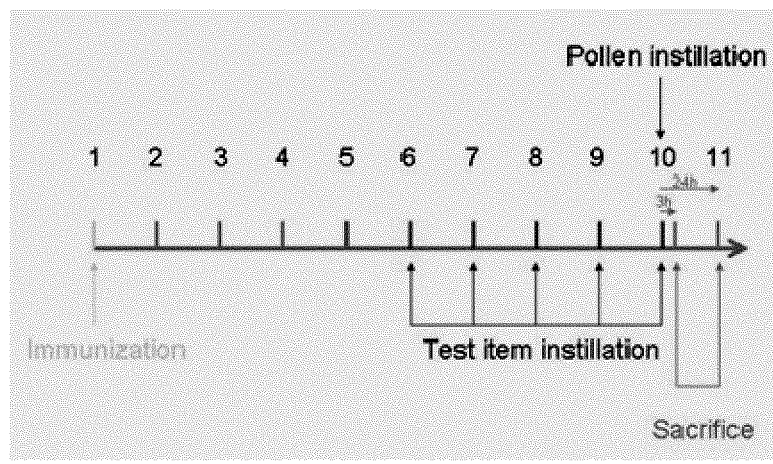
FIG. 8: Schedule of the in vivo assay.

The test item was applied by the topical ocular route to both eyes of the animals once a day over a period of 5 days starting on day 6 (FIG. 8). A separate group of animals was administered with vehicle (PBS) and served as control. Administrations were performed in a dose volume of 5 µL/eye.

2.1.4 Clinical Observations and Collection of Samples

General health status of animals was monitored daily from first administration until sacrifice. Mice were examined for clinical signs of hypersensitivity prior to instillation of topical ocular pollen and at different time-points up to 24h after pollen instillation. Conjunctival chemosis and injection, lid edema, discharge and tearing were graded on a scale 0-3. Clinical scoring was performed by an experimented observer blind to the experimental condition. Animals were sacrificed either 3 or 24h after allergy challenge. Following sacrifice eyes, were isolated and preserved in RNA later.

2.1.5 RNA Isolation and Retrotranscription

Total RNA was isolated from whole eyes, spleen or lymph nodes using RNeasy RNA extraction kit (Invitrogen, CA, USA). 4 µg of total RNA were retrotranscribed using High-Capacity cDNA Archive kit (Applied Biosystems, Inc., Foster City, Calif., USA) according to the manufacturer's instructions and the IT-B-0003-01.

2.1.6 qPCR qPCR was performed using Stepone plus detection system (Applied Biosystems). 500 nanograms of each sample were amplified in a TaqMan 2× Universal Master Mix under the following conditions: 95° C. for 10 min, followed by 40 cycles of 95° C. for 15 s and 60° C. for 1 min. All qPCR amplifications were performed in triplicate and repeated in at least two independent experiments, always including reverse transcription controls and no template controls. PDK1 mRNA levels were analysed by qPCR using the ΔΔCT method of relative quantification using 18S gene as internal standard {Livak and Schmittgen, 2001}.

2.3 Results 2.3.1 Expression of PDK1 in Mouse Eye and Induction in Response to Ocular Allergy.

Figure 9:
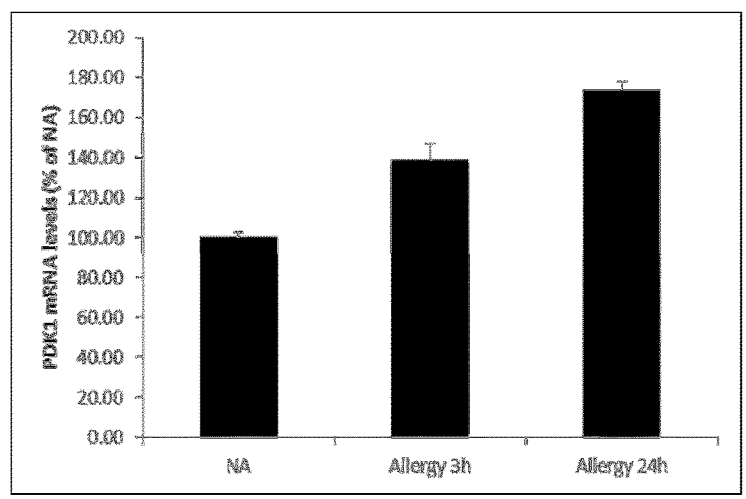
FIG. 9: Levels of PDK1 mRNA in mouse whole eye at different times following induction of ocular allergy. NA: no allergy.

Expression of PDK1 was assessed in eyes of mice at different time points after induction of allergy as mentioned in the methods section. FIG. 9 shows that PDK1 is present in the eye and it is up-regulated over time in response to the allergic challenge; approximately a 1.3-fold increase in PDK1 mRNA levels was observed 3h and a 1.7-fold increase 24 h after administration of ragweed pollen.

Figure 10:
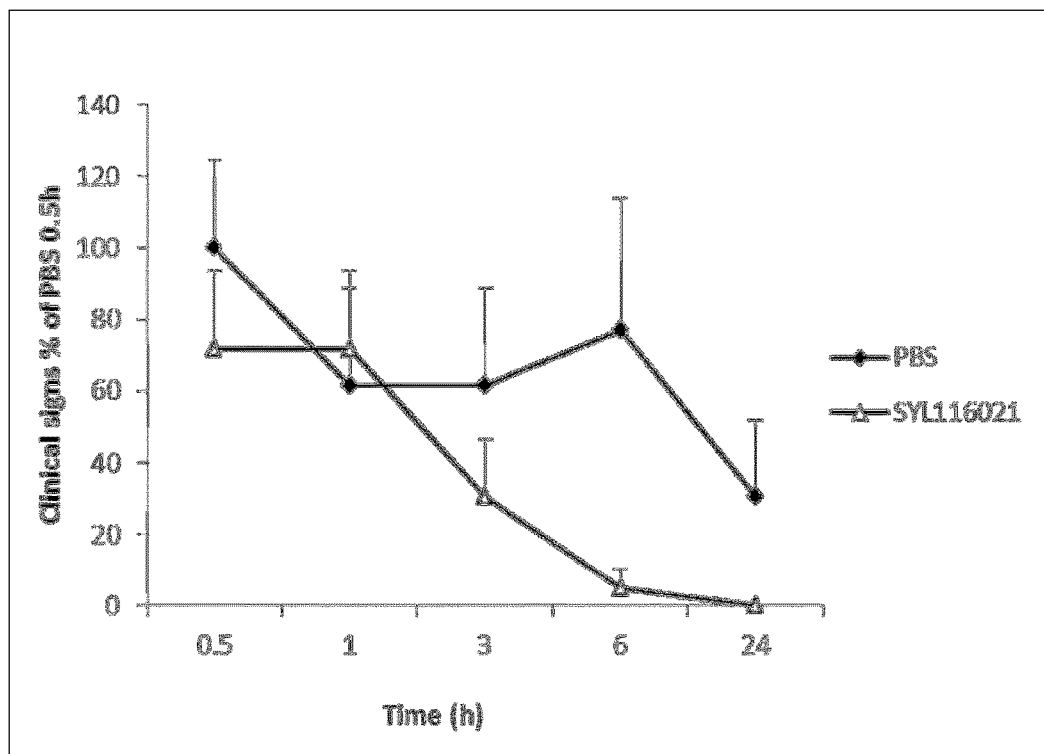
FIG. 10: Ocular clinical signs indicative of ocular allergy. Mice were observed 0.5, 1, 3, 6 and 24 h after induction of ocular allergy. Clinical signs were assessed by grading the following parameters on a scale 0-3: conjunctival chemosis and injection, hyperemia, lid edema, discharge and tearing. Data are expressed as percentage of the clinical scoring at 0.5 h after induction of allergy of the PBS treated group and represent means±s.e.m of 16 animals for PBS and 24 animals for the SEQ ID NO. 688 (SYL116021) treated group.

2.3.2 Efficacy of SEQ ID NO. 688 (SYL116021) in a Mouse Model of Ocular Allergy Two groups of animals were intraperitoneally (IP) injected with a dose of ragweed pollen adsorbed on alum as mentioned in the methods section. Five days after the IP injection one group (A, n=16) received an ocular instillation/day of PBS over a period of five days, the other group received SEQ ID NO. 688 (SYL116021) at the dose of 450 µg/eye/day (low dose) (B, n=24) during the same period of time. Animals were examined for symptoms related to ocular allergy 0.5, 1, 3, 6 and 24 h after ocular instillation of pollen. As shown in FIG. 10 treatment with SEQ ID NO. 688 (SYL116021) significantly reduced the clinical signs of allergy. It is particularly interesting that no clinical signs were observed 6h post-challenge in the group of animals treated with SEQ ID NO. 688 (SYL116021); this means that SEQ ID NO. 688 (SYL116021) was not only able to reduce the intensity of clinical signs but also the duration. Further analysis of the clinical signs indicated that SEQ ID NO. 688 (SYL116021) had an especially potent effect on palpebral edema, tearing and ocular discharge.

REFERENCES

Angaji S. A, Hedayati S. S, Poor R. H, Madani S, Poor S. S. and Panahi S. "Application of RNA interference in treating human diseases" J Genet. 2010. Vol. 89. 4. 527-37.

Bacsi A, Dharajiya N, Choudhury B K, Sur S, Boldogh I. "Effect of pollen-mediated oxidative stress on immediate hypersensitivity reactions and late-phase inflammation in allergic conjunctivitis." J Allergy Clin Immunol. 2005 October; 116(4):836-43.

Bramsen J. B., Laursen M. B., Nielsen A. F., Hansen T. B. et al. 2009 "A large-scale chemical modification screen identifies design rules to generate siRNAs with high activity, high stability and low toxicity" Nucleic Acids Res Vol. 37 Issue: 9 Pages: 2867-81.

Cerutti, L., N. Mian, et al. "Domains in gene silencing and cell differentiation proteins: the novel PAZ domain and redefinition of the Piwi domain." Trends Biochem Sci 2000; 25(10): 481-2.

Collins, R. E. and X. Cheng. "Structural domains in RNAi." FEBS 2005; Lett 579(26): 5841-9.

Chang C. I, Kim H. A, Dua P, Kim S, Li C. J and Lee D. K. "Structural Diversity Repertoire of Gene Silencing Small Interfering RNAs" Nucleic Acid Ther. 2011. Vol. 21. 3. 125-31.

Deleavey G. F and Damha M. J. "Designing chemically modified oligonucleotides for targeted gene silencing". Chem Biol. 2012; Vol. 19. 8. 937-54.

Demo S D, Masuda E, et al. "Quantitative measurement of mast cell degranulation using a novel flow cytometric annexin-V binding assay". Cytometry 1999; 36:340-348.

Doench, J. G. Sharp, P. A. "specificity of microRNA target selection in translational repression" Genes Dev. 18, 504-511; 2004.

Elbashir, S. M., W. Lendeckel, et al. "RNA interference is mediated by 21- and 22-nucleotide RNAs." Genes Dev 2001; 15(2): 188-200.

Fire, A., S. Xu, et al. "Potent and specific genetic interference by double-stranded RNA in Caenorhabditis elegans." Nature 1998; 391(6669): 806-11.

Hutvagner, G. and P. D. Zamore "A microRNA in a multiple-turnover RNAi enzyme complex." Science 2002; 297(5589): 2056-60.

Kari O. and Saari K M. "Updates in the treatment of ocular allergies". Journal of Asthma and Allergy 2010; 3 149-158.

Key B. Allergy and allergic diseases. Part I. N. Engl J Med. 2001; 344:30-37.

Kim D. H., Behlke M. A., Rose S. D., et al. "Synthetic dsRNA Dicer substrates enhance RNAi potency and efficacy" Nat Biotechnol 2005. Vol. 23 Issue: 2 Pages: 222-6.

Kornbrust D, Cavagnaro J, Levin A, et al. "Oligo safety working group exaggerated pharmacology subcommittee consensus document" Nucleic Acid Ther 2013 Vol. 23, 1, Pag: 21-8.

La Rosa M, Lionetti E, et al. "Allergic conjunctivitis: a comprehensive review of the literature" Italian Journal of Pediatrics 2013, 39:18.

Lewis, B. P., Shih I. et al. "Prediction of mammalian micro RNA targets" Cell 2003 115:787-798.

Liu, J., M. A. Carmell, et al. "Argonaute2 is the catalytic engine of mammalian RNAi." Science 2004; 305(5689): 1437-41.

Livak K. J. and Schmittgen T. D., "Analysis of relative gene expression data using real-time quantitative PCR and the 2(-Delta Delta C(T)) Method" Methods. 2001; Vol: 25, Issue: 4, Pages: 402-8.

Magone M T, Chan C C, Rizzo L V, Kozhich A T, Whitcup S M. A novel murine model of allergic conjunctivitis. Clin Immunol Immunopathol 1998; 87:75-84.

Maniatis, T., et al., Molecular Cloning: A Laboratory Manual. Cold Spring Harbor Laboratory, 1982, at pages 387-389.

Nykanen, A., B. Haley, et al. "ATP requirements and small interfering RNA structure in the RNA interference pathway." Cell 2001; 107(3): 309-21.

Ono S J, Abelson M B. "Allergic conjunctivitis: update on pathophysiology and prospects for future treatment" J. Allergy Clin. Immunol. 2005; 75(1), 1 18-122.

Orban, T. I. and E. Izaurralde "Decay of mRNAs targeted by RISC requires XRN1, the Ski complex, and the exosome." Rna 2005; 11(4): 459-69.

Parrish, S., J. Fleenor, et al. "Functional anatomy of a dsRNA trigger: differential requirement for the two trigger strands in RNA interference." Mol Cell 2000; 6(5): 1077-87.

Popescu F D. "Antisense- and RNA interference-based therapeutic strategies in allergy" J Cell Mol Med. 2005 October-December; 9(4):840-53.

Rand, T. A., S. Petersen, et al. "Argonaute2 cleaves the anti-guide strand of siRNA during RISC activation." Cell 2005; 123(4): 621-9.

Sanghvi Y. S. "A status update of modified oligonucleotides for chemotherapeutics applications" Curr Protoc Nucleic Acid Chem. 2011; Vol. 4. 4 1 1-22.

Shumilina E, Zemtsova I M, Heise N, et al. "Phosphoinositide-dependent kinase PDK1 in the regulation of Ca2+ entry into mast cells". Cell Physiol Biochem 2010; 26:699-706.

Song, J. J., S. K. Smith, et al. "Crystal structure of Argonaute and its implications for RISC slicer activity." Science 2004; 305(5689): 1434-7.

Suzuki M, Zheng X, Zhang X, et al. "Inhibition of allergic responses by CD40 gene silencing" Allergy. 2009 March; 64(3):387-97.

Suzuki M, Zheng X, Zhang X, et al. "A novel allergen-specific therapy for allergy using CD40-silenced dendritic cells" J Allergy Clin Immunol. 2010 March; 125(3):737-43.

Walton S. P, Wu M, Gredell J. A and Chan C. "Designing highly active siRNAs for therapeutic applications" FEBS J. 2010. Vol. 277. 23. 4806-13.

The invention claimed is:

1. A method of treating ocular allergy or conjunctivitis in a subject in need thereof, the method comprising:
topically administering to the corneal surface of the eye of the subject an amount of an siRNA molecule which comprises an anti-sense strand that is at least 18 nucleotides in length and at least 85% complementary to a PDK1 mRNA nucleotide sequence, and is effective to decrease the expression and/or activity of PDK1 in cells of the eye and to treat the ocular allergy or conjunctivitis.

2. The method according to claim 1, wherein said ocular allergy or conjunctivitis is selected from the group consisting of seasonal allergic conjunctivitis, perennial allergic conjunctivitis, vernal keratoconjunctivitis, atopic keratoconjunctivitis, giant papillary conjunctivitis, dry eye syndrome and combinations thereof.

3. The method according to claim 1, wherein the siRNA comprises a 19 nucleotide double-stranded region.

4. The method according to claim 3, wherein said siRNA is blunt-ended.

5. The method according to claim 4, wherein said siRNA includes at least one sequence selected from SEQ ID NO. 688 to SEQ ID NO. 1374.

6. The method according to claim 5, wherein at least one nucleotide of said siRNA molecule comprises a chemical modification.

7. The method according to claim 6, wherein said chemical modification is selected from the group consisting of 2'-O-methylation; substitution of uracil ribose nucleotides with deoxythymidine nucleotides; and combinations thereof.

8. The method according to claim 7, wherein said chemical modification is on the sense strand, the antisense strand, or on both the sense and the antisense strand.

9. The method of claim 1, wherein said siRNA molecule is a double stranded, blunt-ended siRNA molecule consisting of 19 base pairs, which comprises a strand that has a sequence selected from SEQ ID NO. 688 to SEQ ID NO. 1374.

10. The method according to claim 9, wherein said eye condition is selected from the group consisting of seasonal allergic conjunctivitis, perennial allergic conjunctivitis, vernal keratoconjunctivitis, atopic keratoconjunctivitis, giant papillary conjunctivitis, dry eye syndrome and combinations thereof.

11. The method according to claim 9, wherein the siRNA molecule has a strand that has the nucleotide sequence set forth in SEQ ID NO. 688.

12. The method according to claim 11, wherein at least one nucleotide of said siRNA molecule comprises a chemical modification.

13. The method according to claim 12, wherein said chemical modification is selected from the group consisting of 2'-O-methylation; substitution of uracil ribose nucleotides with deoxythymidine nucleotides; and combinations thereof.

14. The method according to claim 13, wherein said chemical modification is on the sense strand, the antisense strand, or on both the sense and the antisense strand.

15. The method according to claim 1, wherein said siRNA molecule comprises an anti-sense strand that is at least 18 nucleotides in length and at least 85% complementary to a nucleotide sequence selected from SEQ ID NO:1 to SEQ ID NO: 687.

* * * * *